United States Patent [19]

Baker et al.

[11] Patent Number: 5,462,954
[45] Date of Patent: Oct. 31, 1995

[54] SUBSTITUTED PHENYL PHENOL LEUKOTRIENE ANTAGONISTS

[75] Inventors: S. Richard Baker, Indianapolis; Robert D. Dillard, Zionsville, both of Ind.; Paul E. Floreancig, Mountain View, Calif.; J. Scott Sawyer, Indianapolis; Michael J. Sofia, Carmel, both of Ind.

[73] Assignee: Eli Lilly and Company, Indianapolis, Ind.

[21] Appl. No.: 333,122

[22] Filed: Nov. 1, 1994

Related U.S. Application Data

[63] Continuation of Ser. No. 797,522, Nov. 25, 1991, abandoned.

[51] Int. Cl.⁶ .................. A61K 31/19; A61K 31/41; C07D 257/04; C07D 311/24; C07C 59/68; C07C 65/24

[52] U.S. Cl. .............. 514/381; 514/13; 514/14; 514/15; 514/16; 514/17; 514/18; 514/19; 514/252; 514/318; 514/332; 514/340; 514/343; 514/346; 514/347; 514/351; 514/521; 514/520; 514/570; 514/239.5; 514/239.2; 514/238.8; 514/237.8; 514/233.5; 514/232.8; 548/250; 548/252; 562/463; 562/466; 562/469; 562/471

[58] Field of Search .................... 514/381, 13, 14, 514/15, 16, 17, 18, 19, 235, 252, 318, 332, 340, 343, 346, 347, 351, 520, 521, 570, 571; 548/250, 252; 562/463, 466, 471

[56] References Cited

U.S. PATENT DOCUMENTS

| | | | |
|---|---|---|---|
| 3,652,645 | 3/1972 | Leigh et al. | 562/463 |
| 3,671,580 | 6/1972 | Shen et al. | 562/469 |
| 3,755,603 | 8/1973 | Harrison et al. | 562/469 X |
| 3,882,148 | 5/1975 | Augstein et al. | 260/345.2 |
| 3,972,934 | 8/1976 | Marshall | 260/570.8 |
| 4,136,192 | 1/1979 | Buckle et al. | 424/281 |
| 4,153,807 | 5/1979 | Adams et al. | 562/469 |
| 4,219,668 | 8/1980 | Chiccarelli et al. | 562/469 |
| 4,252,817 | 2/1981 | Closse et al. | 562/469 X |
| 4,281,008 | 7/1981 | Chamberlain et al. | 424/269 |
| 4,424,231 | 1/1984 | Bantick et al. | 424/274 |
| 4,474,788 | 10/1984 | Bantick | 424/258 |
| 4,499,299 | 2/1985 | Bernstein et al. | 514/570 |
| 4,507,498 | 3/1985 | Carson et al. | 562/463 |
| 4,565,882 | 1/1986 | Miyano et al. | 549/399 |
| 4,567,184 | 1/1986 | Musser et al. | 514/227 |
| 4,567,279 | 1/1986 | Chan | 548/491 |
| 4,650,812 | 3/1987 | Cohen et al. | 514/456 |
| 4,661,505 | 4/1987 | Marshall et al. | 514/381 |
| 4,665,203 | 5/1987 | Miyano et al. | 549/402 |
| 4,820,867 | 4/1989 | Belanger et al. | 562/478 |
| 4,853,398 | 8/1989 | Carr et al. | 514/381 |
| 4,874,777 | 10/1989 | Carr et al. | 514/381 |
| 4,899,871 | 12/1989 | Djuric et al. | 514/456 |
| 4,945,099 | 7/1990 | Bollinger et al. | 514/381 |
| 4,952,705 | 8/1990 | Miyano et al. | 548/525 |
| 4,992,576 | 2/1991 | Capinski | 560/52 |
| 4,996,230 | 2/1991 | Gapinski | 514/454 |
| 5,004,743 | 4/1991 | Young et al. | 514/227.8 |
| 5,087,634 | 2/1992 | Reitz et al. | 548/252 X |

FOREIGN PATENT DOCUMENTS

| | | | |
|---|---|---|---|
| 0003847 | 9/1979 | European Pat. Off. | 562/469 |
| 028063 | 5/1981 | European Pat. Off. | 514/381 |
| 056172 | 7/1982 | European Pat. Off. | 514/381 |
| 132366 | 1/1985 | European Pat. Off. | 514/381 |
| 0140684A | 8/1985 | European Pat. Off. | 562/463 |
| 355617 | 2/1990 | European Pat. Off. | 514/381 |
| 405116 | 1/1991 | European Pat. Off. | 514/381 |
| 0544488 | 2/1993 | European Pat. Off. | 562/463 |
| 2173778 | 10/1973 | France | 514/456 |
| 57-35543 | 2/1982 | Japan | 562/469 |
| 1111361 | 4/1968 | United Kingdom | 514/381 |
| 2329037 | 12/1974 | United Kingdom | 562/469 |
| 1396726 | 6/1975 | United Kingdom | 562/469 |

OTHER PUBLICATIONS

*Therapeutic Patents Fast Alert*, 2(17), AG20 (1991).
Buckle, et al., II, *J. Med. Chem.*, 22(2), 158 (1979).
Chemical Abstracts 68:60277j (1968) (Mitsubishi).
LeMahieu, et al., *J. Med. Chem.*, 30(1), 173 (1987).
Krell, et al., *Advances in Prostaglandin, Thromboxane, and Leukotriene Research*, 20, B. Sameulsson, et al., (Raven Press Ltd., New York 1990), p. 119.
Shaw, et al., *J. Med. Chem.*, 34(4), 1235 (1991).
Konno, et al., II, *Advances in Prostaglandin, Thromboxane, and Leukotriene Research*, vol. 21, B. Sameulsson, et al., ed. (Raven Press, Ltd., New York 1990), p. 411.
Djuric et al., II, *J. Med. Chem.*, 32(6), 1145 (1989).
"Leukotrienes and Lipoxygenase", J. Rokach, ed. (Elsevier, Amsterdam 1989), pp. 427–431 and 479–502 (Fitzsimmons et al.).
Siegel, et al., *Monatsh.*, 88, 228 (1957).

*Primary Examiner*—Floyd D. Higel
*Attorney, Agent, or Firm*—Roger S. Benjamin; Robert A. Conrad

[57] ABSTRACT

Antagonists having a substituted phenyl phenol or a substituted phenolic biphenyl structure, and various derivatives thereof, are specific leukotriene antagonists. Their structures, use and synthesis are disclosed. Also, pharmaceutical formulations are disclosed for use in applications treating diseases or conditions characterized by excessive release of leukotriene $B_4$, one of the metabolites of arachidonic acid.

The primary $LTB_4$ antagonistic structures are represented as:

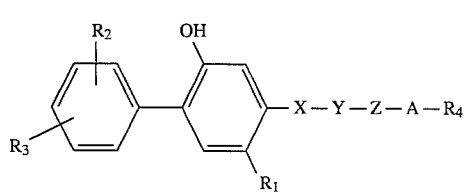

38 Claims, No Drawings

SUBSTITUTED PHENYL PHENOL LEUKOTRIENE ANTAGONISTS

This application is a continuation of application Ser. No. 07/797,522 filed on Nov. 25, 1991, now abandoned.

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A) and have been designated leukotrienes $C_4$, $D_4$, and $E_4$ ($LTC_4$, $LTD_4$, and $LTE_4$, respectively).

Another arachidonic acid metabolite, leukotriene $B_4$ ($LTB_4$), is a proinflammatory lipid which has been implicated in the pathogenesis of psoriasis, arthritis, chronic lung diseases, acute respiratory distress syndrome, shock, asthma, inflammatory bowel diseases, and other inflammatory states characterized by the infiltration and activation of polymorphonuclear leukocytes and other proinflammatory cells. Thus activated, the polymorphonuclear leukocytes liberate tissue-degrading enzymes and reactive chemicals causing the inflammation. Antagonism of $LTB_4$ should therefore provide a novel therapeutic approach to treatment of these conditions.

It is the object of this invention to provide novel chemical agents which are selective leukotriene $B_4$ antagonists that can be used therapeutically in the treatment of inflammation and allergic disorders such as asthma, where leukotrienes are thought to be causal mediators.

SUMMARY OF THE INVENTION

This invention provides compounds of the Formula I

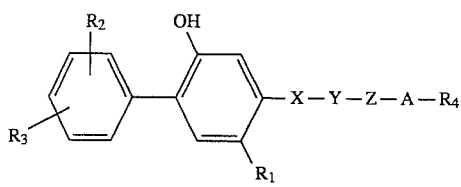

or a pharmaceutically acceptable base addition salt thereof, wherein $R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substitutedphenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)—S(O)$_q$—, trifluoromethyl, or di-($C_1$–$C_3$ alkyl)amino;

X is —O—, —S—, —C(=O)—, or —CH$_2$—;

Y is —O— or —CH$_2$—;

or when taken together, —X—Y— is —CH=CH— or —C≡C—;

Z is a bond or straight or branched chain $C_1$–$C_{10}$ alkylidenyl;

A is a bond, —O—, —S—, —CH=CH—, or —CR$_a$R$_b$—, where R$_a$ and R$_b$ are each independently hydrogen, $C_1$–$C_5$ alkyl, or $R_7$-substituted phenyl, or when taken together with the carbon atom to which they are attached form a $C_4$–$C_8$ cycloalkyl ring;

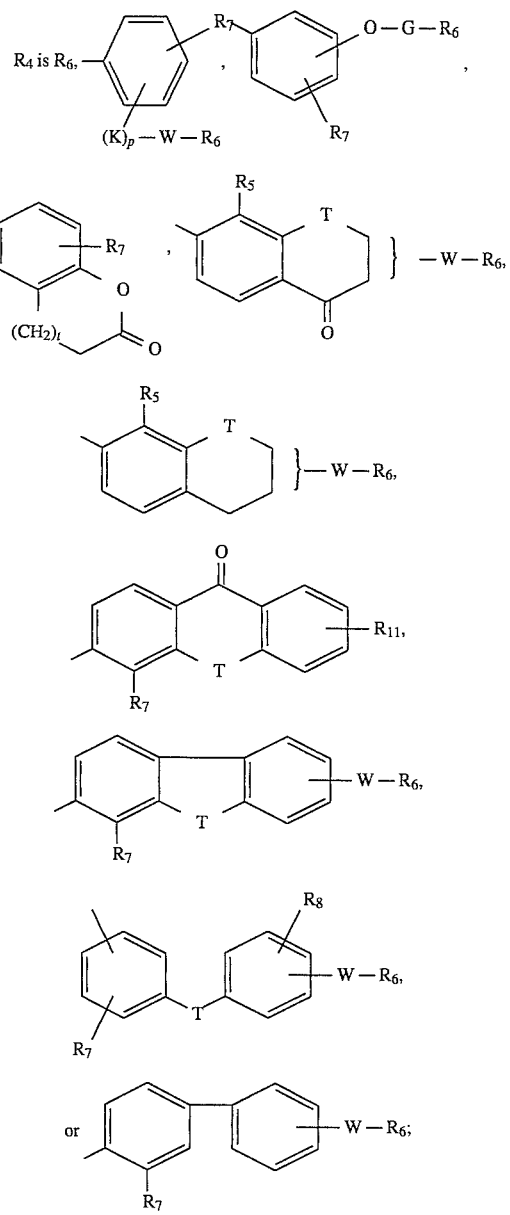

where each $R_5$ is independently hydrogen or $C_1$–$C_4$ alkyl;

each $R_6$ is independently —COOH, 5-tetrazolyl, —CON($R_9$)$_2$, or —CONHSO$_2$$R_{10}$;

each $R_7$ is hydrogen, $C_1$–$C_4$ alkyl, $C_2$–$C_5$ alkenyl, $C_2$–$C_5$ alkynyl, benzyl, methoxy, —W—$R_6$, —T—G—$R_6$, ($C_1$–$C_4$ alkyl)—T—($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, —W—$R_6$, or —T—G—$R_6$;

each W is a bond or a straight or branched chain divalent hydrocarbyl residue of one to eight carbon atoms;

each G is a straight or branched chain divalent hydrocarbyl residue of one to eight carbon atoms;

each T is a bond, —$CH_2$—, —O—, —NH—, —NHCO—, —C(=O)—, or —S(O)$_q$—;

K is —C(=O)— or —CH(OH)—;

each q is independently 0, 1, or 2;

p is 0 or 1; and t is 0 or 1;

provided when X is —O— or —S—, Y may not be —O—;

provided Z and A may not both be a bond when Y is —O—;

provided when A is —O— or —S—, $R_4$ may not be $R_6$;

provided when A is —O— or —S— and Z is a bond, Y may not be —O—;

provided Z may not be a bond when Y is —O—;

and provided W may not be a bond when p is 0.

Further provided by this invention is a method for treating immediate hypersensitivity conditions such as inflammation or asthma comprising the administration of an effective amount of a compound of Formula I.

This invention also provides a pharmaceutical formulation which comprises as an active ingredient a compound of this invention as defined above associated with a pharmaceutically acceptable carrier therefor.

Also provided are intermediates for preparing compounds of Formula I. Such compounds are depicted by Formula II:

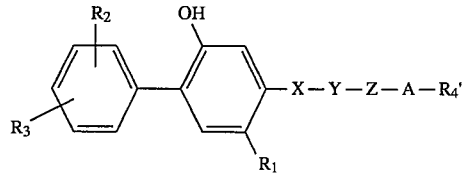

II where $R_1$ is $C_1$-$C_5$ alkyl, $C_2$-$C_5$ alkenyl, $C_2$-$C_5$ alkynyl, $C_1$-$C_4$ alkoxy, ($C_1$-$C_4$ alkyl)thio, halo, or $R_2$-substitutedphenyl;

each $R_2$ and $R_3$ are each independently hydrogen, halo, hydroxy, $C_1$-$C_4$ alkyl, $C_1$-$C_4$ alkoxy, ($C_1$-$C_4$ alkyl)—S(O)$_q$—, trifluoromethyl, or di-($C_1$-$C_3$ alkyl)amino;

X is —O—, —S—, —C(=O)—, or —$CH_2$—;

Y is —O— or —$CH_2$—;

or when taken together, —X—Y— is —CH=CH— or —C≡C—;

Z is a bond or straight or branched chain $C_1$-$C_{10}$ alkylidenyl;

A is a bond, —O—, —S—, —CH=CH—, or —$CR_aR_b$—, where $R_a$ and $R_b$ are each independently hydrogen, $C_1$-$C_5$ alkyl, or $R_7$-substitutedphenyl, or when taken together with the carbon atom to which they are attached form a $C_4$-$C_8$ cycloalkyl ring;

$R_4'$ is $R_6'$,

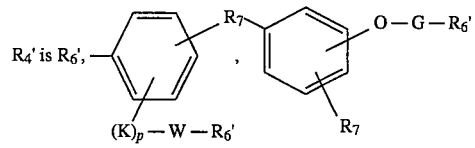

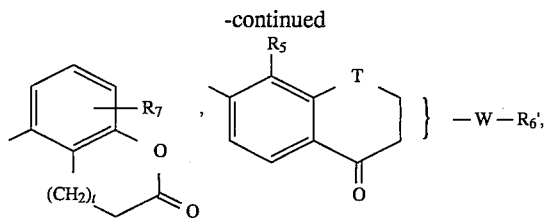

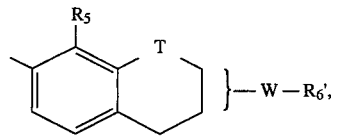

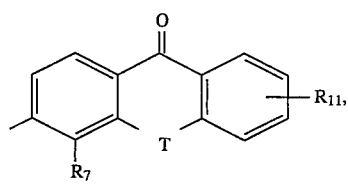

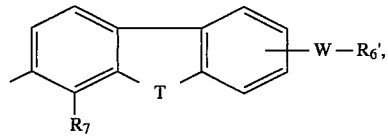

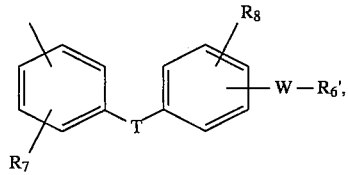

or 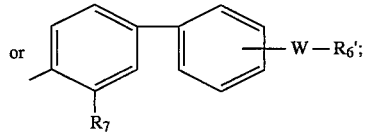

where each $R_5$ is independently hydrogen or $C_1$-$C_4$ alkyl;

each $R_6'$ is independently —COOH, 5-tetrazolyl, —CON($R_9$)$_2$, —CONHSO$_2R_{10}$, —COOR, or —CN;

each $R_7$ is hydrogen, $C_1$-$C_4$ alkyl, $C_2$-$C_5$ alkenyl, $C_2$-$C_5$ alkynyl, benzyl, methoxy, —W—$R_6'$, —T—G—$R_6'$, ($C_1$-$C_4$ alkyl)—T—($C_1$-$C_4$ alkylidenyl)—O—, or hydroxy;

$R_8$ is hydrogen or halo;

each $R_9$ is independently hydrogen, phenyl, or $C_1$-$C_4$ alkyl, or when taken together with the nitrogen atom form a morpholino, piperidino, piperazino, or pyrrolidino group;

$R_{10}$ is $C_1$-$C_4$ alkyl or phenyl;

$R_{11}$ is $R_2$, —W—$R_6'$, or —T—G—$R_6'$;

R is $C_1$-$C_6$ alkyl;

each W is a bond or a straight or branched chain divalent hydrocarbyl residue of one to eight carbon atoms;

each G is a straight or branched chain divalent hydrocarbyl residue of one to eight carbon atoms;

each T is a bond, —$CH_2$—, —O—, —NH—, —NHCO—, —C(=O)—, or —S(O)$_q$—;

K is —C(=O)— or —CH(OH)—;

each q is independently 0, 1, or 2;

p is 0 or 1; and t is 0 or 1;

provided when X is —O— or —S—, Y may not be —O—;

provided Z and A may not both be a bond when Y is —O—;

provided when A is —O— or —S—, $R_4'$ may not be $R_6'$;

provided when A is —O— or —S— and Z is a bond, Y may not be —O—;

provided W may not be a bond when p is 0;

and provided that at least one $R_6'$ must be —COOR or —CN.

DETAILED DESCRIPTION AND PREFERRED EMBODIMENT

The present invention relates to new organic compounds that are useful in the treatment of conditions and diseases associated with the excessive release of leukotriene $B_4$. A preferred group of compounds are the compounds of Formula Ia:

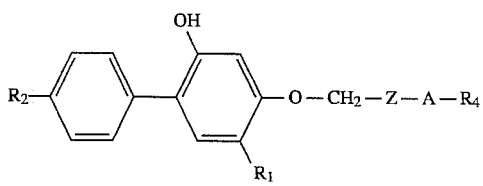

Ia and pharmaceutically acceptable base addition salts thereof. Especially preferred are those compounds wherein $R_2$ is halo, particularly fluoro. Preferred $R_1$ substituents are propyl and especially ethyl.

Preferred Z substituents include $C_2$-$C_4$ alkylidene, particularly —$CH_2CH_2$— and —$CH_2CH_2CH_2CH_2$—. Preferred A groups include —O—, —$CH_2$—, —$CH(R_7$-substitutedphenyl)—, and —$C(CH_3)_2$—. Preferred $R_4$ groups include —COOH, 5-tetrazolyl, or a mono-, di-, or tri-cyclic group as drawn above wherein there is at least one acidic group attached to a ring, such as —W—COOH, —T—G—COOH, or the corresponding tetrazole derivatives. The preferred W moiety is that of a bond or straight chain $C_1$-$C_4$ alkylidene; preferred G moieties are straight chain $C_1$-$C_4$ alkylidene. It is preferred that $R_5$ or $R_7$ be $C_1$-$C_4$ alkyl, especially n-propyl.

Particularly preferred groups are those wherein A is —CH($R_7$-substitutedphenyl)- and $R_4$ is —COOH or 5-tetrazolyl. Also preferred are those compounds wherein A is —O— and $R_4$ is

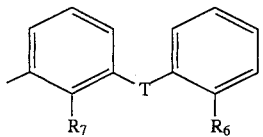

Preferred aspects of this substructure are those therein $R_7$ is $C_1$-$C_4$ alkyl, especially n-propyl, and $R_6$ is —W—COOH. Particularly preferred are those compounds wherein T is —O— or —S— and W is a bond.

The following definitions refer to the various terms used throughout this disclosure. The term "$C_1$-$C_6$ alkyl" refers to the straight and branched aliphatic radicals of 1 to 6 carbon atoms such as methyl, ethyl, propyl, isopropyl, n-butyl, sec-butyl, tert-butyl, n-pentyl, 2,2-dimethylpropyl, hexyl, and the like. Included within this definition are the terms "$C_1$-$C_3$ alkyl", "$C_1$-$C_4$ alkyl" and "$C_1$-$C_5$ alkyl". The term "$C_2$-$C_5$ alkenyl" refers to straight and branched aliphatic radicals of 2 to 5 carbon atoms containing one double bond, such as —$CH=CH_2$, —$CH_2CH=CH_2$, —$CH_2CH_2CH=CH_2$, —$CH_2C(CH_3)=CH_2$, —$CH_2CH=C(CH_3)_2$, and the like. The term "$C_2$-$C_5$ alkynyl" refers to straight and branched aliphatic residues of 2 to 5 carbon atoms containing one triple bond, such as —$C≡CH$, —$CH_2$—$C≡CH$, —$CH_2CH_2C≡CH$, —$CH_2CH(CH_3)C≡CH$, —$CH_2C≡CCH_3$, and the like. The term "$C_1$-$C_4$ alkoxy" refers to methoxy, ethoxy, propoxy, isopropoxy, butoxy, sec-butoxy, and tert-butoxy. The term "halo" refers to fluoro, chloro, bromo, and iodo.

The term "$C_1$-$C_{10}$ alkylidene" refers to a divalent radical derived from a $C_1$-$C_{10}$ alkane such as —$CH_2$—, —$CH(CH_3)$—, —$C(CH_3)_2$—, —$CH(C_2H_5)$—, —$CH_2CH_2$—, —$CH_2CH(CH_3)$—, —$CH(CH_3)CH_2$—, —$CH(CH_3)CH(CH_3)$—, —$CH_2C(CH_3)_2$—, —$CH_2CH(C_2H_5)$—, —$CH_2CH_2CH_2$—, —$CH(CH_3)CH_2CH_2$—, —$CH_2CH(CH_3)CH_2$—, —$CH_2CH(C_2H_5)CH_2$—, —$CH_2CH_2CH(C_2H_5)$—, —$C(CH_3)_2CH_2CH_2$—, —$CH(CH_3)CH_2CH(CH_3)$—, —$CH_2CH_2CH_2CH_2$—, —$CH_2C(CH_3)_2CH_2CH_2$—, —$CH_2C(CH_3)_2CH_2$—, —$CH_2CH_2CH(C_2H_5)CH_2$—, —$CH_2CH_2CH_2CH_2CH_2$—, —$CH(CH_3)CH_2CH_2CH_2CH_2$—, —$CH_2CH_2CH_2CH_2CH_2CH_2$—, —$(CH_2)_{10}$—, and the like. Included within this definition are the terms "$C_1$-$C_4$ alkylidene" and "$C_2$-$C_4$ alkylidene".

The term "$C_4$-$C_8$ cycloalkyl" refers to a cycloalkyl ring of four to eight carbon atoms, such as cyclobutyl, cyclopentyl, cyclohexyl, 4,4-dimethylcyclohexyl, cycloheptyl, cyclooctyl, and the like.

The term "straight or branched chain divalent hydrocarbyl residue of one to eight carbon atoms" refers to a divalent radical derived from a straight or branched alkane, alkene, or alkyne of one to eight carbon atoms. Depending upon the branching and number of carbon atoms, as will be appreciated by organic chemists, such a moiety can contain one, two or three double or triple bonds, or combinations of both. As such, this term can be considered an alkylidene group as defined above containing from 1 to 8 carbon atoms optionally containing one to three double or triple bonds, or combinations of the two, limited as noted in the preceding sentence.

This invention includes the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred. This invention includes both mono-salt forms, ie, a 1:1 ratio of a compound of Formula I with a base as previously described, as well as di-salt forms in those instances where a compound of Formula I has two acidic groups. In addition, this invention includes any solvate forms of the compounds of Formula I or salts thereof, such as ethanol solvates, hydrates, and the like.

It is recognized that in compounds having branched alkyl, alkylidenyl, or hydrocarbyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, ie, (1H)-5-tetrazolyl and (2H)-5-tetrazolyl.

The compounds of this invention may be prepared according to standard methods known in the art. For example, the tetrazole compounds of Formula I (wherein at least one $R_6$ is 5-tetrazolyl) may be prepared from the corresponding intermediate II wherein the corresponding $R_6'$ group is nitrile by any of a variety of standard methods. Generally, the nitrile is reacted with an azide reagent in a non-reactive solvent. Preferred conditions include the use of lithium or ammonium azide in dimethylformamide, sodium azide in diglyme and N,N-dimethylethanolamine hydrochloride, or tri-n-butyltin azide in a non-reactive solvent such as dimethoxyethane or tetrahydrofuran. Under the latter conditions, the reaction is generally heated at or near the reflux temperature of the reaction mixture. The transformation is generally complete under these conditions in 2–3 days. Other operable reaction conditions include the reaction of nitrile II with: an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and DMF.

Similarly, the acids of this invention (Formula I wherein at least one $R_6$ is —COOH) are prepared from the corresponding intermediates II wherein the corresponding $R_6'$ group is —COOR or —CN. Hydrolysis of such esters or nitriles may be accomplished by any of a variety of acidic or basic conditions, preferably under aqueous conditions. Preferred methods involve the use of lithium hydroxide in a solvent mixture of acetone/water, sodium hydroxide in dioxane, or potassium hydroxide or potassium carbonate in a mixture of methanol/water. Under the former conditions, hydrolysis is generally complete in about 12–18 hours at temperatures from about 20°–30° C. whereas the latter reaction is usually complete in one hour at 20°–30° C.

It is generally preferred, in compounds containing both a nitrile and an ester functionality, that the nitrile group be transformed into a tetrazole before hydrolysis of the ester.

The intermediates of Formula II can be prepared by a number of synthetic routes as will be appreciated by skilled artisans depending upon the particular compound desired. For compounds wherein one of X and Y is —O—, the following scheme is generally applicable:

Scheme I

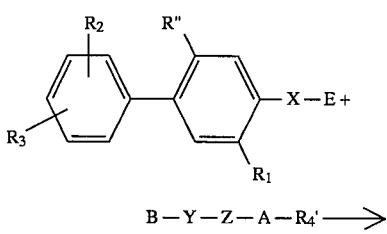

II (one of X and Y is —O—)

where one of —X—E and —Z—B is —OH and the other is —CH$_2$—L, where L is a good leaving group such as halo, especially chloro, bromo or iodo, and R" is hydroxy or preferably a protected hydroxy group, such as benzyloxy.

The reaction of Scheme I is usually performed employing equimolar amounts of the two reactants although ratios other than equimolar amounts are completely operative. The reaction is best carried out in a nonreactive Solvent such as ketones, especially acetone or methyl ethyl ketone, or dimethylformamide, and in the presence of a base, preferably an alkali metal hydride or carbonate, preferably potassium carbonate. Especially when L is chloro, a catalyst such as potassium or sodium iodide may be added to increase the reaction rate. The reaction may be carried out at temperatures of about ambient temperature up to the boiling point of the reaction mixture, the former being preferred.

In the preferred case where the hydroxy group has been protected, the protecting group is removed following the coupling procedure described above. As will be appreciated by skilled artisans in the field, the means for deprotecting the hydroxy group will depend upon the choice of protecting group employed. In the preferred situation where a benzyl group is used, the benzyl group is removed by catalytic hydrogenation, for example, in the presence of 10% palladium on carbon in ethyl acetate, to provide the desired phenol. Generally this step is carried out before converting $R_4'$ into $R_4$; however, as will be appreciated, it is possible this sequence can be reversed depending on the functional groups involved. Thus, coupling as noted above may, under certain circumstances well appreciated in the art, first involve transformation of the $R_4'$ group (eg, nitrile) into $R_4$ (eg, 5-tetrazolyl) followed by deprotection of the phenol.

A similar series of reactions is found in Scheme II:

Scheme II

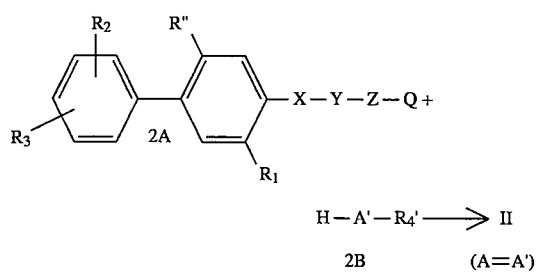

where Q is bromo, chloro, iodo, mesyl, tosyl, or a similar leaving group, and A' is —O— or —S—. Aspects of this reaction scheme and all the variations thereof are generally the same as discussed above regarding Scheme I.

Another way of preparing intermediates II is found in Scheme III:

Scheme III

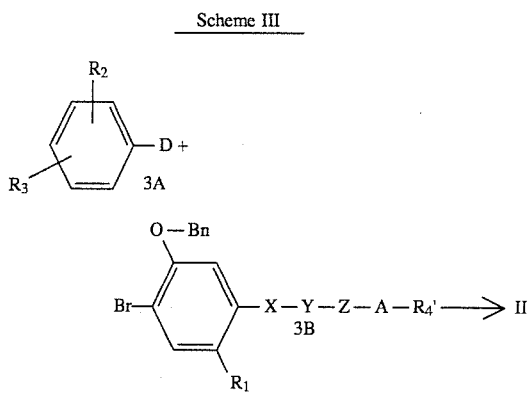

wherein D is B(OH)$_2$, Br, or Cl and Bn is benzyl or a related protecting group.

In the above scheme, an intermediate phenyl bromide (3A, D=Br) can be converted to the corresponding boronic acid (3A, D=B(OH)$_2$) by a number of routes. In one method, the phenyl bromide is treated first with an alkyllithium reagents, such as t-butyl lithium in a non-reactive solvent, followed by reaction with a tri-alkyl borate, such as triisopropyl borate, and hydrolysis with aqueous acid, such as dilute hydrochloric acid. Alternatively, the lithium derivative (3A, D=Li) can be first reacted with a silating reagent, such as trimethylsilyl chloride, to produce an intermediate wherein D is trimethylsilyl; reaction of this intermediate with boron tribromide, followed sequentially with treatment by methanol and aqueous acid similarly produces the desired phenylboronic acid (3A, D=B(OH)$_2$).

The biaryl coupling reaction described by the above scheme can then be performed by reacting substantially equimolar amounts of the phenyl borate (3A, D=B(OH)$_2$) with the phenyl bromide 3B in the presence of tetrakis(triphenylphosphine)palladium(0) and aqueous sodium carbonate in a mixture of ethanol and benzene. When allowed to reacted at elevated temperatures, such as the reflux temperature of the reaction mixture, the reaction is generally complete in 2–18 hours.

Another method of performing the biaryl coupling can be accomplished by reacting one of the two phenyl bromide intermediates 3A or 3B with tert-butyl lithium in a non-reactive solvent such as tetrahydrofuran, followed by treatment with zinc chloride to prepare the corresponding intermediate where the bromo functionality has been converted into a —ZnCl group. This reagent is then reacted with the other bromo (or chloro) intermediate in the presence of tetrakis(triphenylphosphine)palladium(0) to provide the desired product II.

Other variations and combinations of chemical reactions can also be employed to prepare the compounds of this invention. For example, one series of reactions is depicted in Scheme IV; this sequence is drawn for those compounds wherein X is —O—, but as will be appreciated by skilled organic chemists, similar transformations would apply to other variants of X:

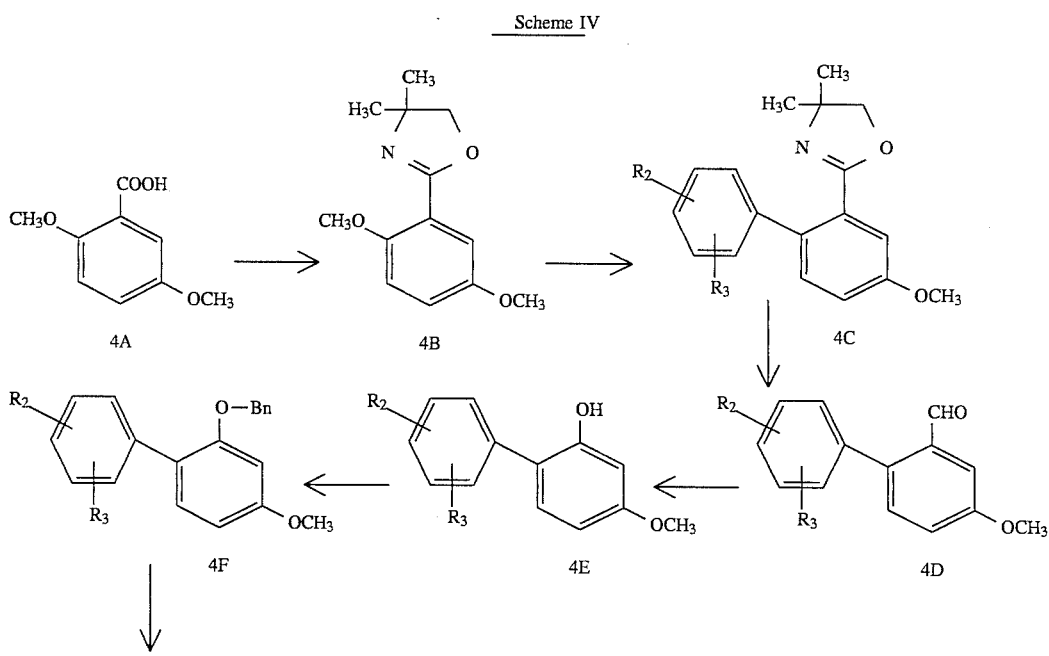

-continued
Scheme IV

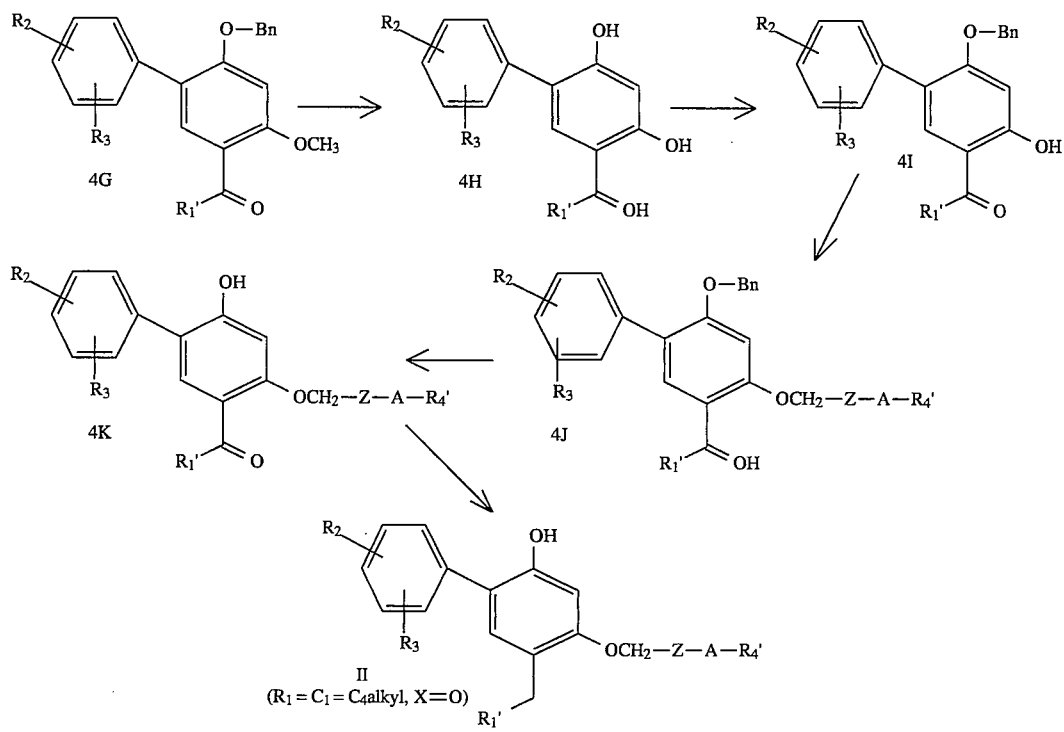

where $R_1'$ is $C_1-C_4$ alkyl and Bn is benzyl or a similar phenol protecting group.

In Scheme IV, 2,5-dimethoxybenzoic acid (4A) is first converted to the corresponding acid halide, for example, the acid chloride upon treatment with thionyl chloride in methylene chloride, which is then allowed to react with 2-amino-2-methyl-1-propanol. Subsequent treatment with, eg, thionyl chloride, completes the protection of the carboxylic acid as the 5,5-dimethyl-2-oxazoline 4B. Treatment of this intermediate with the appropriate substituted phenyl Grignard reagent in a solvent such as tetrahydrofuran provides the biphenyl intermediate 4C. The oxazoline is transformed into the corresponding aldehyde 4D upon sequential treatment with methyl iodide, sodium borohydride in ethanol, and hydrochloric acid in a solvent such as tetrahydrofuran. Treatment of 4D with an oxidizing agent such as meta-chloroperbenzoic acid in methylene chloride yields phenol 4E. The phenol is protected with a benzyl or similar protecting group upon treatment with benzyl bromide (or like reagent) in a solvent such as dimethylformamide and in the presence of an acid scavenger such as potassium carbonate. The resulting intermediate 4F is then acylated with $R_1'$—COCl or a similar reagent in the presence of a Lewis acid, such as stannic chloride, in a solvent such as methylene chloride; cool temperatures, such as −20° to 0° C., are preferred. The resulting acylated intermediate 4G is then doubly deblocked to diphenol 4H upon treatment with a reagent such as boron trichloride in a solvent such as methylene chloride. The benzyl (or similar protecting)group is replaced in the same manner as described above to provide 4I which is then alkylated as described earlier with $R_4'$—A—Z—$CH_2$—L (see Scheme I), especially where L is chloro or iodo, to provide intermediate 4J. The benzyl group is removed by catalytic hydrogenation, for example, in the presence of 10% palladium on carbon in ethyl acetate, to provide phenol 4K. Reduction of the acyl moiety of 4K, for example, upon treatment with triethyl silane and trifluoroacetic acid in a solvent such as carbon tetrachloride, results in the preparation of the corresponding intermediate II which can then be further transformed as described earlier.

A related sequence is depicted in Scheme V; as before, this sequence is drawn for those compounds wherein X is —O—, but as will be appreciated by skilled organic chemists, similar transformations would apply to other variants of X:

Scheme V

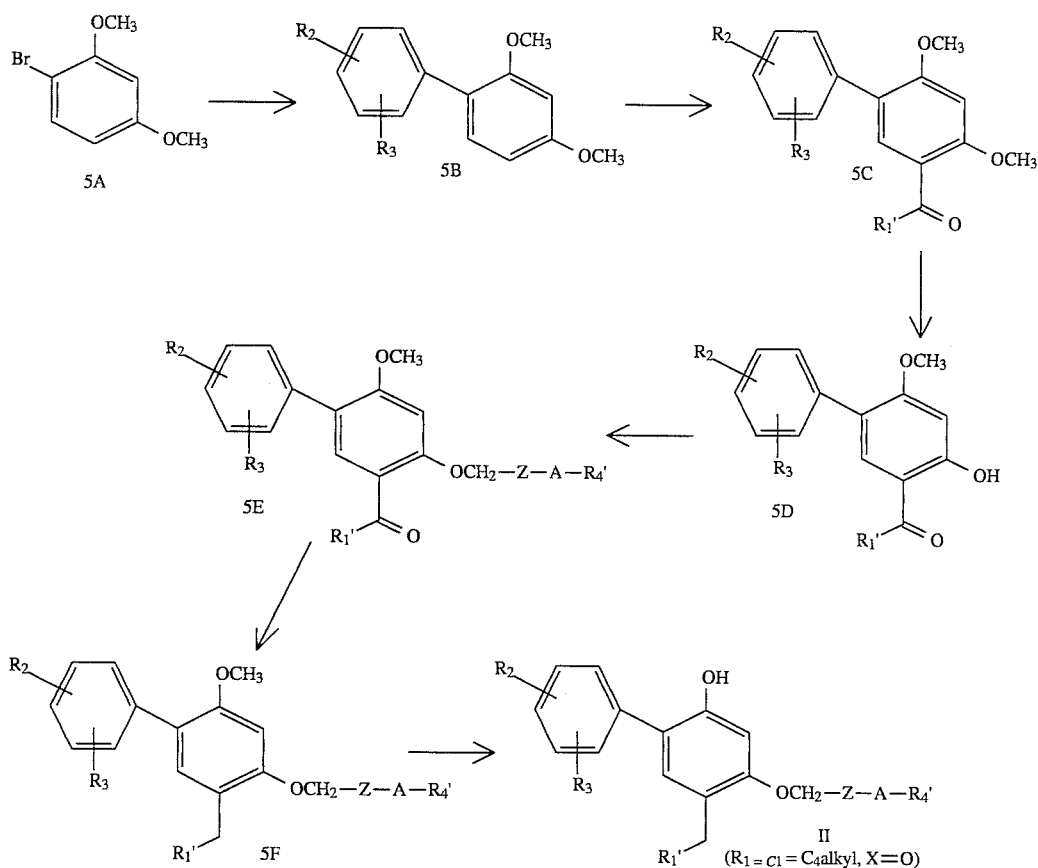

The dimethoxyphenyl bromide 5A is converted to corresponding biphenyl 5B upon treatment with the appropriate boronic acid under standard conditions. In addition to the standard conditions, the use of a catalyst such as bis(triphenylphosphine)-nickel chloride with the corresponding aryl Grignard reagent in refluxing tetrahydrofuran or diethyl ether is an alternative method for effecting this condensation. The biphenyl 5B can then be acylated as described above to prepare 5C, which is then deblocked with boron trichloride as noted above to provide the phenol 5D. In the same manner as described previously, the phenol can be alkylated with $R_4'$—A—Z—$CH_2$—L (see Scheme I), especially where L is chloro or iodo, to provide 5E which, in turn, is reduced to give 5F. The demethylation of 5F to give the corresponding phenol II is accomplished by treatment with sodium thioethoxide in dimethylformamide at elevated temperatures (eg, 90°–100° C.). Alternatively, the demethylation can be effected by treatment with boron tribromide in a solvent such as methylene chloride.

A variation of the process of Scheme V is described below in Scheme VI; as before, this sequence is drawn for those compounds wherein X is —O—, but as will be appreciated by skilled organic chemists, similar transformations would apply to other variants of X:

Scheme VI

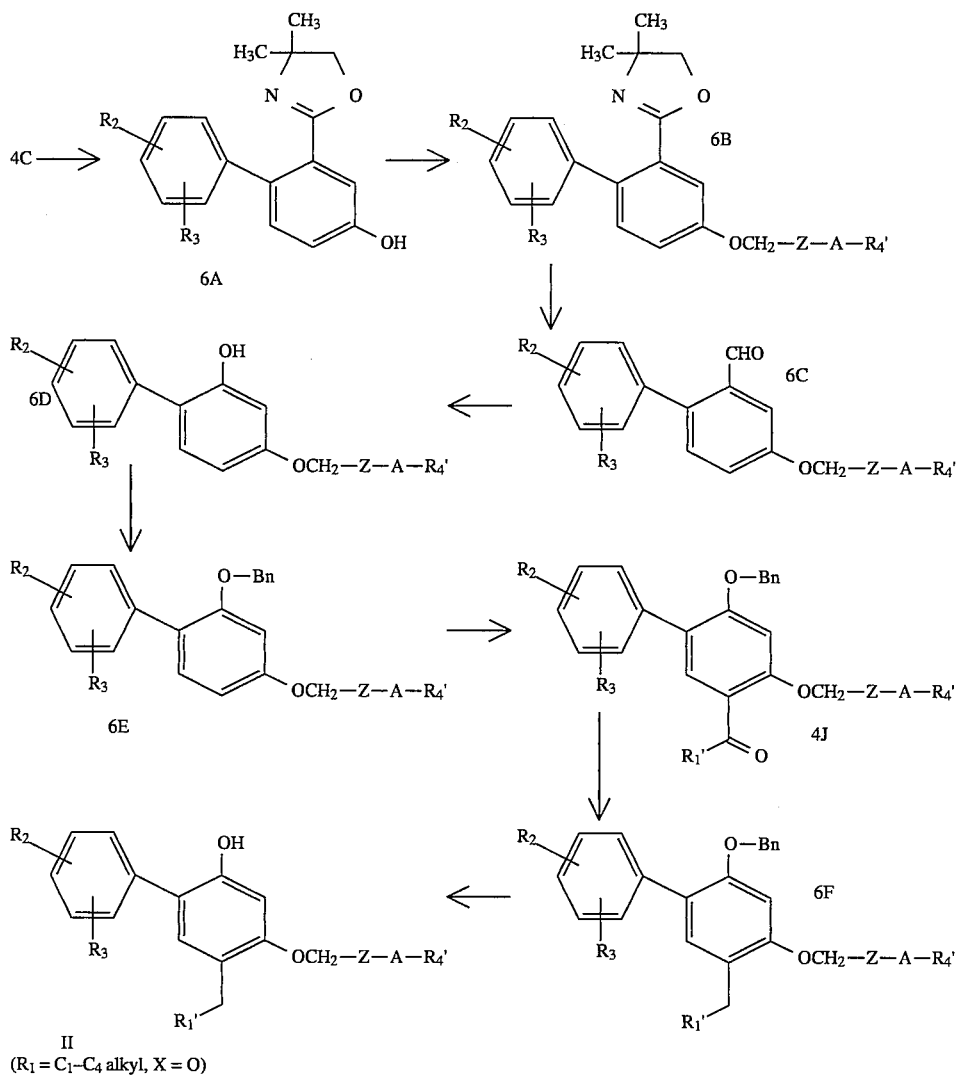

Intermediate 4C (from Scheme IV) is demethylated with boron tribromide in methylene chloride in a manner analogous to the process of converting 4G to 4H. The resulting phenol 6A has the intact oxazoline protecting group and is alkylated with the appropriate agent $R_4'$—A—Z—$CH_2$—L (see Scheme I), especially where L is chloro or iodo, in a solvent such as DMF optionally in the presence of an acid scavenger, such as potassium carbonate. The resulting product 6B is then converted to the benzaldehyde 6C as described above for preparing 4D from 4C, oxidized to the corresponding phenol 6D as described above for the transformation of 4D into 4E, converted to the protected phenol 6E with a group such as benzyl as described for the conversion of 4E into 4F, and acylated to give 4J in the same way as provided in the conversion of 4F to 4G. The intermediate 4J can be first deprotected and then reduced as provided by Scheme IV; alternatively, the steps and be reversed—4J can be reduced to intermediate 6F upon treatment with triethylsilane and trifluoroacetic acid in carbon tetrachloride and then deprotected to give the desired intermediate II.

Another variation of chemical steps is summarized in Scheme VII. Again this sequence is drawn for those compounds wherein X is —O—; in addition, the general Scheme is drawn for compounds wherein $R_a$ is $R_7$-substitutedphenyl, $R_b$ is hydrogen, and $R_4'$ is —CN; as will be appreciated by skilled organic chemists, similar transformations would apply to other variants of X, $R_a$, $R_b$, and $R_4'$:

Scheme VII

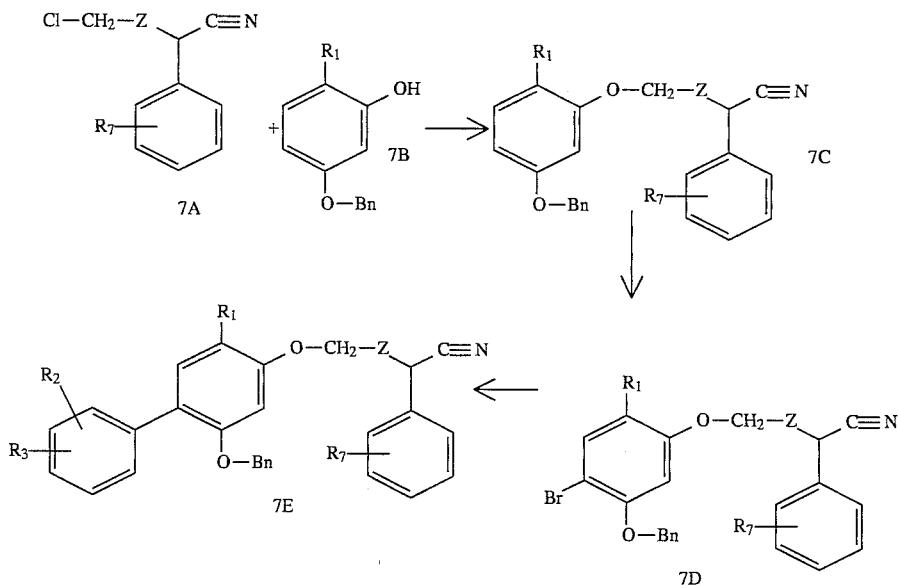

The halo-intermediate 7A is reacted with phenol 7B in the same manner as described above for Scheme I. The resulting product 7C is brominated with an agent such as N-bromosuccinimide in a solvent such as methylene chloride to give the bromo intermediate 7D. This intermediate is then reacted with the appropriate phenyl borate and tetrakis(triphenylphosphine)-palladium(0) as described above in Scheme III to give the coupled product 7E. 7E can then be transformed into the intermediates and final products of this invention by methods previously described, ie, hydrolysis, reaction with azide, debenzylation, etc. Variations of this sequence will also be apparent—for example, this series of transformations can be accomplished using a 7B reactant wherein the $R_1$ group is replaced with $R_1'$—CO, as shown in Schemes IV, V, and VI; the resulting intermediate 7C or later intermediates 7D or 7E can then be reduced to provide compounds wherein the $R_1$ group is $R_1'$—$CH_2$—.

Another variation employing other precursors to some of the more preferred compounds of this invention is generally represented by Scheme VIII—while two examples of such transformations are displayed employing a phenoxy substrate, it will be appreciated that such chemistry is applicable to other aryl groups and side-chains:

Scheme VIII

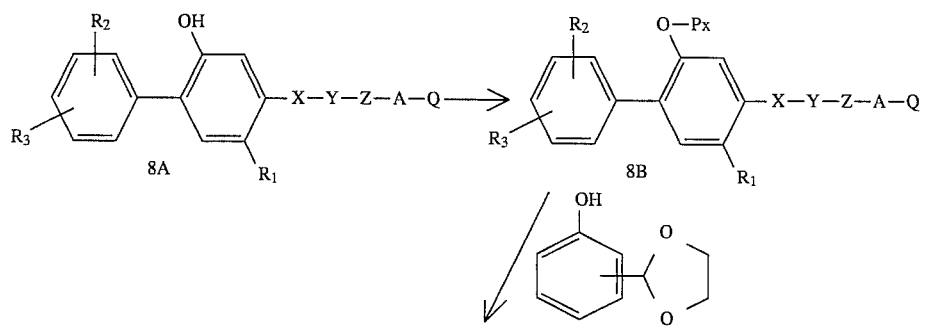

Scheme VIII -continued

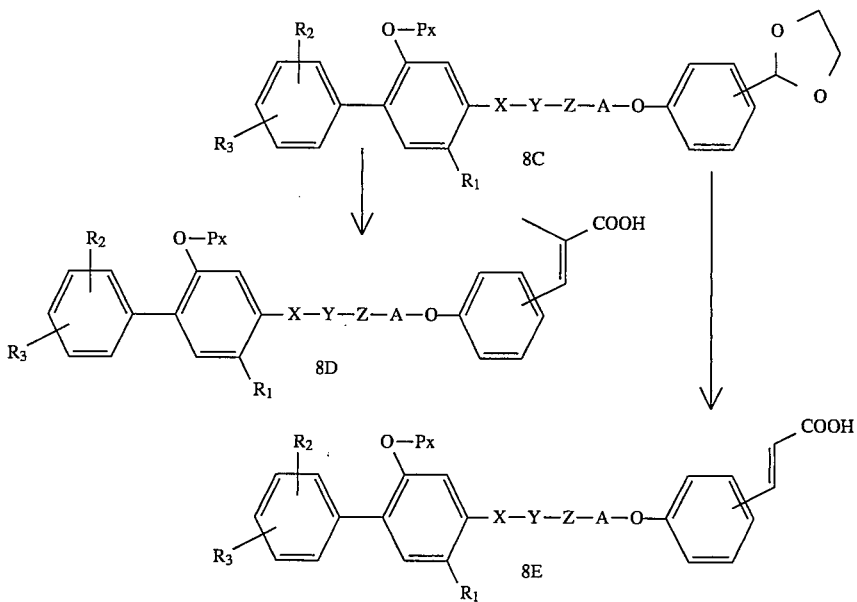

where Px is a protecting group.

In Scheme VIII, 8A is a particular embodiment of compound 2A (Scheme II) wherein R" is —OH. The phenol is protected to give 8B (analogous to 2A wherein R" is a protected hydroxy group). One preferred protecting group for the subsequent transformations is a trimethylsilylethoxymethyl (SEM) group which can be introduced upon treatment of 8A with SEM chloride in the presence of diisopropylethylamine in a solvent such as methylene chloride. Another useful protecting group is an alkanoyl group, such as acetyl, which can simply be introduced upon treatment of 8A with the alkanoyl anhydride (eg, acetic anhydride) in a solvent such as methylene chloride and preferably in the presence of a trialkylamine, such as triethylamine.

The protected intermediate 8B is then reacted with the appropriate precursor intermediate in the same manner as described in Schemes I and II above to give the coupled product 8C. In the illustrative example provided in Scheme VIII, a protected hydroxybenzaldehyde is employed, the aldehyde moiety being protected as a cyclic acetal. In the example of Scheme VIII, in that a phenol is being coupled, Q is preferably a chloro group which is treated with a catalytic amount of an alkali metal iodide to facilitate reaction.

The resulting intermediate 8C can then be transformed into a functionalized compound of this invention upon treatment with a malonic acid derivative. For example, after treatment of the acetal 8C with dilute hydrochloric acid and tetrahydrofuran, the treatment of the resulting benzaldehyde with methylmalonic acid in pyridinium hydrochloride and toluene gives the resulting 2-methylpropenoic acid 8D. In the case of an SEM protecting group, deprotection of the phenol with tetrabutylammonium fluoride in tetrahydrofuran gives a final product of this invention. Similarly, employing malonic acid following hydrolysis of 8C gives the propenoic acid 8E; in the case where the protecting group is an alkanoyl moiety, eg, acetyl, treatment of 8E with potassium carbonate in methanol and water gives the corresponding phenol of this invention.

Many of the intermediates for preparing some of the $R_4$ (or $R_4'$) groups of the more preferred compounds of this invention are known in the art. Many of the $R_4/R_4'$ groups which are diphenyl ethers, diphenyl thioethers, and diphenylamines, can be prepared by any of a number of synthetic routes—however, one general route employed is that of an Ullmann synthesis whereby, for example, a phenol is condensed with and iodo- or bromo-benzene in the presence of pyridine, potassium carbonate, and copper bronze to give the corresponding diphenyl ether. Copper(I) iodide and potassium t-butoxide can be employed in place of the copper bronze and potassium carbonate. In general, these reactions are low yielding and are difficult to work up, especially on a large scale. However, a preferred process for preparing intermediate compounds of the formula

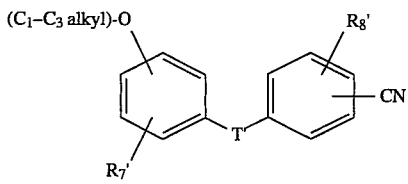

where $R_7'$ is hydrogen, $C_1$–$C_4$ alkyl, $C_1$–$C_4$-alkoxy, or halo, $R_8'$ is hydrogen or halo, T' is —O—, —S—, or —NH—, and the cyano group is either in the 2- or 4-position on the phenyl ring relative to the point of attachment to T', has been discovered. This process, more thoroughly described in copending U.S. patent application Ser. No. 07/797,646 filed Nov. 25, 1991 and now abandoned, and also published in corresponding European Patent Application NO. 0544488A2 at even date herewith) now abandoned, generally involves the reaction of a phenol, thiophenol, or aniline of the formula

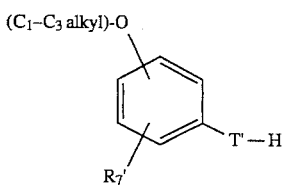

where $R_7'$ and T' are the same as defined above, with a fluorobenzonitrile of the formula

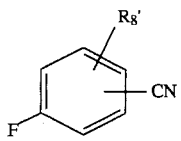

where $R_8'$ and the relative position of the cyano group is the same as defined above, in the presence of a strong base, such as sodium hydride or preferably potassium fluoride on basic aluminium oxide, in an aprotic solvent such as acetonitrile, and preferably in the presence of a catalyst such as tetrabutylammonium bromide or preferably a crown ether such as 18-crown-6. Preferably, relative to the phenol, thiophenol, or aniline, approximately an equimolar amount of the fluorobenzonitrile and an equal weight of the potassium fluoride/aluminum oxide are employed together with a catalytic amount (generally 0.1 equivalents) of the catalyst. When heated at about 90° C. for 1–3 days, almost quantitative yields of the desired diphenyl ether, diphenyl thioether, or diphenylamine are obtained. This intermediate can be dealkylated to give the corresponding phenol which can then be coupled as previously described. The cyano group of this intermediate, once coupled, can be hydrolyzed or treated with an azide reagent as previously described to give the corresponding carboxylic acid or tetrazole group.

The intermediate compounds mentioned above, and any other necessary reagents, are either commercially available, known in the literature, or can be prepared according to methods known in the art as described in further detail below. As will also be appreciated, various intraconversions of the various compounds and intermediates of this invention are possible. For example, carboxylic acids can be esterified by standard means, or converted to acid halides which are then reacted with amines of the formula $(R_9)_2NH$ or $H_2NSO_2R_{10}$ to provide the corresponding amides. Similarly, esters, amides, and nitriles may be hydrolyzed to the carboxylic acid by means as described previously. Nitriles can also be hydrolyzed to the primary amide by treatment with aqueous base.

In addition, precursors to certain $R_1$ functionalities can be used in the synthesis either of the various "halves" of the molecule of after the "halves" are coupled (eg, Schemes I and II). For example, in a precursor compound wherein $R_1$ is alkenyl, the double bond can be oxidized with a peracid to the corresponding epoxide intermediate which, upon catalytic hydrogenation, can be transformed into a hydroxyalkyl derivative. Reduction of a precursor wherein $R_1$ is an alkanoyl group also provides a carbinol analog. Hydrogenation of an alkene derivative or further reduction of the carbinol provides a compound of this invention wherein $R_1$ is alkyl.

The thio derivatives and intermediates of this invention (q is 0) may be transformed into the corresponding sulfoxide (q is 1) compounds upon treatment with a mild oxidizing agent, such as hydrogen peroxide in methanol, meta-chloroperbenzoic acid (MCPBA) in methylene chloride at 0° C., or an alkali metal periodate in aqueous alcohol. The corresponding sulfones (q is 2) are prepared from the thio or sulfoxide compounds on treatment with a strong oxidizing agent such as hydrogen peroxide in acetic acid or m-chloroperbenzoic acid in methylene chloride at 20°– 30° C.

In addition, various compounds of Formula I can be prepared from other compounds, precursors, or intermediates of Formula I by standard methods such as hydrolysis, esterification, alkylation, oxidation, reduction, and the like, as are well known to those skilled in the art. The Schemes noted above are illustrative of the more conventional methods for preparing the compounds of this invention. However, different combinations of these chemical steps and others generally known in the organic chemistry art can effectively be employed; the particular sequence of any such transformations and interconversions will be appreciated by experienced organic chemists in view of the various functional groups to be present in the compound of choice. For example, a tetrazole group can be protected with a group such as trityl; other chemistry can be performed on the remaining portion of the molecule, and the trityl group removed upon treatment with dilute acid to give the unprotected tetrazole. Other variations of this and related transformations will be apparent to skilled artisans in this field.

The following preparations and examples further illustrate the preparation of the intermediates and compounds of this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million ($\partial$) relative to tetramethylsilane. Chemical shifts of aromatic protons of quinoline species in DMSO-$d_6$ are concentration dependent. The following abbreviations are used to denote signal patterns: s= singlet, d=doublet, t=triplet, q=quartet, b=broad, m= multiplet. Infrared spectra were determined on a Nicolet DX10 FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

Preparation 1

Methyl 5-(3-hydroxyphenoxy)pentanoate

A mixture of 11 g of resorcinol, 8.8 g of methyl 5-bromopentanoate, and 13.8 g of potassium carbonate in 150 mL of dimethylformamide was heated in an oil bath at 90° C. for 24 hours. The mixture was cooled, diluted with water, and extracted with ethyl acetate. The organic phase was washed with water, washed with saturated sodium chloride, dried over sodium sulfate, and evaporated in vacuo. The residue was chromatographed on silica gel eluting with hexane/ethyl ether providing the title intermediate in 34% yield, NMR.

Preparations 2–3

The following compounds were prepared according to the procedure of Preparation 1.
5-(3-Hydroxyphenoxy)pentanenitrile, 42% yield, NMR.
Ethyl 5-(3-hydroxyphenoxy)pentanoate, 55% yield, NMR.

Preparation 4

N,N-Dimethyl-4-(3-hydroxyphenyl)butanamide

A mixture of 3.7 g of methyl 4-(3-hydroxyphenyl)pentanoate and 40 mL of 40% dimethylamine in water was stirred for 25 hours. The mixture was acidified with 5N hydrochloric acid and extracted with dichloromethane. The organic phase was washed with a saturated sodium chloride solution, dried over sodium sulfate, and evaporated in vacuo. The residue was chromatographed on silica gel eluting with ethyl ether/methanol to provide 1.62 g (41%) of the title intermediate. NMR Preparation 5

Ethyl 3-(2-hydroxy-6-(4-methoxycarbonylbutyloxy)phenyl)propionate

A mixture of 3.1 g of methyl 4-(3-hydroxyphenoxy)pentanoate, 0.7 g of pivalic acid, and 2.4 g of ethyl orthoacrylate in 50 mL of toluene was refluxed for 2 hours. The mixture was cooled and then stirred with 25 mL of 1 N hydrochloric acid for 2 hours. The organic phase was washed with saturated sodium bicarbonate, dried over sodium sulfate, and evaporated in vacuo. The residue was chromatographed on silica gel eluting with hexane/ethyl ether providing 1.13 g (25%) of the desired title intermediate. NMR Preparations 6–10

The following compounds were prepared according to the procedure of Preparation 5.
Ethyl 3-(2-hydroxy-6-(4-ethoxycarbonylbutyloxy)phenyl)propionate, 25% yield, NMR.
Ethyl 3-(2-hydroxyphenyl)propionate, 84% yield, NMR.
Ethyl 3-(2-hydroxy-6-(4-cyanobutyloxy)phenyl)propionate, 17% yield, NMR.
Ethyl 3-(2-hydroxy-6-(4-dimethylaminocarbonylbutyloxy)phenyl)propionate, 14% yield, NMR.
Ethyl 3-(2-hydroxy-6-methoxyphenyl)propionate, 30% yield, NMR.

Preparation 11

3-Methoxy-1,2-dihydronaphthalene

A mixture of 1.4 g of 2-tetralone, 1.5 mL of methyl orthoformate, and a few crystals of para-toluenesulfonic acid monohydrate in 75 mL of benzene was stirred for 22 hours and then evaporated in vacuo. The residue was chromatographed on Florisil® eluting with hexane/ethyl ether to provide 1.15 g (75%) of the desired title intermediate. NMR.

Preparation 12

3,8-Dimethoxy-1,2-dihydronaphthalene

The title compound was prepared from 5-methoxy-2-tetralone according to the procedure of Preparation 11 in 60% yield. NMR.

Preparation 13

Methyl 3-(2-formylphenyl)propionate

A suspension of 4.5 g of 3-methoxy-1,2-dihydronaphthalene, 1 g of sodium bicarbonate, 20 mL of methanol and 80 mL of dichloromethane was stirred and cooled in a dry ice-acetone bath. A rapid stream of ozone was bubbled into the suspension until a persistent blue coloration was visible. The mixture was flushed with nitrogen and 3.5 mL of methyl sulfide was added. The mixture was stirred in an ice-acetone bath for 1 hour and then 2 hours at room temperature. The organic solution was washed with water, dried over sodium sulfate, and evaporated in vacuo. The residue was chromatographed on silica gel eluting with hexane/ethyl ether to provide 5.0 g (90%) of the desired title intermediate. NMR.

Preparation 14

Methyl 3-(2-formyl-6-methoxyphenyl)propionate

The title compound was prepared according to the procedure of Preparation 13 in 90% yield. NMR.

Preparation 15

2-Methyl-2-cyano-7-(2-ethyl-4-(4-fluorophenyl)-5-benzyloxyphenoxy)heptane

A solution of 1.5 g of 2-methyl-2-cyano-7-(2-ethyl-4-bromo-5-benzyloxyphenoxy)heptane and 0.5 g of tetrakis(triphenylphosphine)palladium(0) in 70 mL of benzene was stirred with 15 mL of 2.0M sodium carbonate. A solution of 1.1 g of 4-fluorophenyl boronic acid in 15 mL of ethanol was added. The mixture was heated at reflux for 16 hours. The mixture was cooled and diluted with ethyl acetate. The organic phase was washed with saturated ammonium chloride, washed with saturated sodium chloride, dried over sodium sulfate, and evaporated in vacuo. The residue was chromatographed on silica gel eluting with hexane/ethyl ether to provide 1.44 g (93%) of the desired title intermediate. NMR.

Preparation 16

2-Methyl-2-cyano-7-(2-ethyl-4-(3-fluorophenyl)-5-benzyloxyphenoxy)heptane

The title compound was prepared following the procedure of Preparation 15 in 91% yield. NMR.

Preparation 17

2-Methyl-2-(1H-tetrazol-5-yl)-7-(2-ethyl-4-(4-fluorophenyl)-5-benzyloxyphenoxy)heptane A mixture of 1.44 g of 2-methyl-2-cyano-7-(2-ethyl-4-(4-fluorophenyl)-5-benzyloxyphenoxy)heptane, 4.1 g of triethylamine hydrochloride, and 1.95 g of sodium azide in 40 mL of dimethylformamide was heated in an oil bath at 125° C. for 17 hours, adding an additional 4 g of triethylamine hydrochloride and 2 g of sodium azide after 5 hours. The mixture was cooled, diluted with water, acidified with 1.0N hydrochloric acid, and extracted with ethyl acetate. The organic phase was washed with water, washed with saturated sodium chloride, dried over sodium sulfate, and evaporated in vacuo. The residue was chromatographed on silica gel eluting with dichloromethane/methanol to provide 1.12 g (72%) of the desired title product. NMR.

Preparation 18

2-Methyl-2-(1H-tetrazol-5-yl)-7-(2-ethyl-4-(3-fluorophenyl)- 5-benzyloxyphenoxy)heptane The title compound was prepared following the procedure of Preparation 17 in 75% yield. NMR.

EXAMPLE 1

2-Methyl-2-(1H-tetrazol-5-yl)-7-(2-ethyl-4-(4-fluorophenyl)- 5-hydroxyphenoxy)heptane

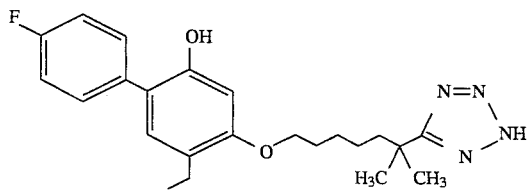

A mixture of 1.1 g of 2-methyl-2-(1H-tetrazol-5-yl)-7 -(2-ethyl-4-(4-fluorophenyl)-5-benzyloxyphenoxy)heptane, 1 g of 10% palladium on carbon, and 200 mL of ethanol was hydrogenated on a Parr™ apparatus at 35–40 psi for 2 hours. The mixture was filtered and the filtrate evaporated in vacuo. The residue was chromatographed on silica gel eluting with dichloromethane/methanol providing 750 mg (84%) of the desired title product. MS, NMR. Crystallization from diethyl ether/hexanes gave material with a melting point of 135°–137° C.; when crystallized from toluene, the melting point was 142°– 143° C.

Analysis for $C_{23}H_{29}FN_4O_2$: Calc: C, 66.97; H, 7.09; N, 13.58; Found: C, 67.18; H, 6.91; N, 13.50.

EXAMPLE 2

2-Methyl-2-(1H-tetrazol-5-yl)-7-(2-ethyl-4-(3-fluorophenyl)- 5-hydroxyphenoxy)heptane

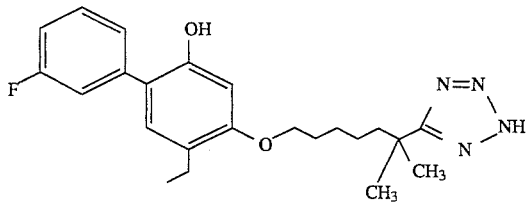

The title compound was prepared from the corresponding nitrile precursor in 73% yield following the procedure of Example 1. NMR.

Preparation 19

3-(2-Ethyl-4-(4-fluorophenyl)-5-benzyloxyphenoxy)propyl chloride

The title intermediate was prepared in 100% yield from 3-( 2-ethyl-4-bromo-5-benzyloxyphenoxy)propyl chloride by the procedure of Preparation 15. NMR.

Preparations 20–24

The following compounds were prepared according to the procedure of Preparation 1 utilizing 3-(2-ethyl-4-(4-fluorophenyl)-5-benzyloxyphenoxy)propyl chloride mixed potassium iodide as the alkylating agent.
Ethyl 3-(2-(3-(2-ethyl-4-(4-fluorophenyl)-5 -benzyloxyphenoxy)propoxy)phenyl)propionate, 40% yield, NMR.
Ethyl 3-(2-(3-(2-ethyl-4-(4-fluorophenyl)-5 -benzyloxyphenoxy)propoxy)-6-(4-ethoxycarbonylbutyloxy)phenyl)propionate, 56% yield, NMR.
Ethyl 3-(2-(3-(2-ethyl-4-(4-fluorophenyl)-5 -benzyloxyphenoxy)propoxy)-6-(4-cyanobutyloxy)phenyl)propionate, 52% yield, NMR.
Ethyl 3-(2-(3-(2-ethyl-4-(4-fluorophenyl)-5 -benzyloxyphenoxy)propoxy)-6-(4-dimethylaminocarbonylbutyloxy)phenyl)propionate, 24% yield, NMR.
Ethyl 3-(2-(3-(2-ethyl-4-(4-fluorophenyl)-5 -benzyloxyphenoxy)propoxy)-6-methoxyphenyl)propionate, 68% yield, NMR.

Preparation 25

Ethyl 3-(2-(3-(2-ethyl-4-(4-fluorophenyl)-5-benzyloxyphenoxy)propoxy)- 6-(4-(1H-tetrazol-5-yl)butyloxy)phenyl)propionate The title compound was prepared in 45% yield from ethyl 3-(2-(3-(2-ethyl-4-(4-fluorophenyl)-5-benzyloxyphenoxy)propoxy)- 6-(4-cyanobutyloxy)phenyl)propionate following the procedure of Preparation 17. NMR.

Preparation 26

3-(2-(3-(2-Ethyl-4-(4-fluorophenyl)-5 -benzyloxyphenoxy)propoxy)phenyl)propionic acid A solution of 375 mg of ethyl 3-(2-(3-(2-ethyl-4-(4 -fluorophenyl)-5-benzyloxyphenoxy)propoxy)phenyl)propionate in 25 mL of ethanol was mixed with 5 mL of 5.0N sodium hydroxide and stirred 16 hours. The mixture was diluted with 1.0N hydrochloric acid and extracted with 3:1 dichloromethane/isopropanol. The organic phase was washed with saturated sodium chloride, dried over sodium sulfate, and evaporated in vacuo providing the desired title product in 93% yield. NMR.

Preparations 27–30

The following compounds were prepared from the corresponding esters according to the procedure of Preparation 26.
3-(2-(3-(2-Ethyl-4-(4-fluorophenyl)-5-benzyloxyphenoxy)propoxy)- 6-(4-carboxybutyloxy)phenyl)propionic acid, 20% yield, NMR.
3-(2-(3-(2-Ethyl-4-(4-fluorophenyl)-5-benzyloxyphenoxy)propoxy)- 6-methoxyphenyl)propionic acid, 80% yield, NMR.

3-(2-(3-(2-Ethyl-4-(4-fluorophenyl)-5-benzyloxyphenoxy)propoxy)- 6-(4-dimethylaminocarbonylbutyloxy)phenyl)propionic acid, 41% yield, NMR.

3-(2-(3-(2-Ethyl-4-(4-fluorophenyl)-5-benzyloxyphenoxy)propoxy)- 6-(4-(1H-tetrazol-5-yl)butyloxy)phenyl)propionic acid, 30% yield, NMR.

EXAMPLES 3–7

The following compounds were prepared from the corresponding benzyloxy precursors according to the procedure of Example 1.

3.  3-(2-(3-(2-Ethyl-4-(4-fluorophenyl)-5-hydroxyphenoxy)propoxy)- 6-(4-dimethylaminocarbonylbutyloxy)phenyl)propionic acid, 42% yield, NMR.

7.  3-(2-(3-(2-Ethyl-4-(4-fluorophenyl)-5-hydroxyphenoxy)propoxy)- 6-(4-(1H-tetrazol-5-yl)butyloxy)phenyl)propionic acid, 34% yield, NMR, MS.

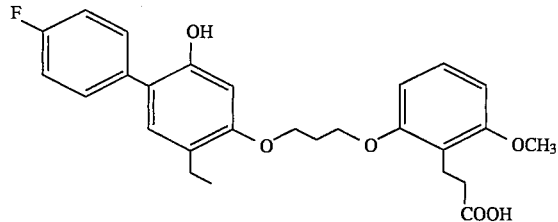

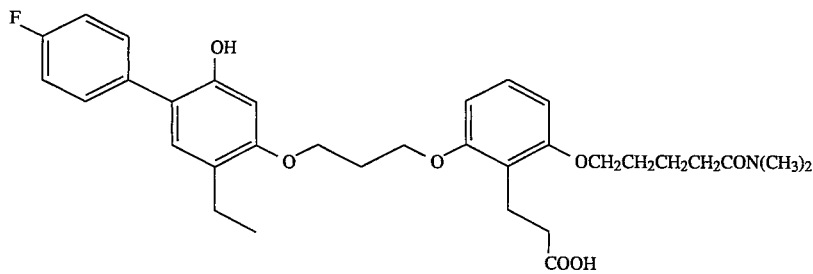

4.  3-(2-(3-(2-Ethyl-4-(4-fluorophenyl)-5-hydroxyphenoxy)propoxy)phenyl)propionic acid, 15% yield, NMR, MS.

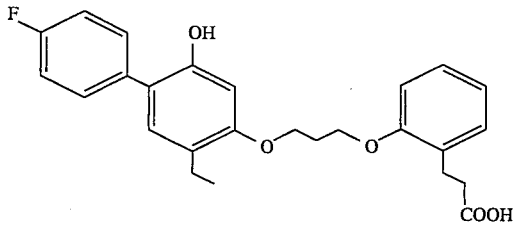

5.  3-(2-(3-(2-Ethyl-4-(4-fluorophenyl)-5-hydroxyphenoxy)propoxy)- 6-(4-carboxybutyloxy)phenyl)propionic acid, yield, NMR, MS.

Analysis for $C_{31}H_{35}FO_8$: Calc: C, 67.14; H, 6.36; Found: C, 66.52; H, 6.54.

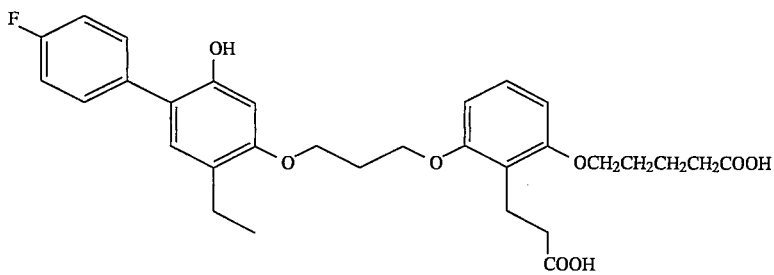

6.  3-(2-(3-(2-Ethyl-4-(4-fluorophenyl)-5-hydroxyphenoxy)propoxy)- 6-methoxyphenyl)propionic acid, 10% yield, NMR, MS.

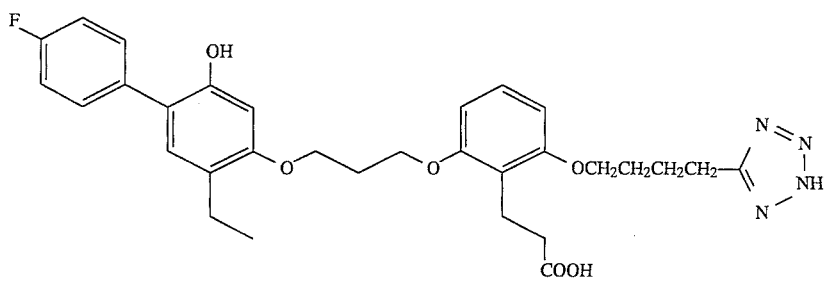

Preparation 31

Methyl 3-(2-(4-(2-ethyl-4-(4-fluorophenyl)-5-benzyloxyphenoxy)-(1-butenyl))-6-methoxyphenyl)propionate To a solution of 900 mg of 3-(2-ethyl-4-(4-fluorophenyl)-5-benzyloxyphenoxy)propyl triphenyl phosphonium iodide in 10 mL of methylsulfoxide and 60 mL of tetrahydrofuran cooled in a dry ice-acetone bath was added 1.5 mL of a 1.6M solution of n-butyl lithium in hexanes. The solution was allowed to warm to −5° C. over 30 minutes and a solution of 225 mg of methyl 3-((2-formyl- 6-methoxy)phenyl)propionate in 3 mL of tetrahydrofuran was added. The solution was stirred 45 minutes at −5° C. and then allowed to warm to room temperature. The mixture was diluted with water, acidified with 1.0N hydrochloric acid, and extracted with ethyl acetate. The organic phase was washed with water, washed with saturated sodium chloride, dried over sodium sulfate, and evaporated in vacuo. The residue was chromatographed on silica gel eluting with hexane/ethyl ether to provide 130 mg (23%) of the desired title intermediate. NMR.

Preparation 32

Methyl 3-(2-(4-(2-ethyl-4-(4-fluorophenyl)-5-benzyloxyphenoxy)-(1-butenyl))phenyl)propionate The title compound was prepared from methyl 3-(2-formylphenyl)propionate according to the procedure of Preparation 31 in 60% yield. NMR.

EXAMPLE 8

Methyl 3-(2-(4-(2-ethyl-4-(4-fluorophenyl)-5-hydroxyphenoxy)-(1-butenyl))phenyl)propionate The title compound was prepared according to the procedure of Preparation 31 utilizing the corresponding debenzylated Wittig salt and an additional equivalent of n-butyl lithium, 28% yield. NMR.

Preparations 33–34

The following compounds were prepared from their corresponding esters according to the procedure of Preparation 26.

3-(2-(4-(2-Ethyl-4-(4-fluorophenyl)-5-benzyloxyphenoxy)-( 1-butenyl))phenyl)propionic acid, 100% yield, NMR, MS.

3-(2-(4-(2-Ethyl-4-(4-fluorophenyl)-5-benzyloxyphenoxy)-( 1-butenyl))-6-methoxyphenyl)propionic acid, 100% yield, NMR, MS.

EXAMPLE 9

3-(2-(4-(2-Ethyl-4-(4-fluorophenyl)-5-hydroxyphenoxy)-(1-butenyl))phenyl)propionic acid

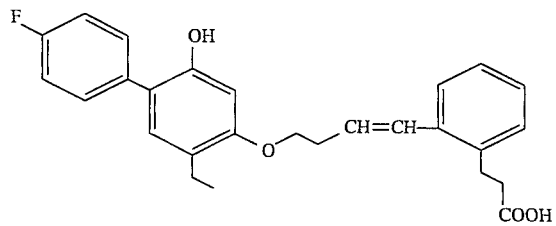

The title product was prepared from the corresponding ester in 100% yield according to the procedure of Preparation 26. NMR. The individual cis and trans isomers were separated and each demonstrated essentially the same in vitro $LTB_4$ activity as found for the mixture.

EXAMPLES 10–11

The following compounds were prepared from the corresponding benzyloxy precursors according to the procedure of Example 1.

10. 3-(2-(4-(2-Ethyl-4-(4-fluorophenyl)-5-hydroxyphenoxy)butyl)phenyl)propionic acid, 61% yield, MS, NMR. Analysis for $C_{27}H_{29}FO_4$: Calc: C, 74.29; H, 6.70; Found: C, 7 4.5 5; H, 6.81.

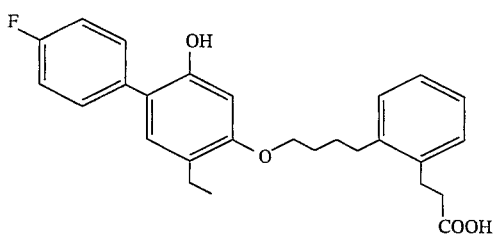

11. 3-(2-(4-(2-Ethyl-4-(4-fluorophenyl)-5-hydroxyphenoxy)butyl)- 6-methoxyphenyl)propionic acid, 75% yield, NMR, MS.

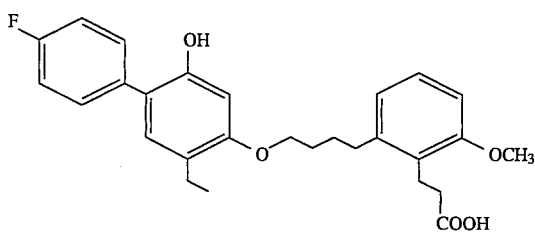

Preparation 35

3-(2-(3-(2-Ethyl-4-(4-fluorophenyl)-5-benzyloxyphenoxy)propoxy)-6-hydroxyphenyl)propionic acid The title compound was prepared from 5-hydroxybenzo-1-pyran-2-one according to the procedure of Preparation 1 in 50% yield, NMR.

Preparation 36

5-(3-(2-Ethyl-4-(4-fluorophenyl)-5-benzyloxyphenoxy)propoxy)benzo-1-pyran-2-one

A solution of 1.2 g of 5-hydroxybenzo-1-pyrane-2-one in 75 mL of tetrahydrofuran and 25 mL of methylsulfoxide was treated with 300 mg of sodium hydride (60% in mineral oil). After stirring for 10 minutes, a solution of 1.1 equivalents of 3-(2-ethyl-4-(4-fluorophenyl)-5-benzyloxyphenyl)propyl iodide in 10 mL of tetrahydrofuran was added. The solution was stirred 19 hours, diluted with a 0.1N hydrochloric acid, and extracted with ethyl acetate. The organic phase was washed with saturated sodium chloride, dried over sodium sulfate, and evaporated in vacuo. The residue was chromatographed on silica gel eluting with hexane/ethyl ether providing 1.80 g (47%) of the desired title intermediate, NMR.

Preparation 37

Methyl 3-(2-(3-(2-ethyl-4-(4-fluorophenyl)-5-benzyloxyphenoxy)propoxy)-6-hydroxyphenyl)propionate To a solution of 1.8 g of 5-(3-(2-ethyl-4-(4-fluorophenyl)-5-benzyloxyphenoxy)propoxy)benzo-1-pyran-2-one in 30 mL of a 1:1 mixture of tetrahydrofuran and methanol was added 40 mL of a 0.06M solution of sodium methoxide in methanol. The mixture was stirred 18 hours, diluted with water, acidified with 1.0N hydrochloric acid, and extracted with ethyl acetate. The organic phase was washed with saturated sodium chloride, dried over sodium sulfate, and evaporated in vacuo. The residue was chromatographed on silica gel eluting with hexane/ethyl ether resulting in 1.8 g (100%) of the desired title intermediate, NMR.

EXAMPLES 12–13

The following compounds were prepared according to the procedure of Example 1 from the respective benzyloxy precursors.

12. Methyl 3-(2-(3-(2-ethyl-4-(4-fluorophenyl)-5-hydroxyphenoxy)propoxy)-6-hydroxyphenyl)propionate, 85% yield, NMR.
13. 3-(2-(3-(2-Ethyl-4-(4-fluorophenyl)-5-hydroxyphenoxy)propoxy)-6-hydroxyphenyl)propionic acid, 30% yield, NMR, MS.

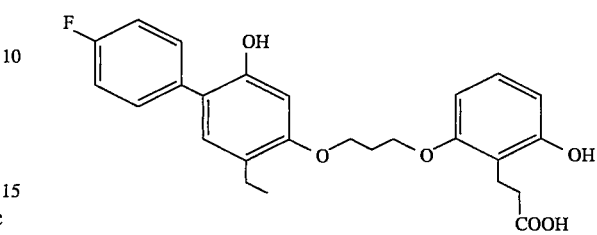

Preparation 38

Methyl 3-(2-(3-(2-ethyl-4-(4-fluorophenyl)-5-benzyloxyphenoxy)propoxy)-6-(4-butyloxy)phenyl)propionate The title compound was prepared from methyl 3-(2-(3-(2-ethyl-4-(4-fluorophenyl)-5-benzyloxyphenoxy)propoxy)-6-hydroxyphenyl)propionate utilizing n-butyl iodide and the procedure of Preparation 36 in 70% yield, NMR.

EXAMPLE 14

3-(2-(3-(2-Ethyl-4-(4-fluorophenyl)-5-hydroxyphenoxy)propoxy)-6-(4-butyloxy)phenyl)propionic acid

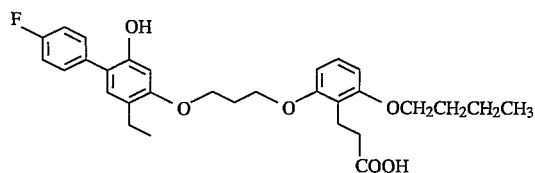

The title compound was prepared from methyl 3-(2-(3-(2-ethyl-4-(4-fluorophenyl)-5-benzyloxyphenoxy)propoxy)-6-(4-butyloxy)phenyl)propionate following, successively, the procedures of Preparation 26 and Example 1 in 87% yield. NMR, MS.

EXAMPLE 15

3-(2-(3-(2-Ethyl-4-(4-fluorophenyl)-5-hydroxyphenoxy)propoxy)-6-(4-methylthiobutyloxy)phenyl)propionic acid

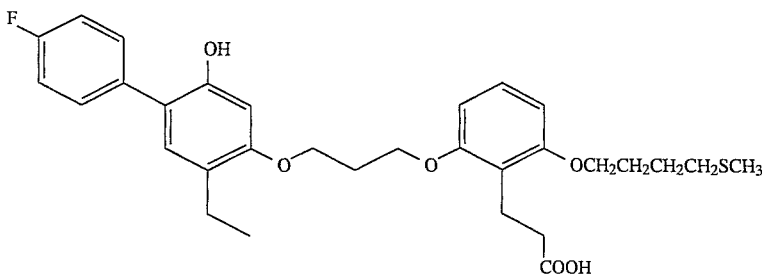

A. Preparation of methyl 3-(2-(3-(2-ethyl-4-(4-fluorophenyl)- 5-benzyloxyphenoxy)propoxy)-6-(4-chlorobutyloxy)phenyl)propionate.

The title compound was prepared in 90% yield from the title compound of Preparation 37 utilizing 4-chlorobutyl bromide and the procedure of Preparation 36. NMR.

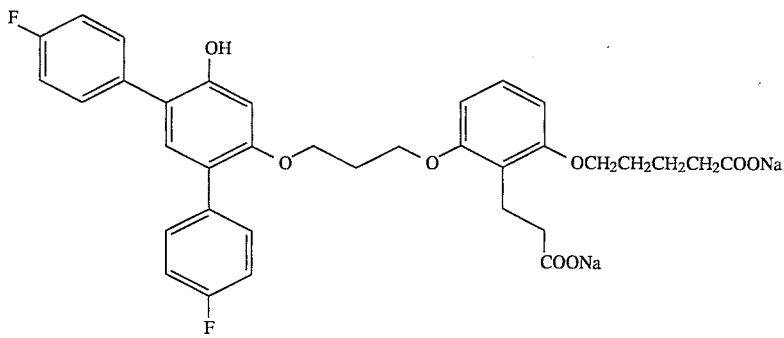

B. Preparation of methyl 3-(2-(3-(2-ethyl-4-(4 -fluorophenyl)-5-hydroxyphenoxy)propoxy)-6-(4-chlorobutyloxy)phenyl)propionate.

The title compound was prepared from methyl 3-(2-(3-(2 -ethyl-4-(4-fluorophenyl)-5-benzyloxyphenoxy)propoxy)-6-(4 -chlorobutyloxy)phenyl)propionate in 60% yield utilizing the procedure of Example 1. NMR.

C. Preparation of methyl 3-(2-(3-(2-ethyl-4-(4 -fluorophenyl)-5-hydroxyphenoxy)propoxy)-6-(4-methylthiobutyloxy)phenyl)propionate.

A solution of 420 mg of methyl 3-(2-(3-(2-ethyl-4-(4 -fluorophenyl)-5-hydroxyphenoxy)propoxy)-6-(4-chlorobutyloxy)phenyl)propionate in 10 mL of tetrahydrofuran was added to 70 mL of a 0.14M solution of sodium methanthiolate in dimethylformamide. The mixture was stirred 2 hours, diluted with water, and extracted with ethyl acetate. The organic phase was washed with a saturated sodium chloride solution, dried over sodium sulfate, and evaporated in vacuo. The residue was chromatographed on silica gel eluting with hexane/ethyl ether to provide the desired title intermediate in 98% yield. NMR.

D. Preparation of 3-(2-(3-(2-ethyl-4-(4-fluorophenyl)- 5-hydroxyphenoxy)propoxy)-6-(4-methylthiobutyloxy)phenyl)propionic acid.

The title compound was prepared in 94% yield from methyl 3-(2-(3-(2-ethyl-4-(4-fluorophenyl)-5-hydroxyphenoxy)propoxy)- 6-(4-methylthiobutyloxy)phenyl)propionate following the procedure of Preparation 26. NMR, MS.

EXAMPLE 16

3-(2-(3-(2,4-Di(4-fluorophenyl)-5-hydroxyphenoxy)propoxy)-6 -(4-carboxybutoxy)phenyl)propionic acid A. Preparation of ethyl 3-(2-(3-(2,4-di(4-fluorophenyl)- 5-benzyloxyphenoxy)propoxy)-6-(4-ethoxycarbonylbutoxy)phenyl)propionate.

The title intermediate was prepared from ethyl 3-(2 -hydroxy-6-(4-ethoxycarbonylbutyloxy)phenyl)propionate and (2,4-di(4-fluorophenyl)-5-benzyloxyphenoxy)propyl iodide following the procedure of Preparation 1. NMR.

B. Preparation of 3-(2-(3-(2,4-di(4-fluorophenyl)-5 -benzyloxyphenoxy)propoxy)-6-(4-carboxybutoxy)phenyl)propionic acid.

The title intermediate was isolated in 100% yield as an oil from ethyl 3-(2-(3-(2,4-di(4-fluorophenyl)-5-benzyloxyphenoxy)propoxy)- 6-(4-ethoxycarbonylbutoxy) phenyl) propionate following the procedure of Preparation 26. NMR.

C. Preparation of 3-(2-(3-(2,4-di(4-fluorophenyl)-5 -hydroxyphenoxy)propoxy)-6-(4-carboxybutoxy)phenyl)propionic acid.

The title compound was prepared in 44% yield from 3-(2 -(3-(2,4-di(4-fluorophenyl)-5-benzyloxyphenoxy)propoxy)- 6-(4 -carboxybutoxy)phenyl)propionic acid following the procedure of Example 1. NMR, MS.

Preparation 39

7-(2-Acetyl-5-benzyloxyphenoxy)-2-methyl-2-n-pentylheptanenitrile

The title intermediate was prepared from 2-hydroxy-5 -benzyloxyacetophenone and 2-methyl-5-n-pentyl-7 -iodoheptanenitrile following the procedure of Preparation 36.

Preparation 40

2-Methyl-2-n-pentyl-7-(2-ethyl-5-benzyloxyphenoxy)heptanenitrile 7-(2-Acetyl-5-benzyloxyphenoxy)-2-methyl-2-n-pentylheptanenitrile was dissolved in carbon tetrachloride containing 6 equivalents of triethylsilane. After addition of 60 equivalents of trifluoroacetic acid, the solution was stirred 24 hours and then evaporated in vacuo. The residue was chromatographed on silica gel eluting with hexane/ethyl ether to provided the title product as an oil in 90% yield, NMR.

Preparation 41

2-Methyl-2-n-pentyl-7-(2-ethyl-4-bromo-5-benzyloxyphenoxy)heptanenitrile

2-Methyl-2-n-pentyl-7-(2-ethyl-5-benzyloxyphenoxy)heptanenitrile and 1.1 equivalents of N-bromosuccinimide in carbon tetrachloride were stirred 1.5 hours, washed with aqueous sodium thiosulfate, washed with saturated sodium chloride, dried over sodium sulfate and evaporated in vacuo. The residue was chromatographed on silica gel eluting with hexane/ethyl ether providing the desired title intermediate in 60% yield, as an oil, NMR.

Preparation 42

2-Methyl-2-n-pentyl-7-(2-ethyl-4-(4-fluorophenyl)-5-benzyloxyphenoxy)heptanenitrile The title intermediate was prepared from 2-methyl-2-n-pentyl- 7-(2-ethyl-4-bromo-5-benzyloxyphenoxy)heptanenitrile in 94% yield by the procedure of Preparation 15 as an oil. NMR.

Preparation 43

6-Methyl-6-(1 H-tetrazol-5-yl)-11-(2-ethyl-4-(4-fluorophenyl)-5-benzyloxyphenoxy)undecane The title compound was isolated as an oil in 42% yield by reacting 2-methyl-2-n-pentyl-7-(2-ethyl-4-(4-fluorophenyl)-5-benzyloxyphenoxy)heptanenitrile according to the procedure of Preparation 17. NMR.

EXAMPLE 17

6-Methyl-6-(1H-tetrazol-5-yl)-11-(2-ethyl-4-(4-fluorophenyl)-5-hydroxyphenoxy)undecane

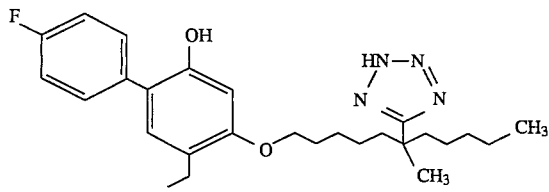

The title compound was prepared from 6-methyl-6-(1H-tetrazol- 5-yl)-11-(2-ethyl-4-(4-fluorophenyl)-5-benzyloxyphenoxy)undecane in 68% yield using the procedure of Example 1. NMR, MS.

Analysis for $C_{27}H_{37}FN_4O_2$: Calc: C, 69.20; H, 7.96; N, 11.96; Found: C, 69.50; H, 8.22; N, 12.00.

EXAMPLE 18

N,N-Dimethyl-3-(2-(3-(2-ethyl-4-(4-fluorophenyl)-5-hydroxyphenoxy)propoxy)phenyl)propionamide

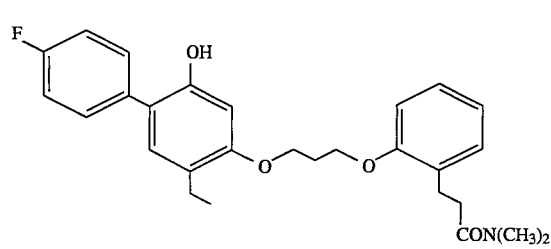

A solution of 3-(2-(3-(2-ethyl-4-(4-fluorophenyl)-5 -hydroxyphenoxy)propoxy)phenyl)propionic acid and several equivalents of thionyl chloride in dichloromethane was kept at room temperature for 3 hours, and then poured into a stirred solution of 40% dimethylamine in water. The organic layer was washed with aqueous hydrochloric acid, washed with saturated sodium chloride, dried over sodium sulfate, and evaporated in vacuo. The residue was chromatographed on silica gel eluting with ethyl acetate to provide the desired title product. NMR, MS.

EXAMPLE 19

N-Methanesulfonyl-3-(2-(3-(2-ethyl-4-(4-fluorophenyl)-5-hydroxyphenoxy)propoxy)phenyl)propionamide

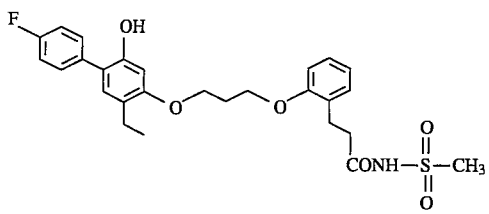

A solution of the acid chloride prepared as in Example 18 in tetrahydrofuran was added to a suspension of 10 equivalents of N-lithiomethanesulfonamide in tetrahydrofuran at −5° C. The mixture was allowed to warm to room temperature, diluted with aqueous hydrochloric acid, and extracted with ethyl acetate. The organic solution was dried and evaporated in vacuo. The residue was chromatographed on silica gel eluting with dichloromethane/methanol to provide the desired title intermediate in 37% yield. NMR.

EXAMPLE 20

N-Phenylsulfonyl-3-(2-(3-(2-ethyl-4-(4-fluorophenyl)-5-hydroxyphenoxy)propoxy)phenyl)propionamide

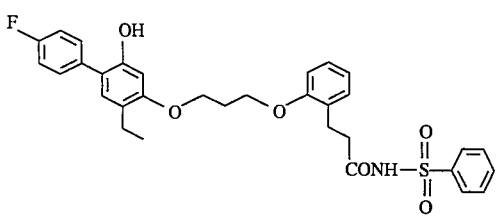

The title product was prepared by the procedure of Example 19 using N-lithiobenzenesulfonamide. The product was isolated by preparative $C_{18}$ reverse phase HPLC. NMR.

Preparation 44

4-(2,4-Dimethoxyphenyl)fluorobenzene

The title compound was an oil prepared in 85% yield from 2,4-dimethoxybromobenzene employing the procedure of Preparation 15. NMR.

Preparation 45

2,4-Dimethoxy-5-(4-fluorophenyl)acetophenone

A solution of 4-(2,4-dimethoxyphenyl)fluorobenzene in dichloromethane at −5° C. was treated with 2 equivalents of stannic chloride and 1.5 equivalents of acetyl chloride. The solution was stirred 2 hours without cooling. The organic solution was dried and evaporated in vacuo to provide the title intermediate as an oil, 97% yield. NMR.

Preparation 46

2,4-Dimethoxybutyrophenone

The title compound was isolated as an oil in 81% yield from 4-(2,4-dimethoxyphenyl)fluorobenzene using the procedure of Preparation 45. NMR.

Preparation 47

2-Hydroxy-4-methoxy-5-(4-fluorophenyl)acetophenone

A dichloromethane solution of 2,4-dimethoxy-5-(4 -fluorophenyl)acetophenone was treated with 1.2 equivalents of boron trichloride at 0° C. for 15 minutes. The organic solution was washed with water, dried, and evaporated in vacuo to provide the desired title intermediate in 96% yield. NMR.

Preparation 48

2-Hydroxy-4-methoxy-5-(4-fluorophenyl)butyrophenone

The title compound was prepared in 97% yield from 2,4 -dimethoxybutyrophenone by the procedure of Preparation 47. NMR.

Preparation 49

2-(3-Chloropropoxy)-4-methoxy-5-(4 -fluorophenyl)acetophenone

The title compound was isolated as an oil in 53% yield from 2-hydroxy-4-methoxy-5-(4-fluorophenyl)acetophenone and 3-chloropropyl bromide by the procedure of Preparation 36. NMR.

Preparation 50

2-(3-Chloropropoxy)-4-methoxy-5-(4 -fluorophenyl)butyrophenone

The title compound was isolated as an oil in 64% yield from 2-hydroxy-4-methoxy-5-(4-fluorophenyl)butyrophenone and 3-chloropropyl bromide by the procedure of Preparation 36. NMR.

Preparation 51

1-(2-(3-Chloropropoxy)-4-methoxy-5-(4-fluorophenyl)phenyl)butane

The title compound was isolated as an oil in 89% yield from 2-(3-chloropropoxy)-4-methoxy-5-(4-fluorophenyl)butyrophenone employing the procedure of Preparation 40. NMR.

Preparation 52

Ethyl 3-(2-(3-(2-butyl-4-(4-fluorophenyl)-5 -methoxyphenoxy)propoxy)phenyl)propionate The title intermediate was prepared from 1-(2-(3 -chloropropoxy)-4-methoxy-5-(4-fluorophenyl)phenyl)butane and ethyl 3-(2-hydroxy)phenylpropionate according to the procedure of Preparation 36; the product was as oil obtained in 80% yield. NMR.

EXAMPLE 21

3-(2-(3-(2-Butyl-4-(4-fluorophenyl)-5 -hydroxyphenoxy)propoxy)phenyl)propionic acid

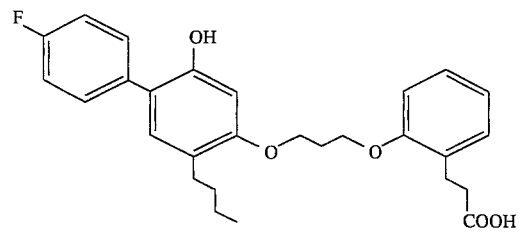

Ethyl 3-(2-(3-(2-butyl-4-(4-fluorophenyl)-5 -methoxyphenoxy)propoxy)phenyl)propionate in dichloromethane was treated with 2 equivalents of boron tribromide at −75° C. The mixture was stirred without cooling for 18 hours, washed with water, dried, and evaporated in vacuo. The residue was chromatographed on silica gel eluting with dichloromethane/methanol to provide the desired title product in 56% yield. NMR.

EXAMPLE 21

Alternate Synthesis 3-(2-(3-(2-Butyl-4-(4-fluorophenyl)-5 -hydroxyphenoxy)propoxy)phenyl)propionic acid A solution of ethyl 3-(2-(3-(2-butyl-4-(4-fluorophenyl)-5-methoxyphenoxy)propoxy)phenyl)propionate and 5 equivalents of sodium ethanthiolate in dimethylformamide was heated at 110° C. for 2 hours, cooled, diluted with aqueous hydrochloric acid, and extracted with ethyl acetate. The organic solution was washed with water, dried, and evaporated in vacuo. The residue was chromatographed on silica gel eluting with ethyl ether and with ethyl acetate providing the desired title product in 66% yield. NMR.

Preparation 53

Ethyl 3-(2-(4-iodobutoxy)phenyl)propionate

The title compound was prepared in 85% yield from ethyl 3-(2-hydroxyphenyl)propionate and 4-chlorobutyl bromide according to the procedure of Preparation 36 followed by treatment with sodium iodide; the product was an oil. NMR.

Preparation 54

Ethyl 3-(2-(4-(2-acetyl-5-benzyloxyphenoxy)butyloxy)phenyl)propionate

The title intermediate was isolated as an oil in 71% yield from ethyl 3-(2-(4-iodobutoxy)phenyl)propionate and 2-hydroxy- 4-benzyloxyacetophenone according to the procedure of Preparation 36. NMR.

Preparation 55

Ethyl 3-(2-(4-(2-ethyl-5-benzyloxyphenoxy)butyloxy)phenyl)propionate

The title intermediate was isolated as an oil in 85% yield from ethyl 3-(2-(4-(2-acetyl-5-benzyloxyphenoxy)butyloxy)phenyl)propionate following the procedure of Preparation 40. NMR.

Preparation 56

Ethyl 3-(2-(4-(2-ethyl-4-bromo-5-benzyloxyphenoxy)butyloxy)phenyl)propionate The title intermediate was isolated as an oil in 85% yield from ethyl 3-(2-(4-(2-ethyl-5-benzyloxyphenoxy)butyloxy)phenyl)propionate following the procedure of Preparation 41. NMR.

Preparation 57

Ethyl 3-(2-(4-(2-ethyl-4-(4-fluorophenyl)-5-benzyloxyphenoxy)butyloxy)phenyl)propionate The title intermediate was isolated as an oil in 84% yield from ethyl 3-(2-(4-(2-ethyl-4-bromo-5-benzyloxyphenoxy)butyloxy)phenyl)propionate following the procedure of Preparation 15. NMR.

EXAMPLE 22

Ethyl 3-(2-(4-(2-ethyl-4-(4-fluorophenyl)-5-hydroxyphenoxy)butyloxy)phenyl)propionate The title intermediate was isolated as an oil in 100% yield from ethyl 3-(2-(4-(2-ethyl-4-(4-fluorophenyl)-5-benzyloxyphenoxy)propoxy)phenyl)propionate following the procedure of Example 1. NMR.

EXAMPLE 23

3-(2-(4-(2-Ethyl-4-(4-fluorophenyl)-5-hydroxyphenoxy)butyloxy)phenyl)propionic acid

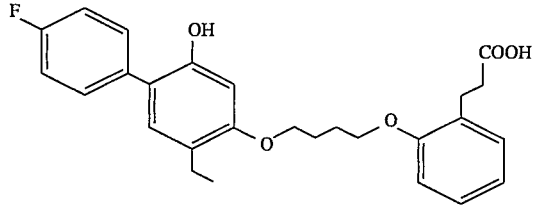

The title product was prepared in 72% yield following the procedure of Preparation 26 employing ethyl 3-(2-(4-(2-ethyl- 4-(4-fluorophenyl)-5-hydroxyphenoxy)butyloxy)phenyl), propionate as the reactant. NMR.

Preparation 58

Methyl 4-(3-allyloxyphenoxy)benzoate

The title compound was prepared in 96% yield as an oil from methyl 4-(3-hydroxyphenoxy)benzoate and allyl bromide by the procedure of Preparation 36. NMR.

Preparation 59

Methyl 4-(2-allyl-3-hydroxyphenoxy)benzoate and

Methyl 4-(4-allyl-3-hydroxyphenoxy)benzoate

A solution of methyl 4-(3-allyloxyphenoxy)benzoate in N,N-dimethylaniline was heated at 190° C. for 19 hours, cooled, diluted with ethyl acetate, washed with aqueous hydrochloric acid, dried, and evaporated in vacuo. The residue was chromatographed on silica gel eluting with hexane/ethyl ether to give a 40:60 mixture of the title compounds as an oil in 92% yield. NMR.

Preparation 60

Methyl 4-(2-(3-hydroxypropyl)-3-hydroxyphenoxy)benzoate and

Methyl 4-(3-hydroxy-4-(3-hydroxypropyl)phenoxy)benzoate

A tetrahydrofuran solution of the title compounds of Preparation 59 was treated with 3.4 equivalents of 9-borabicyclononane for 16 hours. The mixture was cooled to −5° C., treated with 50 equivalents of aqueous sodium acetate and then with 5.0 equivalents of hydrogen peroxide. The mixture was stirred without cooling for 6 hours, diluted with aqueous sodium thiosulfate, acidified with hydrochloric acid, and extracted with ethyl acetate. The organic solution was dried and evaporated in vacuo. The residue was chromatographed on silica gel eluting with dichloromethane/methanol to give a mixture of the title compounds in essentially quantitative yield. NMR.

Preparation 61

Methyl 3-(2-hydroxy-6-(4-(methoxycarbonyl)phenoxy)phenyl)propionate and

Methyl 3-(2-hydroxy-4-(4-(methoxycarbonyl)phenoxy)phenyl)propionate

A solution of the title compounds of Preparation 60 in acetone at −5° C. was treated with a large excess of Jones reagent and then stirred without cooling for 1.5 hours. The excess oxidizing agent was destroyed with isopropanol and the mixture extracted with ethyl acetate. The organic solution was dried and evaporated in vacuo. The residue was dissolved in methanol containing a few drops of sulfuric acid and refluxed for 5 hours, cooled, concentrated in vacuo, diluted with ethyl acetate, washed with aqueous sodium bicarbonate, dried and evaporated in vacuo. The residue was chromatographed on silica gel eluting with hexane/ethyl ether to give a mixture of the title compounds as an oil in 70% yield. NMR.

Preparation 62

Methyl 3-(2-(3-(2-ethyl-4-(4-fluorophenyl)-5-benzyloxyphenoxy)-propoxy)-6-(4-(methoxycarbonyl)phenoxy)phenyl)propionate and Methyl 3-(2-(3-(2-ethyl-4-(4-fluorophenyl)-5-benzyloxyphenoxy)-propoxy)-4-(4-(methoxycarbonyl)phenoxy)phenyl)propionate Reacting the compounds of Preparation 61 and 3-(2-ethyl-4-(4-fluorophenyl)-5-benzyloxyphenoxy)propyl iodide following the procedure of Preparation 36 gave a 40:60 mixture of the title compounds as an oil in 30% yield. NMR.

EXAMPLE 24

Methyl 3-(2-(3-(2-ethyl-4-(4-fluorophenyl)-5-hydroxyphenoxy)propoxy)-6-(4-(methoxycarbonyl)phenoxy)phenyl)propionate and Methyl 3-(2-(3-(2-ethyl-4-(4-fluorophenyl)-5-hydroxyphenoxy)propoxy)-4-(4-(methoxycarbonyl)phenoxy)phenyl)propionate The title esters were prepared from the compounds of Preparation 62 according to the procedure of Example 1 giving a mixture of the title compounds as an oil, 100% yield. NMR.

EXAMPLES 25 AND 26

3-(2-(3-(2-Ethyl-4-(4-fluorophenyl)-5-hydroxyphenoxy)propoxy)-6-(4-carboxyphenoxy)phenyl)propionic acid

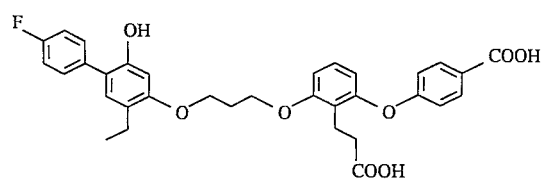

and 3-(2-(3-(2-Ethyl-4-(4-fluorophenyl)-5-hydroxyphenoxy)propoxy)-4-(4-carboxyphenoxy)phenyl)propionic acid

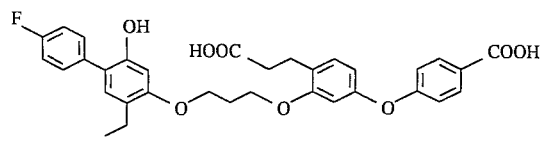

Hydrolyzing the title compounds of Example 24 according to the procedure of Preparation 26 gave a mixture of the title products which were separated by preparative reverse phase HPLC on a $C_{18}$ column.

25. 3-(2-(3-(2-Ethyl-4-(4-fluorophenyl)-5-hydroxyphenoxy)propoxy)- 6-(4-carboxyphenoxy)phenyl)propionic acid, 49% yield, NMR.
26. 3-(2-(3-(2-Ethyl-4-(4-fluorophenyl)-5-hydroxyphenoxy)propoxy)- 4-(4-carboxyphenoxy)phenyl)propionic acid, 34% yield, NMR.

Preparation 63

3,3-Dimethyl-3-(2-(3-(2-ethyl-4-(4-fluorophenyl)-5-benzyloxyphenoxy)propoxy)phenyl)propionic acid A solution of 4,4-dimethylbenzopyran-2-one in dimethylsulfoxide was treated with 2.0 equivalents of potassium hydroxide for 16 hours. A solution of 2.0 equivalents of 3-(2-ethyl-4-(4-fluorophenyl)-5-benzyloxyphenoxy)propyl iodide in a mixture of dimethylsulfoxide and tetrahydrofuran was added and stirred for 1 hour, diluted with aqueous hydrochloric acid, and extracted with ethyl acetate. The organic solution was washed with water, dried, and evaporated in vacuo. The residue was chromatographed on silica gel eluting with hexane/ethyl ether giving the desired title intermediate as an oil, 29% yield, NMR.

Also isolated was the title compound esterified by the alkyl iodide, oil, 50% yield, NMR.

EXAMPLE 27

3,3-Dimethyl-3-(2-(3-(2-ethyl-4-(4-fluorophenyl)-5-hydroxyphenoxy)propoxy)phenyl)propionic acid

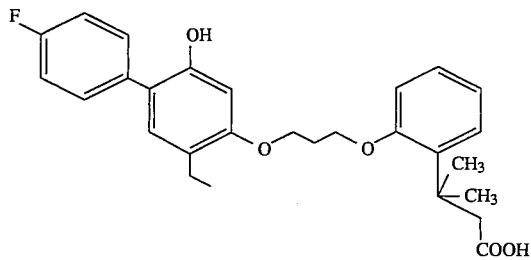

The title compound was prepared in 75% yield from 3,3-dimethyl-3-(2-(3-(2-ethyl-4-(4-fluorophenyl)-5-benzyloxyphenoxy)propoxy)phenyl)propionic acid following the procedure of Example 1. NMR.

Preparation 64

2-Cyano-2-methyl-3-(2-(3-(2-ethyl-4-(4-fluorophenyl)-5-benzyloxyphenoxy) propoxy) phenyl) propane The title intermediate was isolated as an oil in 77% yield from 2-cyano-2-methyl-3-(2-hydroxy)phenylpropane and 3-(2-ethyl-4-(4-fluorophenyl)-5-benzyloxyphenoxy)propyl iodide following the procedure of Preparation 36. NMR.

Preparation 65

2-Methyl-2-(1H-tetrazol-5-yl)-3-(2-(3-(2-ethyl-4-(4-fluorophenyl)-5-benzyloxyphenoxy)propoxy)phenyl)propane The title intermediate was isolated as an oil in 77% yield from 2-cyano-2-methyl-3-(2-(3-(2-ethyl-4-(4-fluorophenyl)-5-benzyloxyphenoxy)propoxy)phenyl)propane following the procedure of Preparation 17. NMR.

EXAMPLE 28

2-Methyl-2-(1H-tetrazol-5-yl)-3-(2-(3-(2-ethyl-4-(4-fluorophenyl)-5-hydroxyphenoxy) propoxy) phenyl)propane

Preparation 66

2-(3-(2-Ethyl-4-(4-fluorophenyl)-5-benzyloxy)propoxy)benzaldehyde

The title intermediate was prepared from salicylaldehyde in 71% yield by the procedure of Preparation 36. NMR

Preparation 67

(±)-2,2-Di methyl-3-hydroxy-3-(2-(3-(2-ethyl-4-(4-fluorophenyl)-5-benzyloxyphenoxy)propoxy)phenyl)pentanenitrile A solution of 1.3 mL of isobutyronitrile in 100 mL of toluene at −5° C. was treated with one equivalent of lithium diisopropylamide and then allowed to warm to room temperature. A solution of 690 mg of the title compound of Preparation 66 in 10 mL of toluene was added and the suspension was stirred for one hour, poured into dilute aqueous hydrochloric acid and extracted with ethyl acetate. The organic phase was washed, dried, and evaporated in vacuo. The residue was chromatographed on silica gel eluting with dichloromethane to provide the title intermediate in 91% yield. NMR

Preparation 68

2-Methyl-2-(1H-tetrazol-5-yl)-3-hydroxy-3-(2-(3-(2-ethyl-4-(4-fluorophenyl)-5-benzyloxyphenoxy)propoxy)phenyl)propane A solution of 715 mg of the title compound of Preparation 67 and 8 mL of tri-n-butyltin azide was heated at 95° C. for 92 hours, cooled, diluted with 5 mL tetrahydrofuran, 25 mL acetonitrile, and 10 mL acetic acid, and then stirred 3.5 hours. The solution was washed well with hexane and then evaporated in vacuo. The residue was chromatographed on silica gel eluting with dichloromethane/methanol to provide the title compound in 87% yield. NMR

EXAMPLE 29

2-Methyl-2-(1H-tetrazol-5-yl)-3-hydroxy-3-(2-(3-(2-ethyl-4-(4-fluorophenyl)-5-hydroxyphenoxy)propoxy)phenyl)propane

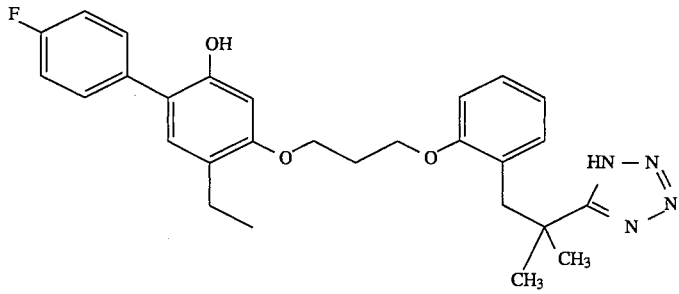

The debenzylation of 2-methyl-2-(1H-tetrazol-5-yl)-3-(2-(3-(2-ethyl-4-(4-fluorophenyl)-5-benzyloxyphenoxy)propoxy)phenyl)propane following the procedure of Example 1 gave the title compound in 76% yield. NMR.

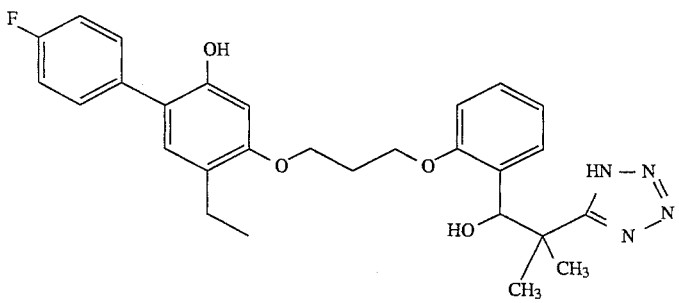

The title compound was prepared in 67% yield from the title compound of Preparation 68 by the procedure of Example 1. NMR, MS Analysis for $C_{28}H_{31}FN_4O_4$: Calc: C, 66.34; H, 6.17; N, 11.06; Found: C, 66.41; H, 6.34; N, 11.07.

Preparation 69

4-(2,4-Dimethoxy-5-bromophenyl)fluorobenzene

The title intermediate was prepared from 4-(2,4-dimethoxyphenyl)fluorobenzene in 97% yield by the procedure of Preparation 41. NMR Preparation 70

4-(2-Methoxy-4-hydroxy-5-bromophenyl)fluorobenzene and 4-(2-Hydroxy-4-methoxy-5-bromophenyl)fluorobenzene Each of the title compounds were isolated in 35% yield from transforming the title compound of Preparation 69 by the procedure of Example 21. NMR Preparation 71

3-(4-(4-Fluorophenyl)-2-bromo-5-methoxyphenoxy)propyl chloride

The title intermediate was prepared from 4-(2-methoxy-4-hydroxy-5-bromophenyl)fluorobenzene and 3-bromopropyl chloride in 84% yield by the procedure of Preparation 36. NMR Preparation 72

Ethyl 3-(2-(3-(2-bromo-4-(4-fluorophenyl)-5-methoxyphenoxy)propoxy)phenyl)propionate The title intermediate was prepared from 3-(4-(4-fluorophenyl)-2-bromo-5-methoxyphenoxy)propyl chloride and ethyl 3-(2-hydroxyphenyl)propionate in 76% yield by the procedure of Preparation 36. NMR

EXAMPLES 30–31

3-(2-(3-(2-Bromo-4-(4-fluorophenyl)-5-hydroxyphenoxy)propoxy)phenyl)propionic acid

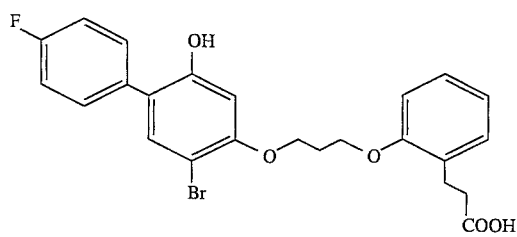

and 3-(2-(3-(2-Ethylthio-4-(4-fluorophenyl)-5-hydroxyphenoxy)propoxy)phenyl)propionic acid

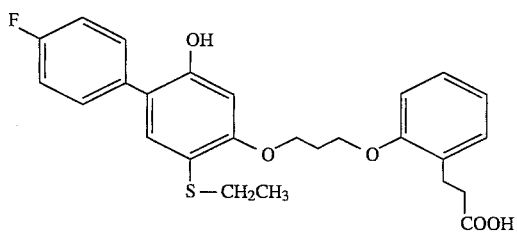

The title compounds were prepared from the title compound of Preparation 72 by the procedure of Example 21 (Alternate Synthesis).

30. 3-(2-(3-(2-Bromo-4-(4-fluorophenyl)-5-hydroxyphenoxy)propoxy)phenyl)propionic acid, 18% yield, NMR
Analysis for: $C_{24}H_{22}BrFO_5$: Calc: C, 58.91; H, 4.53; Br, 16.33; Found: C, 59.17; H, 4.72; Br, 16.48.

31. 3-(2-(3-(2-Ethylthio-4-(4-fluorophenyl)-5-hydroxyphenoxy)propoxy)phenyl)propionic acid, 10% yield, NMR

EXAMPLE 32

Methyl 3-(2-hydroxy-3-(4-methoxycarbonylbutyl)-6-(3-(2-ethyl-4-(4-fluorophenyl)-5-hydroxyphenoxy)propoxy)phenyl)propionate A mixture 250 mg of ethyl 3-(2-hydroxy-3-(4-methoxycarbonylbutyl)-6-(3-(2-ethyl-4-(4-fluorophenyl)-5-hydroxyphenoxy)propoxy)phenyl)propionate, 0.1 gm of 10% palladium on carbon, and several drops of concentrated sulfuric acid in 125 mL of methanol was hydrogenated on a Parr™ apparatus at 45 psi for 18 hours. The mixture was filtered and the filtrate was evaporated in vacuo giving the title intermediate in 80% yield, NMR

EXAMPLE 33

5-(3-(2-Ethyl-4-(4-fluorophenyl)-5-hydroxyphenoxy)propoxy)-8-(4-carboxybutyl)dihydrocoumarin

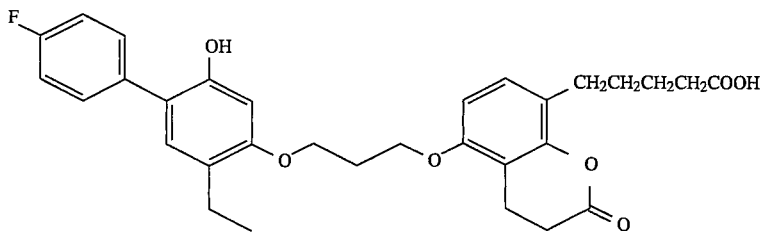

The title product was prepared from methyl 3-(2-hydroxy-3-(4-methoxycarbonylbutyl)-6-(3-(2-ethyl-4-(4-fluorophenyl)-5-hydroxyphenoxy)propoxy)phenyl)propionate by the procedure of Preparation 26. The title compound was purified by preparative reverse phase HPLC and isolated in 15% yield. NMR

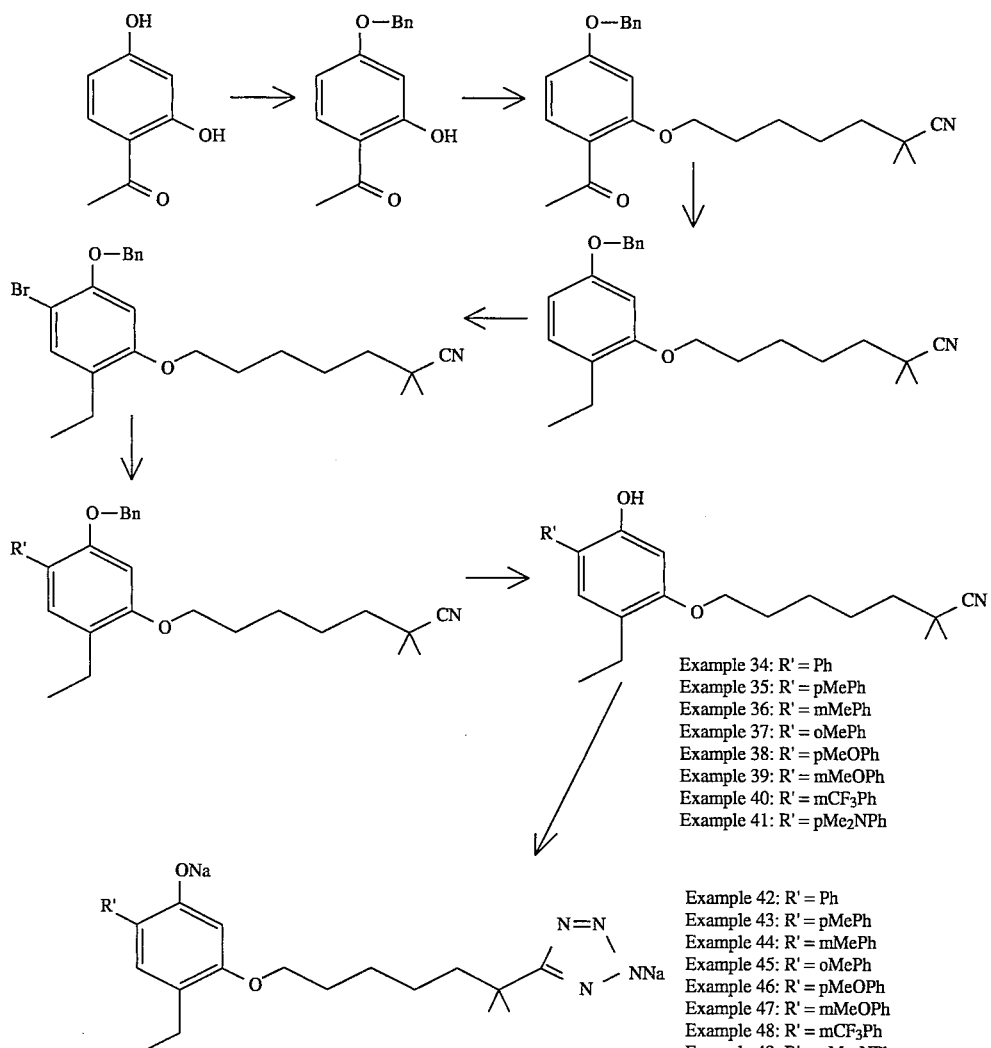

Example 34: R' = Ph
Example 35: R' = pMePh
Example 36: R' = mMePh
Example 37: R' = oMePh
Example 38: R' = pMeOPh
Example 39: R' = mMeOPh
Example 40: R' = mCF$_3$Ph
Example 41: R' = pMe$_2$NPh Example 42: R' = Ph
Example 43: R' = pMePh
Example 44: R' = mMePh
Example 45: R' = oMePh
Example 46: R' = pMeOPh
Example 47: R' = mMeOPh
Example 48: R' = mCF$_3$Ph
Example 49: R' = pMe$_2$NPh Preparation 73

1-Benzyloxy-2-phenyl-4-ethyl-5-(6-methyl-6-cyanoheptyloxy)benzene

A. Preparation of 4-benzyloxy-2-hydroxyacetophenone.

In a dry round-bottom flask under nitrogen, 2,4-dihydroxyacetophenone (15.2 g, 100 mmol) was dissolved in methyl ethyl ketone (400 mL) and dimethylsulfoxide (100 mL). To this solution were added benzyl bromide (17.0 g, 100 mmol) and potassium carbonate (27.6 g, 200 mmol). The reaction was heated to reflux and stirred for 15 hours. The methyl ethyl ketone was removed in vacuo, and the dimethylsulfoxide solution was diluted with ethyl acetate and washed several times with brine. The organic material was collected, dried (magnesium sulfate), filtered, and concentrated to provide a dark solid. The solid was recrystallized from hexane/toluene to provide the title benzyl ether as a tan solid (12.8 g, 55.7%); mp 143°–144.5° C.; NMR (CDCl$_3$) $\partial$12.77 (s, 1H), 7.70 (d, 1H, J=7 Hz), 7.3–7.5 (m, 5H), 6.54 (d, 1H, J=7 Hz), 6.53 (s, 1H), 5.11 (s, 2H), 2.58 (s, 3H).

Analysis for C$_{15}$H$_{12}$O$_3$: Calc: C, 74.36; H, 5.82; Found: C, 74.52; H, 5.97.

B. Preparation of 2-(6-methyl-6-cyanoheptyloxy)-4-benzyloxyacetophenone.

To a solution of 4-benzyloxy-2-hydroxyacetophenone (9.65 g, 42 mmol) in dimethylformamide (150 mL) were added the appropriate alkyl chloride (6.86 g, 40 mmol), potassium carbonate (10.6 g, 77 mmol), and potassium iodide (1.6 g, 9.6 mmol). The stirred reaction was heated to 90° C. for 24 hours. The solids were removed by filtration, and the dimethylformamide was removed in vacuo. The residue was purified by Prep-500 HPLC, using a gradient of 5% ethyl acetate in hexane to 20% over 30 minutes as a mobile phase to yield the title ether as a clear oil (12.1 g, 79.8%); NMR (CDCl$_3$) $\partial$7.85 (d, 1H, J=7.4 Hz), 7.3–7.5 (m, 5H), 6.60 (dd, 1H, J=7.4, 1.8 Hz), 6.53 (d, 1 H, J=1.8 Hz), 5.12 (s, 2H), 4.04 (t, 2H, J=5.3 Hz), 2.61 (s, 3H), 1.85–1.95 (m, 2H), 1.5–1.6 (m, 6H), 1.37 (s, 6H); IR (CHCl$_3$) 2943, 2238, 1601 cm$^{-1}$; MS (m/e) 379.

C. Preparation of 4-benzyloxy-2-(6-methyl-6-cyanoheptyloxy)ethylbenzene.

To a solution of 2-(6-methyl-6-cyanoheptyloxy)-4-benzyloxyacetophenone (12.1 g, 31.6 mmol) in carbon tetrachloride (30 mL) were added trifluoroacetic acid (44.4 g, 390 mmol) and triethylsilane (21.8 g, 188 mmol). The reaction was stirred at room temperature for 1.5 hours, then was worked-up by diluting with ethyl acetate and washing with aqueous sodium carbonate. The organic material was collected, dried (magnesium sulfate), filtered, and concentrated in vacuo. The residue was purified by Prep-500 HPLC using a 3% ethyl acetate in hexane to 5% grade over 15 minutes, then holding at 5%. Concentration of the appropriate fractions provided the desired title product (10.6 g, 91.5%) as a clear liquid. NMR (CDCl$_3$) $\partial$7.35–7.5 (m, 5H), 7.06 (d, 1H, J=6.5 Hz), 6.53 (s, 1H), 6.52 (dd, 1H, J=6.5, 2 Hz), 5.06 (s, 2H), 3.96 (t, 2H, J=5.3 Hz), 2.60 (q, 2H, J=6.3 Hz), 1.8–1.85 (m, 2H), 1.5–1.6 (m, 6H), 1.37 (s, 6H), 1.20 (t, 3H, J=6.3 Hz).

D. Preparation of 1-bromo-2-benzyloxy-4-(6-methyl-6-cyanoheptyloxy)-5-ethylbenzene.

To a stirred solution of 4-benzyloxy-2-(6-methyl-6-cyanoheptyloxy)ethylbenzene (10.6 g, 28.9 mmol) in carbon tetrachloride (125 mL) was added N-bromosuccinimide (6.0 g, 33.3 mmol). Stirring was continued for 6 hours at room temperature. The mixture was then diluted with methylene chloride and washed with water. The organic material was collected, dried (magnesium sulfate), filtered, and concentrated in vacuo. The residue was recrystallized from hexane/ethyl acetate to provide the title aryl bromide (12.6 g, 97.8%) as a pale yellow solid. NMR (CDCl$_3$) $\partial$7.35–7.5 (m, 5H), 7.22 (s, 1H), 6.50 (s, 1H), 5.17 (s, 2H), 3.90 (t, 2H, J=5.3 Hz), 2.58 (q, 2H, J=6.3 Hz), 1.75–1.85 (m, 2H), 1.50–1.65 (m, 6H), 1.37 (s, 6H), 1.18 (t, 3H, J=6.3 Hz); IR (CHCl$_3$) 3020, 2981, 2946, 2238, 1662, 1600 cm$^{-1}$; MS (m/e) 444, 445, 446.

E. Representative procedures for the biaryl coupling reaction.

Method A

In a round-bottom flask, the appropriate aryl bromide (1 equivalent) was dissolved in benzene. To this solution were added Pd(PPh$_3$)$_4$ (10 mol %) and a 2.0M aqueous solution of sodium carbonate (10 eq.). In a separate flask, the aryl boronic acid (2 eq.) was dissolved in ethanol. To the aryl boronic acid solution was added the the aryl bromide solution, and the mixture was heated to reflux and stirred for 16 hours. The mixture was diluted with ethyl acetate and washed with saturated aqueous ammonium chloride. The organic material was collected, dried (magnesium sulfate), filtered, and concentrated. The residue was purified by flash chromatography (6% ethyl acetate in hexane) to provide the desired biaryl.

Method B

A solution of the appropriate aryl bromide in tetrahydrofuran was cooled to −78° C. To this solution was added tert-butyl lithium (2 eq). The reaction was stirred at −78° C. for 30 minutes, then a tetrahydrofuran solution of zinc chloride (1 eq) was added. The mixture was warmed to room temperature and stirred for 15 minutes. In a separate flask, a solution was prepared containing the appropriate aryl halide (1 eq) and Pd(PPh$_3$)$_4$ (10 mole%) in tetrahydrofuran. This solution was added to the aryl zinc solution, and the mixture was stirred at room temperature for 2–18 hours. The reaction was diluted with ethyl acetate and washed with aqueous ammonium chloride. The organic material was dried (magnesium sulfate), filtered, and concentrated. The residue was purified by flash chromatography (6% ethyl acetate in hexane) to provide the desired biaryl.

F. Preparation of 1-benzyloxy-2-phenyl-4-ethyl-5-(6-methyl-6-cyanoheptyloxy)benzene.

This compound was prepared in 75% yield by Method A. NMR (CDCl$_3$) $\partial$7.60 (d, 2H, J=6.5 Hz), 7.3–7.5 (m, 8H), 7.18 (s, 1H), 6.59 (s, 1H), 5.04 (s, 2H), 3.95 (t, 2H, J=5.3 Hz), 2.63 (q, 2H, J= 6.3 Hz), 1.8–1.9 (m, 2H), 1.5–1.65 (m, 6H), 1.38 (s, 6H), 1.25 (t, 3H, J=6.3 Hz); IR (CHCl$_3$) 3013, 2977, 2943, 2238, 1611, 1488 cm$^{-1}$; MS (m/e) 439.

Analysis for C$_{30}$H$_{35}$NO$_2$: Calc: C, 81.59; H, 7.99; N, 3.17; Found: C, 81.34; H, 8.18; N, 3.05.

Preparations 74–80

The following intermediates were prepared as noted following the procedures as described for Preparation 73 employing the appropriate aryl boronic acid or aryl halide.

1-Benzyloxy-2-(4-methylphenyl)-4-ethyl-5-(6-methyl-6-cyanoheptyloxy)benzene, 58% yield by Method A. NMR (CDCl$_3$) $\partial$7.49 (d, 2H, J=7.0 Hz), 7.3–7.4 (m, 5H), 7.22 (d, 2H, J= 7.0 Hz), 7.15 (s, 1H), 6.56 (s, 1H), 5.05 (s, 2H), 3.96 (t, 2H, J=5.3 Hz), 2.64 (q, 2H, J=6.3 Hz), 2.41 (s, 3H), 1.8–1.9 (m, 2H), 1.5–1.65 (m, 6H), 1.38 (s, 6H), 1.22 (t, 3H, J=6.3 Hz); IR (CHCl$_3$) 3018, 2977, 2934, 2878, 2238, 1611, 1496, 1219 cm$^{-1}$; MS (m/e) 456.

Analysis for C$_{31}$H$_{37}$NO$_2$: Calc: C, 81.72; H, 8.18; N, 3.07; Found: C, 81.92; H, 8.41; N, 3.13.

1-Benzyloxy-2-(3-methylphenyl)-4-ethyl-5-(6-methyl-6- cyanoheptyloxy)benzene, 75% yield by Method A. NMR (CDCl$_3$) ∂7.29–7.44 (m, 8H), 7.18 (s, 1H), 7.16 (d, 1H, J=6.0 Hz), 6.60 (s, 1H), 5.06 (s, 2H), 4.00 (t, 2H, J=5.3 Hz), 2.66 (q, 2H, J= 6.3 Hz), 2.42 (s, 3H), 1.8–1.9 (m, 2H) 1.55–1.65 (m, 6H), 1.39 (s, 6H), 1.22 (t, 3H, J=6.3 Hz); IR (CHCl$_3$) 2944, 2238, 1612, 1504, 1471 cm$^{-1}$; MS (m/e) 455.

Analysis for C$_{31}$H$_{37}$NO$_2$: Calc: C, 81.72; H, 8.18; N, 3.07; Found: C, 81.48; H, 8.22; N, 3.17.

1-Benzyloxy-2-(2-methylphenyl)-4-ethyl-5-(6 -methyl-6-cyanoheptyloxy)benzene, 40% yield by Method A. NMR (CDCl$_3$) ∂7.2–7.5 (m, 9H), 6.99 (s,1 H), 6.57 (s, 1H), 4.98 (s, 2H), 3.99 (t, 2H, J=5.3 Hz), 2.63 (q, 2H, J=6.3 Hz), 2.23 (s, 3H), 1.8– 1.9 (m, 2H), 1.55–1.65 (m, 6H), 1.37 (s, 6H), 1.22 (t, 3H, J=6.3 Hz); IR (CHCl$_3$) 3026, 2943, 2238, 1613, 1455 cm$^{-1}$; MS (m/e) 455.

Analysis for C$_{31}$H$_{37}$NO$_2$: Calc: C, 81.72; H, 8.18; N, 3.07; Found: C, 81.49; H, 7.95; N, 3.00.

1-Benzyloxy-2-(4-methoxyphenyl)-4-ethyl-5-(6 -methyl-6-cyanoheptyloxy)benzene, 82% yield by Method A. NMR (CDCl$_3$) ∂7.53 (d, 2H, J=7.0 Hz), 7.3–7.4 (m, 5H), 7.14 (s, 1H), 6.96 (d, 2H, J=7.0 Hz), 6.57 (s, 1H), 5.04 (so 2H), 3.97 (t, 2H, J= 5.3 Hz), 3.87 (s, 3H), 2.64 (q, 2H, J=6.3 Hz), 1.8–1.9 (m, 2H), 1.5– 1.7 (m, 6H), 1.38 (s, 6H), 1.22 (t, 3H, J=6.3 Hz); IR (CHCl$_3$) 2971, 2942, 2238, 1610, 1496, 1245 cm$^{-1}$; MS (e/m) 472;.

Analysis for C$_{31}$H$_{37}$NO$_3$: Calc: C, 78.95; H, 7.91; N, 2.97; Found: C, 78.67; H, 7.99; N, 2.81.

1-Benzyloxy-2-(3-methoxyphenyl)-4-ethyl-5-(6 -methyl-6-cyanoheptyloxy)benzene, 53% yield by Method A. NMR (CDCl$_3$) ∂7.3–7.45 (m, 6H), 7.15–7.20 (m, 3H), 6.87 (dd, 1H, J=6, 2 Hz), 6.58 (s, 1H), 5.04 (s, 2H), 3.99 (t, 2H, J=5.3 Hz), 3.79 (s, 3H), 2.64 (q, 2H, J=6.3 Hz), 1.8–1.9 (m, 2H), 1.5–1.65 (m, 6H), 1.38 (s, 6H), 1.24 (t, 3H, J=6.3 Hz); IR (CHCl$_3$) 2943, 2238, 1610, 1467, 1251 cm$^{-1}$; MS (m/e) 471.

Analysis for C$_{31}$H$_{37}$NO$_3$: Calc: C, 78.95; H, 7.91; N, 2.97; Found: C, 77.12; H, 7.83; N, 3.32.

1-Benzyloxy-2-(3-trifluoromethylphenyl)-4-ethyl- 5-(6-methyl-6-cyanoheptyloxy)benzene, 55% yield by Method B. NMR (CDCl$_3$) ∂7.88 (s, 1H), 7.71 (d, 1H, J=5 Hz), 7.3–7.5 (m, 7H), 7.14 (s, 1H), 6.60 (s, 1H), 5.06 (s, 2H), 4.01 (t, 2H, J=5.3 Hz), 2.64 (q, 2H, J=6.3 Hz), 1.8–1.9 (m, 2H), 1.5–1.7 (m, 6H), 1.38 (s, 6H), 1.22 (t, 3H, J=6.3 Hz); IR (CHCl$_3$) 2944, 2872, 2238, 1612, 1507, 1333 cm$^{-1}$; MS (m/e) 509.

1-Benzyloxy-2-(3-dimethylaminophenyl)-4-ethyl-5 -(6-methyl-6-cyanoheptyloxy)benzene, 94% yield by Method A. NMR (CDCl$_3$) ∂7.54 (d, 2H, J=7.0 Hz), 7.3–7.5 (m, 5H), 7.16 (s, 1H), 6.82 (s, 2H, J=7.0 Hz), 6.55 (s, 1H), 5.03 (s, 2H), 3.95 (t, 2H, J=5.3 Hz), 3.00 (s, 6H), 2.62 (q, 2H, J=6.3 Hz), 1.8–1.9 (m, 2H), 1.5–1.7 (m, 6H), 1.38 (s, 6H), 1.22 (t, 3H, J=6.3 Hz); IR (CHCl$_3$) 3009, 2944, 2868, 2238, 1612, 1498 cm$^{-1}$; MS (m/e) 484.

Analysis for C$_{32}$H$_{40}$N$_2$O$_2$: Calc: C, 79.30; H, 8.32; N, 5.78; Found: C, 77.04; H, 8.07; N, 5.67.

EXAMPLE 34–41

Representative Procedure for the Debenzylation

To a solution of the aryl benzyl ether in ethyl acetate was added 10% Pd on carbon. The atmosphere of the reaction was exchanged for hydrogen gas (1 Atm) and the reaction stirred at room temperature for 2–48 hours. The dispersion was filtered over Celite® and washed with ethyl acetate several times. The resulting solution was concentrated in vacuo and purified by flash chromatography (15% ethyl acetate in hexane) to provide the desired phenol.

34. 2-Phenyl-4-ethyl-5-(6-methyl-6-cyanoheptyloxy)phenol, 79.4% yield. NMR (CDCl$_3$) ∂7.4–7.5 (m, 5H), 7.03 (s, 1H), 6.53 (s, 1H), 5.22 (s, 1H), 4.00 (t, 3H, J=5.3 Hz), 2.63 (q, 2H, J= 6.3 Hz), 1.8–1.9 (m, 2H), 1.55–1.65 (m, 6H), 1.38 (s, 6H), 1.21 (t, 3H, J=6.3 Hz); IR (CHCl$_3$) 3558, 3019, 2843, 2237, 1624, 1408, 1219 cm$^{-1}$; MS (m/e) 351.

Analysis for C$_{23}$H$_{29}$NO$_2$: Calc: C, 78.63; H, 8.26; N, 3.99; Found: C, 79.04; H, 8.41; N, 4.24.

35. 2-(4-Methylphenyl)-4-ethyl-5-(6-methyl-6-cyanoheptyloxy)phenol, 44.5% yield. NMR (CDCl$_3$) ∂7.35 (d, 2H, J=7.0 Hz), 7.29 (d, 2H, J=7.0 Hz), 7.00 (s, 1H), 6.52 (s, 1H), 5.21 (s, 1H), 4.00 (t, 2H, J=5.3 Hz), 2.62 (q, 2H, J=6.3 Hz), 2.42 (s, 3H), 1.8–1.9 (m, 2H), 1.5–1.7 (m, 6H), 1.38 (s, 6H), 1.21 (t, 3H, J=6.3 Hz); IR (CHCl$_3$) 3554, 3020, 2843, 2237, 1624, 1587, 1497; MS (m/e ) 365.

Analysis for C$_{24}$H$_{31}$NO$_2$: Calc: C, 78.86; H, 8.55; N, 3.83; Found: C, 76.84; H, 8.44; N, 3.84.

36. 2-(3-Methylphenyl)-4-ethyl-5-(6-methyl-6 -cyanoheptyloxy)phenol, 80.1% yield. NMR (CDCl$_3$) ∂7.2 (m, 4H), 7.01 (s, 1H), 6.52 (s, 1H), 5.30 (s, 1H), 4.00 (t, 2H, J=5.3 Hz), 2.61 (q, 2H, J=6.3 Hz), 2.43 (s, 3H), 1.8–1.9 (m, 2H), 1.5–1.6 (m, 6H), 1.37 (s, 6H), 1.20 (t, 3H, J=6.3 Hz); IR (CHCl$_3$) 3553, 3023, 2977, 2943, 2872, 2237, 1625 cm$^{-1}$: MS (m/e) 365.

Analysis for C$_{24}$H$_{30}$NO$_2$: Calc: C, 79.08; H, 8.30; N, 3.84; Found: C, 78.89; H, 8.84; N, 3.92.

37. 2-(2-Methylphenyl)-4-ethyl-5-(6-methyl-6 -cyanoheptyloxy)phenol, 46.9% yield. NMR (CDCl$_3$) ∂7.2–7.4 (m, 4H), 6.87 (s, 1H), 6.51 (s, 1H), 4.69 (s, 1H), 4.00 (t, 2H, J=5.3 Hz), 2.61 (q, 2H, J=6.3 Hz), 2.20 (s, 3H), 1.8–1.9 (m, 2H), 1.55– 1.65 (m, 6H), 1.38 (s, 1H), 1.20 (t, 3H, J=6.3 Hz); IR (CHCl$_3$) 3551, 3019, 2944, 2871, 2238, 1625, 1586, 1502 cm$^{-1}$; MS (m/e ) 365.

Analysis for C$_{24}$H$_{31}$NO$_2$: Calc: C, 78.86; H, 8.55; N, 3.83; Found: C, 78.11; H, 8.52; N, 3.78.

38. 2-(4-Methoxyphenyl)-4-ethyl-5-(6-methyl-6 -cyanoheptyloxy)phenol, quantitative yield. NMR (CDCl$_3$) ∂7.38 (d, 2H J=8.6 Hz), 7.15 (d, 2H, J=8.6 Hz), 6.99 (s, 1H), 6.52 (s, 1H), 5.27 (s, 1H), 3.99 (t, 2H, J=6.2 Hz), 3.87 (s, 3H), 2.62 (q, 2H, J= 7.5 Hz), 1.8–1.9 (m, 2H), 1.55–1.65 (m, 6H), 1.37 (s, 6H), 1.21 (t, 2H, J=7.5 Hz); IR (CHCl$_3$) 3600, 3019, 2977, 2943, 2238, 1609, 1496, 1241 cm$^{-1}$; MS (m/e) 381.

Analysis for C$_{24}$H$_{31}$NO$_3$: Calc: C, 75.56; H, 8.19; N, 3.67; Found: C, 75.38; H, 8.32; N, 3.50.

39. 2-(3-Methoxyphenyl)-4-ethyl-5-(6-methyl-6 -cyanoheptyloxy)phenol, 72.3% yield. NMR (CDCl$_3$) ∂7.40 (t, 1 H, J= 6.8 Hz), 6.90–7.05 (m, 4H), 6.52 (s, 1H), 5.33 (s, 1H), 4.00 (t, 2H, J=5.3 Hz), 3.86 (s, 1H), 2.62 (q, 2H, J=6.3 Hz), 1.8–1.9 (m, 2H), 1.55–1.65 (m, 6H), 1.38 (s, 6H), 1.21 (t, 3H, J=6.3 Hz); IR (CHCl$_3$) 3550, 3023, 2943, 2238, 1597, 1485, 1287 cm$^{-1}$; MS (m/e) 382.

Analysis for C$_{24}$H$_{31}$NO$_3$: Calc: C, 75.56; H, 8.17; N, 3.67; Found: C, 73.95; H, 8.08; N, 2.59.

40. 2-(3-Trifluoromethylphenyl)-4-ethyl-5-(6-methylcyanoheptyloxy)phenol, 56.3% yield. NMR (CDCl$_3$) ∂7.75 (s, 1H), 7.5–7.7 (m, 3H), 7.03 (s, 1H), 6.50 (s, 1H), 5.09 (s, 1H), 4.01 (t, 2H, J=5.3 Hz), 2.62 (q, 2H, J=6.3 Hz), 1.8–1.9 (m, 2H), 1.5–1.65 (m, 6H), 1.38 (s, 6H), 1.21 (t, 3H, J=6.3 Hz); IR (CHCl$_3$) 2943, 2238, 1378, 1239 cm$^{-1}$; MS (m/e) 419, 420.

Analysis for C$_{24}$H$_{28}$F$_3$NO$_2$: Calc: C, 68.72; H, 6.73; N, 3.34; Found: C, 68.72; H, 7.02; N, 3.38.

41. 2-(4-Dimethylaminophenyl)-4-ethyl-5-(6-methyl-6 -cyanoheptyloxy)phenol, 38.5% yield. NMR (CDCl$_3$) ∂7.32

(d, 2H, J= 7.3 Hz), 6.99 (s, 1H), 6.85 (d, 2H, J=7.3 Hz), 6.52 (s, 1H), 3.99 (t, 2H, J=5.3 Hz), 3.01 (s, 6H), 1.8–1.9 (m, 2H), 1.5–1.6 (m, 6H), 1.37 (s, 6H), 1.20 (t, 3H, J=6.3 Hz); IR (CHCl$_3$) 3600, 3020, 2900, 2238, 1612, 1498 cm$^{-1}$; MS (m/e) 394, 395.

Analysis for C$_{25}$H$_{34}$N$_2$O$_2$: Calc: C, 76.10; H, 8.69; N, 7.10; Found: C, 74.10; H, 8.57; N, 7.91.

EXAMPLES 42–49

Representative Procedure for the Tetrazole Synthesis

To a solution of the nitrile (1 eq.) in diglyme were added N,N-dimethylethanolamine hydrochloride (2 eq.) and sodium azide (4 eq.). The suspension was heated to 130° C. and stirred for 8–72 hours. The mixture was diluted with methylene chloride and acidified with dilute hydrochloride acid. The organic material was collected, dried (magnesium sulfate), filtered and concentrated in vacuo. The resulting material was dissolved in ethanol, and to this solution was added aqueous sodium hydroxide (4 eq.). This reaction was stirred at room temperature for 30 minutes, then the solvents were removed in vacuo. An HP-20 reverse phase MPLC system was used to purify the residue, first using water as the mobile phase, then using 40% water in methanol. The desired fractions were combined and concentrated in vacuo. The residue was then lyophilized to produce the tetrazole as its sodium salt.

42. 2-Phenyl-4-ethyl-5-[6-(2H-tetrazol-5-yl)-6 -methylheptyloxy]phenol sodium salt, 34.3% yield. NMR (DMSO-d6) ∂7.55 (d, 2H, J=6.5 Hz), 7.35 (t, 2H, J=6.5 Hz), 7.20 (t, 1 H, J= 6.5 Hz), 6.98 (s, 1H), 6.60 (s, 1H), 3.82 (t, 2H, J=5.3 Hz), 2.65 (q, 2H, J=6.3 Hz), 1.55–1.70 (m, 6H), 1.25–1.35 (m, 8H), 1.10 (t, 3H, J=6.3 Hz); IR (KBr) 3192, 2970, 2937, 1617, 1488, 1453, 1214 cm$^{-1}$; MS (m/e) 439.

Analysis for C$_{23}$H$_{29}$N$_4$NaO$_2$.2H$_2$O: Calc: C, 59.87; H, 7.16; N, 12.25; Found: C, 60.28; H, 7.45; N, 12.07.

43. 2-(4-Methylphenyl)-4-ethyl-5-[6-methyl-6-(2H-tetrazol- 5-yl)heptyloxy]phenol disodium salt, 29.0% yield. NMR (DMSO-d6) ∂7.40 (d, 2H, J=6.0 Hz), 7.15 (d, 2H, J=6.0 Hz), 6.95 (s, 1H), 6.60 (s, 1H), 3.82 (t, 2H, J=5.3 Hz), 2.45 (q, 2H, J=6.3 Hz), 2.32 (s, 3H), 1.5–1.7 (m, 6H), 1.2–1.4 (m, 8H), 1.07 (t, 3H, J= 6.3 Hz); IR (KBr) 2935, 1616, 1502, 1443 cm$^{-1}$; MS (m/e) 409.

Analysis for C$_{24}$H$_{30}$N$_4$Na$_2$O$_2$.1.5H$_2$O: Calc: C, 60.13; H, 6.89; N, 11.69; Found: C, 59.99; H, 6.71; N, 11.98.

44. 2-(3-Methylphenyl)-4-ethyl-5-[6-methyl-6-(2H-tetrazol- 5-yl)heptyloxy]phenol sodium salt, 26.8% yield. NMR (DMSO-d6) ∂7.32 (s, 1H), 7.30 (d, 1 H, J=6.3 Hz), 7.20 (t, 1H, J= 6.3 Hz), 7.00 (d, 1H, J=6.3 Hz), 6.94 (s, 1H), 6.61 (s, 1H), 3.82 (t, 2H, J=5.3 Hz), 2.46 (q, 2H, J=6.3 Hz), 2.30 (s, 3H), 1.5–1.7 (m, 6H), 1.2–1.4 (m, 8H), 1.10 (t, 3H, J=6.3 Hz); IR (KBr) 2935, 1616, 1486, 1140 cm$^{-1}$; MS (m/e) 453.

Analysis for C$_{24}$H$_{30}$N$_4$Na$_2$O$_2$.0.5H$_2$O: Calc: C, 62.34; H, 6.71; N, 12.12; Found: C, 61.91; H, 8.02; N, 11.64.

45. 2-(2-Methylphenyl)-4-ethyl-5-[6-methyl-6-(2H-tetrazol- 5-yl)heptyloxy]phenol disodium salt, 34.9% yield. NMR (DMSO-d6) ∂7.04–7.12 (m, 4H), 6.71 (s, 1H), 6.59 (s, 1H), 3.83 (t, 2H, J=5.3 Hz), 2.43 (q, 2H, J=6.3 Hz), 2.08 (s, 3H), 1.55–1.7 (m, 4H), 1.1–1.25 (m, 6H), 1.08 (t, 3H, J=6.3 Hz); IR (KBr) 2935, 1617, 1486, 1326, 1243 cm$^{-1}$; MS (m/e) 431.

Analysis for C$_{24}$H$_{30}$N$_4$Na$_2$O$_2$.2H$_2$O: Calc: C, 59.02; H, 6.97; N, 11.48; Found; C, 59.61; H, 7.41; N, 11.96.

46. 2-(4-Methoxyphenyl)-4-ethyl-5-[6-methyl-6-(2H-tetrazol- 5-yl)heptyloxy]phenol sodium salt, 29.0% yield. NMR (DMSO-d6) ∂7.43 (d, 2H, J=7.3 Hz), 6.91 (s, 1H), 6.89 (d, 2H, J= 7.3 Hz), 6.57 (s, 1H), 3.81 (t, 2H, J=5.3 Hz), 3.74 (s, 3H), 2.43 (q, 2H, J=6.3 Hz), 1.7–1.9 (m, 6H), 1.2–1.4 (m, 8H), 1.06 (t, 3H, J= 6.3 Hz); IR (KBr) 3009, 2969, 2937, 1609, 1497, 1242 cm$^{-1}$; MS (m/e) 425.

Analysis for C$_{24}$H$_{30}$N$_4$Na$_2$O$_3$.2H$_2$O: Calc: C, 57.14; H, 6.75; N, 11.11; Found: C, 57.53; H, 7.57; N, 10.20.

47. 2-(3-Methoxyphenyl)-4-ethyl-5-[6-methyl-6-(2H-tetrazol- 5-yl)heptyloxy]phenol sodium salt, 15.9% yield. NMR (DMSO-d6) ∂7.26 (t, 1H, J=6 Hz), 7.05–7.10 (m, 2H), 6.98 (s, 1H), 6.80 (dd, 1H, J=2,6 Hz), 6.60 (s, 1H), 3.84 (t, 2H, J=5.3 Hz), 3.76 (s, 3H), 2.46 (q, 2H, J=6.3 Hz), 1.5–1.7 (m, 6H), 1.2–1.4 (m, 8H) 1.08 (t, 3H, J=6.3 Hz); IR (KBr) 3416, 2961, 2936, 2869, 1608, 1487, 1140 cm$^{-1}$; MS (m/e) 469.

Analysis for C$_{24}$H$_{30}$N$_4$Na$_2$O$_3$.1.5H$_2$O: Calc: C, 58.18; H, 6.67; N, 11.31; Found: C, 58.40; H, 7.73; N, 10.69.

48. 2-(4-Trifluoromethylphenyl)-4-ethyl-5-[6-methyl-6-(2H-tetrazol-5-yl)heptyloxy]phenol disodium salt, 29.0% yield. NMR (DMSO-d6) ∂7.8–7.9 (m, 2H), 7.55–7.6 (m, 1H), 7.55 (s, 1H), 7.04 (s, 1H), 6.65 (s, 1H), 3.84 (t, 2H, J=5.3 Hz), 2.48 (q, 2H, J= 6.3 Hz), 1.7–1.9 (m, 6H), 1.2–1.4 (m, 8H), 1.05 (t, 3H, J=6.3 Hz); IR (KBr) 3412, 2965, 2937, 2870, 1617, 1336 cm$^{-1}$; MS (m/e) 507.

Analysis for C$_{24}$H$_{27}$F$_3$N$_4$Na$_2$O$_2$.H$_2$O: Calc: C, 54.96; H, 5.53; N, 1 0.69; Found: C, 55.26; H, 6.23; N, 10.10.

49. 2-(3-Dimethylaminophenyl)-4-ethyl-5-[6-methyl-6 -(2H-tetrazol-5-yl)heptyloxy]phenol disodium salt, 28.8% yield. NMR (DMSO-d6) ∂7.36 (d, 2H, J=7.3 Hz), 6.89 (s, 1H), 6.71 (d, 2H, J=7.3 Hz), 6.53 (s, 1H), 3.81 (t, 2H, J=5.3 Hz), 2.45 (q, 2H, J= 6.3 Hz), 1.5–1.7 (m, 6H), 1.2–1.4 (m, 8H), 1.06 (t, 3H, J=6.3 Hz); IR (KBr) 3412. 2963, 2935, 2867, 1613, 1505 cm$^{-1}$; MS (m/e) 437, 438.

Analysis for C$_{25}$H$_{33}$N$_5$Na$_2$O$_2$.2H$_2$O: Calc: C, 58.48; H, 7.21; N, 13.65; Found: C, 58.63; H, 6.66; N, 12.53.

EXAMPLE 50

3-(5-(6-(4-Phenyl-5-hydroxy-2-ethylphenoxy)propoxy)-2 -carboxymethyl-1,2,3,4-tetrahydronaphthalen-1(2H)- one)propanoic acid

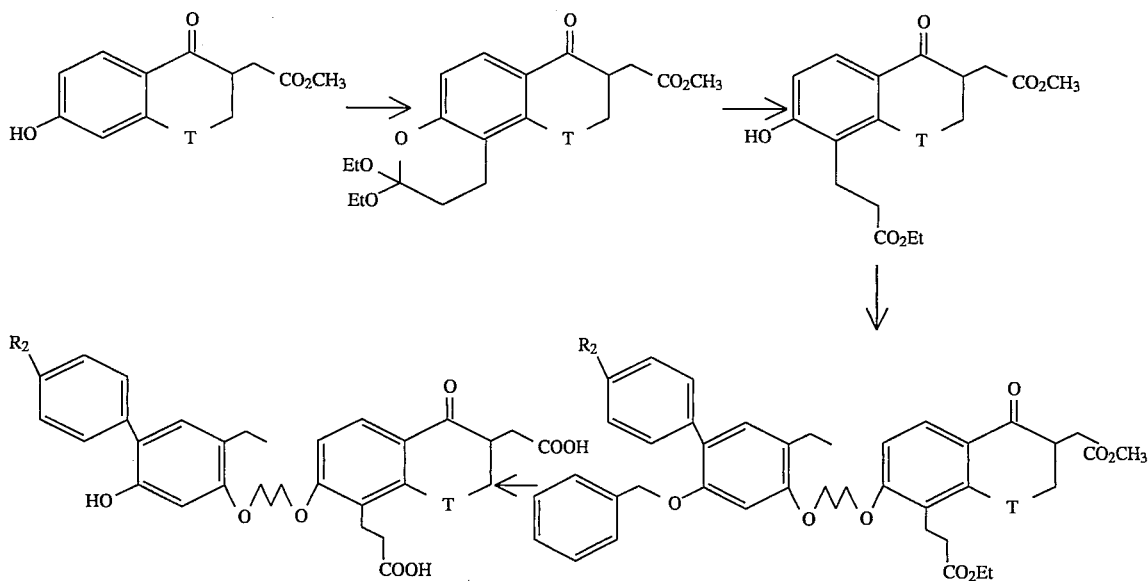

R₂ = H, T = CH₂ - Example 50
R₂ = F, T = CH₂ - Example 51
R₂ = F, T = bond - Example 52

A. Preparation of 3-(2-carbomethoxymethyl-6-hydroxy-1,2,3,4-tetrahydronaphthalen-1(2H)-one-5-yl)propanoic acid, ethyl ester.

A mixture of 6.4 g (0.027 mol) of 6-hydroxy-1,2,3,4-tetrahydronaphthalen-1(2H)-one-2-acetic acid, methyl ester, 9.5 g (0.055 mol) of triethyl orthoacrylate and 1.4 g (0.00137 mol) of pivalic acid in 50 mL of toluene was heated to maintain reflux for 20 hours. After cooling, the reaction mixture was washed with water, dried (sodium sulfate), and chromatographed over silica gel eluting with a gradient (toluene to toluene/ethyl acetate, 9:1) providing 6.5 g of a yellow oil. This oil was crystallized from 45 mL of methanol to give 3.9 g (40%) of a white crystalline solid. A portion of this solid (2.1 g) was stirred in 20 mL of ethyl acetate containing 1 mL of 1N hydrochloric acid for 15 minutes. The mixture was washed with water, dried (sodium sulfate), and concentrated at reduced pressure to give 1.8 g of the desired title product (93% yield), NMR (CDCl₃) ∂1.28 (t, 3), 1.93 (m, 1), 2.23–2.50 (m, 2), 2.72 (t, 2), 2.95–3.10 (m, 6), 3.75 (s, 3), 4.20 (q, 2), 6.9 (d, 1), 7.95 (d, 1), 8.30 (s, 1).

B. Preparation of 3-(5-(6-(4-phenyl-5-benzyloxy-2-ethylphenoxy)propoxy)-2-carbomethoxymethyl-1,2,3,4-tetrahydronaphthalen-1(2H)-one)propanoic acid, ethyl ester.

A mixture of 3-(2-carbomethoxymethyl-6-hydroxy-1,2,3,4-tetrahydronaphthalen-1(2H)-one-5-yl)propanoic acid, ethyl ester (0.67 g, 1.9 mmol), 0.76 g (2 mmol) of 1-phenyl-2-benzyloxy-4-(3-chloropropoxy)-6-ethylbenzene, 0.2 g of potassium iodide and 1.38 g (10.0 mmol) of potassium carbonate in 25 mL of methyl ethyl ketone was heated to maintain reflux for 20 hours. The reaction mixture was cooled, diluted with ethyl acetate, washed with water, and dried (sodium sulfate). The product was isolated by silica gel chromatography eluting with toluene to give 0.73 g (54%) of the title intermediate. NMR (CDCl₃) ∂1.14 (t, 3), 1.23 (t, 3), 1.90 (m, 1), 2.23–2.60 (m, 8), 2.85–3.20 (m, 6), 3.75 (s, 3), 4.12 (m, 4), 4.25 (t, 2), 5.15 (s, 2), 6.55 (s, 1), 6.90 (d, 1), 7.15–7.55 (m, 11), 8.02 (d, 1).

C. Preparation of 3-(5-(6-(4-phenyl-5-hydroxy-2-ethylphenoxy)propoxy)-2-carboxymethyl-1,2,3,4-tetrahydronaphthalen-1(2H)-one)propanoic acid.

A mixture of 50 mL of 90% aqueous methanol, 0.36 g (6.45 mmol) of potassium hydroxide, and 0.73 g (1.08 mmol) of 3-(5-(6-(4-phenyl-5-benzyloxy-2-ethylphenoxy)propoxy)-2-carbomethoxymethyl-1,2,3,4-tetrahydronaphthalen-1(2H)-one)propanoic acid, ethyl ester was stirred for 24 hours at 25° C. The reaction mixture was diluted with 100 mL of water, made acidic with 5N hydrochloric acid and extracted with ethyl acetate. This solution was dried (sodium sulfate), and concentrated at reduced pressure to give 0.48 g (70% yield) of an oil. This oil was dissolved in 50 mL of ethyl acetate and hydrogenated under 30 psi of hydrogen with 0.48 g of 5% Pd/C as catalyst. After filtering off the catalyst and concentrating at reduced pressured, the desired title product was obtained (0.31 g, 75% yield) by chromatography on R-18 resin eluting with methanol/water, mp 72°–76° C., NMR (CDCl₃) ∂1.10 (t, 3), 1.91 (m, 1), 2.25–2.65 (m, 6), 2.86–3.20 (m, 8), 4.21 (t, 2), 4.28 (t, 2), 6.58 (s, 1), 6.90 (d, 1), 7.02 (s, 1), 7.32–7.52 (m, 5), 8.03 (d, 1).

Analysis for C₃₂H₃₄O₈: Calc: C, 70.32; H, 6.27; Found: C, 70.13; H, 6.31.

EXAMPLE 51

3-(5-(6-(4-(4-Fluorophenyl)-5-hydroxy-2-ethylphenoxy)propoxy)-2-carboxymethyl-1,2,3,4-tetrahydronaphthalen-1(2H)-one)propanoic acid A. Preparation of 3-(5-(6-(4-(4-fluorophenyl)-5-benzyloxy-2-ethylphenoxy)propoxy)-2-carbomethoxymethyl-1,2,3,4-tetrahydronaphthalen-1(2H)-one)propanoic acid ethyl ester.

Using the procedure described for the synthesis of Example 50(B), 0.91 g (2.72 mmol) of 3-(2-carbomethoxymethyl-6-hydroxy-1,2,3,4-tetrahydronaphthalen-1(2H)-one-5-yl)propanoic acid, ethyl ester and 1.09 g (2.73 mmol) of 1-(4-fluorophenyl)- 2-benzyloxy-4-(3-chloropropoxy)-6-ethylbenzene were reacted to give 1.08 g of the title product (57% yield), NMR (CDCl₃) ∂ 1.20 (m, 6), 1.90 (m, 1), 2.22–2.68 (m, 8), 2.90–3.20 (m, 6), 3.75 (s, 3), 4.12 (q, 23), 4.22 (t, 2), 4.30 (t, s), 5.03 (s, 2), 6.63 (s, 1), 6.90 (d, 1), 7.03–7.55 (m, 10), 8.02 (d, 1).

B. Preparation of 3-(5-(6-(4-(4-fluorophenyl)-5 -hydroxy-2-ethylphenoxy)propoxy)-2-carboxymethyl-1,2,3,4 -tetrahydronaphthalen-1(2H)-one)propanoic acid.

3-(5-(6-(4-(4-Fluorophenyl)-5-benzyloxy-2-ethylphenoxy)propoxy)- 2-carbomethoxymethyl-1,2,3,4-tetrahydronaphthalen- 1(2H)-one)propanoic acid ethyl ester was reacted by the method used for Example 50(C) to give 0.47 g (77% yield) of the desired title product, mp 68°–72° C., NMR (CDCl$_3$) ∂1.15 (t, 3), 1.91 (m, 1), 2.23–2.62 (m, 8), 2.85–3.18 (m, 6), 4.21 (t, 2), 4.28(t, 2), 6.55 (s, 1), 6.88 (d, 1), 7.10 (t, 2), 7.41 (m, 2), 8.02 (d, 1).

Analysis for $C_{32}H_{33}FO_8$: Calc: C, 68.07; H, 5.89; Found: C, 67.84; H, 6.14.

EXAMPLE 52

3-(4-(5-(4-(4-Fluorophenyl)-5-hydroxy-2-ethylphenoxy)propoxy)-2-carboxymethyl-2,3-dihydroinden-1(2H)-one)propanoic acid A. Preparation of 3-(4-(2-carbomethoxymethyl)-5 -hydroxy-2,3-dihydroinden-1(2H)-one)propanoic acid, ethyl ester.

C. Preparation of 3-(4-(5-(4-(4-fluorophenyl)-5 -hydroxy-2-ethylphenoxy)propoxy)-2-carboxymethyl-2,3 -dihydroinden-1(2H)-one)propanoic acid.

3-(4-(5-(4-Fluorophenyl)-5-benzyloxy-2-ethylphenoxy)propoxy)- 2-carbomethoxymethyl-2,3-dihydroinden-1(2H)-one)propanoic acid (0.55 g, 0.8 mmol) was reacted using the method described for Example 50(C) to give 0.16 g (30% yield) of the title product, mp 78°–81° C., NMR (CDCl$_3$) ∂1.20 (t, 3), 2.30– 3.05 (m, 12), 3.45 (m, 1), 4.22 (t, 2), 4.32 (t, 2), 6.55 (s, 1), 6.88– 7.45 (m, 6), 7.70 (d, 1).

Analysis for $C_{31}H_{31}FO_8$: Calc: C, 67.63; H, 5.67; Found: C, 67.44; H, 5.92.

EXAMPLE 53

3,3-Dimethyl-5-(3-(2-carboxyethyl)-4-(3-(4-fluorophenyl)-5 -hydroxy-2-ethylphenoxy)propoxy)phenyl)- 5-oxopentanoic acid

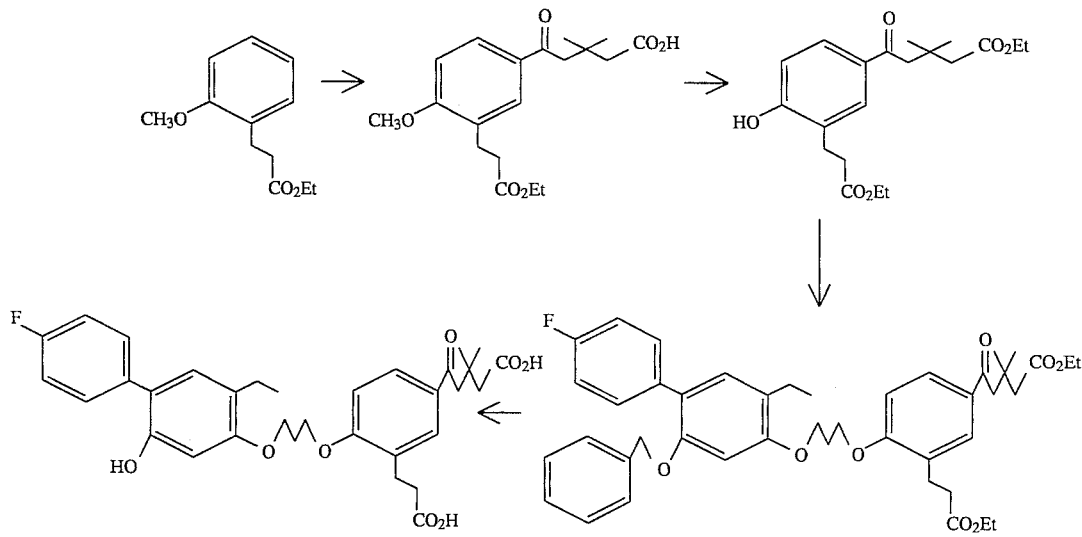

Using the method described for Example 50(A), 4.8 g (21.8 mmol) of 5-hydroxy-2,3-dihydroinden-1(2H)-one-2-acetic acid, methyl ester was converted to 1.6 g of the title intermediate in 76% yield, NMR (CDCl$_3$) ∂1.25 (t, 3), 2.50–2.80 (m, 4), 2.80–3.10 (m, 4), 3.36 (m, 1), 3.73 (s, 3), 4.15 (m, 2), 6.94 (d, 1), 7.58 (d, 1), 8.75 (s, 1).

B. Preparation of 3-(4-(5-(4-fluorophenyl)-5 -benzyloxy-2-ethylphenoxy) propoxy)-2-carbomethoxymethyl-2,3 -dihydroinden-1(2H)-one)propanoic acid.

Using the method described for Example 50(B), 0.93 g (2.91 mmol) of 3-(4-(2-carbomethoxymethyl)-5-hydroxy-2,3 -dihydroinden-1(2H)-one)propanoic acid, ethyl ester and 1.16 g (2.9 mmol) of 1-(4-fluorophenyl)-2-benzyloxy-4-(3 -chloropropoxy)-6-ethylbenzene were converted to 0.58 g (30% yield) of the title intermediate. NMR (CDCl$_3$) ∂1.20 (m, 6), 2.15– 3.10 (m, 12), 3.47 (m, 1), 3.73 (s, 3), 4.10 (q, 2), 4.22 (t, 2), 4.32 (t, 2), 5.03 (s, 2), 6.62 (s,1), 6.94–7.56 (m, 11), 7.70 (d, 1).

A. Preparation of 5-(3-(2-carbethoxyethyl)-4 -methoxyphenyl)-3,3-dimethyl-5-oxopentanoic acid.

Aluminum chloride (41.4 g, 0.3 mol) was added in portions to a mixture of 20.8 g (0.1 mol) of 1-(2-methoxyphenyl)propanoic acid, ethyl ester and 14.2 g (0.1 mol) of β,β-dimethylglutaric anhydride in 250 mL of methylene chloride cooled with an ice-water bath. Stirring was maintained for four hours while slowly warming to 25° C. The mixture was poured into 500 g of ice and 50 mL of concentrated hydrochloric acid. The organic layer was separated, washed with water, and dried over magnesium sulfate. After removing the solvent at reduced pressure, 28 g of crude 5-(3-(2-carbethoxyethyl)-4-methoxyphenyl)-3,3 -dimethyl-5-oxopentanoic acid were obtained.

B. Preparation of 5-(3-(2-carbethoxyethyl)-4 -hydroxyphenyl)-3,3-dimethyl-5-oxopentanoic acid, ethyl ester.

Crude 5-(3-(2-carbethoxyethyl)-4-methoxyphenyl)-3,3 -dimethyl-5-oxopentanoic acid (0.08 mol) was placed in 300 g of pyridine hydrochloride and the mixture heated at 180° C. in an oil bath for 20 hours. After cooling, the mixture was taken up in water, made strongly acidic with 2N hydrochloric acid, and extracted three times with ethyl acetate. The combined ethyl acetate was washed with water and dried (sodium sulfate). The solvent was removed at reduced pressure and the residue dissolved in 200 mL of ethanol. Methanesulfonic acid (0.5 mL) was added and the mixture heated to maintain reflux for 20 hours. After concentrating in vacuo, the residue was taken up in ethyl acetate, washed with Water, and dried (sodium sulfate). The solvent was removed at reduced pressure and the title ester (19.1 g, 66% yield) was obtained by silica gel chromatography, eluting with toluene/ethyl acetate, 17:3., NMR (DMSO-$d_6$) ∂0.94 (s, 6) 0.97 (t, 3), 0.98 (t, 3), 2.44 (s, 2), 2.56 (t, 2), 2.82 (t, 2), 2.97 (s, 2), 4.02 (m, 4), 6.85 (d, 1), 7.70 (m, 2), 10.36 (s, 1).

C. Preparation of 3,3-dimethyl-5-(3-(2-carbethoxyethyl)- 4-(4-(4-fluorophenyl)-5-benzyloxy-2-ethylphenoxy)propoxy)- 5-oxopentanoic acid, ethyl ester.

By the method described for Example 50(B), 1.6 g (4.4 mmol) of 5-(3-(2-carbethoxyethyl)-4-hydroxyphenyl)-3,3-dimethyl-5-oxopentanoic acid, ethyl ester and 1.75 g (4.4 mmol) of 1-(4-fluorophenyl)-2-benzyloxy-4-(3-chloropropoxy)-6 -ethylbenzene were converted to 1.1 g (35% yield) of the desired title intermediate. NMR (CDCl$_3$) ∂1.20 (m, 15), 2.34 (t, 2), 2.54 (s, 2), 2.61 (m, 4), 3.00 (t, 2), 3.07 (s, 2), 4.10 (m, 4), 4.20 (t, 2), 4.28 (t, 2), 5.02 (s, 2), 6.63 (s, 1), 6.91 (d, 1), 7.07 (m, 3), 7.30 (m, 5), 7.51 (m, 3), 7.81 (s, 1), 7.86 (d, 1).

D. Preparation of 3,3-dimethyl-5-(3-(2-carboxyethyl)- 4-(3-(4-fluorophenyl)-5-hydroxy-2-ethylphenoxy)propoxy)phenyl)-5 -oxopentanoic acid.

Using the method described for Example 50(C), 3,3-dimethyl-5-(3-(2-carbethoxyethyl)-4-(4-(4-fluorophenyl)-5-benzyloxy-2-ethylphenoxy)propoxy)-5-oxopentanoic acid, ethyl ester (0.6 g, 0.9 mmol) was converted to 0.41 g (51% yield) of the title product, mp 52°–55° C., NMR (CDCl$_3$) ∂1.16 (m, 9), 2.35 (t, 2), 2.50–2.72 (m, 6), 3.02 (m, 4), 4.19 (t, 2), 4.28 (t, s), 6.55 (s, 1), 6.93 (d, 1), 7.00 (s, 1), 7.12 (m, 2), 7.42 (m, 2), 7.85 (s, 1), 7.90 (d, 1).

Analysis for $C_{33}H_{37}FO_8$: Calc: C, 68.26; H, 6.42; Found: C, 67.60; H, 6.63.

EXAMPLE 54

7-[3-[(5-Ethyl-2-hydroxy[1,1'-biphenyl]-4-yl)oxy]propoxy]-3,4-dihydro-8-propyl-2H-1-benzopyran-2-carboxylic acid

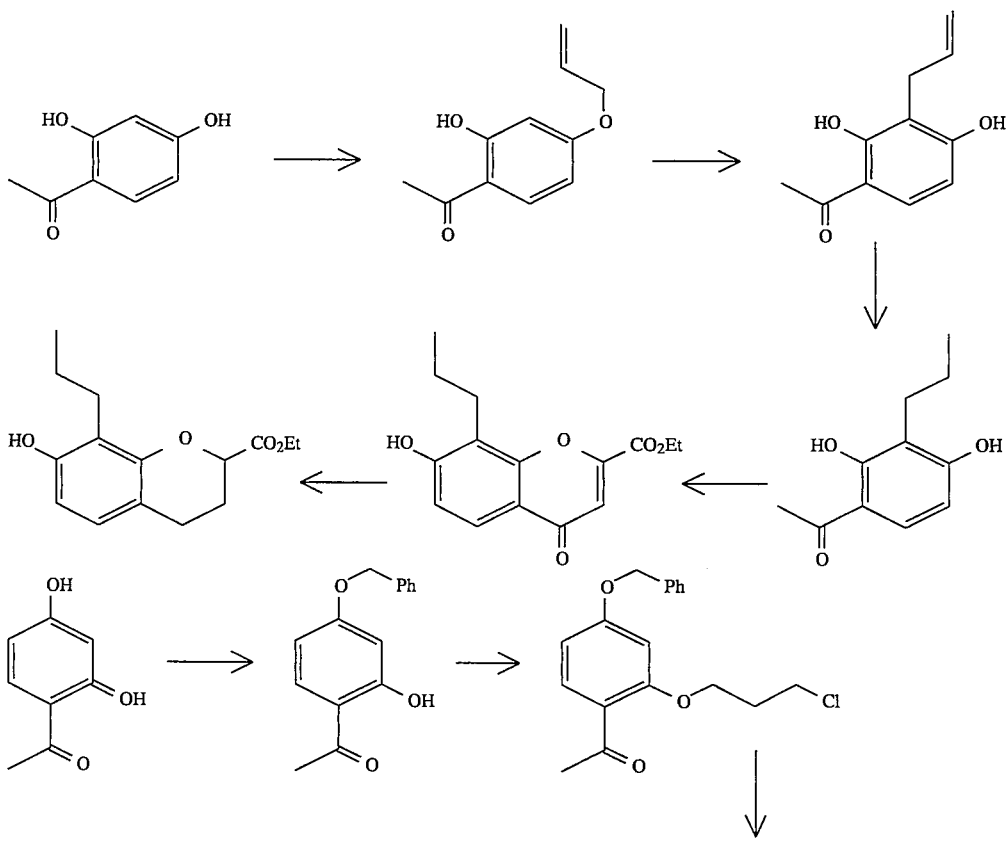

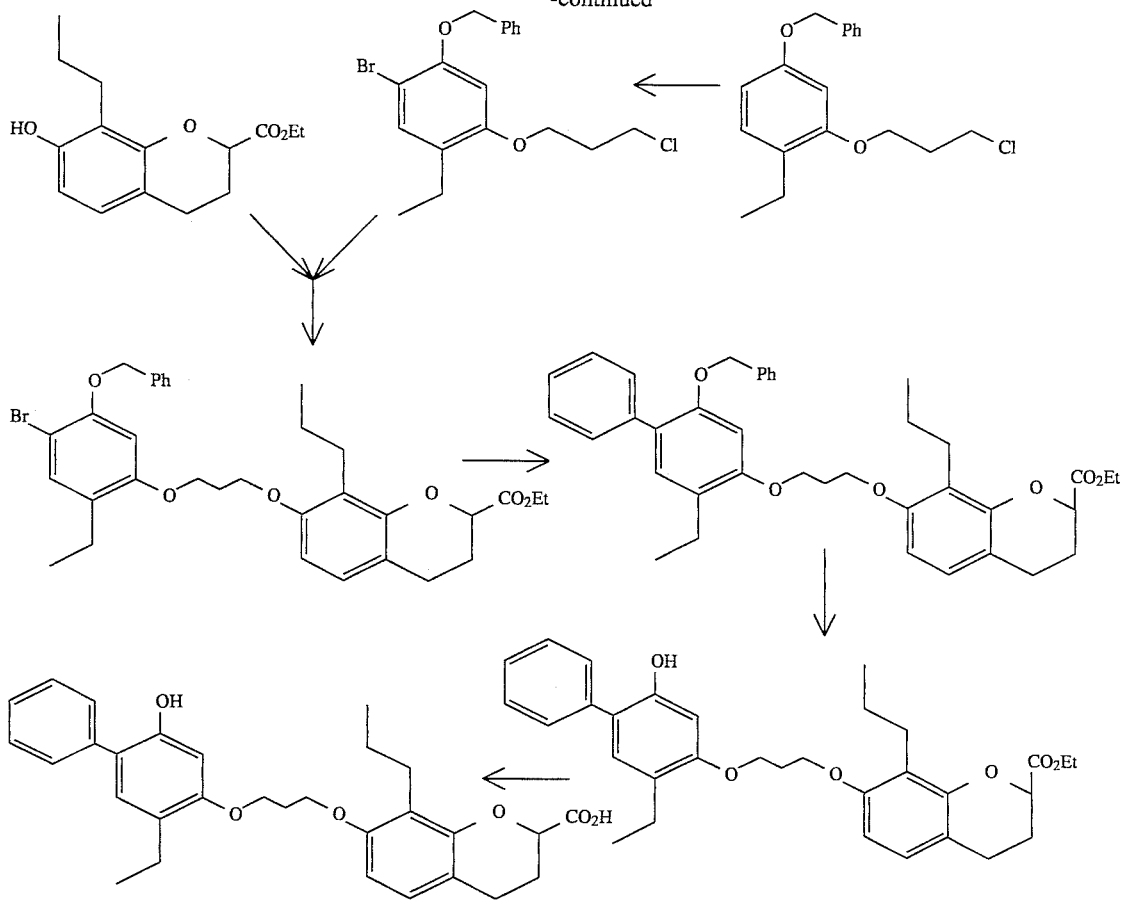

-continued

A. Preparation of ethyl 7-hydroxy-8-propyl-2H-1-benzopyran-2-carboxylate.

To a solution of 225 mL of absolute ethanol under an argon atmosphere and at room temperature were added 16.56 g of sodium metal over a 1 hour period. After all of the sodium was added, the reaction mixture was heated at reflux for 1 hour, then cooled to room temperature. A mixture of 2,4-dihydroxy-3-propylacetophenone (34.82 g, 0.180 mol), diethyloxylate (54.57 mL, 0.41 mol), absolute ethanol (45 mL), and diethyl ether (45 mL) was added to the sodium ethoxide solution over a 25 minute period. The resulting deep maroon reaction mixture was heated at reflux for 2.5 hours and then cooled to room temperature. The reaction mixture was poured into approximately 600 mL of 1N hydrochloric acid and then extracted several times with diethyl ether. The ether was removed in vacuo and the resulting gum was dissolved in 135 mL of ethanol. To this solution was then added 2.25 mL of concentrated hydrochloric acid. This mixture was subsequently refluxed for 45 minutes. The reaction was cooled to room temperature and ethanol was removed under reduced pressure leaving a brown solid. This solid was dissolved in ethyl acetate and washed once with water, twice with a saturated sodium bicarbonate solution, once with water, and then dried over magnesium sulfate. Filtration and solvent removal gave 87 g of a brown solid which was recrystallized from ethyl acetate/petroleum ether. Recrystallization provided 24.07 g (48%) of the title intermediate as a tan solid.

TLC: Rf=0.27 (40% ethyl acetate/hexane).

NMR (CDCl$_3$) $\delta$8.80 (br s, 1), 7.98 (d, 1, J=8.78 Hz), 7.13 (d, 1, J=8.78 Hz), 7.13(s, 1), 4.47 (q, 2, J=7.11 Hz), 2.96 (t, 2, J=7.25 Hz), 1.73 (m, 2), 1.46 (t, 3, J=7.16 Hz), 1.02 (t, 3, J=7.11 Hz).

B. Preparation of ethyl 3,4-dihydro-7-hydroxy-8-propyl-2H-1-benzopyran-2-carboxylate.

In a Parr™ bottle, ethyl 7-hydroxy-8-propyl-2H-1-benzopyran-2-carbohydrate (12.07 g, 0.044 mol) was dissolved in 210 mL of acetic acid. 10% Palladium-on-carbon (7.2 g) catalyst was added to this solution and the bottle was pressurized with 52 psi of hydrogen gas. The reaction was agitated for 23 hours. The catalyst was removed by filtration through a Celite® pad in a sintered glass funnel. The catalyst was washed with ethyl acetate. The solvent was removed from the filtrate, and the resulting oil was azeotroped with toluene providing 12 g of brown oil. The material was purified on a Waters Prep 500 HPLC, equipped with silica gel cartridges, running a 5% to 40% ethyl acetate/hexane gradient over 50 minutes at a flow rate of 250 mL/minute and collecting 500 mL fractions. The purified title chroman intermediate was obtained as a pink oil (10 g, 86%).

TLC: Rf=0.50 (40% ethyl acetate/hexane).

NMR (CDCl$_3$) $\delta$6.73 (d, 1, J=8.20 Hz), 6.37 (d, 1, J=8.20 Hz), 4.78 (br s, 1), 4.75 (m, 1), 4.25 (m, 2), 2.68 (m, 4), 2.16 (m, 2), 1.60 (m, 2), 1.29 (t, 3, J=7.07 Hz), 0.99 (t, 3, J=7.34 Hz).

C. Preparation of 4-benzyloxy-2-(3-chloro-1-propyloxy)acetophenone.

A suspension of sodium hydride (80 mg of 60% oil dispersion, 2.0 mmol) in 5 mL of dry dimethylformamide was stirred under a nitrogen atmosphere. To this suspension at room temperature was added a 2 mL solution of 4-benzyloxy-2-hydroxyacetophenone (242 mg, 1.0 mmol). The reaction was stirred for 25 minutes at room temperature. A solution of the 1-bromo-3-chloropropane (625 mg, 4 mmol) in 3 mL of dimethylformamide was added to the generated alkoxide followed by the 18-crown-6 (26 mg, 0.1 mmol). The reaction was stirred for 19 hours at room temperature after which it was diluted with ethyl acetate and washed twice with a saturated aqueous sodium chloride solution. The organic material was dried over magnesium sulfate, filtered and concentrated under vacuum. The resulting material was chromatographed on silica gel eluting with 20% ethyl acetate/hexane to give the the title chloropropyl ether (170 mg, 53%).

NMR (CDCl$_3$) ∂7.84 (d, 1, J=9.0 Hz), 7.40 (m, 5), 6.61 (dd, 1, J= 3.0, 9.0 Hz), 6.56 (d, 1, J=3.0 Hz), 5.12 (s, 2), 4.20 (t, 2, J=6.0 Hz), 3.78 (t, 2, J=6.0 Hz), 2.58 (s, 3), 2.30 (m, 2); IR (CHCl$_3$) 3019, 2930, 1663, 1600, 1574, 1499, 1435 cm$^{-1}$; Mass Spec (FD) (m/z) 318 (M$^+$).

Analysis for C$_{18}$H$_{19}$O$_3$Cl: Calc: C, 76.82; H, 6.01; Found: C, 76.56; H, 5.99.

D. Preparation of 1-benzyloxy-4-ethyl-3-(3-chloro-1-propyloxy) benzene.

4-Benzyloxy-2-(3-chloro-1-propyloxy)acetophenone (1.0 g) was dissolved in carbon tetrachloride (3 mL). At room temperature under a nitrogen atmosphere, trifluoroacetic acid (3 mL) was added followed by triethylsilane (3 mL). After stirring for 1.5 hours, the reaction was diluted with methylene chloride and the organic layer was washed several times with a saturated aqueous sodium bicarbonate solution. The organic material was dried over magnesium sulfate, filtered and concentrated under vacuum. The resulting residue was purified by flash chromatography on silica gel eluting with 1% ethyl acetate/hexane giving 0.620 g of desired title compound.

NMR (CDCl$_3$) ∂7.38 (m, 5), 7.04 (d, 1, J=8.0 Hz), 6.72 (s, 1), 6.70 (dd, 1, J=8.0 Hz), 5.02 (s, 2), 4.07 (t, 2, J=7.0 Hz), 3.74 (t, 2, J= 7.0 Hz), 2.56 (q, 2, J=8.0 Hz), 2.25 (m, 2), 1.16 (t, 3, J=8.0 Hz); IR (CHCl$_3$) 3011, 2958, 2912, 2876, 1612, 1505, 1455 cm$^{-1}$.

E. Preparation of 2-benzyloxy-1-bromo-5-ethyl-4-(3-chloro-1-propyloxy)benzene.

To a solution of 1-benzyloxy-4-ethyl-3-(3-chloro-1-propyloxy)benzene (39.5 g, 0.13 mol) in carbon tetrachloride (500 mL) at room temperature was added solid N-bromosuccinimide (23.1 g, 0.13 mol). The solution was stirred at room temperature for 15 hours. The reaction was diluted with methylene chloride and washed with water. The organic extract was dried over magnesium sulfate, filtered and concentrated in vacuo. The crude material was chromatographed on a Waters Prep 500 HPLC. The desired title aryl bromide (27.1 g) was obtained in 55% yield.

NMR (CDCl$_3$) ∂7.50–7.22 (m, 7), 6.50 (s, 1), 5.13 (s, 2), 4.04 (t, 2, J=8.0 Hz), 3.74 (t, 2, J=8.0 Hz), 2.53 (q, 2, J=8.0 Hz), 2.22 (m, 2), 1.14 (t, 3, J=8.0 Hz); IR (CHCl$_3$) 3012, 2971, 1602, 1500, 1454 cm$^{-1}$; Mass Spec (FD) (m/z) 384 (M$^+$), 304.

Analysis for C$_{18}$H$_{20}$O$_2$BrCl: Calc: C, 56.34; H, 5.25; Found: C, 56.55; H, 5.36.

F. Preparation of ethyl 7-[3-[(2-benzyloxy-1-bromo-5-ethyl-4-yl)oxy]propoxy]-3,4-dihydro-8-propyl-2H-1-benzopyran-2-carboxylate.

2-Benzyloxy-1-bromo-5-ethyl-4-(3-chloro-1-propyloxy)benzene (5.09 g, 13.3 mmol) was dissolved in methyl ethyl ketone (60 mL), and solid sodium iodide (20 g, 133 mmol) was added. The reaction mixture was refluxed under an argon atmosphere for 18 hours. The reaction was cooled to room temperature, quenched with water, then extracted three times with diethyl ether. The organic extracts were combined, dried over magnesium sulfate, and filtered to give 6.27 g of a yellow oil.

A solution of ethyl 3,4-dihydro-7-hydroxy-8-propyl-2H-1-benzopyran-2-carboxylate (2.1 g, 8.1 mmol) in dimethylformamide (5 mL) was added to a suspension of sodium hydride (324 mg, 8.1 mol, 60% oil dispersion) in 10 mL of dry dimethylformamide under a nitrogen atmosphere. After stirring the reaction mixture for 30 minutes, a mixture of the alkyl iodide (3.8 g, 8.1 mmol) prepared above and 18-crown-6(110 mg, 0.4 mmol) was added. The reaction was stirred for 1.5 hours at room temperature. The reaction was quenched with water and then extracted several times with ethyl acetate. The organic material was dried over magnesium sulfate, filtered and concentrated under vacuum. The resulting product was purified by flash chromatography on silica gel eluting with 6% ethyl acetate/hexane to give 2.5 g (86.3%) of desired title product.

TLC: Rf=0.61 (20% ethyl acetate/hexane).

NMR (CDCl$_3$) ∂7.60–7.30 (m, 6), 6.85 (d, 1, J=8.50 Hz), 6.55 (s, 1), 6.46 (d, 1, J=8.50 Hz), 5.13 (s, 2), 4.75 (m, 1), 4.40–4.10 (m, 6), 2.90–2.50 (m, 6), 2.40–2.10 (m, 4), 1.60 (m, 2), 1.30 (t, 3, J= 7.40 Hz), 1.15 (t, 3, J=7.50 Hz), 0.95 (t, 3, J=7.30 Hz); IR (CHCl$_3$) 3019, 2969, 1730, 1590, 1492 cm$^{-1}$; Mass Spec. (FAB) (m/z) 611 (M$^+$).

Analysis for C$_{33}$H$_{39}$O$_6$Br: Calc: C, 64.81; H, 6.42; Br, 13.07; Found: C, 65.10; H, 6.52; Br, 12.89.

G. Preparation of ethyl 7-[3-[(2-benzyloxy-5-ethyl[1,1'-biphenyl]-4-yl)oxy]propoxy]-3,4-dihydro-8-propyl-2H-1-benzopyran-2-carboxylate.

Ethyl 7-[3-[(2-benzyloxy-1-bromo-5-ethyl-4-yl)oxy]propoxy]-3,4-dihydro-8-propyl-2H-1-benzopyran-2-carboxylate (1.3 g, 2.24 mmol) was stirred in 40 mL of benzene under an argon atmosphere. To this solution was added tetrakis(triphenylphosphine)palladium(0) (0.40 g, 0.35 mmol) and sodium bicarbonate (10 mL of a 2M aqueous solution). An ethanol solution (10 mL) of phenylboronic acid (1.3 g, 10.7 mmol) was added to the above reaction mixture, and then the reaction mixture was refluxed for 21 hours. The reaction was cooled to room temperature, quenched with a saturated aqueous ammonium chloride solution, diluted with water and then extracted with ethyl acetate. The organic layer was dried over magnesium sulfate and filtered. The filtrate was concentrated under vacuum providing 1.3 g of a brown solid. The solid was dissolved in 20% ethyl acetate/hexane and filtered through 35 g of Merck 60 silica gel eluting with 500 mL of 20% ethyl acetate/hexane. The resulting 1.0 g of yellow oil was purified by flash chromatography on silica gel eluting with 18% ethyl acetate/hexane. The desired title ester (0.875 g, 64%) was obtained as a yellow oil.

TLC: Rf=0.65 (30% ethyl acetate/hexane).

NMR (CDCl$_3$) ∂7.72 (d, 2, J=7.13 Hz), 7.46 (m, 8), 7.29 (s,1), 6.93 (d, 1, J=8.40 Hz) , 6.75 (s,1), 6.60 (d, 1, J=8.40), 5.13 (s, 2), 4.85 (m, 1), 4.31 (m, 6), 2.80 (m, 6), 2.35 (m, 4), 1.75 (m, 2), 1.39 (t, 3, J=7.10 Hz), 1.35 (t, 3, J=7.50 Hz), 1.11 (t, 3, J=7.33 Hz); IR (CHCl$_3$) 3010, 2965, 1769, 1612, 1409 cm$^{-1}$, Mass Spec (FAB) (m/z) 608 (M$^+$), 519.

Analysis for C$_{39}$H$_{44}$O$_6$: Calc: C, 76.94; H, 7.29; Found: C, 75.70; H, 7.39.

H. Preparation of ethyl 7-[3-[(5-ethyl-2-hydroxy[1,1'-biphenyl]-4-yl)oxy]propoxy]-3,4-dihydro-8-propyl-2H-1-benzopyran-2-carboxylate.

Hydrogen gas was bubbled for 15 minutes through a 10 mL ethyl acetate solution of ethyl 7-[3-[(2-benzyloxy-5-ethyl[1,1'-biphenyl]-4-yl)oxy]propoxy]-3,4-dihydro-8-propyl-2H-1-benzopyran-2-carboxylate (0.850 g, 1.4 mmol) containing 0.14 g of 10% Pd/C catalyst. A hydrogen atmosphere was maintained over the reaction mixture, and the reaction was stirred for 4 days. The reaction was filtered through a Celite® pad in a sintered glass funnel and the catalyst was washed with ethyl acetate. The solvent was removed from the filtrate providing a clear oil. The oil was purified by flash chromatography on silica gel eluting with 20% ethyl acetate/hexane. The desired title phenol (0.354 g, 49%) was obtained as a clear oil.

TLC: Rf=0.32 (30% ethyl acetate/hexane).

NMR (CDCl$_3$) $\partial$7.51 (d, 4, J=4.43 Hz), 7.40 (m, 1), 7.08 (s, 1), 6.86 (d, 1, J=8.26 Hz), 6.60 (s, 1), 6.54 (d, 1, J=8.29 Hz), 5.41 (s, 1), 4.80 (m, 1), 4.26 (m, 6), 2.73 (m, 6), 2.30 (m, 4), 1.65 (m, 2), 1.33 (t, 3, J=6.94 Hz), 1.26 (t, 3, J=7.39 Hz), 1.02 (t, 3, J= 7.33 Hz); IR (CHCl$_3$) 3026, 2967, 1749, 1612, 1488 cm$^{-1}$; Mass Spec. (FAB) (m/z) 519 (M$^+$+1), 518 (M$^+$), 305.

Analysis for C$_{32}$H$_{38}$O$_6$: Calc: C, 74.11; H, 7.39; Found: C, 72.40; H, 7.14.

I. Preparation of 7-[3-[(5-ethyl-2-hydroxy[1,1' -biphenyl]-4-yl)oxy]propoxy]-3,4-dihydro-8-propyl-2H-1 -benzopyran-2-carboxylic acid.

A solution of ethyl 7-[3-[(5-ethyl-2-hydroxy[1,1' -biphenyl]-4-yl)oxy]propoxy]-3,4-dihydro-8-propyl-2H-1 -benzopyran-2-carboxylate (0.367 g, 0.71 mmol) in 4 mL of dioxane was treated with 1.10 mL of 2N sodium hydroxide solution and stirred at room temperature. After 1.25 hours at room temperature, the dioxane was removed under vacuum and the remaining aqueous solution was diluted with water an acidified to pH 1 with 5N hydrochloric acid. The resulting suspension was extracted with ethyl acetate. The organic extract was dried over magnesium sulfate and filtered. The resulting white solid was recrystallized from toluene/hexane. The title acid was obtained as a white crystalline solid (0.245 g, 71%).

TLC: Rf=0.25 (10% methanol/methylene chloride, streak).

NMR (CDCl$_3$) $\partial$7.45 (m, 6), 7.02 (s,1), 6.86 (d, 1, J=8.57 Hz), 6.56 (s, 1), 6.53 (d, 1, J=8.28 Hz), 5.30 (br s, 1), 4.78 (dd, 1, J= 3.70, 7.50 Hz), 4.20 (t, 2, J=6.02 Hz), 4.18 (t, 2, J=6.04 Hz), 2.69 (m, 8), 2.26 (m, 6), 1.55 .(m, 2), 1.19 (t, 3, J=7.48 Hz), 0.96 (t, 3, J=7.31 Hz); IR (KBr) 3426, 2959, 2870, 1718, 1615 cm$^{-1}$; Mass Spec (FAB) (m/z) 491 (M$^+$+ 1), 490 (M$^+$), 277.

Analysis for C$_{30}$H$_{34}$O$_6$: Calc: C, 73.45; H, 6.99; Found: C, 73.53; H, 6.82.

EXAMPLE 55

8-Propyl-7-[3-[4-(4-fluorophenyl)-2-ethyl-5 -hydroxyphenoxy]propoxy]-3,4-dihydro-2H-1-benzopyran-2 -carboxylic acid A. Preparation of ethyl 8-propyl-7-[3-[2-ethyl-4-(4 -fluorophenyl)-5-benzyloxyphenoxy]propoxy]-3,4-dihydro-2H-1 -benzopyran-2-carboxylate.

Tetrakis(triphenylphosphine)palladium(0) (0.659 g, 0.6 mmol) and aqueous sodium carbonate solution (20 mL of a 2M solution) were added to a 30 mL benzene solution of ethyl 7-[3 -[(2-benzyloxy-1-bromo-5-ethyl-4-yl)oxy]propoxy]-3,4-dihydro-b 8-propyl-2H-1-benzopyran-2-carboxylate (2.163 g, 3.5 mmol) under an argon atmosphere. The reaction was refluxed for 17 hours, then cooled to room temperature and extracted with ethyl acetate. The organic extract was dried over magnesium sulfate, filtered and the solvent removed under vacuum. The crude product was purified by Waters Prep 500 silica gel chromatography eluting with a gradient of 5% to 20% ethyl acetate/hexane over 50 minutes. The desired title biphenyl was obtained as a clear oil (1.722 g, 78%).

NMR (CDCl$_3$) $\partial$7.51 (m, 2), 7.32 (m, 5), 7.09 (m, 3), 6.83 (d, 1, J= 8.32 Hz), 6.62 (s, 1), 6.49 (d, 1, J=8.50 Hz), 5.02 (s, 2), 4.75 (dd, 1, J=4.10, 6.50 Hz), 4.22 (m, 6), 2.69 (m, 6), 2.25 (m, 4), 1.59 (m, 2), 1.30 (t, 3, J=7.10 Hz), 1.21 (t, 3, J=7.42 Hz), 0.96 (t, 3, J=7.33 Hz); IR (CHCl$_3$) 3019, 2968, 1745, 1611, 1495 cm$^{-1}$; Mass Spec. (FAB) (m/z) 627 (M$^+$+1), 626 (M$^+$), 536.

Analysis for C$_{39}$H$_{43}$O$_6$: Calc: C, 74.74; H, 6.91; F, 3.03; Found: C, 74.98; H, 7.05; F, 3.39.

B. Preparation of ethyl 8-propyl-7-[3-[4-(4 -fluorophenyl)-2-ethyl-5-hydroxyphenoxy]propoxy]-3,4-dihydro- 2H-1-benzopyran-2-carboxylate.

Hydrogen gas was bubbled for 10 minutes through a solution of ethyl 8-propyl-7-[3-[2-ethyl-4-(4-fluorophenyl)-5 -benzyloxy-phenoxy]propoxy]-3,4-dihydro-2H-1-benzopyran-2 -carboxylate (1.610 g, 2.57 mmol) in 30 mL of ethyl acetate containing 1.0 g of 10% Pd/C catalyst. The reaction was stirred at room temperature under an atmosphere of hydrogen for 2 hours. The reaction mixture was filtered through a Celite® pad in a sintered glass funnel and the catalyst was washed with ethyl acetate. The solvent was-removed from the filtrate providing 1.242 g of a clear oil. The oil was purified by flash chromatography on Merck silica gel eluting with 20% ethyl acetate/hexane. The desired title phenol was obtained in 74% yield (1.020 g) as a white solid.

TLC: Rf=0.35 (30% ethyl acetate/hexane).

NMR (CDCl$_3$) $\partial$7.43 (m, 2), 7.16 (dd, 2, J=5.97, 5.97 Hz), 6.98 (s,1), 6.82 (d, 1, J=8.44 Hz), 6.53 (s, 1), 6.46 (d, 1, J=9.43 Hz), 5.07 (s, 1), 4.76 (m, 1), 4.21 (m, 6), 2.67 (m, 6), 2.26 (m, 4), 1.58 (m, 2), 1.29 (t, 3, J=6.96 Hz), 1.91 (t, 3, J=7.35 Hz), 0.96 (t, 3, J=7.27 Hz); IR (KBr) 3434, 2962, 2869, 1738, 1614, 1588, 1502 cm$^{-1}$; Mass Spec (FAB) (m/z) 537 (M$^+$+1), 536 (M$^+$).

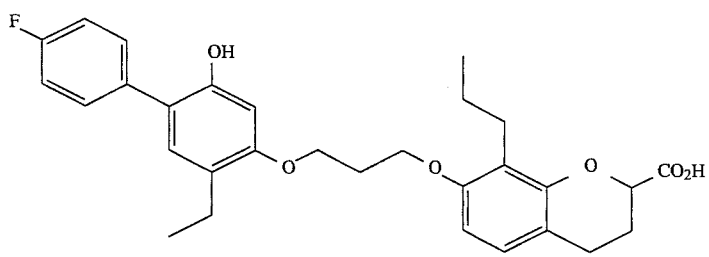

Analysis for C$_{32}$H$_{37}$O$_6$: Calc: C, 71.62; H, 6.95; Found: C, 71.63; H, 7.06.

67

C. Preparation of 8-propyl-7-[3-[4-(4-fluorophenyl)-2-ethyl-5-hydroxyphenoxy]propoxy]-3,4-dihydro-2H-1-benzopyran-2-carboxylic acid.

A dioxane (12 mL) solution of ethyl 8-propyl-7-[3-[4-(4-fluorophenyl)-2-ethyl-5-hydroxyphenoxy]propoxy]-3,4-dihydro-2H-1-benzopyran-2-carboxylate (0.968 g, 1.8 mmol) was treated with sodium hydroxide (2.71 mL of a 2N solution) and stirred at room temperature. After 2.5 hours at room temperature, the dioxane was removed from the reaction mixture and the remaining material was diluted with water and acidified to pH 1 with 5N hydrochloric acid. The resulting white milky suspension was then stirred with ethyl acetate and subsequently extracted with ethyl acetate. The organic extract was dried over magnesium sulfate, filtered and the solvent removed to give a white solid (1.098 g). The solid was recrystallized from ethyl acetate/hexane to give the title acid as white needle-like crystals (0.568 g, 62%).

TLC: Rf=0.31 (10% methanol/methylene chloride).

NMR (CDCl$_3$) ∂7.42 (m, 2), 7.15 (dd, 2, J=8.68), 6.98 (s, 1), 6.85 (d, 1, J=8.30 Hz), 6.53 (s, 1), 6.52 (d, 1, J=6.98 Hz), 4.77 (dd, 1, J=3.63, 7.43 Hz), 4.18 (m, 4), 2.70 (m, 6), 2.27 (m, 4), 1.56 (m, 2), 1.19 (t, 3, J=7.42 Hz), 0.95 (t, 3, J=7.30 Hz); IR (KBr) 3421, 2959, 2871, 1706, 1 615, 1500 cm$^{-1}$; Mass Spec (FAB) (m/z) 509 (M$^+$+1), 508 (M$^+$).

Analysis for C$_{30}$H$_{33}$O$_6$: Calc: C, 70.78; H, 6.54; Found: C, 70.05; H, 6.82.

68

EXAMPLE 56

2-[3-[3-[(5-Ethyl-2-hydroxy[1,1'-biphenyl]-4-yl)oxy]propoxy]-2-propylphenoxy]propanoic acid

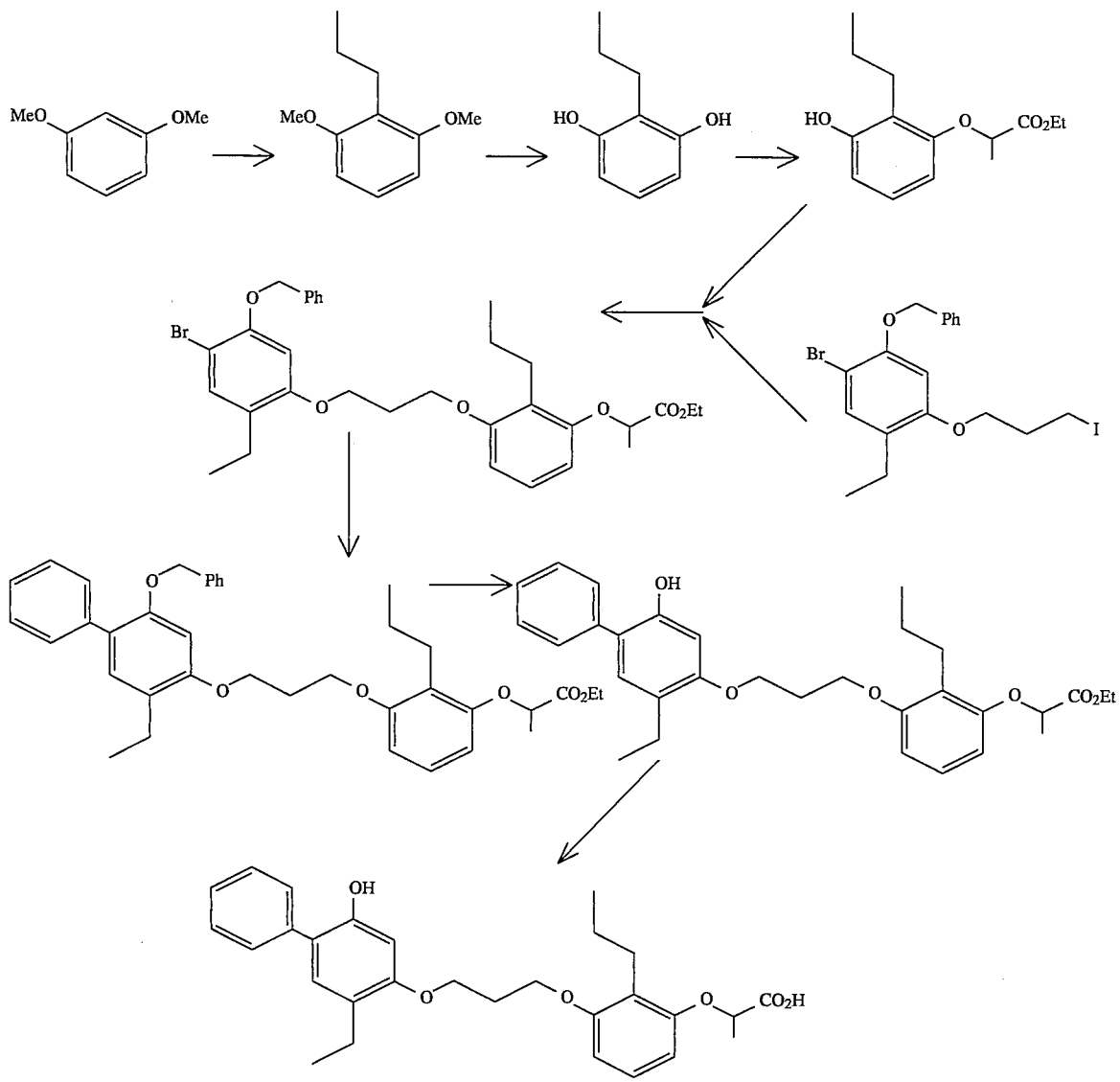

A. Preparation of 2-propyl-1,3-dimethoxybenzene.

1,3-Dimethoxybenzene (20 g, 145 mmol) in 200 mL of dry tetrahydrofuran was cooled to −10° C. To this solution at −10° C. was added n-butyllithium (100 mL of a 1.6M solution in hexane, 160 mmol) over 20 minutes. The reaction was then stirred for 2.5 hours at 0° C. At 0° C., propyl iodide (24.65 g, 145 mmol) was added slowly over 15 minutes. When the addition was complete, the reaction was allowed to warm to room temperature and stirred overnight. After stirring overnight, the reaction was refluxed for 1.5 hours, then cooled to room temperature and quenched with ice. The tetrahydrofuran was removed under vacuum, and the resulting aqueous layer was extracted several times with diethyl ether. The organic extract was dried over magnesium sulfate and filtered to give a clear oil after solvent removal (26.11 g). The oil was purified by vacuum distillation to provide the title intermediate (24.0 g, 92%).

Bp 80°–82° C. at 10 mm Hg.

NMR (CDCl$_3$) ∂7.16 (t,1, J=8.30 Hz), 6.58 (d, 2, J=8.30 Hz), 3.85 (s, 6), 2.67 (t, 2, J=7.57 Hz), 1.56 (m, 2), 0.99 (t, 3, J=7.35 Hz).

B. Preparation of 2-propyl-1,3-dihydroxybenzene.

A mixture of solid 1,3-dimethoxy-2-propylbenzene (33.70 g, 190 mmol) and solid pyridine hydrochloride (150 g, 1.30 mol) was warmed to 180° C. After 7.5 hours the reaction was cooled to 110° C. and 50 mL of water was added slowly. After the reaction cooled to room temperature, it was diluted with 100 mL of water and extracted several times with ethyl acetate. The ethyl acetate extract was washed once with 2N hydrochloric acid and then dried over magnesium sulfate. Filtration and solvent removal gave 38.5 g of an orange solid. The title product was purified by recrystallization from dichloromethane providing 11.86 g (41%) of yellow crystals.

NMR (CDCl$_3$) ∂6.94 (t, 1, J=8.10 Hz), 6.40 (d, 2, J=8.10 Hz), 4.84 (s, 2), 2.63 (t, 2, J=7.57 Hz), 1.62 (m, 2), 1.01 (t, 3, J= 7.33 Hz).

C. Preparation of ethyl 2-(2-propyl-3-hydroxyphenoxy)propanoate.

Sodium hydride (1.08 g of a 60% oil dispersion, 27 mmol) under an argon atmosphere was washed with 15 mL of dry hexane. The hexane supernatant was removed via syringe. Dry tetrahydrofuran (60 mL) was added to the sodium hydride and, with stirring at room temperature, the 2-propyl-1,3-dihydroxybenzene (4.08 g, 27 mmol) was added as a 40 mL tetrahydrofuran solution. After stirring at room temperature for 25 minutes, the ethyl 2-bromopropionate (4.64 g, 26 mmol) was added rapidly. After stirring at room temperature for 17 hours, the reaction was quenched with a saturated aqueous ammonium chloride solution and the tetrahydrofuran was removed under vacuum. The resulting aqueous mixture was extracted several times with ethyl acetate. The organic extract was dried over magnesium sulfate. Filtration and solvent removal gave an orange oil. This oil was purified by flash chromatography on Merck silica gel eluting with 20% ethyl acetate/hexane. The desired title ester was obtained as a white solid (2.43 g, 36%).

TLC: Rf=0.47 (30% ethyl acetate/hexane).

NMR (CDCl$_3$) ∂6.93 (dd, 1, J=8.00 Hz), 6.45 (d, 1, J=8.00 Hz), 6.30 (d, 1, J=8.00 Hz), 5.77 (s, 1), 4.76 (q, 1, J=6.76 Hz), 4.23 (q, 2, J=7.02 Hz), 2.69 (m, 2), 1.63 (d, 3, J=6.70 Hz), 1.60 (m, 2), 1.28 (t, 3, J=7.50 Hz), 0.99 (t, 3, J=7.50 Hz); IR (KBr) 3435, 2955, 2872, 1733, 1600, 1500, 1465 cm$^{-1}$; Mass Spec. (FD) (m/z) 253 (M$^+$+1).

Analysis for C$_{14}$H$_{20}$O$_4$: Calc: C, 66.65; H, 7.99; Found: C, 66.41; H, 8.04.

D. Preparation of ethyl 2-[3-[3-[(2-benzyloxy-1-bromo-5-ethyl-4-yl)oxy]propoxy]-2-propylphenoxy]propanoate.

The title compound was prepared using ethyl 2-(2-propyl-3-hydroxyphenoxy)propanoate as described for Example 54(F). The title intermediate was obtained in 68% yield (2.90 g) as a clear oil.

TLC: Rf=0.47 (30% ethyl acetate/hexane).

NMR (CDCl$_3$) ∂7.56–7.37 (m, 6), 7.12 (t, 1, J=8.20 Hz), 6.62 (d, 1, J=8.35 Hz), 6.59 (s, 1), 6.45 (d, 1, J=8.31 Hz), 5.16 (s, 2), 4.80 (q, 1, J=6.90 Hz), 4.26 (q, 2, J=7.20 Hz), 4.18 (dd, 4, J= 5.91, 12.02 Hz), 2.80 (m, 2), 2.62 (q, 2, J=7.47 Hz), 2.31 (m, 2), 1.69 (m, 2, J=6.70 Hz), 1.65 (m, 2), 1.30 (t, 3, J=7.20 Hz), 1.22 (t, 3, J=7.54 Hz), 1.03 (t, 3, J=7.35 Hz); IR (CHCl$_3$) 3015, 2967, 2930, 2780, 1752, 1595, 1500, 1464 cm$^{-1}$; Mass Spec. (FAB) (m/z) 599 (M$^+$).

Analysis for C$_{32}$H$_{39}$O$_6$Br: Calc: C, 64.11; H, 6.56; Br, 13.33; Found: C, 64.01; H, 6.56; Br, 13.06.

E. Preparation of ethyl 2-[3-[3-[(2-benzyloxy-5-ethyl[1,1'-biphenyl]-4-yl)oxy]propoxy]-2-propylphenoxy]propanoate.

Prepared from ethyl 2-[3-[3-[(2-benzyloxy-1-bromo-5-ethyl-4-yl)oxy]propoxy]-2-propylphenoxy]propanoate as described for Example 54(G). The title intermediate was obtained in 47% yield as a clear oil.

TLC: Rf=0.48 (30%. ethyl acetate/hexane).

NMR (CDCl$_3$) ∂7.10 (d, 2, J=8.06 Hz), 7.44 (m, 8), 7.27 (s, 1), 7.15 (t, 1, J=8.14 Hz), 6.72 (s, 1), 6.66 (d, 1, J=8.27 Hz), 6.48 (d, 1, J= 8.27 Hz), 5.11 (s, 2), 4.83 (q, 1, J=6.71 Hz), 4.28 (m, 6), 2.78 (m, 4), 2.38 (m, 2), 1.72 (d, 3, J=6.96 Hz), 1.69 (m, 2), 1.32 (t, 3, J=7.29 Hz), 1.31 (t, 3, J=7.30 Hz), 1.08 (t, 3, J=7.36 Hz); IR (CHCl$_3$) 3015, 2966, 2930, 2880, 1750, 1594, 1488, 1464 cm$^{-1}$; Mass Spec. (FAB) (m/z) 597 (M$^+$+1), 596 (M$^+$).

Analysis for C$_{38}$H$_{44}$O$_6$: Calc: C, 76.48; H, 7.43; Found: C, 76.42; H, 7.52.

F. Preparation of ethyl 2-[3-[3-[(5-ethyl-2-hydroxy[1,1'-biphenyl]-4-yl)oxy]propoxy]-2-propylphenoxy] propanoate.

Prepared from ethyl 2-[3-[3-[(2-benzyloxy-5-ethyl[1,1'-biphenyl]-4-yl)oxy]propoxy]-2-propylphenoxy]propanoate as described for Example 54(H). The title intermediate was obtained in 53% yield as a clear oil.

TLC: Rf=0.36 (30% ethyl acetate/hexane).

NMR (CDCl$_3$) ∂7.43 (m, 5), 7.06 (d, 1, J=8.84 Hz), 6.56 (s, 1), 6.37 (d, 1, J=8.28 Hz), 5.20 (s, 1), 4.74 (q, 1, J=6.73 Hz), 4.20 (m, 6), 2.71 (m, 2), 2.61 (q, 2, J=7.58 Hz), 2.33 (t, 2, J=6.05 Hz), 1.61 (d, 3, J=6.94 Hz), 1.58 (m, 2), 1.25 (t, 3, J=7.30 Hz), 1.19 (t, 3, J=7.40 Hz), 0.96 (t, 3, J=7.35 Hz); IR (CHCl$_3$) 3558, 3029, 3011, 2964, 2935, 2873, 1745, 1625, 1593, 1488, 1464 cm$^{-1}$; Mass Spec. (FAB) (m/z) 507 (M$^+$+1), 506 (M$^+$).

Analysis for C$_{31}$H$_{38}$O$_6$: Calc: C, 73.49; H, 7.56; Found: C, 73.70; H, 7.67.

G. Preparation of 2-[3-[3-[(5-ethyl-2-hydroxy[1,1'-biphenyl]-4-yl)oxy]propoxy]-2-propylphenoxy]propanoic acid.

Prepared from ethyl 2-[3-[3-[(5-ethyl-2-hydroxy[1,1'-biphenyl]-4-yl)oxy]propoxy]-2-propylphenoxy]propanoate as described for Example 54(I). The title product was crystallized from toluene/hexane and obtained as white tufts (0.582 g, 80%).

TLC: Rf=0.21 (10% methanol/methylene chloride).

NMR (CDCl$_3$) ∂7.45 (m, 5), 7.09 (t, 1, J=8.16 Hz), 7.03 (s, 1), 6.60 (d, 1, J=8.28 Hz), 6.56 (s, 1), 6.42 (d, 1, J=8.29 Hz), 4.79 (q, 1, J=7.00 Hz), 4.20 (m, 4), 2.70 (m, 2), 2.62 (q, 2, J=7.49 Hz), 2.33 (t, 2, J=6.00 Hz), 1.67 (d, 3, J=6.93 Hz), 1.56 (m, 2), 1.20 (t, 3, J=7.39 Hz), 0.96 (t, 3, J=7.30 Hz); IR (KBr) 3381, 2964, 2871, 1707, 1615, 1594, 1490, 1461 cm$^{-1}$; Mass Spec. (FAB) (m/z) 479 (M$^+$+1), 478 (M$^+$).

Analysis for C$_{29}$H$_{34}$O$_6$: Calc: C, 72.78; H, 7.16; Found: C, 73.39; H, 7.29.

EXAMPLE 57

2-(4-Chlorophenyl)-4-ethyl-5-[6-methyl-6-(2H-tetrazol-5-yl)heptyloxy]phenol monosodium salt

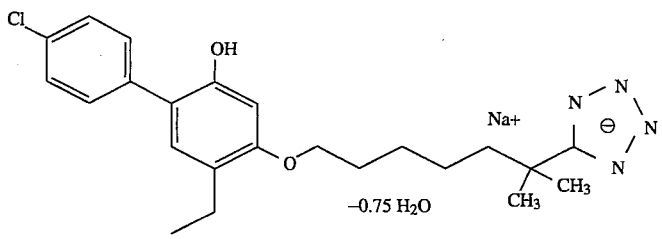

A. Preparation of 1-benzyloxy-2-(4-chlorophenyl)-4 -ethyl-5-[6-methyl-6-cyanoheptyloxy]benzene.

The title intermediate was prepared from 1-benzyloxy-2-bromo-4-ethyl-5-[6-methyl-6-cyanoheptyloxy]benzene and 4 -chlorophenyl boronic acid via the biaryl coupling procedure Method A (Preparation 73(E)). The title intermediate was obtained as a white solid in 67% yield.

TLC Rf=0.51 (30% ethyl acetate/hexane).

NMR (CDCl$_3$) ∂7.52 (d, 2, J=8.95 Hz), 7.32 (m, 7), 7.12 (s, 1), 6.75 (s, 1), 5.05 (s, 2), 3.98 (t, 2, J=6.15 Hz), 2.63 (q, 2, J=7.54 Hz), 1.85 (m, 2), 1.58 (br s, 6), 1.38 (s, 6), 1.22 (t, 3, J=7.49 Hz); IR (KBr)2973, 2937, 2858, 2235, 1609, 1580, 1561, 1518, 1498 cm$^{-1}$; Mass Spec (FD) (m/z) 476 (M$^+$+1).

Analysis for C$_{30}$H$_{34}$NO$_2$Cl: Calc: C, 75.69; H, 7.20; N, 2.94; Cl, 7.45; Found: C, 75.95; H, 7.29; N, 2.78; Cl, 7.68.

B. Preparation of 2-(4-chlorophenyl)-4-ethyl-5-[6 -methyl-6-cyanoheptyloxy]phenol.

Prepared in 97% yield from 1-benzyloxy-2-(4-chlorophenyl)- 4-ethyl-5-[6-methyl-6-cyanoheptyl]oxybenzene via catalytic hydrogenation as described in Example 54(H). White solid.

TLC Rf=0.33 (30% ethyl acetate/hexane).

NMR (CDCl$_3$) ∂7.43 (m, 4), 7.00 (s, 1), 6.50 (s, 1), 5.11 (s, 1), 3.99 (t, 2, J=6.22 Hz), 2.62 (q, 2, J=7.45 Hz), 1.87 (t, 2, J=6.64 Hz), 1.63 (br s, 6), 1.38 (s, 6), 1.20 (t, 3, J=7.63 Hz); IR (KBr) 3400, 2940, 2860, 2237, 1618, 1514, 1489, 1468 cm$^{-1}$; Mass Spec (FD) (m/z) 385 (M$^+$), 350.

Analysis for C$_{23}$H$_{28}$NO$_2$Cl: Calc: C, 71.58; H, 7.31; N, 3.63; Cl, 9.19; Found: C, 71.73; H, 7.55; N, 3.87; Cl, 9.11.

C. Preparation of 2-(4-chlorophenyl)-4-ethyl-5-[6 -methyl-6-(2H-tetrazol-5-yl)heptyloxy]phenol monosodium salt.

The title product was prepared in 38% yield from 2-(4 -chlorophenyl)-4-ethyl-5-[6-methyl-6-cyanoheptyloxy]phenol via the procedure of Examples 42–49 and obtained as a white lyophilate.

TLC Rf=0.26 (10% methanol/methylene chloride).

NMR (DMSO-d6) ∂7.57 (d, 2, J=8.53 Hz), 7.37 (d, 2, J=8.38 Hz), 6.98 (s, 1), 6.67 (s, 1), 3.82 (t, 2, J=6.5 Hz), 1.20 (m, 5), 1.24 (s, 6), 1.07 (t, 3, J=7.42 Hz); IR (KBr) 3300 (br), 2936, 1616, 1489 cm$^{-1}$; Mass Spec (FAB) (m/z) 473 (M$^+$+ 1+2Na), 451 (M$^+$+1+Na).

Analysis for C$_{23}$H$_{28}$N$_4$O$_2$ClNa.0.75 H$_2$O: Calc: C, 59.42; H, 6.40; N, 12.06; Cl, 7.53; Found: C, 59.57; H, 6.43; N, 11.89; Cl, 7.08.

EXAMPLE 58

2-(3,5-Dichlorophenyl)-4-ethyl-5-[6-methyl-6-(2H-tetrazol-5 -yl)heptyloxy]phenol monosodium salt

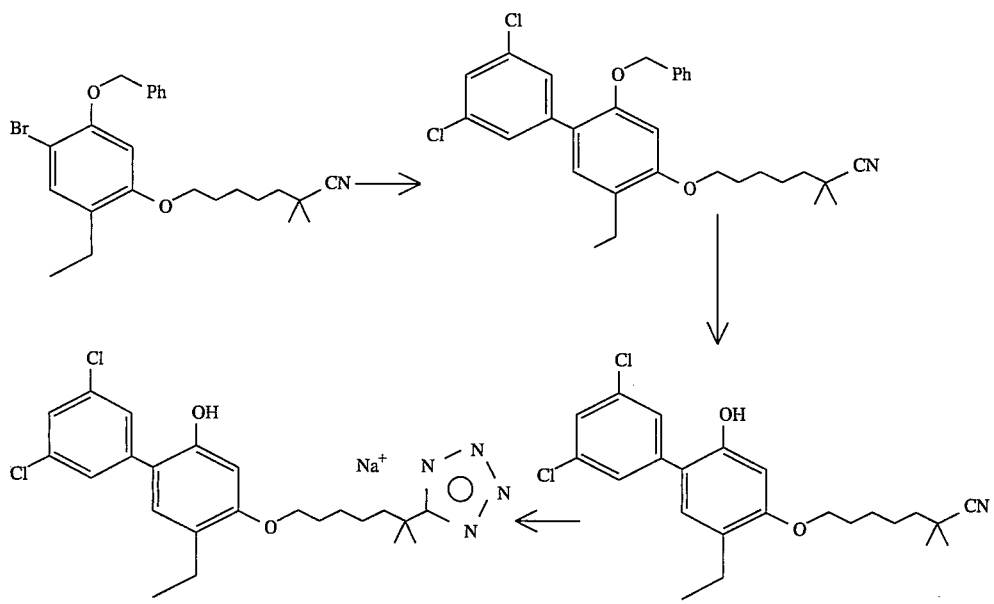

A. Preparation of 1-benzyloxy-2-(3,5-dichlorophenyl)-4-ethyl-5-[6-methyl-6-cyanoheptyloxy]benzene.

The title dichlorobiphenyl was prepared from 1-benzyloxy- 2-bromo-4-ethyl-5-[6-methyl-6-cyanoheptyloxy]benzene and 3,5-dichlorophenyl boronic acid via the biaryl coupling procedure Method A. The title product was obtained as a white solid in 54% yield.

TLC Rf=0.47 (30% ethyl acetate/hexane).

NMR (CDCl₃) ∂7.55 (d, 2, J=2.14 Hz), 7.37 (m, 6), 7.17 (s, 1), 6.63 (s, 1), 5.13 (s, 2), 4.04 (t, 2, J=6.22 Hz), 2.70 (q, 2, J=7.54 Hz), 1.90 (m, 2), 1.63 (m, 4), 1.42 (s, 6), 1.29 (t, 3, J=7.44 Hz); IR (KBr)2972, 2941, 2859, 2233, 1612, 1583, 1558, 1506, 1484, 1387 cm⁻¹; Mass Spec. (FD) (m/z) 510 (M⁺+1).

Analysis for $C_{30}H_{33}NO_2Cl_2$: Calc: C, 70.58; H, 6.52; N, 2.74; Cl, 13.89; Found: C, 70.58; H, 6.60; N, 2.58; Cl, 13.54.

B. Preparation of 2-(3,5-dichlorophenyl)-4-ethyl-5-[6-methyl-6-cyanoheptyloxy]phenol.

The title phenol was prepared in 72% yield from 1-benzyloxy-2-(3,5-dichlorophenyl)-4-ethyl-5-[6-methyl-6-cyanoheptyloxy]-benzene via catalytic hydrogenation as described in Example 54(H). White solid.

TLC Rf=0.37 (30% ethyl acetate/hexane).

NMR (CDCl₃) ∂7.36 (d, 2, J=1.3 Hz), 7.31 (s, 1), 6.97 (s, 1), 6.45 (s, 1), 5.11 (s, 1), 3.97 (t, 2, J=6.26 Hz), 2.58 (q, 2, J=7.49 Hz), 1.85 (m, 2), 1.56 (m, 6), 1.35 (s, 6), 1.17 (t, 3, J=7.49 Hz); IR (KBr) 3360, 2977, 2940, 2856, 2247, 161 7, 1582, 1554, 1516, 1468 cm⁻¹; Mass Spec. (FD) (m/z) 419 (M⁺).

Analysis for $C_{23}H_{27}NO_2Cl_2$: Calc: C, 65.71; H, 6.47; N, 3.33; Cl, 16.88; Found: C, 65.58; H, 6.44; N, 3.15; Cl, 17.05.

C. Preparation of 2-(3,5-dichlorophenyl)-4-ethyl-5-[6-methyl-6-(2H-tetrazol-5-yl)heptyloxy]phenol monosodium salt.

The title product was prepared in 13% yield from 2-(3,5-dichlorophenyl)-4-ethyl-5-[6-methyl-6-cyanoheptyl)oxyphenol via the procedure of Examples 42–49 and obtained as a white lyophilate.

TLC Rf=0.26 (10% methanol/methylene chloride).

NMR (d⁶-DMSO) ∂7.61 (d, 2, J=1.96 Hz), 7.39 (m, 1), 7.06 (s, 1), 6.66 (s, 1), 3.82 (m, 2), 3.38 (br s, 1), 2.44 (q, 2, J=7.48 Hz), 1.59 (m, 3), 1.26 (m, 6), 1.24 (s, 6), 1.06 (t, 3, J=7.46 Hz); IR (KBr) 3408, 2936, 161 7, 1585, 1557, 151 2, 1376 cm⁻¹; Mass Spec. (FAB) (m/z) 485 (M⁺+1+Na), 463 (M⁺).

Analysis for $C_{23}H_{27}N_4O_2Cl_2Na$: Calc: C, 56.91; H, 5.61; N, 11.54; Cl, 14.61; Found: C, 56.80; H, 5.73; N, 11.39; Cl, 14.37.

EXAMPLE 59

3-[2-[3-[(5-Ethyl-2-hydroxy[1,1'-biphenyl]-4-yl)oxy]propoxy]-1-dibenzofuran]propanoic acid disodium salt

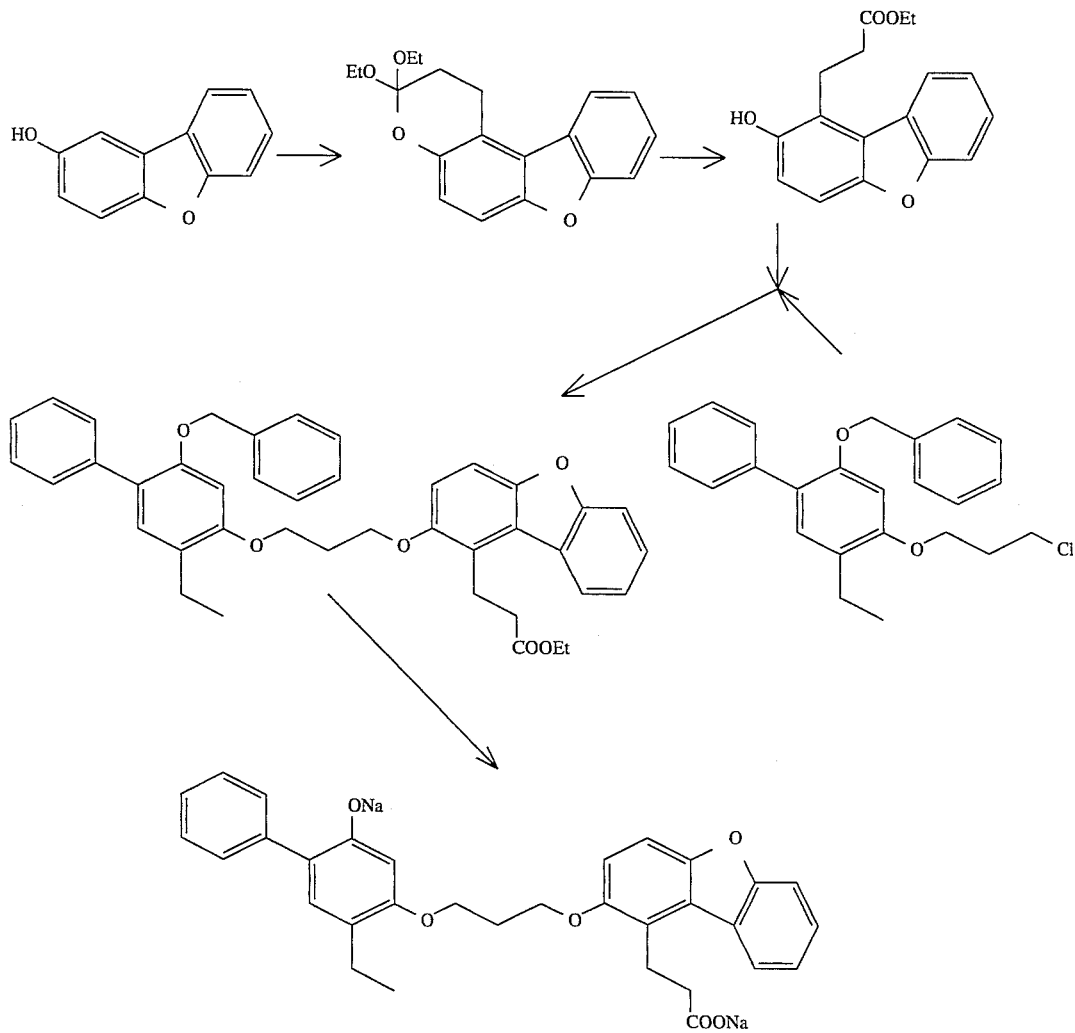

A. Preparation of 3,3-diethoxy-2,3-dihydro-1H-benzofuro-[3,2-f][1]benzopyran.

A solution of 2-hydroxydibenzofuran (5.00 g, 27.2 mmol), triethylorthoacrylate (10.1 g, 54.3 mmol) and pivalic acid (1.39 g, 13.6 mmol) in toluene (100 mL) was refluxed for 18 hours. The mixture was cooled to room temperature and washed once with water and once with a saturated sodium bicarbonate solution, dried over sodium sulfate, filtered and concentrated in vacuo to provide an orange oil. This material was diluted with hexane and maintained at −20° C. for 18 hours. The resulting crystals were collected via vacuum filtration to provide 5.67 g (67%) of the desired title intermediate, mp 64° C.; NMR (CDCl$_3$) 7.96 (d, J=7.8 Hz, 1H), 7.57 (d, J=8.0 Hz, 1H), 7.46 (t, J=8 Hz, 1H), 7.35 (m, 2H), 7.06 (d, J=8.8 Hz, 1H), 3.82 (q, J=7.2 Hz, 2H), 3.73 (q, J=6.8 Hz, 2H), 3.35 (t, J=6.9 Hz, 2H), 2.29 (t, J=7.0 Hz, 2H), 1.23 (t, J=7.1 Hz, 6H); MS-FD m/e 312 (p); IR (CHCl$_3$, cm$^{-1}$) 2982, 1494, 1476, 1451, 1434, 1251, 1090, 1054, 975.

Analysis for $C_{19}H_{20}O_4$: Calc: C, 73.06; H, 6.45; Found: C, 72.81; H, 6.72.

B. Preparation of 3-[1-(2-hydroxydibenzofuran)]propanoic acid ethyl ester.

A mixture of 3,3-diethoxy-2,3-dihydro-1H-benzofuro-[3,2-f][1]benzopyran (3.50 g, 11.2 mmol) and 10% aqueous hydrochloric acid (5 mL) in ethyl acetate (30 mL) was stirred at room temperature for 1 hour. The resulting mixture was washed once with water, dried over sodium sulfate, filtered and concentrated in vacuo to provide a tan solid. Recrystallization from hexane/ethyl acetate provided 3.11 g (98%) of the desired title intermediate as an off-white crystalline material: mp 128°–131° C.; NMR (CDCl$_3$) 7.88 (d, J=7.7 Hz, 1H), 7.59 (d, J=8.4 Hz, 1H), 7.47 (t, J=7.2 Hz, 1H), 7.37 (d, J=8.9 Hz, 1H), 7.36 (t, J= 6.6 Hz, 1H), 7.13 (d, J=8.8 Hz, 1 H), 7.13 (q, J=8.8 Hz, 1H), 3.43 (t, J=5.8 Hz, 2H), 3.01 (t, J=7.7 Hz, 2H), 1.23 (t, J=7.2 Hz, 3H); MS-FD m/e 284 (100, p), 256 (65), 238 (17); IR (KBr, cm$^{-1}$) 2985 (b), 1701, 1430, 1226, 1183, 1080.

Analysis for $C_{17}H_{16}O_4$: Calc: C, 71.82; H, 5.67; Found: C, 71.90; H, 5.43.

C. Preparation of 3-[2-[3-[[5-ethyl-2-(phenylmethoxy)[1,1'-biphenyl]-4-yl]oxy]propoxy]-1-dibenzofuran]propanoic acid ethyl ester.

3-[1-(2-Hydroxydibenzofuran)]propanoic acid ethyl ester (625 mg, 2.20 mmol) was dissolved in dimethylformamide (10 mL) and carefully treated at room temperature with 95% sodium hydride (58 mg, 2.4 mmol). When gas evolution had ceased, 2-benzyloxy-1-phenyl-5-ethyl-4-(3-chloro-1-propyloxy)benzene (836 mg, 2.20 mmol) was added and the resulting mixture was stirred for 18 hours. The mixture was diluted with ether and washed once with water. The organic layer was dried over sodium sulfate, filtered, and concentrated in vacuo to provide a dark oil. Silica gel chromatography (ethyl acetate/hexane) provided 200 mg (14%) of the desired titled intermediate as a colorless oil: NMR (CDCl$_3$) 8.11 (d, J=7.7 Hz, 1H), 7.57 (m, 3H), 7.48 (t, J=7.3 Hz, 1H), 7.20–7.44 (m, 10 H), 7.17 (s, 1H), 7.08 (d, J=8.9 Hz, 1H), 6.67 (s, 1H), 5.05 (s, 2H), 4.29 (t, J=6.2 Hz, 2H), 4.26 (t, J=6.1 Hz, 2H), 4.15 (q, J=7.2 Hz, 2H), 3.54 (t, J=8.5 Hz, 2H), 2.67 (m, 4H), 2.37 (t, J=6.0 Hz, 2H), 1.21 (m, 6H).

D. Preparation of 3-[2-[3-[(5-ethyl-2-hydroxy[1,1'-biphenyl]-4-yl)oxy]propoxy]-1-dibenzofuran]propanoic acid disodium salt.

To a nitrogen-purged solution of 3-[2-[3-[[5-ethyl-2-(phenylmethoxy)[1,1'-biphenyl]-4-yl]oxy]propoxy]-1-dibenzofuran]propanoic acid ethyl ester (200 mg, 0.318 mmol) in a 1:1 mixture of methanol/tetrahydrofuran (40 mL) was added 10% palladium on carbon (25 mg). The resulting suspension was hydrogenated at 1 atm pressure for 24 hours at room temperature. The mixture was filtered through a short pad of Florisil® and the filtrate concentrated in vacuo. The residue was dissolved in a 1:1 mixture of methanol/tetrahydrofuran (20 mL) and treated with 5N sodium hydroxide solution (2 mL) at room temperature for 24 hours. The resulting mixture was extracted once with diethyl ether. The aqueous layer was acidified with 5N hydrochloric acid solution and extracted twice with methylene chloride. The combined methylene chloride fractions were concentrated in vacuo. The residue was dissolved in a minimum of 1N sodium hydroxide solution and purified on HP-20 resin to provide 53 mg (30%) of the desired title product as a fluffy white solid: NMR (DMSO-d$_6$) 8.12 (d, J=6.9 Hz, 1H), 7.64 (d, J=8.2 Hz, 1H), 7.37–7.57 (m, 5H), 7.30 (m, 2H), 7.14 (m, 2H), 6.96 (s, 1H), 6.93 (s, 1H), 4.30 (t, J=7.3 Hz, 2H), 4.14 (t, J= 5.4 Hz, 2H), 2.48 (m, 4H), 2.23 (m, 4H), 1.10 (t, J=7.6 Hz, 3H); MS-FAB m/e 555 (88, p+1), 533 (62); IR (CHCl$_3$, cm$^{-1}$) 3384 (b), 2969, 1566, 1428, 1257, 1181.

Analysis for $C_{32}H_{28}O_6Na_2$: Calc: C, 69.31; H, 5.09; Found: C, 69.51; H, 5.39.

EXAMPLE 60

7-Carboxy-9-oxo-3-[3-(2-ethyl-5-hydroxy-4-phenylphenoxy)propoxy]-9H-xanthene-4-propanoic acid disodium salt monohydrate

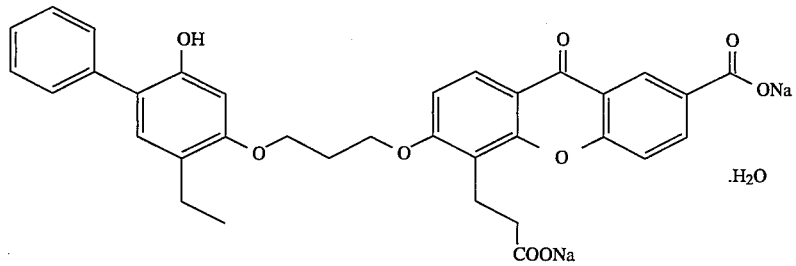

A mixture of 2-benzyloxy-1-phenyl-5-ethyl-4-(3-chloro-1-propyloxy)benzene (749 mg, 1.97 mmol), ethyl 7-carboethoxy-3-hydroxy-9-oxo-9H-xanthene-4-propanoate (729 mg, 1.97 mmol), potassium carbonate (1.36 g, 9.85 mmol) and potassium iodide (33 mg, 0.20 mmol) was refluxed for 24 hours. Dimethylsulfoxide (2 mL) was added and heating continued for 24 hours. The reaction mixture was cooled to room temperature, diluted with ethyl acetate, and washed once with water. The organic layer was dried over sodium sulfate, filtered and concentrated in vacuo to reveal a tan solid. This material was dissolved in ethyl acetate (30 mL)

and the resulting solution purged with nitrogen. To this solution was added 10% palladium on carbon (120 mg) and the resulting suspension hydrogenated at 1 atmosphere of pressure. The solution was filtered and concentrated in vacuo to provide a colorless oil. This material was dissolved in a solution of 1:1 methanol/tetrahydrofuran (30 mL) and treated with 5N sodium hydroxide solution (2 mL) at room temperature for 18 hours. The resulting solution was extracted once with diethyl ether and the aqueous layer acidified with 5N hydrochloric acid solution. The resulting precipitate was collected via suction filtration. This material was converted to the di-sodium salt and purified as described above for the preparation of Example 59(D) to provide 390 mg (56%) of the desired title product as a fluffy white solid: NMR (DMSO-$d_6$) 12.65 (s, 1H, —OH), 8.65 (s, 1H), 8.28 (dd, J=8.5, 2.0 Hz, 1H), 8.01 (d, J=8.9 Hz, 1H), 7.50 (m, 3H), 7.29 (t, J=7.8 Hz, 2H), 7.17 (m, 2H), 6.93 (s, 1H), 6.89 (s, 1H), 4.26 (m, 4H), 3.12 (m, 2H), 2.47 (m, 2H), 2.23 (m, 2H), 1.10 (t, J=7.4 Hz, 3H); MS-FAB m/e 627 (24, p), 605 (40), 583 (24), 331 (24), 309 (100); IR (KBr, cm$^{-1}$) 3419 (b), 2962, 1 61 2, 1558, 1443, 1390, 1277, 1084.

Analysis for $C_{34}H_{28}O_9Na_2 \cdot H_2O$: Calc: C, 63.34; H, 4.69; Found: C, 63.36; H, 4.50.

EXAMPLE 61

2-[2-Propyl-3-[3-(2-ethyl-5-hydroxy-4-phenylphenoxy)propoxy] phenoxy]benzoic acid sodium salt hemihydrate cm$^3$) Florisil® column. The resulting solution was washed twice with a saturated copper sulfate solution and concentrated in vacuo. The residue was dissolved in methylene chloride, washed once with a 0.5N sodium hydroxide solution, and washed once with a dilute sodium hydroxide solution. The organic layer was dried over sodium sulfate, filtered, and concentrated in vacuo to provide a clear brown oil. Silica gel chromatography (ethyl acetate/hexane) provided 45.4 g (32%) of the desired title intermediate as a white solid: mp 80° C.; NMR (CDCl$_3$) 7.92 (dd, J=7.8, 1.6 Hz, 1H), 7.42 (t, J=8.4 Hz, 1H), 7.13 (t, J=7.2 Hz, 1H), 6.97 (t, J=8.1 Hz, 1H), 6.86 (d, J=8.1 Hz, 1H), 6.62 (d, J=8.0 Hz, 1H), 6.51 (d, J= 8.0 Hz, 1H), 5.65 (bs, 1 H, —OH), 3.88 (s, 3H), 2.66 (t, J=7.6 Hz, 2H), 1.62 (hextet, J=7.6 Hz, 2H), 0.96 (t, J=7.4 Hz, 3H); MS-FD m/e 286 (p); IR (CHCl$_3$, cm$^{-1}$) 3350 (b), 2950, 1718, 1602, 1480, 1306, 1255, 1086, 981.

Analysis for $C_{17}H_{18}O_4$: Calc: C, 71.31; H, 6.34; Found: C, 71.53; H, 6.37.

B. Preparation of 2-[2-propyl-3-[3-(2-ethyl-5-hydroxy-4-phenylphenoxy)propoxy]phenoxy]benzoic acid sodium salt hemihydrate.

2-(3-Hydroxy-2-propylphenoxy)benzoic acid methyl ester (450 mg, 1.57 mmol) was alkylated with 2-benzyloxy-1-phenyl- 5-ethyl-4-(3-chloro-1-propyloxy)benzene, de-benzylated, and hydrolyzed as described above for the preparation of Example 60 except that dimethylsulfoxide was omitted. Salt formation and purification as described above for the preparation of Example 59(D) provided 200 mg (21%) of the desired title product as a fluffy white solid:

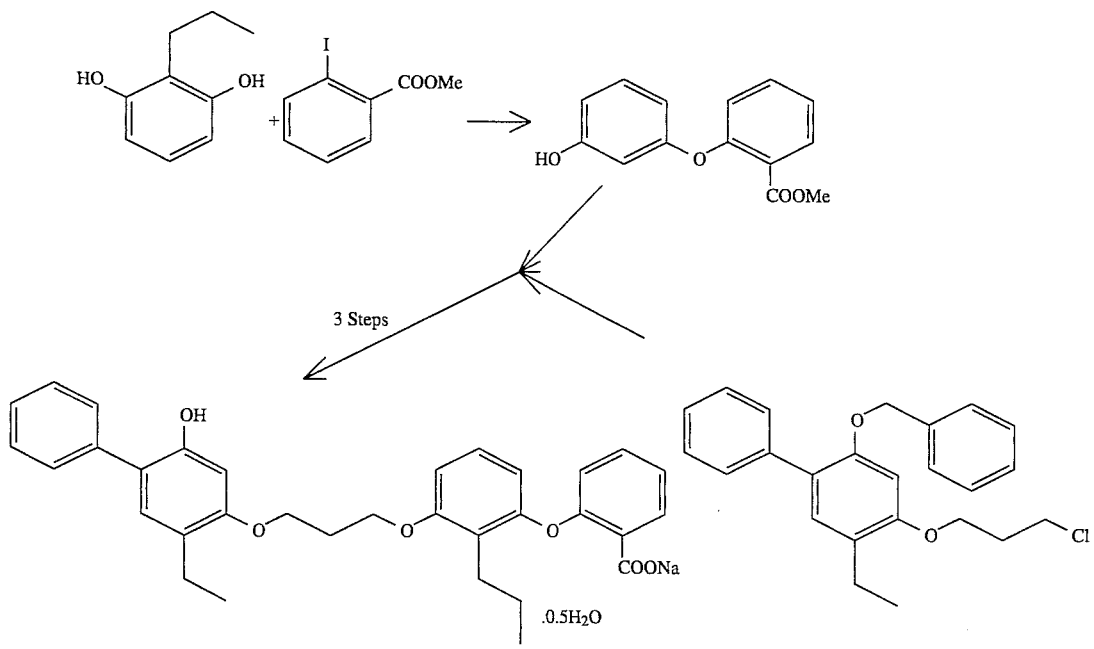

A. Preparation of 2-(3-hydroxy-2-propylphenoxy)benzoic acid methyl ester.

A mixture of 1,3-dihydroxy-2-propylbenzene (75.0 g, 0.490 mol), methyl 2-iodobenzoate (129 g, 0.490 mol), copper bronze (47.0 g, 0.740 mol) and potassium carbonate (81.7 g, 0.592 mol) in dry pyridine (1L) was thoroughly de-gassed with nitrogen, then refluxed for 6 hours. The mixture was cooled to room temperature, filtered, and concentrated in vacuo to reveal a dark sludge. This material was dissolved in ethyl acetate and passed down a short (~500

NMR (DMSO-$d_6$) 7.48 (d, J=7.5 Hz, 2H), 7.42 (d, J=7.2 Hz, 1H), 7.31 (t, J=7.4 Hz, 2H), 7.18 (t, J=7.5 Hz, 1H), 7.16 (t, J=7.1 Hz, 1H), 6.98 (m, 3H), 6.64 (t, J=7.2 Hz, 2H), 6.60 (s, 1H), 6.24 (d, J=7.9 Hz, 1H), 4.15 (m, 2H), 4.02 (m, 2H), 2.61 (m, 2H), 2.49 (m, 2H), 2.16 (t, J=5.5 Hz, 2H), 1.46 (hextet, J=6.6 Hz, 2H), 1.07 (t, J=7.4 Hz, 3H), 0.82 (t, J=7.4 Hz, 3H); MS-FAB m/e 549 (100, p+1), 526 (32), 295 (28), 252 (34), 227 (20), 213 (21); IR (CHCl$_3$, cm$^{-1}$) 3450 (b), 2974, 1602, 1586, 1461, 1393, 1240, 1113, 1048.

Analysis for $C_{33}H_{32}O_6Na \cdot 0.5H_2O$: Calc: C, 71.22; H, 5.94; Found: C, 71.4 2; H, 6.16.

EXAMPLE 62

3-[3-(2-Ethyl-5-hydroxy-4-phenylphenoxy)propoxy][1,1'-biphenyl]-4-propanoic acid disodium salt monohydrate

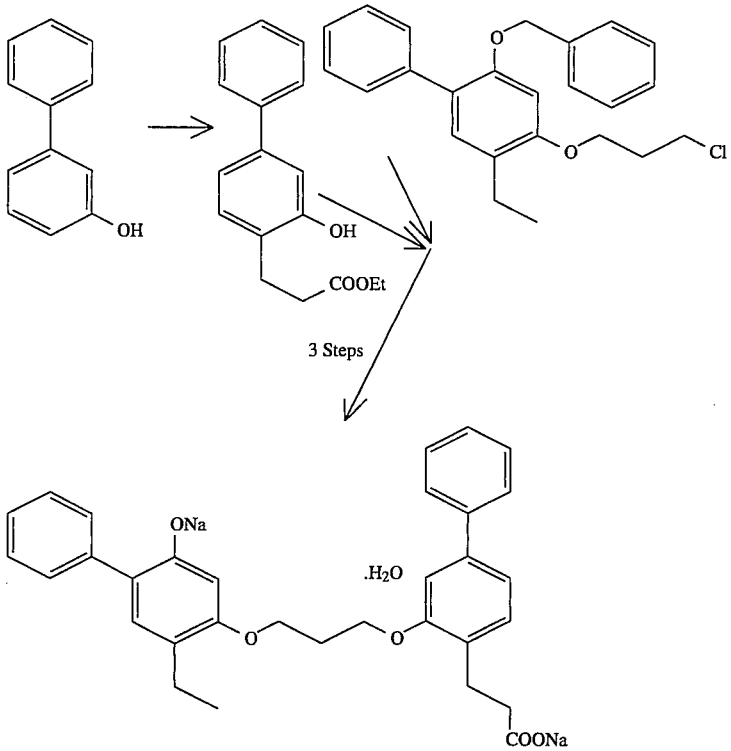

A. Preparation of 3-[(2-hydroxy-4-phenyl)phenyl] propanoic acid ethyl ester.

A mixture of 3-phenylphenol (5.00 g, 29.4 mmol), triethylorthoacrylate (10.9 g, 58.8 mmol) and pivalic acid (1.50 g, 14.7 mmol) in toluene (100 mL) was refluxed for 24 hours. The resulting solution was cooled to room temperature and washed once with water and once with dilute sodium hydroxide solution. The organic layer was dried over sodium sulfate, filtered, and concentrated in vacuo to provide a colorless oil. The resulting solid was dissolved in tetrahydrofuran (25 mL) and treated at room temperature with 1N hydrochloric acid solution (0.5 mL) for 5 minutes. The mixture was diluted with ether, washed once with water, filtered, and concentrated in vacuo to provide a waxy solid: NMR (CDCl$_3$) 7.57 (m, 3H), 7.44 (t, J=7.1 Hz, 2H), 7.35 (d, J=7.3 Hz, 1H), 7.17 (m, 2H), 4.19 (q, J=7.2 Hz, 2H), 2.97 (t, J=6.8 Hz, 2H), 2.77 (t, J=6.8 Hz, 2H), 1.27 (t, J= 5.4 Hz, 3H); MS-FD m/e 270 (p); IR (CHCl$_3$, cm$^{-1}$) 3328 (b), 3013, 1708, 1564, 1485, 1411, 1379, 1237, 1166.

Analysis for $C_{17}H_{18}O_3$: Calc: C, 75.53; H, 6.71; Found: C, 75.80; H, 6.60.

B. Preparation of 3-[3-(2-ethyl-5-hydroxy-4-phenylphenoxy)propoxy] [1,1'-biphenyl]-4-propanoic acid disodium salt monohydrate.

3-[(2-Hydroxy-4-phenyl)phenyl]propanoic acid ethyl ester (354 mg, 1.31 mmol) was alkylated with 2-benzyloxy-1-phenyl-5-ethyl-4-(3-chloro-1-propyloxy)benzene, de-benzylated and hydrolyzed as described above for the preparation of Example 60, except that dimethylsulfoxide was omitted. Salt formation and purification as described above for the preparation of Example 59(D) provided 32 mg (4%) of the desired title product: NMR (DMSO-d$_6$) 7.62 (d, J=7.9 Hz, 2H), 7.53 (d, J=8.0 Hz, 2H), 7.42 (t, J=7.9 Hz, 2H), 7.25 (m, 3H), 7.12 (m, 4H), 6.93 (s, 1H), 6.90 (s, 1H), 4.26 (m, 2H), 4.19 (m, 2H), 2.79 (m, 2H), 2.48 (m, 2H), 2.18 (m, 4H), 1.09 (t, J=7.7 Hz, 3H); MS-FAB m/e 540 (51, p), 518 (76); IR (CHCl$_3$, cm$^{-1}$) 3480 (b), 2975, 1602, 1408, 1049.

Analysis for $C_{32}H_{30}O_5Na_2 \cdot H_2O$: Calc: C, 66.62; H, 5.95; Found: C, 66.25; H, 5.67.

EXAMPLE 63

5-Ethyl-4-[3-[2-propyl-3-[2-(2H-tetrazol-5-yl)phenoxy]phenoxy]propoxy][1,1'-biphenyl]-2-ol disodium salt sesquihydrate

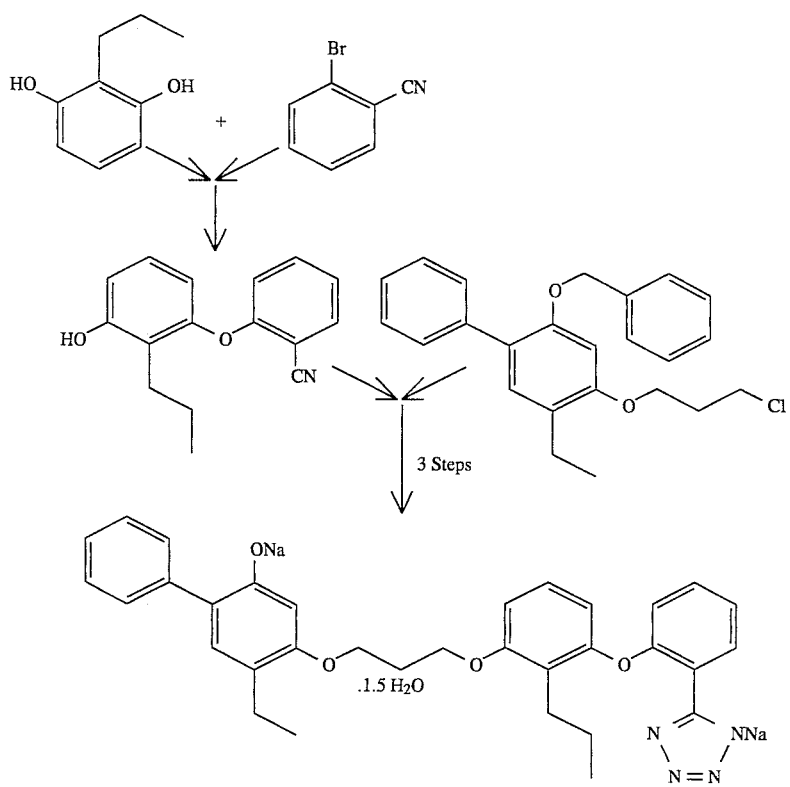

A. Preparation of 3-(2-cyanophenoxy)-2-propylphenol.

A mixture of 3-hydroxy-2-propylphenol (7.50 g, 49.3 mmol), 2-bromobenzonitrile (8.97 g, 49.3 mmol), copper bronze (3.76 g, 59.2 mmol), and potassium carbonate (6.80 g, 49.3 mmol) in pyridine (250 mL) was refluxed for 72 hours. The mixture was cooled to room temperature, filtered, and concentrated in vacuo. The residue was dissolved in ethyl acetate and washed once with water and three times with a saturated copper sulfate solution. The organic layer was dried over sodium sulfate, filtered, and concentrated in vacuo to provide a dark oil. Silica gel chromatography provided a white solid. Sublimation of this material (bulb-to-bulb distillation apparatus, 200° C.) to remove excess 3-hydroxy-2-propylphenol provided 1.79 g (14%) of the desired title intermediate as an off-white crystalline material: mp 103°–107° C.; NMR (CDCl$_3$) 7.68 (d, J=8 Hz, 1H), 7.47 (t, J=7 Hz, 1H), 7.12 (t, J=8 Hz, 1H), 7.10 (t, J=8 Hz, 1H), 6.80 (d, J=9 Hz, 1H), 6.71 (d, J=9 Hz, 1H), 6.58 (d, J=9 Hz, 1H), 4.95 (s, 1H, —OH), 2.62 (t, J=7 Hz, 2H), 1.60 (hextet, J=6 Hz, 2H), 0.96 (t, J= 7 Hz, 3H); MS-FD m/e 253 (p); IR (CHCl$_3$, cm$^{-1}$) 3300 (b), 2967, 2234, 1600, 1485, 1483, 1450, 1247, 1097, 980.

Analysis for C$_{16}$H$_{15}$NO$_2$: Calc: C, 75.87; H, 5.97; N, 5.53; Found: C, 75.09; H, 5.88; N, 5.58.

B. Preparation of 5-ethyl-4-[3-[2-propyl-3-[2-(2H-tetrazol-5-yl)phenoxy]phenoxy]propoxy][1,1'-biphenyl]-2-ol disodium salt sesquihydrate.

3-(2-Cyanophenoxy)-2-propylphenol (1.66 g, 6.56 mmol) was alkylated with 2-benzyloxy-1-phenyl-5-ethyl-4-(3-chloro-1-propyloxy)benzene as described above for the preparation of Example 60. The crude product was dissolved in hexane/ethyl acetate and passed through a short silica gel column. The solution was concentrated in vacuo and the residue dissolved in 2-methoxyethanol (50 mL). To this solution was added lithium azide (1.38 g, 24.2 mmol) and triethylammonium bromide (1.30 g, 7.14 mmol). The resulting mixture was refluxed for 48 hours, cooled to room temperature, and passed down a short silica gel column. The column was washed with excess ethyl acetate and the combined washings were concentrated in vacuo. The resulting material was de-benzylated as described above for the preparation of Example 60. The crude tetrazole was converted to the sodium salt and purified as described above for the preparation of Example 59(D) to provide 320 mg (8%) of the desired title product as a fluffy white solid: NMR (DMSO-d$_6$) 7.81 (dd, J=7.7, 1.5 Hz, 1H), 7.49 (d, J=7.5 Hz, 2H), 7.33 (t, J= 7.5 Hz, 2H), 7.21 (m, 2H), 7.11 (t, J=7.3 Hz, 1H), 6.99 (m, 2H), 6.76 (d, J=8.1 Hz, 1H), 6.68 (d, J=8.2 Hz, 1H), 6.56 (s, 1H), 6.22 (d, J=8.2 Hz, 1H), 4.16 (t, J=5.8 Hz, 2H), 4.10 (t, J=5.9 Hz, 2H), 2.61 (t, J=6.5 H, 2H), 2.48 (m, 2H), 2.22 (m, 2H), 1.45 (hextet, J=7.4 Hz, 2H), 1.08 (t, J=7.4 Hz, 3H), 0.79 (t, J=7.3 Hz, 3H); MS-FAB m/e 595 (35, p+1), 574 (39), 573 (100), 551(99); IR (KBr, cm$^{-1}$) 3418 (b), 2962, 1577, 1458, 1243, 1229, 1147, 1117. Analysis for C$_{33}$H$_{32}$N$_4$O$_4$Na$_2$·1.5 H$_2$O: Calc: C, 63.76; H, 5.68; N, 9.01; Found: C, 63.63; H, 5.59; N, 8.80.

EXAMPLE 64

3-[4-[3-[3-(2-Ethyl-5-hydroxy-4-phenylphenoxy)propoxy]-9-oxo-9H-xanthene]]propanoic acid sodium salt hemihydrate

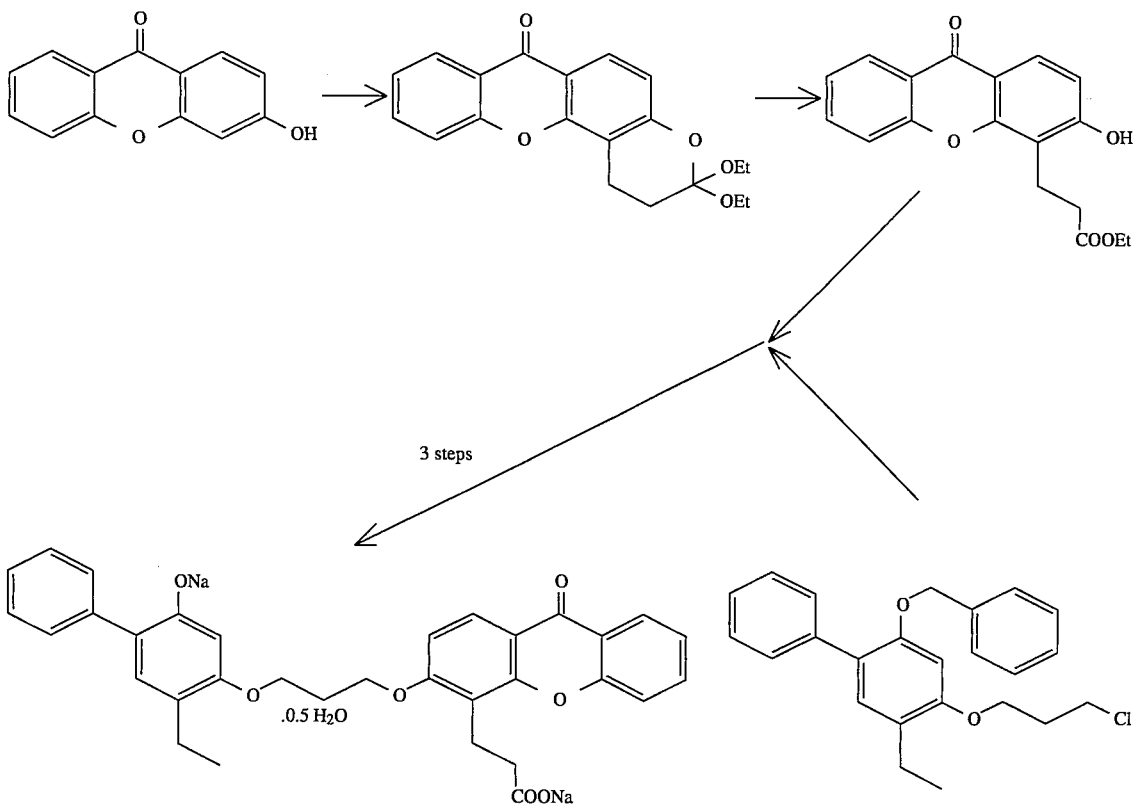

A. Preparation of 3,3-diethoxy-2,3-dihydro-1H,7 H-pyrano[2,3-c]xanthen-7-one.

A mixture of 3-hydroxy-9-oxo-9H-xanthene (3.00 g, 14.2 mmol), triethylorthoacrylate (5.26 g, 28.4 mmol), and pivalic acid (0.720 g, 7.06 mmol) in toluene (75 mL) was refluxed for 16 hours. The mixture was cooled to room temperature and diluted with ether. The resulting mixture was washed once with water and once with dilute sodium hydroxide solution, dried over sodium sulfate, filtered, and concentrated in vacuo. Recrystallization (hexane/ethyl acetate) of the residue provided 4.31 g (90%) of the desired title intermediate as a white crystalline material: mp 156° C.; NMR (CDCl$_3$) 8.33 (dd, J=8.0 Hz, 1H), 8.15 (d, J=8.8 Hz, 1H), 7.69 (t, J=6.9 Hz, 1H), 7.48 (d, J=8.6 Hz, 1H), 7.37 (t, J=7.7 Hz, 1H), 6.93 (d, J=8.8 Hz, 1H), 3.76 (m, 4H), 3.11 (t, J=6.9 Hz, 2H), 2.22 (t, J=6.9 Hz, 2H), 1.23 (t, J=7.1 Hz, 6H); MS-FD m/e 340 (p); IR (CHCl$_3$, cm$^{-1}$) 2980, 1650, 1622, 1606, 1466, 1437, 1 230, 1089, 1045. Analysis for C$_{20}$H$_{20}$O$_5$: Calc: C, 70.58; H, 5.92; Found: C, 70.83; H, 5.84.

B. Preparation of 3-[4-(3-hydroxy-9-oxo-9 H-xanthene)] propanoic acid ethyl ester.

3,3-Diethoxy-2,3-dihydro-1H,7H-pyrano[2,3-c]xanthen-7-one (3.40 g, 10.0 mmol) was dissolved in tetrahydrofuran (30 mL) and treated at room temperature with 1N hydrochloric acid solution (0.20 mL) for 1 hour. The reaction was diluted with ethyl acetate and washed once with water. The organic layer was dried over sodium sulfate, filtered, and concentrated in vacuo. The residue was recrystallized from hexane/ethyl acetate to provide 3.09 g (99%) of the desired title intermediate as a white micro-crystalline material: mp 181° C.; NMR (CDCl$_3$)9.10 (s, 1H, —OH), 8.34 (dd, J=7.9, 2.0 Hz, 1H), 8.17 (d, J=8.8 Hz, 1H), 7.71 (t, J=8 Hz, 1H), 7.50 (d, J=8.0 Hz, 1H), 7.34 (t, J=7.8 Hz, 1H), 7.03 (d, J=8.1 Hz, 1H), 4.19 (q, J=7.2 Hz, 2H), 3.22 (t, J=5.7 Hz, 2H), 2.90 (t, J=6.6 Hz, 2H), 1.25(t, J=7.3 Hz, 3H); MS-FD m/e 312 (p); IR (CHCl$_3$, cm$^{-1}$) 3260 (b), 3025, 1648, 1620, 1607, 1467, 1328, 1242. Analysis for C$_{18}$H$_{16}$O$_5$: Calc: C, 69.22; H, 5.16; Found: C, 69.13; H, 5.22.

C. Preparation of 3-[4-[3-[3-[2-ethyl-4-phenyl- 5-(phenylmethoxy)phenoxy]propoxy]-9-oxo-9H-xanthene]]propanoic acid ethyl ester.

3-[4-(3-Hydroxy-9-oxo-9H-xanthene)]propanoic acid ethyl ester (0.821 g, 2.63 mmol) was alkylated with 2-benzyloxy- 1-phenyl-5-ethyl-4-(3-chloro-1-propyloxy)benzene as described above for the preparation of Example 60 to provide crude product as an orange oil. Silica gel chromatography provided 1.48 g (86%) of the desired title intermediate as a white solid: mp 99°–102° C.; NMR (CDCl$_3$) 8.35 (d, J=7.7 Hz, 1H), 8.28 (d, J=8.9 Hz, 1H), 7.73 (t, J=7 Hz, 1H), 7.54 (m, 3H), 7.25–7.50 (m, 9H), 7.18 (s, 1H), 7.04 (d, J=9.0 Hz, 1H), 6.66 (s, 1H), 5.05 (s, 2H), 4.39 (t, J=6 Hz, 2H), 4.25 (t, J=5.8 Hz, 2H), 4.12 (q, J=7.1 Hz, 2H), 3.34 (t, J=7.5 Hz, 2H), 2.64 (m, 4H), 2.39 (t, J=5.9 Hz, 2H), 1.20 (m, 6H); MS-FD m/e 656 (100, p), 362 (9); IR (CHCl$_3$, cm$^{-1}$) 3000, 1727, 1652, 1618, 1604, 1466, 1434, 1276, 1149, 1087. Analysis for C$_{42}$H$_{40}$O$_7$: Calc: C, 76.81; H, 6.14; Found: C, 77.05; H, 6.24.

D. Preparation of 3-[4-[3-[3-(2-ethyl-5-hydroxy- 4-phenylphenoxy)propoxy]-9-oxo-9H-xanthene]]propanoic acid sodium salt hemihydrate.

De-benzylation, hydrolysis, salt formation, and purification of 3-[4-[3-[3-[2-ethyl-4-phenyl- 5-(phenylmethoxy)phenoxy]propoxy]-9-oxo-9H-xanthene]]propanoic acid ethyl ester (1.24 g, 1.89 mmol) proceeded as described above for the preparation of Example 59 to provide 817 mg (73%) of the desired title product as a fluffy white solid: NMR (DMSO-$d_6$) 8.48 (d, J=8.0 Hz, 1H), 8.00 (d, J=8.9 Hz, 1H), 7.80 (t, J=7.2 Hz, 1H), 7.62 (d, J=8.3 Hz, 1H), 7.52 (d, J=7.8 Hz, 2H), 7.41 (t, J=7.8 Hz, 1H), 7.29 (t, J=7.8 Hz, 2H), 7.16 (t, J=8.7 Hz, 2H), 6.94 (s, 1H), 6.86 (s, 1H), 4.26 (m, 4H), 3.10 (m, 2H), 2.48 (q, J=7.3 Hz, 2H), 2.23 (m, 4H), 1.09 (t, J=7.6 Hz, 3H); MS-FAB m/e 583 (7, p), 561 (54), 539 (100); IR (KBr, cm$^{-1}$) 3410 (b), 2961, 1605, 1433, 1278, 1147, 1087, 766, 699. Analysis for $C_{33}H_{28}O_7Na_2 \cdot 0.5\ H_2O$: Calc: C, 67.00; H, 4.94; Found: C, 67.26; H, 5.12.

EXAMPLE 65

2-Fluoro-6-[2-propyl-3-[3-(2-ethyl-5-hydroxy-4-phenylphenoxy)propoxy]phenoxy]benzoic acid disodium salt A. Preparation of 2-fluoro-6-(3-hydroxy- 2-propyl-phenoxy)benzoic acid methyl ester.

2-Fluoro-6-iodobenzoic acid methyl ester (13.1 g, 46.8 mmol) was submitted to the Ullmann conditions described above for the preparation of Example 61(A). This procedure provided 3.10 g (22%) of the desired title intermediate as an oil: NMR (CDCl$_3$) 7.26 (m, 1H), 7.03 (t, J=8.1 Hz, 1H), 6.83 (t, J=8.6 Hz, 1H), 6.65 (d, J=8.0 Hz, 1H), 6.56 (d, J=7.8 Hz, 1H), 6.53 (d, J=7.6 Hz, 1H), 5.30 (bs, 1H, —OH), 3.93 (s, 3H), 2.59 (t, J=7.3 Hz, 2H), 1.56 (hextet, J=7.6 Hz, 2H), 0.94 (t, J=7.4 Hz, 3H).

B. Preparation of 2-fluoro-6-[2-propyl-3-[3-( 2-ethyl-5-hydroxy-4-phenylphenoxy)propoxy]phenoxy]benzoic acid disodium salt.

2-Fluoro-6-(3-hydroxy-2-propylphenoxy)benzoic acid methyl ester (0.660 g, 2.17 mmol) was alkylated with 2-benzyloxy-1-phenyl-5-ethyl-4-(3-chloro-1-propyloxy-)benzene as described above for the preparation of Example 60 to provide crude product as an oil. De-benzylation and hydrolysis proceeded as described above for the preparation of Example 60. Salt formation and purification as described above for the preparation of Example 59(D) provided 468 mg (37%) of the desired title product as a fluffy white solid: NMR (DMSO-$d_6$) 7.49 (d, J=8.8 Hz, 2H), 7.32 (t, J=7.5 Hz, 2H), 7.18 (t, J=7.4 Hz, 1H), 6.85–7.10 (m, 3H), 6.74 (t, J=8.1 Hz, 2H), 6.62 (s, 1H), 6.42 (d, J=8.1 Hz, 1H), 6.33 (d, J=8.2 Hz, 1H), 4.13 (t, J=6.0 Hz, 2H), 4.04 (t, J=5.8 Hz, 2H), 2.40–2.63 (m, 4H), 2.15 (m, 2H), 1.41 (hextet, J=7.3 Hz, 2H), 1.07 (t, J=7.4 Hz, 3H), 0.79 (t, J=7.2 Hz, 3H); MS-FAB m/e 589 (16, p), 568 (36), 567 (100), 546 (30), 527 (15); IR (CHCl$_3$, cm$^{-1}$) 2975, 1601, 1456, 1395, 1115, 1047. Analysis for $C_{33}H_{31}O_6FNa_2$: Calc: C, 67.34; H, 5.31; F, 3.23; Found: C, 67.43; H, 5.59; F, 2.99.

EXAMPLE 66

2-[2-Propyl-3-[3-[2-ethyl-4-(4-fluorophenyl)-5-hydroxyphenoxy]propoxy]phenoxy]benzoic acid sodium salt

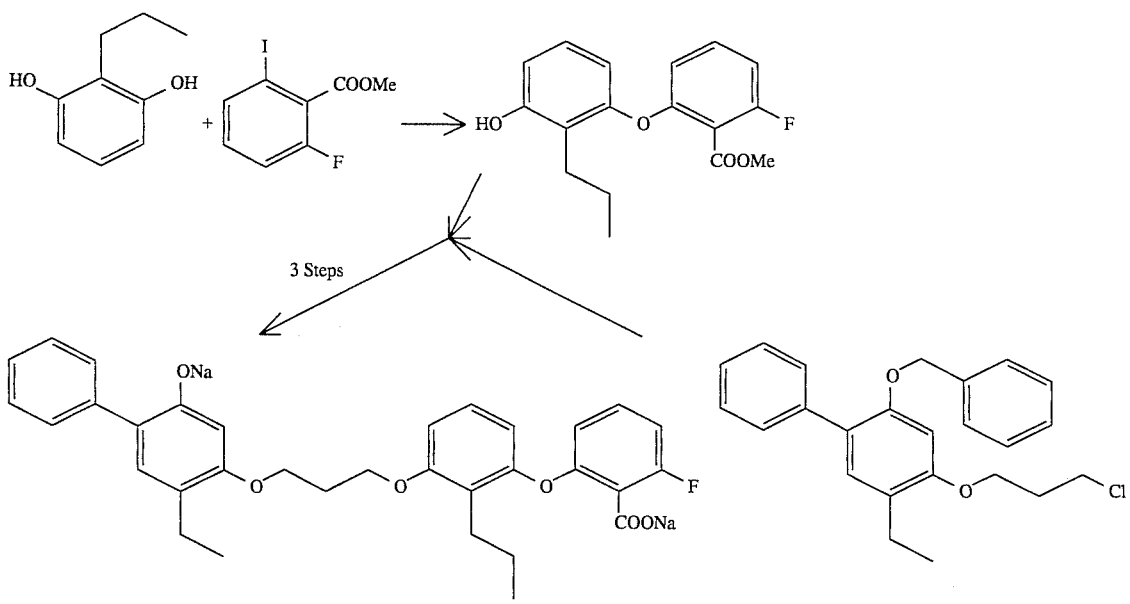

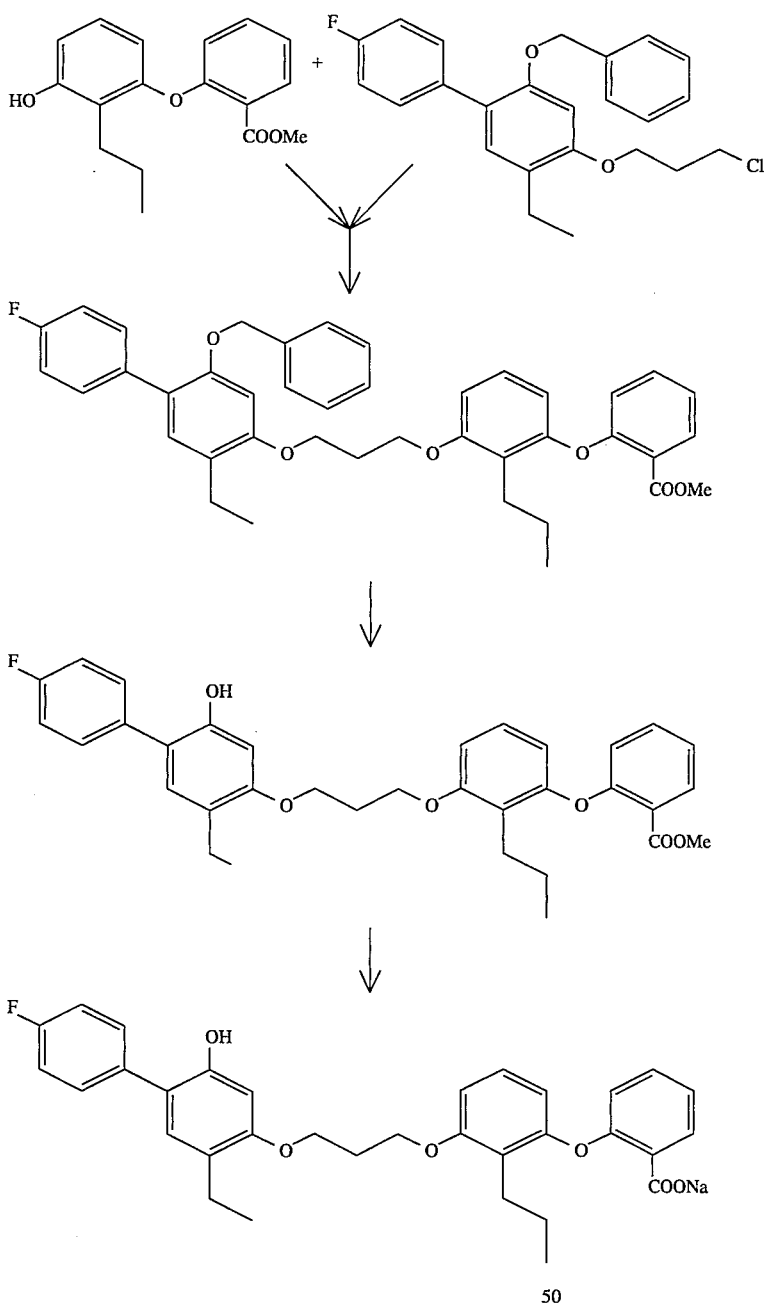

A. Preparation of 2-[2-propyl-3-[3-[2-ethyl-4-( 4-fluorophenyl)-5-(phenylmethoxy)phenoxy]propoxy]phenoxy]benzoic acid methyl ester.

A mixture of 2-benzyloxy-1-(4-fluorophenyl)-5-ethyl-4-(3-chloro-1-propyloxy)benzene (20.0 g, 50.2 mmol) and sodium iodide (75.3 g, 502 mmol) in 2-butanone (200 mL) was refluxed for 6 hours. The mixture was diluted with ether and washed once with water. The organic layer was dried over sodium sulfate, filtered, and concentrated in vacuo to provide a colorless oil. This material was dissolved in dimethylformamide (100 mL) and treated with 2-(3-hydroxy-2-propylphenoxy)benzoic acid methyl ester (14.4 g, 50.2 mmol) and potassium carbonate (20.8 g, 151 mmol) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (d, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p); IR (CHCl$_3$, cm$^{-1}$) 2960, 1740, 1604, 1497, 1461, 1112. Analysis for C$_{41}$H$_{41}$O$_6$F: Calc: C, 75.91; H, 6.37; Found: C, 7 6.15; H, 6.45.

B. Preparation of 2-[2-propyl-3-[3-[2-ethyl-4-( 4-fluorophenyl)-5-hydroxyphenoxy]propoxy]phenoxy]benzoic acid methyl ester.

2-[2-Propyl-3-[3-[2-ethyl-4-(4-fluorophenyl)- 5-(phenyl-methoxy)phenoxy]propoxy]phenoxy]benzoic acid methyl ester (33.0 g, 50.9 mmol) was de-benzylated as described above for the preparation of Example 60 to provide 27.3 g (96%) of the title intermediate as an amber oil: NMR (CDCl$_3$) 7.90 (dd, J=7.8, 1.7 Hz, 1H), 7.42 (m, 3H), 7.05–7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, —OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p); IR (CHCl$_3$, cm$^{-1}$) 2965, 1727, 1603, 1496, 1458, 1306, 1112. Analysis for C$_{34}$H$_{35}$O$_6$F: Calc: C, 73.10; H, 6.31; Found: C, 73.17; H, 6.42.

C. Preparation of 2-[2-propyl-3-[3-[2-ethyl-4-( 4-fluorophenyl)-5-hydroxyphenoxy]propoxy]phenoxy]benzoic acid sodium salt.

2-[2-Propyl-3-[3-[2-ethyl-4-(4-fluorophenyl)- 5-hydroxyphenoxy]propoxy]phenoxy]benzoic acid methyl ester (21.5 g, 38.5 mmol) was hydrolyzed as described above for the preparation of Example 60. The acid was converted to the sodium salt and purified as described above for the preparation of Example 59(D) to provide 16.7 g (77%) of the desired title product as a white amorphous solid: NMR (DMSO-d$_6$) 10.50 (bs, 1H, —OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9 Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112. Analysis for C$_{33}$H$_{32}$O$_6$FNa: Calc: C, 69.95; H, 5.69; F, 3.35; Found: C, 69.97; H, 5.99; F, 3.52.

EXAMPLE 67

3-[4-[7-Carboxy-9-oxo-3-[3-[2-ethyl-4-(4-fluorophenyl)-5-hydroxyphenoxy]propoxy]-9H-xanthene]]propanoic acid disodium salt trihydrate off-white crystalline material: mp 100° C.; NMR (CDCl$_3$) 9.02 (s, 1H), 8.38 (d, J=8.8 Hz, 1H), 8.28 (d, J=9.0 Hz, 1H), 7.58 (d, J=8.8 Hz, 1H), 7.52 (d, J=5.9 Hz, 1H), 7.50 (d, J=5.5 Hz, 1H), 7.32 (m, 5H), 7.07 (m, 4H), 6.64 (s, 1H), 5.03 (s, 2H), 4.40 (t, J=5.7 Hz, 2H), 4.24 (t, J=5.5 Hz, 2H), 4.10 (q, J=7.3 Hz, 2H), 3.99 (s, 3H), 3.32 (t, J=8.0 Hz, 2H), 2.64 (m, 4H), 2.39 (t, J=5.8 Hz, 2H), 1.19 (m, 6H); MS-FD m/e 731 (p–1); IR (CHCl$_3$, cm$^{-1}$)2950, 1724, 1661, 1610, 1497, 1435, 1276, 1084. Analysis for C$_{44}$H$_{41}$O$_9$F: Calc: C, 72.12; H, 5.64; Found: C, 72.34; H, 5.87.

B. Preparation of 3-[4-[7-carboxy-9-oxo-3-[3-[ 2-ethyl-4-(4-fluorophenyl)-5-hydroxyphenoxy]propoxy]-9 H-xanthene]]propanoic acid disodium salt trihydrate.

Ethyl 3-[4-[7-carbomethoxy-9-oxo-3-[3-[2-ethyl-4-( 4-fluorophenyl)-5-(phenylmethoxy)phenoxy]propoxy]-9 H-xanthene]]propanoate (550 mg, 0.751 mmol) was de-benzylated and hydrolyzed as described above for the preparation of Example 60 except that a Parr™ apparatus was used at 2 atmospheres hydrogen pressure. The acid was converted to the sodium salt and purified as described for the preparation of Example 59(D) to provide 242 mg (46%) of the desired title product as a fluffy white solid: NMR (DMSO-d$_6$) 8.65 (d, J=1.8 Hz, 1H), 8.29 (dd, J=8.6, 1.8 Hz, 1H), 8.00 (d, J=8.9 Hz, 1H), 7.52 (m, 3H), 7.11 (m, 3H), 6.92 (s, 1H), 6.89 (s, 1H), 4.26 (m, 4H), 3.10 (m, 2H), 2.48 (q, J=7.2 Hz, 2H), 2.21 (m, 4H), 1.09 (t, J=7.5 Hz, 3H); MS-FAB m/e 645 (18, p), 624 (30), 623 (61), 601 (74), 309 (100), 307 (54); IR (KBr, cm$^{-1}$) 3414 (b), 2926, 1609, 1391, 1276, 1101, 785. Analysis for C$_{34}$H$_{27}$O$_9$FNa$_2$.3 H$_2$O: Calc: C, 58.61; H, 4.74; Found: C, 58.34; H, 4.34.

EXAMPLE 68

3-[4-[9-Oxo-3-[3-[2-ethyl-4-(4-fluorophenyl)-5-hydroxyphenoxy]propoxy]-9H-xanthene]]propanoic acid

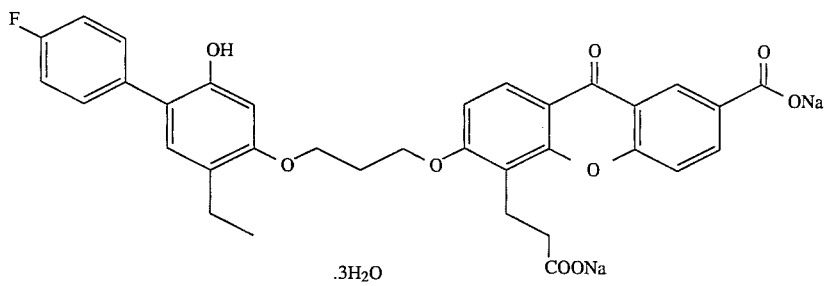

A. Preparation of ethyl 3-[4-[7-carbomethoxy-9-oxo-3-[3-[2-ethyl-4-(4-fluorophenyl)-5-(phenylmethoxy)phenoxy]-propoxy]- 9H-xanthene]]propanoate.

2-Benzyloxy-1-(4-fluorophenyl)-5-ethyl-4-(3-chloro-1-propyloxy)benzene (0.593 g, 1.49 mmol) was converted to the corresponding iodide and reacted with ethyl 7-carboethoxy- 3-hydroxy-9-oxo-9H-xanthene-4-propanoate as described above for the preparation of Example 66(A). The crude product was recrystallized (hexane/ethyl acetate) to provide 755 mg (69%) of the title intermediate as an

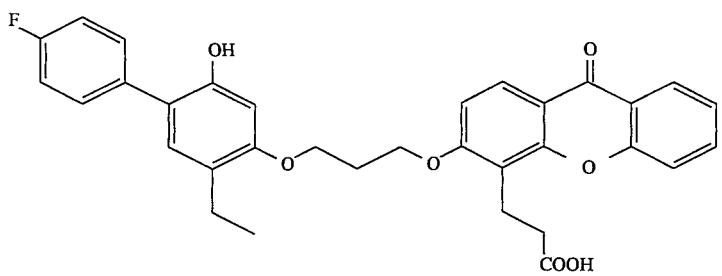

A. Preparation of ethyl 3-[4-[9-oxo-3-[3-[2-ethyl-4-(4-fluorophenyl)-5-(phenylmethoxy)phenoxy]propoxy]-9 H-xanthene]]propanoate.

2-Benzyloxy-1-(4-fluorophenyl)-5-ethyl-4-(3-chloro-1-propyloxy)benzene (0.593 g, 1.49 mmol) was converted to the corresponding iodide and reacted with 3-[4-(3-hydroxy-9-oxo-9 H-xanthene)]propanoic acid ethyl ester as described above for the preparation of Example 66(A). The crude product was recrystallized (hexane/ethyl acetate) to provide 610 mg (61%) of the desired title intermediate as an off-white crystalline material: mp 115° C.; NMR (CDCl$_3$) 8.34 (dd, J=7.9, 1.6 Hz, 1H), 8.27 (d, J=8.9 Hz, 1H), 7.73 (t, J=7.0 Hz, 1H), 7.52 (m, 3H), 7.39 (t, 7.9 Hz, 1H), 7.31 (m, 5H), 7.01–7.13 (m, 4H), 6.64 (s, 1H), 5.04 (s, 2H), 4.39 (t, J=6.0 Hz, 2H), 4.24 (t, J=5.8 Hz, 2H), 4.10 (q, J=7.1 Hz, 2H), 3.32 (t, J=7.6 Hz, 2H), 2.64 (m, 4H), 2.39 (quintet, J=5.9 Hz, 2H), 1.19 (m, 6H); MS-FD m/e 674 (p); IR (CHCl$_3$, cm$^{-1}$) 2973, 1727, 1653, 1618, 1604, 1497, 1466, 1434, 1275, 1146, 1087. Analysis for $C_{42}H_{39}O_7F$: Calc: C, 74.76; H, 5.83; F, 2.82; Found: C, 74.49; H, 5.72; F, 2.65.

B. Preparation of 3-[4-[9-oxo-3-[3-[2-ethyl-4-( 4-fluorophenyl)-5-hydroxyphenoxy]propoxy]-9H-xanthene]]-propanoic acid.

Ethyl 3-[4-[9-oxo-3-[3-[2-ethyl-4-(4-fluorophenyl)-5-(phenylmethoxy)phenoxy]propoxy]-9H-xanthene]]propanoate (500 mg, 0.742 mmol) was de-benzylated and hydrolyzed as described above for the preparation of Example 60. Recrystallization (toluene/ethyl acetate) provided 278 mg (67%) of the title product as a white crystalline material: mp 205° C.; NMR (DMSO-d$_6$) 12.38 (bs, 1H, —COOH), 9.36 (s, 1H, —OH), 8.14 (dd, J=7.9, 1.6 Hz, 1H), 8.07 (d, 8.9 Hz, 1H), 7.82 (t, J=8.7 Hz, 1H), 7.63 (d, J=8.4 Hz, 1H), 7.38–7.52 (m, 2H), 7.08–7.30 (m, 4H), 6.97 (s, 1H), 6.55 (s, 1H), 4.37 (t, J=6.1 Hz, 2H), 4.13 (t, J=6.0 Hz, 2H), 3.15 (t, J=8.2 Hz, 2H), 2.48 (m, 4H), 2.28 (quintet, J=3.7 Hz, 2H), 1.06 (t, J=7.5 Hz, 3H); MS-FD m/e 556 (p); IR (CHCl$_3$, cm$^{-1}$) 2974, 1711, 1652, 1618, 1604, 1498, 1466, 1434, 1277, 1146, 1088. Analysis for $C_{33}H_{29}O_7F$: Calc: C, 71.21; H, 5.25; Found: C, 71.14; H, 5.23.

EXAMPLE 69

3-[2-[1-[2-Ethyl-4-(4-fluorophenyl)-5-hydroxyphenoxy]propoxy]-4-(5-oxo-5-morpholinopentanamido)phenyl]propanoic acid

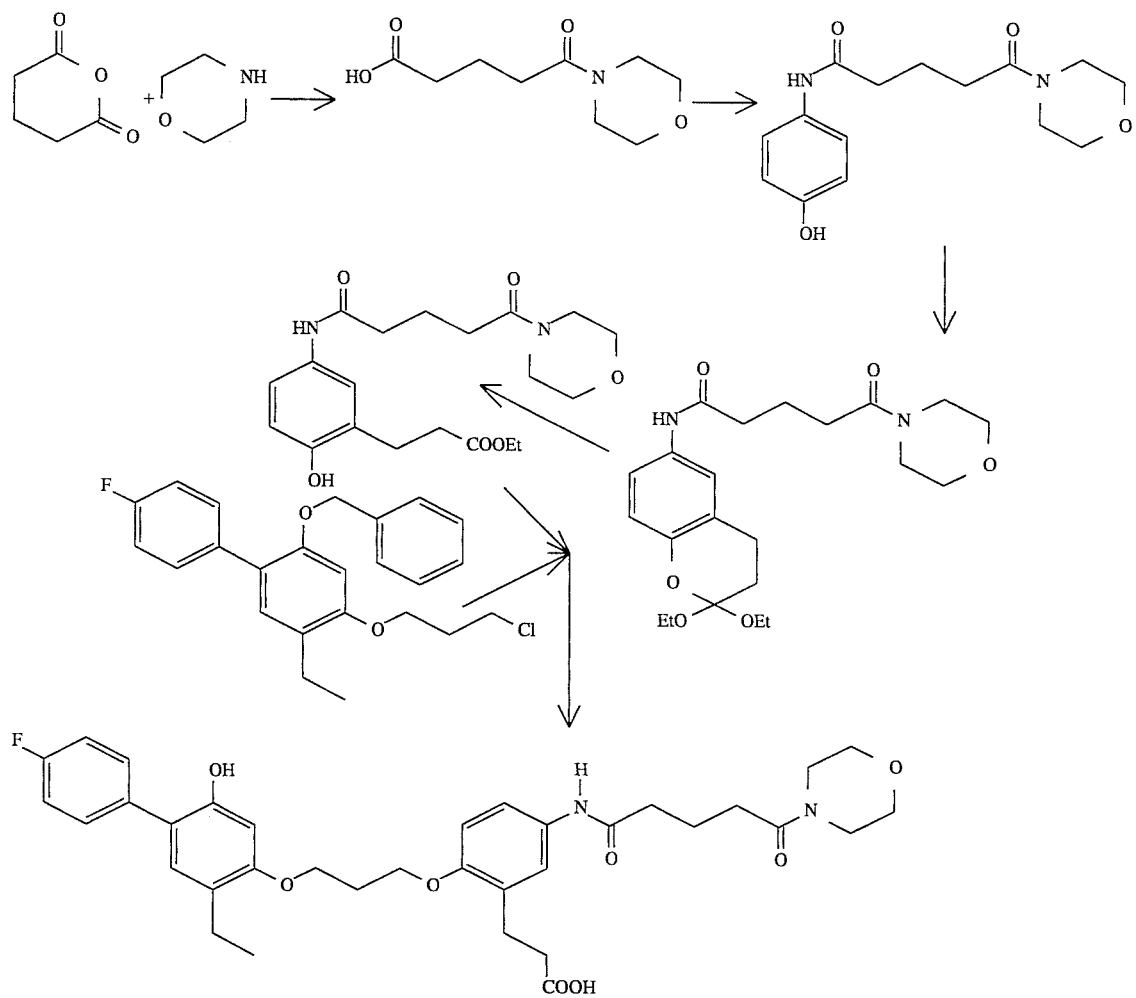

A. Preparation of 5-oxo-5-morpholinopentanoic acid.

A mixture of glutaric anhydride (28.8 g, 253 mmol) and morpholine (20.0 g, 230 mmol) in xylenes (500 mL) was refluxed for 45 minutes. The mixture was concentrated in vacuo to provide the title intermediate in quantitative yield as a light orange oil that crystallized upon standing: mp 81°–83° C.; NMR (CDCl$_3$) 9.80 (bs, 1H, —OH), 3.67 (m, 4H), 3.61 (m, 2H), 2.44 (m, 4H), 1.98 (quintet, J=6 Hz, 2H); MS-FD m/e 202 (p); IR (CHCl$_3$, cm$^{-1}$) 3100 (b), 3020, 1711, 1635, 1439, 1272, 1237, 1116, 1033.

B. Preparation of 4-(5-oxo-5-morpholinopentanamido)-phenol.

5-Oxo-5-morpholinopentanoic acid (20.0 g, 99.8 mmol) was dissolved in methylene chloride (250 mL) and carefully treated with oxalyl chloride (15.2 g, 200 mmol) at room temperature. After gas evolution had subsided (approximately 1 hour) the mixture was concentrated in vacuo. The residue was dissolved in a fresh portion of methylene chloride (50 mL) and added dropwise over 2 hours to a suspension of 4-aminophenol (9.88 g, 99.8 mmol) and triethylamine (11.1 g, 110 mmol) cooled to 0° C. After stirring for 2 hours the mixture was washed twice with water. The aqueous layer was back-extracted with three fresh portions of ethyl acetate. The combined organic layers were dried over sodium sulfate, filtered, and concentrated in vacuo to provide a dark oil. Silica gel chromatography (ethyl acetate/hexane) provided 9.70 g (34%) of the title intermediate as a colorless oil: NMR (CDCl$_3$) 8.58 (bs, 1H), 8.50 (bs, 1H), 7.24 (d, J=8 Hz, 2H), 6.70 (d, J=8 Hz, 2H), 3.55 (m, 6H), 3.38 (m, 2H), 2.32 (q, J=6 Hz, 4H), 1.90 (m, 2H).

C. Preparation of 2,2-diethoxy-3,4-dihydro-6-( 5-oxo-5-morpholinopentanamido)-2H-1-benzopyran.

4-(5-Oxo-5-morpholinopentanamido)phenol (3.00 g, 10.3 mmol) was converted to the desired title intermediate as described above for the preparation of Example 59(A). Recrystallization (ethyl acetate/hexane) provided 3.51 g (81%) of the desired title intermediate as a white crystalline solid: mp 141°–143° C.; NMR (CDCl$_3$) 7.88 (bs, 1H, —NH), 7.40 (d, J=2.4 Hz, 1H), 7.15 (dd, J=8.7, 2.6 Hz, 1H), 6.83 (d, J=8.7 Hz, 1H), 3.70 (m, 10H), 3.51 (m, 2H), 2.86 (t, J=6.8 Hz, 2H), 2.48 (m, 4H), 2.07 (4H, m), 1.20 (t, J=7.1 Hz, 6H); MS-FD m/e 421 (p+1, 24), 420 (p, 100); IR (CHCl$_3$, cm$^{-1}$) 3010, 1629, 1499, 1116, 1086, 1048. Analysis for $C_{22}H_{32}N_2O_6$: Calc: C, 62.84; H, 7.67; N, 6.66; Found: C, 62.64; H, 7.38; N, 6.47.

D. Preparation of 3-[2-[1-hydroxy-4-(5-oxo- 5-morpholinopentanamido)phenyl]]propanoic acid ethyl ester.

To a solution of 2,2-diethoxy-3,4-dihydro-6-(5-oxo-5-morpholinopentanamido)-2H-1-benzopyran (1.33 g)in tetrahydrofuran (25 mL) was added 1N aqueous hydrochloric acid (0.15 mL). The mixture was stirred for 1 hour at room temperature then diluted with water and extracted three times with ethyl acetate. The combined organic layers were dried over sodium sulfate, filtered, and concentrated in vacuo to provide an off-white solid. Recrystallization from hexane/ethyl acetate provided 1.03 g (83%) of the desired title ester: mp 77°–79° C.; NMR (CDCl$_3$) 7.98 (bs, 1H,—NH), 7.35 (d, J=2.5 Hz, 1H), 7.14 (dd, J=8.5, 2.5 Hz, 1H), 6.82 (d, J=8.5 Hz, 1H), 4.14 (q, J=7.1 Hz, 2H), 3.64 (m, 6H), 3.50 (m, 2H), 2.87 (t, J=6.6 Hz, 2H), 2.69 (t, J=6.6 Hz, 2H), 2.48 (t, J=6.9 Hz, 2H), 2.43 (t, J=7.7 Hz, 2H), 2.02 (m, 2H), 1.24 (t, J=7.2 Hz, 3H); MS-FD m/e 393 (p); IR (CHCl$_3$, cm$^{-1}$) 3350 (b), 3020, 1629, 1503, 1234, 1116. Analysis for $C_{20}H_{28}N_2O_6$: Calc: C, 61.21; H, 7.19; N, 7.14; Found: C, 61.10; H, 7.18; N, 7.14.

E. Preparation of 3-[2-[1-[2-ethyl-4-(4-fluorophenyl)-5-(phenylmethoxy)phenoxy]propoxy]-4-(5-oxo-5-morpholinopentanamido)phenyl]propanoic acid ethyl ester.

2-Benzyloxy-1-(4-fluorophenyl)-5-ethyl-4-(3-chloro-1-propyloxy)benzene (1.00 g, 2.51 mmol) was converted to the corresponding iodide and reacted with 3-[2-[1-hydroxy-4-(5-oxo-5-morpholinopentanamido)phenyl]]propanoic acid ethyl ester (980 mg, 2.51 mmol) as described above for the preparation of Example 66(A). The crude product was purified by silica gel chromatography to provide 800 mg (32%) of the title ester intermediate as a colorless oil: NMR (CDCl$_3$) 9.66 (bs, 1H, —NH), 7.50 (m, 2H), 7.25–7.42 (m, 7H), 7.16 (t, J=8.9 Hz, 2H), 7.04 (s, 1H), 6.89 (d, J=8.8 Hz, 1H), 6.81 (s, 1H), 5.10 (s, 2H), 4.20 (t, J=6.1 Hz, 2H), 4.12 (t, J=5.8 Hz, 2H), 3.96 (q, J=7.2 Hz, 2H), 3.52 (m, 4H), 3.40 (m, 4H), 2.76 (t, J=7.3 Hz, 2H), 2.48 (m, 6H), 2.28 (m, 4H), 2.18 (quintet, J=7 Hz, 2H), 1.07 (m, 6H); MS-FD m/e 755 (p); IR (CHCl$_3$, cm$^{-1}$)3420 (b), 2975, 1604, 1500, 1234, 1145, 1117, 1042. Analysis for $C_{44}H_{51}N_2O_8F$: Calc: C, 70.01; H, 6.81; N, 3.71; Found: C, 69.77; H, 6.89; N, 3.77.

F. Preparation of 3-[2-[1-[2-ethyl-4-(4-fluorophenyl)-5-hydroxyphenoxy]propoxy]-4-(5-oxo-5-morpholino-pentanamido)phenyl]propanoic acid.

3-[2-[1-[2-ethyl-4-(4-fluorophenyl)-5-(phenylmethoxy)phenoxy]propoxy]-4-(5-oxo-5-morpholinopentanamido)phenyl]-propanoic acid ethyl ester (800 mg, 1.06 mmol) was subjected to de-benzylation and hydrolysis as described above for the preparation of Example 60. This procedure provided 450 mg (46%) of the title product as an off-white crystalline material: mp 78°–80° C.; NMR (CDCl$_3$) 8.48 (bs, 1H, —NH), 7.45 (m, 3H), 7.20 (s, 1H), 7.06 (m, 2H), 6.99 (s, 1H), 6.75 (d, J=8.8 Hz, 1H), 6.56 (s, 1H), 4.10 (m, 4H), 3.58 (m, 6H), 3.35 (m, 2H), 2.88 (t, J=7.5 Hz, 2H), 2.55 (m, 4H), 2.37 (m, 4H), 2.24 (t, J=5.5 Hz, 2H), 1.92 (m, 2H), 1.16 (t, J=7.5 Hz, 3H); MS-FD m/e 638 (p+1, 63), 637 (p, 100); IR (CHCl$_3$, cm$^{-1}$) 2973, 1618, 1502, 1235, 1146, 1117. Analysis for $C_{35}H_{41}N_2O_8F$: Calc: C, 66.02; H, 6.49; N, 4.40; Found: C, 66.29; H, 6.72; N, 4.26.

EXAMPLE 70

2-Fluoro-6-[2-propyl-3-[3-[2-ethyl-5-hydroxy-4-(4-fluorophenyl)phenoxy]propoxy]phenoxy]benzoic acid disodium salt hydrate

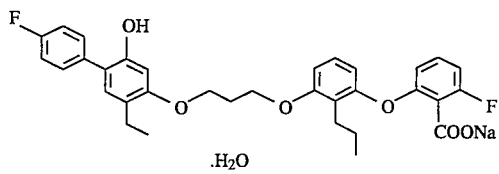

A. Preparation of 2-fluoro-6-[2-propyl-3-[3-[4-bromo-2-ethyl-5-(phenylmethoxy)phenoxy]propoxy]phenoxy]benzoic acid methyl ester.

2-Fluoro-6-(3-hydroxy-2-propylphenoxy)benzoic acid methyl ester (1.84 g, 4.80 mmol) was alkylated with 2-benzyloxy-1-bromo-5-ethyl-4-(3-chloro-1-propyloxy)benzene as described above for the preparation of Example 60 to provide crude product as an oil. Silica gel chromatography provided 2.05 g (66%) of the purified title intermediate as a colorless oil: NMR (CDCl$_3$) 7.49 (d, J=7.1 Hz, 2H), 7.20–7.45 (m, 5H), 7.14 (t, J=8.2 Hz, 1H), 6.82 (t, J=8.5 Hz, 1H), 6.73 (d, J=8.3 Hz, 1H), 6.60 (d, J=8.4 Hz, 1H), 6.53 (s, 1H), 6.52 (d, J=8.5 Hz, 1H), 5.13 (s, 2H), 4.20 (t, J=6.0 Hz, 2H), 4.13 (t, J=6.0 Hz, 2H), 3.92 (s, 3H), 2.58 (m, 4H), 2.30 (quintet, J=6.0 Hz, 2H), 1.51 (hextet, J=7.6 Hz, 2H), 1.16 (t, J=7.9 Hz, 3H), 0.90 (t, J=7.3 Hz, 3H).

B. Preparation of 2-fluoro-6-[2-propyl-3-[3-[2-ethyl-5-hydroxy-4-(4-fluorophenyl)phenoxy]propoxy]phenoxy]benzoic acid disodium salt hydrate.

To a solution of 2-fluoro-6-[2-propyl-3-[3-[4-bromo-2-ethyl-5-(phenylmethoxy)phenoxy]propoxy]phenoxy]benzoic acid methyl ester (1.77 g, 2.72 mmol) in benzene (12 mL) was added tetrakis(triphenylphosphine)palladium(0) (0.33 g, 0.30 mmol) and 2.0M aqueous sodium carbonate (4 mL). To this mixture was added a solution of 4-fluorophenylboronic acid (4.10 g, 8.16 mmol) in ethanol (5 mL). The resulting mixture was refluxed for 4 hours then cooled to room temperature. The mixture was diluted with ethyl acetate and shaken. The organic layer was washed once with water and once with 1N aqueous sodium hydroxide, dried over sodium sulfate, filtered, and concentrated in vacuo to provide an oil. De-benzylation and hydrolysis proceeded as described above for the preparation of Example 60. Salt formation and purification as described above for the preparation of Example 59(D) provided 403 mg (25%) of the desired title product as a fluffy white solid: NMR (DMSO-d$_6$) 9.83 (bs, 1H), 7.50 (m, 2H), 6.96–7.16 (m, 4H), 6.96 (s, 1H), 6.74 (t, J=8.4 Hz, 2H), 6.57 (s, 1H), 6.40 (d, J=8.3 Hz, 1H), 6.35 (d, J=8.3 Hz, 1H), 4.16 (t, J=5.7 Hz, 2H), 4.05 (t, J=5.5 Hz, 2H), 2.40–2.58 (m, 4H), 2.18 (quintet, J=4.1 Hz, 2H), 1.41 (hextet, J=7.4 Hz, 2H), 1.07 (t, J=7.5 Hz, 3H), 0.80 (t, J=7.3 Hz, 3H); MS-FAB m/e 586 (p+1, 35), 585 (p, 100), 562 (33), 313 (30). IR (CHCl$_3$, cm$^{-1}$) 3300 (b), 2967, 1616, 1455, 1398, 1115. Analysis for $C_{33}H_{31}O_6F_2Na \cdot H_2O$: Calc: C, 65.77; H, 5.52; Found: C, 65.81; H, 5.41.

EXAMPLE 71

4-Fluoro-2-[2-propyl-3-[3-[2-ethyl-5-hydroxy-4-(4-fluorophenyl)phenoxy]propoxy]phenoxy]benzoic acid

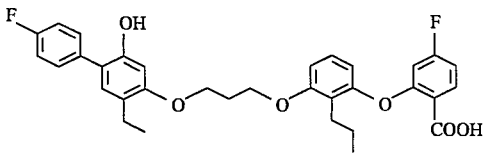

A. Preparation of 4-fluoro-2-(3-hydroxy-2-propylphenoxy)benzoic acid methyl ester.

To a solution of 2-propylresorcinol (10.0 g, 65.7 mmol) in pyridine (120 mL) was added potassium tert-butoxide (7.00 g, 62.5 mmol) at room temperature with stirring. To this was added a mixture of methyl 2-bromo-4-fluorobenzoate (7.60 g, 32.6 mmol) and copper(I) iodide (12.5 g, 65.7 mmol) in pyridine (120 mL). The resulting mixture was gently refluxed for 4 hours. The reaction was cooled to room temperature and stirred for 18 hours. The mixture was concentrated in vacuo and the resulting material dissolved in ethyl ether. The solution was washed once with 5N aqueous hydrochloric acid. The aqueous layer was extracted once with fresh ethyl ether and the combined organic layers were washed twice with 5N aqueous ammonium hydroxide. The organic layer was washed once with a saturated sodium chloride solution, dried over sodium sulfate, filtered, and concentrated in vacuo. Silica gel chromatography of the resulting residue provided 1.45 g (15%) of the desired intermediate product as a light tan solid: mp 92°–94° C.; NMR (CDCl$_3$) 7.95 (m, 1H), 7.04 (t, J=9.5 Hz, 1H), 6.79 (t, J=9 Hz, 1H), 6.65 (d, J=9.5 Hz, 1H), 6.50 (m, 2H), 5.25 (bs, 1H, —OH), 3.88 (s, 3H), 2.60 (t, J=8.7 Hz, 2H), 1.55 (hextet, J=7.8 Hz, 2H), 0.92 (t, J=7.8 Hz, 3H); MS-FD m/e 305 (p+1, 40), 304 (p, 100); IR. Analysis for $C_{17}H_{17}O_4F$: Calc: C, 67.10; H, 5.63; Found: C, 67.32; H, 5.78.

B. Preparation of 4-fluoro-2-[2-propyl-3-[ 3-[4-(4-fluorophenyl)-2-ethyl-5-(phenylmethoxy)phenoxy] propoxy] phenoxy]benzoic acid methyl ester.

4-Fluoro-6-(3-hydroxy-2-propylphenoxy)benzoic acid methyl ester (0.534 g, 1.75 mmol) was alkylated with 2-benzyloxy-1-(4-fluorophenyl)-5-ethyl- 4-(3-chloro-1-propyloxy)benzene as described above for the preparation of Example 66(A) to provide crude product as an oil. Purification via silica gel chromatography provided 640 mg (55%) of the desired title intermediate as a white crystalline solid: mp 77°–78° C.; NMR (CDCl$_3$) 7.95 (t, J=7.8 Hz, 1H), 7.53 (m, 2H), 7.32 (m, 4H), 7.03–7.20 (m, 3H), 6.77 (m, 2H), 6.62 (s, 1H), 6.55 (d, J=8 Hz, 1H), 6.50 (d, J=9 Hz, 1H), 5.05 (s, 2H), 4.25 (m, 4H), 3.89 (s, 3H), 2.65 (m, 4H), 2.34 (quintet, J=6 Hz, 4H), 1.55 (hextet, J=6 Hz, 2H), 1.22 (t, J=7 Hz, 3H), 0.92 (t, J=7 Hz, 3H); MS-FD m/e 666 (p); IR (CHCl$_3$, cm$^{-1}$)2960, 1730, 1600, 1499, 1461, 1268, 1110. Analysis for $C_{44}H_{40}O_6F_2$: Calc: C, 73.86; H, 6.05; Found: C, 73.17; H, 6.44.

C. Preparation of 4-fluoro-2-[2-propyl-3-[3-[ 4-(4-fluorophenyl)-2-ethyl-5-hydroxyphenoxy]propoxy] phenoxy] benzoic acid methyl ester.

4-Fluoro-2-[2-propyl-3-[3-[ 4-(4-fluorophenyl)-2-ethyl-5-(phenylmethoxy)phenoxy]propoxy]phenoxy]benzoic acid methyl ester (590 mg) was dissolved in ethyl acetate (25 mL) containing 10% palladium on carbon (118 mg) and hydrogenated at 2 atmospheres for 18 hours. The mixture was filtered through Celite® and concentrated in vacuo to provide an oil. Purification of the crude material via silica gel chromatography provided 400 mg (79%) of the title intermediate as a glass: NMR (CDCl$_3$) 7.97 (t, J=7.8 Hz, 1H), 7.44 (m, 2H), 7.17 (m, 3H), 7.03 (s, 1H), 6.79 (m, 2H), 6.45–6.63 (m, 3H), 5.38 (bs, 1H, —OH), 4.22 (m, 4H), 3.92 (s, 3H), 2.65 (m, 4H), 2.35 (quintet, J=5 Hz, 2H), 1.57 (hextet, J=7 Hz, 2H), 1.24 (t, J=7.8 Hz, 3H), 0.95 (t, J=7.8 Hz, 3H); MS-FD m/e 578 (p+2, 50), 577 (p+1, 90), 576 (p, 100); IR (CHCl$_3$, cm$^{-1}$) 3563 (b), 2965, 1722, 1604, 1585, 1497, 1461, 1267, 1251, 1152, 1110. Analysis for $C_{34}H_{34}O_6F_2$: Calc: C, 70.82; H, 5.94; Found: C, 71.12; H, 5.96.

D. Preparation of 4-fluoro-2-[2-propyl-3-[3-[ 2-ethyl-5-hydroxy-4-(4-fluorophenyl)phenoxy]propoxy]phenoxy] benzoic acid.

4-Fluoro-2-[2-propyl-3-[3-[4-(4-fluorophenyl)-2-ethyl-5-hydroxyphenoxy]propoxy]phenoxy]benzoic acid methyl ester (350 mg) was hydrolyzed as described for the preparation of Example 60 to provide 310 mg (91%) of the desired title product as a white solid: mp 62°–64° C.; NMR (CDCl$_3$) 8.21 (t, J=7.8 Hz, 1H), 7.35 (m, 2H), 7.10–7.30 (m, 3H), 7.97 (s, 1H), 6.84 (m, 2H), 6.63 (d, J=6.8 Hz, 1H), 6.52 (s, 1H), 6.41 (d, J=9 Hz, 1H), 5.10 (bs, 1H, —OH), 4.23 (m, 4H), 2.57 (m, 4H), 2.34 (quintet, J=5 Hz, 2H), 1.50 (hextet, J=6 Hz, 2H), 1.17 (t, J=7.8 Hz, 3H), 0.88 (t, =7.8 Hz, 3H); MS-FD m/e 564 (p+2, 30), 562 (p, 100); IR (CHCl$_3$, cm$^{-1}$) 3379 (b), 2963, 1699, 1607, 1500, 1268, 1247, 1146, 1110, 839. Analysis for $C_{33}H_{32}O_6F_2$: Calc: C, 70.45; H, 5.73; Found: C, 70.15; H, 5.81.

EXAMPLE 72

2-[2-Propyl-3-[5-[2-ethyl-5-hydroxy-4-(4-fluorophenyl)phenoxy]pentoxy]phenoxy]benzoic acid

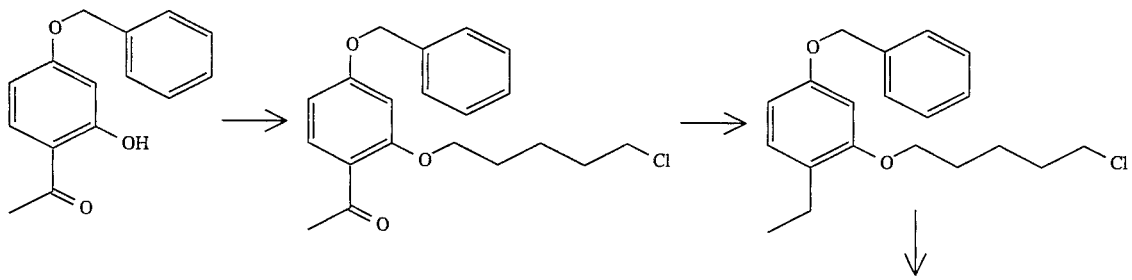

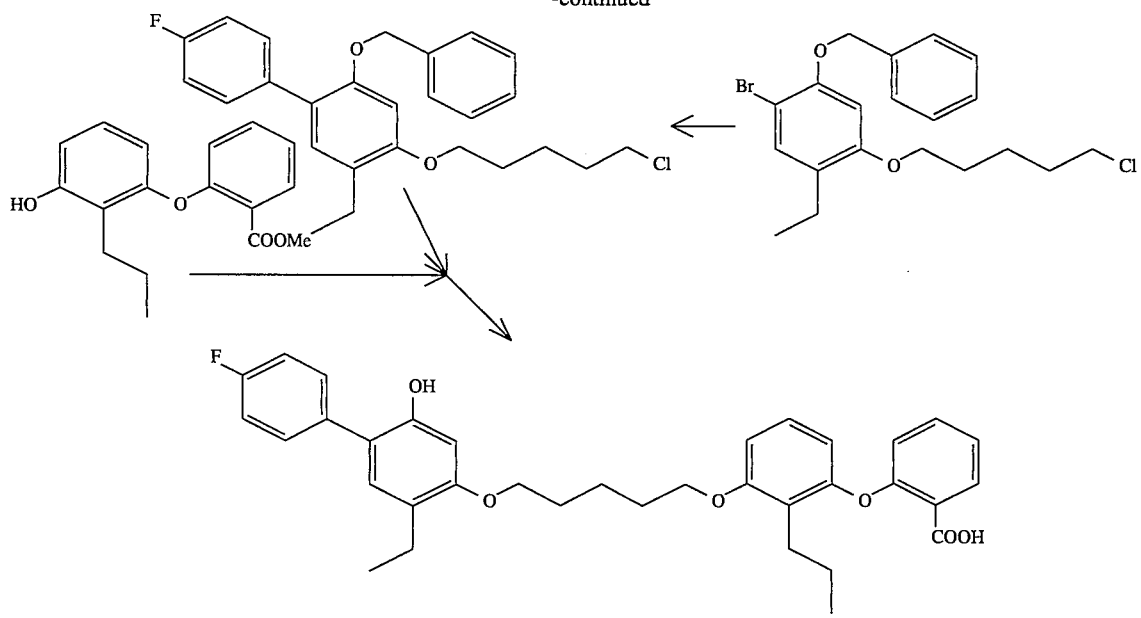

-continued

A. Preparation of 2-(5-chloropentoxy)- 4-(phenylmethoxy) acetophenone.

A mixture of 2-hydroxy-4-(phenylmethoxy)acetophenone (15.5 g, 64.0 mmol), potassium carbonate (8.83 g, 64.0 mmol), and dimethylsulfoxide (15 mL) in 2-butanone (145 mL) was stirred at room temperature for 30 minutes. 1-Bromo-5-chloropentane (11.9 g, 64.0 mmol) was added and the resulting mixture heated at reflux for 18 hours. The reaction mixture was cooled, diluted with water, and extracted with ethyl acetate. The organic layer was washed once with a saturated sodium chloride solution, dried over sodium sulfate, filtered, and concentrated in vacuo to provide a waxy solid. Purification via silica gel chromatography (ethyl acetate/hexane) provided 16.1 g (73%) of the title intermediate as a white solid: mp 76°–77° C.; NMR (CDCl$_3$) 7.85 (d, J=8.7 Hz, 1H), 7.43 (m, 5H), 6.59 (d, J=8.5 Hz, 1H), 6.53 (s, 1H), 5.11 (s, 2H), 4.05 (t, J=6 Hz, 2H), 3.61 (t, J=6 Hz, 2H), 2.60 (s, 3H), 1.90 (m, 4H), 1.69 (m, 2H); MS-FD m/e 348 (p+2, 65), 346 (p, 100); IR (CHCl$_3$, cm$^{-1}$) 3025, 1662, 1598, 1268, 1184, 1139, 1027.

B. Preparation of 2-(5-chloropentoxy)- 4-(phenylmethoxy)ethylbenzene.

To a solution of 2-(5-chloropentoxy)-4-(phenylmethoxy)- acetophenone (15.0 g, 43.2 mmol) in trifluoroacetic acid (33.3 mL) at 0° C. was added triethylsilane (11.0 g, 95.1 mmol) dropwise. The resulting mixture was stirred at 0° C. for 2.5 hours then treated with excess saturated sodium bicarbonate solution. The mixture was extracted with ether. The organic layer was washed once with a saturated sodium chloride solution, dried over sodium sulfate, filtered, and concentrated in vacuo to reveal a yellow oil. Purification via silica gel chromatography (ethyl acetate/hexane) provided 10.45 g (73%) of the title intermediate as a faint yellow oil: NMR (CDCl$_3$) 7.20–7.55 (m, 5H), 7.08 (d, J=9.7 Hz, 1H), 6.53 (s, 1H), 6.51 (d, J=8.7 Hz, 1H), 5.05 (s, 2H), 3.95 (t, J=6.8 Hz, 2H), 3.60 (t, J=6.8 Hz, 2H), 2.59 (q, J=7.8 Hz, 2H), 1.75–1.95 (m, 4H), 1.69 (quintet, J=6 Hz), 1.18 (t, J=7.8 Hz, 3H); MS-FD m/e; IR (CHCl$_3$, cm$^1$) 2937, 1613, 1587, 1505, 1289, 1258, 1172, 1132, 1028. Analysis for C$_{20}$H$_{25}$O$_2$Cl: Calc: C, 72.12; H, 7.57; Found: C, 71.24; H, 7.64.

C. Preparation of 3-bromo-6-(5-chloropentoxy)- 4-(phenylmethoxy)ethylbenzene.

A mixture of 2-(5-chloropentoxy)-4-(phenylmethoxy)ethylbenzene (10.0 g, 31.0 mmol) and N-bromosuccinimide (5.35 g, 30.1 mmol) in carbon tetrachloride (100 mL) was warmed slightly for 2 hours, then stirred at room temperature for 18 hours. The mixture was washed sequentially with water, 1N aqueous sodium thiosulfate solution, and saturated sodium chloride solution. The organic layer was dried over sodium sulfate, filtered, and concentrated in vacuo to provide a white solid. Recrystallization from hexane provided 10.0 g (81%) of the desired title intermediate as a white crystalline solid: mp 54°–55° C.; NMR (CDCl$_3$) 7.50 (m, 2H), 7.25–7.48 (m, 4H), 6.48 (s, 1H), 5.15 (s, 2H), 3.91 (t, J=6 Hz, 2H), 3.58 (t, J=6 Hz, 2H), 2.55 (q, J=7 Hz, 2H), 1.85 (m, 4H), 1.65 (m, 2H), 1.16 (t, J=7.8 Hz, 3H); MS-FD m/e 414 (p+2, 25), 412 (p, 100), 410 (p–2, 85); IR (CHCl$_3$, cm$^{-1}$)2950, 1602, 1501, 1450, 1370, 1300, 1163. Analysis for C$_{20}$H$_{24}$O$_2$BrCl: Calc: C, 58.34; H, 5.87; Found: C, 58.31; H, 6.04.

D. Preparation of 6-(5-chloropentoxy)-2-( 4-fluorophenyl)-4-(phenylmethoxy)ethylbenzene.

3-Bromo-6-(5-chloropentoxy)-4-(phenylmethoxy)ethylbenzene (8.80 g, 26.4 mmol) was coupled to 4-fluorophenylboronic acid as described above for the preparation of Example 70(B). Purification via silica gel chromatography (ethyl acetate/hexane) followed by recrystallization from hexane provided 7.04 g (77%) of the intermediate title product as a white solid: mp 55°–56° C.; NMR (CDCl$_3$) 7.54 (m, 2H), 7.33 (m, 5H), 7.11 (m, 3H), 6.59 (s, 1H), 5.07 (s, 2H), 3.99 (t, J=6 Hz, 2H), 3.62 (t, J=6 Hz, 2H), 2.65 (q, J=8 Hz, 2H), 1.90 (m, 4H), 1.70 (m, 2H), 1.14 (t, J=8 Hz, 3H); IR (CHCl$_3$, cm$^{-1}$) 2938, 1613, 1497, 1143, 1027. Analysis for C$_{26}$H$_{28}$O$_2$ClF: Calc: C, 73.14; H, 6.61; Found: C, 72.91; H, 6.69.

E. Preparation of 2-[2-propyl-3-[5-[2-ethyl-4-( 4-fluorophenyl)-5-(phenylmethoxy)phenoxy]pentoxy]phenoxy] benzoic acid methyl ester.

2-(3-Hydroxy-2-propylphenoxy)benzoic acid methyl ester (2.00 g, 6.99 mmol) was alkylated with 6-(5-chloropentoxy)- 2-(4-fluorophenyl)-4-(phenylmethoxy)ethylbenzene as described above for the preparation of Example 66(A) to provide crude product as an oil. Purification via silica gel chromatography (ethyl acetate/hexane) provided 3.90 g (83%) of title intermediate as a colorless oil: NMR (CDCl$_3$) 7.94 (d, J=8 Hz, 1H), 7.55 (m, 2H), 7.35 (m, 6H), 7.11 (m, 5H), 6.85 (d, J=9 Hz, 1H), 6.70 (d, J=9 Hz, 1H), 6.60 (s, 1H), 6.48 (d, J=9 Hz, 1H), 5.07 (s, 2H), 4.08 (t, J=5 Hz, 2H), 4.03 (t, J=5 Hz, 2H), 3.89 (s, 3H), 2.70 (m, 4H), 1.95 (m, 4H), 1.76 (m, 2H), 1.62 (m, 2H), 1.24 (t, J=7 Hz, 3H), 0.95 (t, J=7 Hz, 3H); MS-FD m/e 677 (p+1, 65), 676 (p, 100); IR (CHCl$_3$, cm$^{-1}$) 2965, 1740, 1604, 1497, 1461, 1453, 1306, 1111. Analysis for C$_{42}$H$_{45}$O$_6$F: Calc: C, 76.31; H, 6.70; Found: C, 76.24; H, 6.83.

F. Preparation of 2-[2-propyl-3-[5-[2-ethyl- 5-hydroxy-4-(4-fluorophenyl)phenoxy]pentoxy]phenoxy]benzoic acid.

2-[2-Propyl-3-[5-[2-ethyl-4-(4-fluorophenyl)- 5-(phenylmethoxy)phenoxy]pentoxy]phenoxy]benzoic acid methyl ester (3.60 g, 5.32 mmol) was submitted to de-benzylation and hydrolysis as described above for the preparation of Example 60. The product was isolated via vacuum filtration as a white crystalline solid: mp 65° C. (dec); NMR (CDCl$_3$) 8.25 (dd, J=7.9, 1.7 Hz, 1H), 7.44 (m, 3H), 7.18 (m, 4H), 6.97 (s, 1H), 6.80 (d, J=8.2 Hz, 1H), 6.75 (d, J=8.5 Hz, 1H), 6.65 (d, J=8.1 Hz, 1H), 6.54 (s, 1H), 5.15 (bs, 1H, —OH), 4.10 (t, J=6.1 Hz, 2H), 4.05 (t, J=5.6 Hz, 2H), 2.61 (m, 4H), 1.93 (m, 4H), 1.75 (m, 2H), 1.54 (hextet, J=7.4 Hz, 2H), 1.18 (t, J=7.4 Hz, 3H), 0.89 (t, J=7.3 Hz, 3H); MS-FD m/e 572 (p); IR (CHCl$_3$, cm$^{-1}$) 3350 (b), 2965, 1739, 1605, 1496, 1455, 1238, 1108. Analysis for C$_{35}$H$_{37}$O$_6$F: Calc: C, 73.41; H, 6.51; Found: C, 73.13; H, 6.59.

EXAMPLE 73

2-[2-Propyl-3-[4-[2-ethyl-5-hydroxy-4-(4-fluorophenyl)phenoxy]butoxy]phenoxy]benzoic acid sesquihydrate

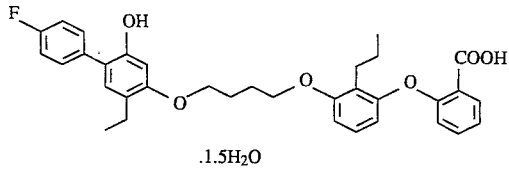

.1.5H$_2$O

A. Preparation of 2-(4-chlorobutoxy)-4-(phenylmethoxy)acetophenone.

2-Hydroxy-4-(phenylmethoxy)acetophenone (9.20 g, 37.9 mmol) was alkylated with 1-bromo-4-chlorobutane as described above for the preparation of Example 72(A). The crude material was purified via silica gel chromatography (ethyl acetate/hexane) to provide 7.70 g (61%) of the desired title product as a white solid: mp 58°–60° C.; NMR (CDCl$_3$) 7.83 (d, J=9 Hz, 1H), 7.33–7.47 (m, 5H), 6.59 (dd, J=9, 2 Hz, 1H), 6.53 (d, J=2 Hz, 1H), 5.10 (s, 2H), 4.05 (t, J=5 Hz, 2H), 3.62 (t, J=5 Hz, 2H), 2.57 (s, 3H), 2.02 (m, 4H); MS-FD m/e 334 (p+1, 50), 333 (p, 28), 332 (p−1,100); IR (CHCl$_3$, cm$^{-1}$) 3013, 1663, 1599, 1267, 1184, 1027. Analysis for C$_{19}$H$_{21}$O$_3$Cl: Calc: C, 68.57; H, 6.36; Found: C, 68.77; H, 6.60.

B. Preparation of 2-(4-chlorobutoxy)-4-(phenylmethoxy)ethylbenzene.

2-(4-Chlorobutoxy)-4-(phenylmethoxy)-acetophenone (3.50 g, 10.5 mmol) was reduced as described above for the preparation of Example 72(B). Purification via silica gel chromatography (ethyl acetate/hexane) provided 2.60 g (79%) of the desired title intermediate as a colorless oil: NMR (CDCl$_3$) 7.13–7.55 (m, 5H), 7.08 (d, J=8.9 Hz, 1H), 6.54 (m, 2H), 5.07 (s, 2H), 3.99 (d, J=5.7 Hz, 2H), 3.65 (t, J=6.0 Hz, 2H), 2.65 (q, J=7.5 Hz, 2H), 2.00 (m, 4H), 1.22 (t, J=7.5 Hz, 3H); MS-FD m/e; IR (CHCl$_3$, cm$^{-1}$) 2966, 1613, 1506, 1289, 1171, 1132, 1028. Analysis for C$_{19}$H$_{23}$O$_2$Cl: Calc: C, 71.57; H, 7.27; Found: C, 71.78; H, 7.40.

C. Preparation of 3-bromo-6-(4-chlorobutoxy)- 4-(phenylmethoxy)ethylbenzene.

2-(4-Chlorobutoxy)-4-(phenylmethoxy)ethylbenzene (2.50 g, 7.84 mmol) was brominated as described above for the preparation of Example 72(C). Recrystallization of the crude product from hexane provided 2.52 g (81%) of the desired title product: mp 65°–66° C.; NMR (CDCl$_3$) 7.50 (d, J=8 Hz, 2H), 7.34–7.48 (m, 3H), 7.32 (s, 1H), 6.49 (s, 1H), 5.15 (s, 2H), 3.92 (t, J=5.6 Hz, 2H), 3.64 (t, J=5.9 Hz, 2H), 2.55 (q, J=7.5 Hz, 2H), 1.97 (m, 4H), 1.15 (t, J=7.5 Hz, 3H); MS-FD m/e 398 (p, 100), 396 (p−2, 70); IR (CHCl$_3$, cm$^{-1}$) 2967, 1602, 1501, 1455, 1389, 1285, 1163, 1060. Analysis for C$_{19}$H$_{22}$O$_2$BrCl: Calc: C, 57.38; H, 5.57; Found: C, 57.27; H, 5.62.

D. Preparation of 6-(4-chlorobutoxy)-2-( 4-fluorophenyl)-4-(phenylmethoxy)ethylbenzene.

3-Bromo-6-(4-chlorobutoxy)-4-(phenylmethoxy)ethylbenzene (2.30 g, 26.4 mmol) was coupled to 4-fluorophenylboronic acid as described above for the preparation of Example 70(B). Purification via silica gel chromatography (ethyl acetate/hexane) followed by trituration with methanol provided 2.07 g (87%) of the titled intermediate product as a white solid: mp 48°–49° C.; NMR (CDCl$_3$) 7.55 (m, 2H), 7.35 (m, 5H), 7.12 (m, 3H), 6.59 (s, 1H), 5.08 (s, 2H), 4.03 (t, J=5.3 Hz, 2H), 3.68 (t, J=5.3 Hz, 2H), 2.67 (q, J=7.5 Hz, 2H), 2.02 (m, 4H), 1.24 (t, J=7.5 Hz, 3H); MS-FD m/e 412 (p); IR. Analysis for C$_{25}$H$_{26}$O$_2$ClF: Calc: C, 72.72; H, 6.35; Found: C, 72.59; H, 6.46.

E. Preparation of 2-[2-propyl-3-[4-[2-ethyl-4-( 4-fluorophenyl)-5-(phenylmethoxy)phenoxy]butoxy]phenoxy] benzoic acid methyl ester.

2-(3-Hydroxy-2-propylphenoxy)benzoic acid methyl ester (1.40 g, 4.84 mmol) was alkylated with 6-(4-chlorobutoxy)- 2-(4-fluorophenyl)-4-(phenylmethoxy)ethylbenzene as described above for the preparation of Example 66(A) to provide crude product as an oil. Purification via silica gel chromatography (ethyl acetate/hexane) provided 2.40 g (75%) of the title intermediate as a colorless oil: NMR (CDCl$_3$) 7.93 (dd, J=6.2, 1.7 Hz, 1H), 7.54 (m, 2H), 7.25–7.45 (m, 6H), 7.13 (m, 5H), 6.88 (d, J=8.8 Hz, 1H), 6.70 (d, J=8.8 Hz, 1H), 6.63 (s, 1H), 6.50 (d, J=8.3 Hz, 1H), 5.07 (s, 2H), 4.12 (m, 4H), 3.89 (s, 3H), 2.68 (m, 4H), 2.09 (m, 4H), 1.63 (hextet, J=7.4 Hz, 2H), 1.15 (t, J=7.4 Hz, 3H), 0.97 (t, J=7.4 Hz, 3H); MS-FD m/e 663 (p+1, 35), 662 (p, 100); IR (CHCl$_3$, cm$^{-1}$)3470, 2950, 1760, 1740, 1461, 1305, 1135, 1071. Analysis for C$_{42}$H$_{43}$O$_6$F: Calc: C, 76.11; H, 6.54; Found: C, 76.36; H, 6.65.

F. Preparation of 2-[2-propyl-3-[4-[2-ethyl- 5-hydroxy-4-(4-fluorophenyl)phenoxy]butoxy]phenoxy]benzoic acid sesquihydrate.

2-[2-Propyl-3-[4-[2-ethyl-4-(4-fluorophenyl)- 5-(phenylmethoxy)phenoxy]butoxy]phenoxy]benzoic acid methyl ester (2.20 g, 3.32 mmol) was submitted to de-benzylation and hydrolysis as described above for the preparation of Example 60. This procedure provided 1.00 g (85%) of the title product as a white solid: mp 65°–68° C.; NMR (CDCl$_3$)

8.26 (dd, J=6.0, 1.8 Hz, 1H), 7.43 (m, 3H), 7.12–7.29 (m, 4H), 6.99 (s, 1H), 6.81 (d, J=8 Hz, 1H), 6.75 (d, J=8.2 Hz, 1H), 6.65 (d, J=8 Hz, 1H), 6.53 (s, 1H), 5.08 (bs, 1H, —OH), 4.12 (m, 4H), 2.63 (m, 4H), 2.08 (m, 4H), 1.55 (hextet, J=7.4 Hz, 2H), 1.20 (t, J=7.4 Hz, 3H), 0.90 (t, J=7.4 Hz, 3H); MS-FD m/e 559 (p+1, 57), 558 (p, 100); IR (CHCl$_3$, cm$^{-1}$) 3350 (b), 2950, 1739, 1625, 1496, 1455, 1237, 1108. Analysis for C$_{34}$H$_{35}$O$_6$F.1.5 H$_2$O: Calc: C, 69.73; H, 6.43; Found: C, 69.74; H, 6.54.

EXAMPLE 74

2-[2-(2-Methylpropyl)-3-[3-[2-ethyl-5-hydroxy-4-( 4-fluorophenyl)phenoxy]propoxy]phenoxy]benzoic acid

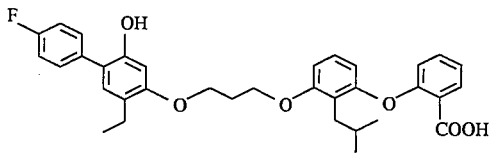

A. Preparation of 2-(2-methylpropyl)-1,3-dimethoxybenzene.

To a solution of 1,3-dimethoxybenzene (38.0 g, 272 mmol) in tetrahydrofuran (380 mL) at 0° C. was added a 1.6M solution of butyllithium in hexane (188 mL, 299 mmol). The resulting mixture was stirred at 0° C. for 2 hours. 1-Iodo-2-methylpropane (50.0 g, 272 mmol) was added and the reaction mixture warmed to room temperature, then refluxed for 36 hours. The mixture was cooled to room temperature, diluted with saturated ammonium chloride solution, and extracted twice with ethyl acetate. The organic layer was dried over sodium sulfate, filtered, and concentrated in vacuo. Purification via silica gel chromatography (ethyl acetate/hexane) provided 13.8 g (26%) of title intermediate product as a colorless oil: NMR (CDCl$_3$) 7.22 (t, J=9 Hz, 1H), 6.33 (d, J=10 Hz, 2H), 3.89 (s, 6H), 2.66 (d, J=9 Hz, 2H), 2.03 (heptet, J=8 Hz, 1H), 1.00 (d, J=8 Hz, 6H); IR (CHCl$_3$, cm$^{-1}$) 2959, 1593, 1474, 1261, 1133, 1075.

B. Preparation of 2-(2-methylpropyl)-1,3-dihydroxybenzene.

2-(2-Methylpropyl)-1,3-dimethoxybenzene (18.0 g, 92.8 mmol) was melted with pyridinium hydrochloride (90 g) and stirred at 180° C. for 8 hours. The mixture was cooled to room temperature, diluted with water, and extracted twice with ethyl acetate. The organic phase was washed with dilute aqueous hydrochloric acid, dried over sodium sulfate, filtered and concentrated in vacuo. Purification via silica gel chromatography (ether/hexane) provided 15.0 g (98%) of title intermediate as a light yellow oil: NMR (CDCl$_3$) 6.97 (t, J=9 Hz, 1H), 6.43 (d, J=10 Hz, 2H), 5.68 (s, 2H, —OH), 2.59 (d, J=9 Hz, 2H), 2.03 (heptet, J=8 Hz, 1H), 1.00 (d, J=8 Hz, 6H); MS-FD m/e 166 (p); IR (CHCl$_3$, cm$^{-1}$) 3603, 3349 (b), 2959, 1601, 1466, 1298, 1104, 987. Analysis for C$_{10}$H$_{14}$O$_2$: Calc: C, 72.26; H, 8.49; Found: C, 72.37; H, 8.75.

C. Preparation of 2-[3-hydroxy-2-(2-methylpropyl)phenoxy] benzoic acid methyl ester.

2-(2-Methylpropyl)-1,3-dihydroxybenzene (14.5 g, 87.3 mmol) was submitted to Ullmann coupling conditions with methyl 2-iodobenzoate as described above for the preparation of Example 61(A). Purification of the crude product via silica gel chromatography (ether/hexane) provided 3.11 g (12%) of the desired title intermediate as a light yellow oil: NMR (CDCl$_3$) 7.91 (d, J=8 Hz, 1H), 7.23 (t, J=8 1 Hz, 1H), 7.16 (t, J=8 Hz, 1H), 6.99 (t, J=8 Hz, 1H), 6.86 (d, J=9 Hz, 1H), 6.63 (d, J=9 Hz, 1H), 6.39 (d, J=9 Hz, 1H), 5.42 (bs, 1H, —OH), 3.84 (s, 3H), 2.58 (d, J=9 Hz, 2H), 2.08 (heptet, J=8 Hz, 1H), 0.99 (d, J=8 Hz, 6H); MS-FD m/e 300 (p); IR (CHCl$_3$, cm$^{-1}$) 3625, 3360 (b), 2950, 1718, 1602, 1453, 1306, 1235, 1107, 910. Analysis for C$_{18}$H$_{20}$O$_4$: Calc: C, 71.98; H, 6.71; Found: C, 72.19; H, 6.86.

D. Preparation of 2-[2-(2-methylpropyl)-3-[3-[ 2-ethyl-5-(phenylmethoxy)-4-(4-fluorophenyl)phenoxy]propoxy] phenoxy]benzoic acid methyl ester.

2-[3-Hydroxy-2-(2-methylpropyl)phenoxy]benzoic acid methyl ester (750 mg, 2.51 mmol) was alkylated with 2-benzyloxy-1-(4-fluorophenyl)-5-ethyl-4-(3-chloro- 1-propyloxy)benzene as described above for the preparation of Example 66(A) to provide crude product as an oil. Purification via silica gel chromatography (ether/hexane) provided 620 mg (35%) of title intermediate product as an off-white solid: mp 82°–84° C.; NMR (CDCl$_3$) 7.99 (d, J=8 Hz, 1H), 7.62 (t, J=7 Hz, 2H), 7.38 (m, 6H), 7.18 (m, 5H), 6.90 (d, J=9H, 1H), 6.78 (d, J=9 Hz, 1H), 6.71 (s, 1H), 6.53 (d, J=9 Hz, 1H), 5.09 (s, 2H), 4.27 (m, 4H), 3.91 (s, 3H), 2.70 (m, 4H), 2.39 (quintet, J=8 Hz, 2H), 2.10 (heptet, J=8 Hz, 1H), 1.30 (t, J=9 Hz, 3H), 1.00 (d, J=8 Hz, 6H); MS-FD m/e 663 (p+1, 42), 662 (p, 100); IR (KBr, cm$^{-1}$) 3425 (b), 2959, 2864, 1733, 1604, 1580, 1500, 1447, 1246, 1080, 837. Analysis for C$_{42}$H$_{43}$O$_6$F: Calc: C, 76.11; H, 6.54; Found: C, 76.20; H, 6.83.

E. Preparation of 2-[2-(2-methylpropyl)-3-[3-[ 2-ethyl-5-hydroxy-4-(4-fluorophenyl)phenoxy]propoxy]phenoxy] benzoic acid.

2-[2-(2-Methylpropyl)-3-[2-ethyl- 5-(phenylmethoxy)-4-(4-fluorophenyl)phenoxy]propoxy]phenoxy] benzoic acid methyl ester (600 mg, 0.906 mmol) was submitted to de-benzylation conditions as described above for the preparation of Example 71(C). Hydrolysis of the resulting ester as described above for the preparation of Example 60 provided 250 mg (57%) of title product as an off-white solid: mp 48°–49° C.; NMR (CDCl$_3$) 8.25 (d, J=9 Hz, 1H), 7.44 (m, 3H), 7.20 (m, 4H), 7.05 (s, 1H), 6.85 (d, J=9 Hz, 1H), 6.76 (d, J=9 Hz, 1H), 6.64 (d, J=9 Hz, 1H), 6.59 (s, 1H), 5.32 (bs, 1H, —OH), 4.28 (m, 4H), 2.63 (q, J=8 Hz, 2H), 2.52 (d, J=8 Hz, 2H), 2.38 (quintet, J=8 Hz, 2H), 1.96 (heptet, J=8 Hz, 1H), 1.23 (t, J=9 Hz, 3H), 0.98 (d, J=8 Hz, 6H); MS-FD m/e 559 (p+1, 39), 558 (p, 100); IR (KBr, cm$^1$) 3350 (b), 2958, 1699, 1604, 1457, 1222, 1112, 1062, 838, 756. Analysis for C$_{34}$H$_{35}$O$_6$F: Calc: C, 73.10; H, 6.31; Found: C, 73.32; H, 6.50.

EXAMPLE 75

2-[2-Butyl-3-[3-[2-ethyl-5-hydroxy-4-( 4-fluorophenyl)phenoxy]propoxy]phenoxy]benzoic acid hydrate

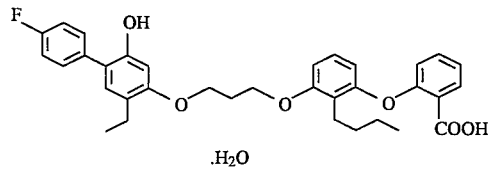

.H$_2$O

A. Preparation of 2-butyl-1,3-dimethoxybenzene.

1,3-Dimethoxybenzene (15.0 g, 109 mmol) was alkylated with 1-iodobutane as described above for the preparation of Example 74(A) except that the final reaction mixture was not refluxed. Purification via silica gel chromatography (ethyl acetate/hexane) provided 15.0 g (71%) of the title intermediate product as a yellow oil: NMR (CDCl$_3$) 7.18 (t, J=8.2 Hz, 1H), 6.59 (d, J=9.7 Hz, 2H), 3.84 (s, 6H), 2.70 (t, J=8.7 Hz, 2H), 1.50 (hextet, J=6 Hz, 2H), 1.44 (quintet, J=6 Hz, 2H), 0.98 (t, J=8.2 Hz, 3H); MS-FD m/e 194 (p).

B. Preparation of 2-(3-hydroxy-2-butylphenoxy)benzoic acid methyl ester.

2-Butyl-1,3-dimethoxybenzene (14.98 g, 77.6 mmol) was de-methylated as described above for the preparation of Example 74(B) to provide 19 g crude product as a brown oil. A solution of 15 g of this material and potassium tert-butoxide (9.70 g, 86.5 mmol) in pyridine (150 mL) was added to a second solution of methyl 2-iodobenzoate (11.9 g, 180 mmol) and copper(I) iodide (17.3 g, 91.0 mmol) in pyridine (150 mL). The resulting mixture was refluxed for 36 hours. The mixture was cooled to room temperature, diluted with water, and extracted three times with diethyl ether The combined ether fractions were filtered through a mat of Celite®, washed once with 5N aqueous hydrochloric acid, once with 2N aqueous sodium hydroxide, and filtered again through a mat of Celite®. The resulting solution was dried over magnesium sulfate, filtered, and evaporated in vacuo. Silica gel chromatography (ethyl acetate/hexane) provided provided 3.02 g (11%) of the title intermediate product as an orange oil: NMR (CDCl$_3$) 7.91 (d, J=8 Hz, 1H), 7.41 (t, J=8 Hz, 1H), 7.14 (t, J=8 Hz, 1H), 6.97 (t, J=9 Hz, 1H), 6.83 (d, J=8 Hz, 1H), 6.59 (d, J=8 Hz, 1H), 6.39 (d, J=8 Hz, 1H), 5.04 (bs, 1H, —OH), 3.83 (s, 3H), 2.66 (t, J=9 Hz, 2H), 1.54 (quintet, J=5 Hz, 2H), 1.35 (hextet, J=5 Hz, 2H), 0.91 (t, J=8 Hz, 3H); MS-EI m/e 300 (p, 34), 225 (100), 213 (42), 197 (53), 107 (38); IR (mull, cm$^{-1}$) 3410, 2926, 1709, 1600, 1463, 1234, 1107, 1090, 992. Analysis for C$_{18}$H$_{20}$O$_4$: Calc: C, 71.98; H, 6.71; Found: C, 70.82; H, 6.67.

C. Preparation of 2-[2-butyl-3-[3-[2-ethyl-4-(4-fluorophenyl)-5-(phenylmethoxy)phenoxy]propoxy]phenoxy]benzoic acid methyl ester.

2-(3-Hydroxy-2-butylphenoxy)benzoic acid methyl ester (700 mg, 1.76 mmol) was alkylated with 2-benzyloxy-1-(4-fluorophenyl)-5-ethyl-4-(3-chloro-1-propyloxy)benzene as described above for the preparation of Example 66(A) to provide crude product as an oil. Purification via silica gel chromatography (ethyl acetate/hexane) provided 700 mg (60%) of the title intermediate product as a yellow oil: NMR (CDCl$_3$) 7.91 (d, J=9 Hz, 1H), 7.58 (m, 2H), 7.38 (m, 6H), 7.18 (m, 5H), 6.88 (d, J=10 Hz, 1H), 6.76 (d, J=9 Hz, 1H), 6.68 (s, 1H), 6.47 (d, J=9 Hz, 1H), 5.09 (s, 2H), 4.25 (m, 4H), 3.91 (s, 3H), 2.72 (m, 4H), 2.40 (quintet, J=5 Hz, 2H), 1.60 (hextet, J=5 Hz, 2H), 1.38 (m, 2H), 1.24 (t, J=8 Hz, 3H), 0.99 (t, J=8 Hz, 3H); IR (CHCl$_3$, cm$^{-1}$) 3024, 1717, 1602, 1465, 1453, 1306, 1234, 1086, 1014. Analysis for C$_{42}$H$_{43}$O$_6$F: Calc: C, 76.11; H, 6.54; Found: C, 75.82; H, 6.50.

D. Preparation of 2-[2-butyl-3-[3-[2-ethyl-5-hydroxy-4-(4-fluorophenyl)phenoxy]propoxy]phenoxy]benzoic acid hydrate.

2-[2-Butyl-3-[3-[2-ethyl-4-(4-fluorophenyl)-5-(phenylmethoxy)phenoxy]propoxy]phenoxy]benzoic acid methyl ester (690 mg, 1.04 mmol) was submitted to de-benzylation conditions as described above for the preparation of Example 71(C). Hydrolysis of the resulting ester as described above for the preparation of Example 60 provided 114 mg (30%) of the title product as an off-white solid: mp 62°–64° C.; NMR (DMSO-d$_6$) 12.75 (bs, 1H, —COOH), 9.60 (bs, 1H, —OH), 7.69 (d, J=7.3 Hz, 1H), 7.50 (m, 2H), 7.35 (t, J=7.4 Hz, 1H), 7.00–7.18 (m, 4H), 6.96 (s, 1H), 6.69 (m, 2H), 6.56 (s, 1H), 6.31 (d, J=8.2 Hz, 1H), 4.17 (t, J=5.1 Hz, 2H), 4.09 (t, J=5.4 Hz, 2H), 2.58 (t, J=7.3 Hz, 2H), 2.48 (m, 2H), 2.21 (quintet, J=5.0 Hz, 2H), 1.37 (hextet, J=6.8 Hz, 2H), 1.21 (m, 2H), 1.06 (t, J=7.4 Hz, 3H), 0.74 (t, J=7.1 Hz, 3H); MS-FD m/e 559 (p+1, 55), 558 (p, 100); IR (KBr, cm$^{-1}$) 3350 (b), 2963, 2933, 1738, 1605, 1497, 1461, 1455, 1236, 1118. Analysis for C$_{34}$H$_{35}$O$_6$F.H$_2$O: Calc: C, 70.81; H, 6.47; Found: C, 71.19; H, 6.52.

EXAMPLE 76

2-[2-(Phenylmethyl)-3-[3-[2-ethyl-5-hydroxy-4-(4-fluorophenyl)phenoxy]propoxy]phenoxy]benzoic acid

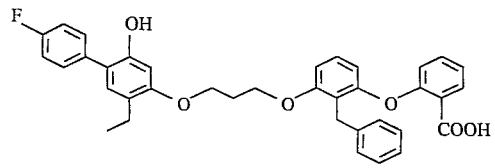

A. Preparation of 2-(phenylmethyl)-1,3-dimethoxybenzene.

1,3-Dimethoxybenzene (75.0 g, 391 mmol) was alkylated with benzyl bromide as described above for the preparation of Example 74(A) except that the final reaction mixture was not refluxed. Purification via silica gel chromatography (ether/hexane) provided 18.8 g (8%) of intermediate product as a white solid: 53°–55° C.; NMR (CDCl$_3$) 7.15–7.37 (m, 6H), 6.62 (d, J=10 Hz, 2H), 4.12 (s, 2H), 3.87 (s, 6H); MS-FD m/e 229 (p+1, 17), 228 (p, 100); IR (KBr, cm$^{-1}$) 2925, 2839, 1594, 1476, 1435, 1259, 1197, 1106, 700. Analysis for C$_{15}$H$_{16}$O$_2$: Calc: C, 78.92; H, 7.06; Found: C, 79.21; H, 7.33.

B. Preparation of 2-(phenylmethyl)-1,3-dihydroxybenzene.

2-(Phenylmethyl)-1,3-dimethoxybenzene (15.0 g, 65.8 mmol) was de-methylated as described above for the preparation of Example 74(B). Purification via silica gel chromatography (ethyl acetate/hexane) provided 7.76 g (60%) of title intermediate product as an off-white crystalline material: mp 81°–83° C.; NMR (CDCl$_3$) 7.18–7.23 (m, 5H), 7.01 (t, J=9 Hz, 1H), 6.43 (d, J=10 Hz, 2H), 5.38 (bs, 2H, —OH), 4.18 (s, 2H); MS-FD m/e 201 (p+1, 23), 200 (p, 100); IR (KBr, cm$^{-1}$) 3505 (b), 1618, 1464, 1360, 1292, 1183, 1012, 739. Analysis for C$_{13}$H$_{12}$O$_2$: Calc: C, 77.98; H, 6.04; Found: C, 77.69; H, 5.99.

C. Preparation of 2-[3-hydroxy-2-(phenylmethyl)phenoxy] benzoic acid methyl ester.

2-(Phenylmethyl)-1,3-dihydroxybenzene (14.5 g, 87.3 mmol) was submitted to Ullmann coupling conditions with methyl 2-iodobenzoate as described above for the preparation of Example 61(A). Purification of the crude product via silica gel chromatography (ethyl acetate/hexane) provided 900 mg (7%) of title intermediate product as a white crystalline material: mp 79°–81° C.; NMR (CDCl$_3$) 7.93 (d, J=9 Hz, 1H), 7.35 (m, 3H), 7.27 (m, 2H), 7.13 (m, 2H), 7.04 (d, J=9 Hz, 1H), 6.83 (d, J=9 Hz, 1H), 6.63 (d, J=9 Hz, 1H), 6.41 (d, J=9 Hz, 1H), 5.43 (bs, 1H, —OH), 4.14 (s, 2H), 3.79 (s, 3H); MS-FD m/e 335 (p+1, 23), 334 (p, 100); IR (KBr, cm$^{-1}$) 3327 (b), 1687, 1598, 1453, 1315, 1233, 1008, 754. Analysis for $C_{21}H_{18}O_4$: Calc: C, 75.43; H, 5.43; Found: C, 75.21; H, 5.57.

D. Preparation of 2-[2-(phenylmethyl)-3-[3-[2-ethyl-4-(4-fluorophenyl)-5-(phenylmethoxy)phenoxy]propoxy]phenoxy]benzoic acid methyl ester.

2-[3-Hydroxy-2-(phenylmethyl)phenoxy]benzoic acid methyl ester (840 mg, 2.51 mmol) was alkylated with 2-benzyloxy-1-(4-fluorophenyl)-5-ethyl-4-(3-chloro- 1-propyloxy)benzene as described above for the preparation of Example 66(A). Purification via silica gel chromatography (ethyl acetate/hexane) provided 680 mg (40%) of desired title intermediate product as a glass: NMR (CDCl$_3$) 8.01 (d, J=8 Hz, 1H), 7.65 (m, 2H), 7.40 (m, 8H), 7.15–7.30 (m, 8H), 6.88 (d, J=10 Hz, 1H), 6.80 (d, J=10 Hz, 1H), 6.63 (s, 1H), 6.48 (d, J=9 Hz, 1H), 5.09 (s, 2H), 4.34 (t, 7 Hz, 2H), 4.22 (s, 2H), 4.20 (t, J=7 Hz, 2H), 3.84 (s, 3H), 2.77 (q, J=8 Hz, 2H), 2.40 (quintet, J=8 Hz, 2H), 1.38 (t, J=9 Hz, 3H); MS-FD m/e 698 (p+1, 48), 697 (p, 100); IR (CHCl$_3$, cm$^{-1}$) 3015, 2975, 1717, 1604, 1496, 1453, 1306, 1081. Analysis for $C_{45}H_{41}O_6F$: Calc: C, 77.57; H, 5.93; Found: C, 77.80; H, 6.08.

E. Preparation of 2-[2-(phenylmethyl)-3-[3-[2-ethyl-5-hydroxy-4-(4-fluorophenyl)phenoxy]propoxy]phenoxy]benzoic acid.

2-[2-(Phenylmethyl)-3-[3-[2-ethyl-4-(4-fluorophenyl)-5-(phenylmethoxy)phenoxy]propoxy]phenoxy]benzoic acid methyl ester (660 mg, 0.947 mmol) was submitted to de-benzylation conditions and hydrolysis as described above for the preparation of Example 60. Purification via silica gel chromatography (ethyl acetate/hexane) provided 450 mg (80%) the desired title product as a glass: NMR (CDCl$_3$) 8.16 (dd, J=7.8, 1.8 Hz, 1H), 7.43 (m, 2H), 7.35 (m, 1H), 7.05–7.32 (m, 9H), 7.02 (s, 1H), 6.86 (d, 8.4 Hz, 1H), 6.66 (d, J=8.4 Hz, 1H), 6.61 (d, J=8.2 Hz, 1H), 6.46 (s, 1H), 4.28 (t, J=4.6 Hz, 2H), 4.10 (t, J=4.1 Hz, 2H), 4.08 (s, 2H), 2.64 (q, J=7.5 Hz, 2H), 2.33 (quintet, J=5.1 Hz, 2H), 1.22 (t, J=7.5 Hz, 3H); MS-FD m/e 593 (p, 100), 592 (p−1, 89); IR (CHCl$_3$, cm$^{-1}$) 3375 (b), 3020, 2970, 1738, 1605, 1496, 1455, 1068. Analysis for $C_{37}H_{33}O_6F$: Calc: C, 74.98; H, 5.61; Found: C, 75.21; H, 5.72.

EXAMPLE 77

2-[2-Propyl-3-[3-[2-ethyl-5-hydroxy-4-(4-fluorophenyl)phenoxy]propoxy]phenoxy]phenylacetic acid

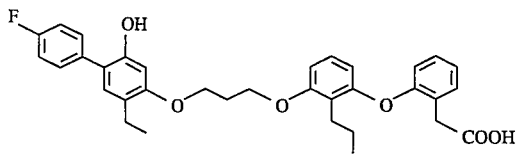

A. Preparation of 2-(3-hydroxy-2-propylphenoxy)phenylacetic acid methyl ester.

1,3-Dihydroxy-2-propylbenzene (6.07 g, 39.9 mmol) was submitted to Ullmann coupling conditions with methyl 2-iodophenylacetate as described above for the preparation of Example 61(A). Purification of the crude product via silica gel chromatography (ethyl acetate/hexane) provided 1.27 g (11%) of title product as a yellow oil: NMR (CDCl$_3$) 7.34 (d, J=9 Hz, 1H), 7.23 (t, J=8 Hz, 1H), 7.08 (t, J=8 Hz, 1H), 6.97 (t, J=8 Hz, 1H), 6.77 (d, J=8 Hz, 1H), 6.58 (d, J=8 Hz, 1H), 3.68 (d, J=9 Hz, 1H), 3.75 (s, 2H), 3.66 (s, 3H), 2.63 (t, J=6 Hz, 2H), 1.61 (hextet, J=6 Hz, 2H), 0.97 (t, J=7 Hz, 3H); MS-FD m/e 300 (p); IR (CHCl$_3$, cm$^{-1}$) 3350 (b), 3020, 2962, 1736, 1455, 1236, 1107, 982.

B. Preparation of 2-[2-propyl-3-[3-[2-ethyl-4-( 4-fluorophenyl)-5-(phenylmethoxy)phenoxy]propoxy]phenoxy]phenylacetic acid methyl ester.

2-(3-Hydroxy-2-propylphenoxy)phenylacetic acid methyl ester (750 mg, 2.51 mmol) was alkylated with 2-benzyloxy-1-(4-fluorophenyl)-5-ethyl-4-(3-chloro-1-propyloxy)benzene as described above for the preparation of Example 66(A). Purification via silica gel chromatography (ethyl acetate/hexane) provided 750 mg (45%) of the title intermediate as a colorless oil: NMR (CDCl$_3$) 7.53 (m, 2H), 7.25–7.40 (m, 6H), 7.19 (t, J=8 Hz, 2H), 7.04–7.17 (m, 4H), 6.72 (d, J=8.7 Hz, 1H), 6.69 (d, J=8.2 Hz, 1H), 6.62 (s, 1H), 6.45 (d, J=8.2 Hz, 1H), 5.03 (s, 2H), 4.22 (m, 4H), 3.75 (s, 2H), 3.66 (s, 3H), 2.65 (m, 4H), 2.34 (quintet, J=6.0 Hz, 2H), 1.54 (hextet, J=7.4 Hz, 2H), 1.21 (t, J=7.5 Hz, 3H), 0.93 (t, J=7.3 Hz, 3H); MS-FD m/e 663 (p+1, 57), 662 (p, 100); IR (CHCl$_3$, cm$^{-1}$) 2975, 1750, 1602, 1496, 1454, 1231, 1116. Analysis for $C_{42}H_{43}O_6F$: Calc: C, 76.11; H, 6.54; Found: C, 76.36; H, 6.71.

C. Preparation of 2-[2-propyl-3-[3-[2-ethyl-5-hydroxy-4-(4-fluorophenyl)phenoxy]propoxy]phenoxy]phenylacetic acid.

2-[2-Propyl-3-[3-[2-ethyl-4-(4-fluorophenyl)- 5-(phenylmethoxy)phenoxy]propoxy]phenoxy]-phenylacetic acid methyl ester (630 mg, 1.10 mmol) was submitted to debenzylation conditions and hydrolysis as described above for the preparation of Example 60. Purification via silica gel chromatography provided 320 mg (60%) of the title product as a glass: NMR (CDCl$_3$) 7.48 (m, 2H), 7.33 (d, J=7.4 Hz, 1H), 7.00–7.30 (m, 6H), 6.76 (d, J=7.8 Hz, 1H), 6.73 (d, J=8.1 Hz, 1H), 6.57 (s, 1H), 6.52 (d, J=8.2 Hz, 1H), 4.25 (m, 4H), 3.82 (s, 2H), 2.78 (m, 4H), 2.38 (quintet, J=5.9 Hz, 2H), 1.60 (hextet, J=7.5 Hz, 2H), 1.25 (t, J=7.5 Hz, 3H), 0.95 (t, J=7.4 Hz, 3H); MS-FD m/e 559 (p+1, 65), 558 (p, 100); IR (CHCl$_3$, cm$^{-1}$) 3570, 2966, 2934, 2873, 1714, 1582, 1496, 1463, 1230, 1116. Analysis for $C_{34}H_{35}O_6F$: Calc: C, 73.10; H, 6.31; Found: C, 73.24; H, 6.41.

EXAMPLE 78

2-[2-Propyl-3-[3-[2-ethyl-5-hydroxy-4-( 4-fluorophenyl)phenoxy]propoxy]benzoyl]benzoic acid

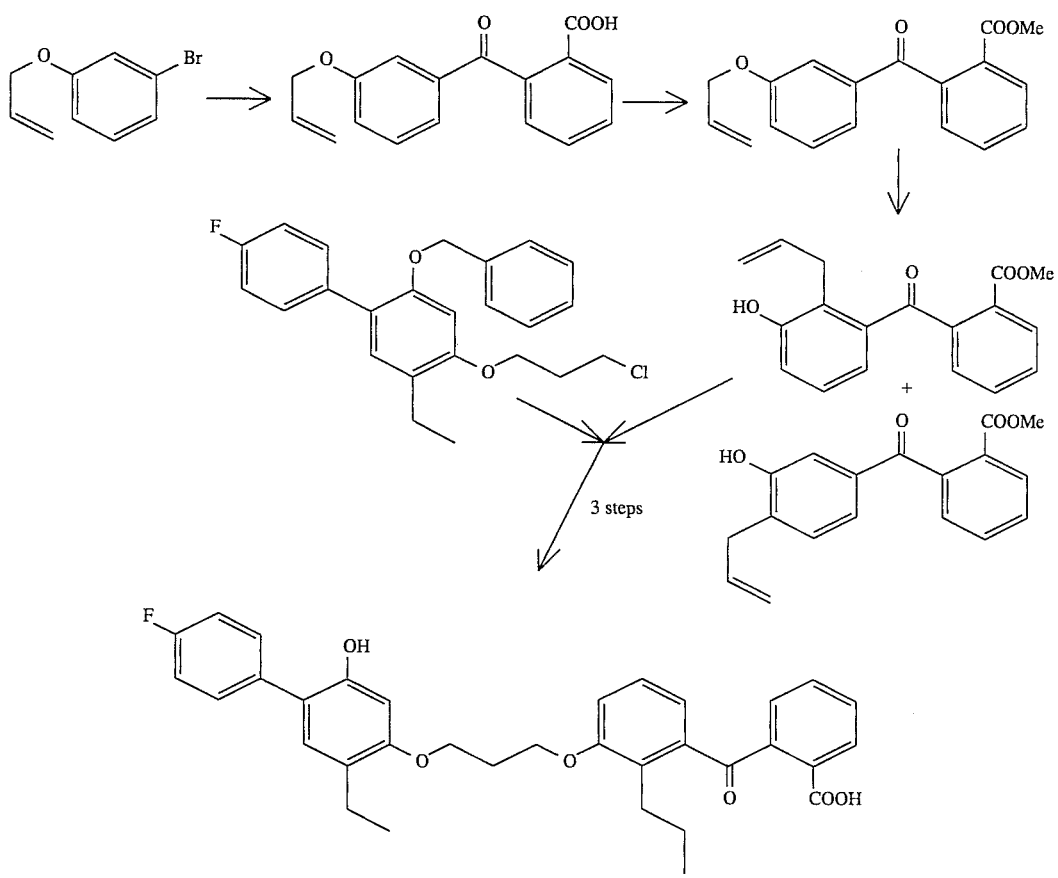

A. Preparation of 2-[3-(allyloxy)benzoyl]benzoic acid.

To a solution of 3-(allyloxy)bromobenzene (15.0 g, 70.5 mmol) in tetrahydrofuran (750 mL) at −70° C. was added 1.6M n-butyllithium (44.1 mL, 70.5 mmol). After stirring for 1 hour, a solution of phthalic anhydride (11.4 g, 77.0 mmol) in tetrahydrofuran (100 mL, previously cooled to −70° C.) was added over 1 hour. The mixture was allowed to warm to room temperature and stirred for 3 hours. The mixture was diluted with saturated ammonium chloride solution and extracted with diethyl ether. The organic layer was washed three times with 1N sodium hydroxide solution and the combined aqueous layers were back-extracted with a fresh portion of diethyl ether. The aqueous layer was adjusted to pH~3 with aqueous hydrochloric acid and extracted three times with fresh diethyl ether. The combined organic layers were washed once with water, once with saturated sodium chloride solution, dried over sodium sulfate, filtered, and concentrated in vacuo to reveal an off-white solid. Recrystallization from ether/hexane provided 10.3 g (52%) of the title intermediate as a white crystalline material: mp 109° C.; NMR (CDCl$_3$) 8.20 (d, J=8 Hz, 1H), 7.65 (t, J=8 Hz, 1H), 7.60 (t, J=8 Hz, 1H), 7.30–7.45 (m, 3H), 7.28 (d, J=8 Hz, 1H), 7.20 (d, J=8 Hz, 1H), 6.02 (m, 1H), 5.35 (d, J=16 Hz, 1H), 5.30 (d, J=11 Hz, 1H), 4.55 (d, J=6 Hz, 2H); MS-FD m/e 283 (p+1, 27), 282 (p, 100). Analysis for C$_{17}$H$_{14}$O$_4$: Calc: C, 72.33; H, 5.00; Found: C, 7 2.0 7; H, 5.22.

B. Preparation of 2-[3-(allyloxy)benzoyl]benzoic acid methyl ester.

A solution of 2-[3-(allyloxy)benzoyl]benzoic acid (9.00 g, 31.9 mmol) in methanol (100 mL) was saturated with hydrogen chloride gas. The resulting solution was stirred at room temperature for 18 hours. The reaction mixture was concentrated in vacuo and diluted with diethyl ether. The resulting solution was washed sequentially with a saturated sodium bicarbonate solution, water, and a saturated sodium chloride solution. The organic layer was dried over sodium sulfate, filtered, and concentrated in vacuo. The resulting pale yellow oil solidified upon standing to provide 9.45 g (100%) of the desired title product as a white solid: mp 50°–52° C.; NMR (CDCl$_3$) 8.05 (d, J=7.8 Hz, 1H), 7.65 (t, J=8 Hz, 1H), 7.56 (t, J=8 Hz, 1H), 7.40 (m, 2H), 7.32 (t, J=8 Hz, 1H), 7.22 (d, J=8 Hz, 1H), 7.14 (d, J=8 Hz, 1H), 6.08 (m, 1H), 5.40 (d, J=16 Hz, 1H), 5.30 (d, J=11 Hz, 1H), 4.78 (d, J=4 Hz, 2H), 3.62 (s, 3H); MS-FD m/e 297 (p+1, 40), 296 (p, 100); IR. Analysis for C$_{18}$H$_{16}$O$_4$: Calc: C, 72.46; H, 5.44; Found: C, 72.75; H, 5.58.

C. Preparation of 2-[3-hydroxy-2-[3-(1-propenyl)]benzoyl] benzoic acid methyl ester and 2-[3-hydroxy-4-[3-(1-propenyl)] benzoyl]benzoic acid methyl ester.

2-[3-(Allyloxy)benzoyl]benzoic acid methyl ester (6.70 g, 20.2 mmol) was heated neat at 175° C. for 30 hours. The product mixture was cooled to room temperature and purified via silica gel chromatography (95:5 methylene chloride/ethyl acetate) to provide 3.62 g (54%) of 2-[3-hydroxy-2-[3-(1-propenyl)]benzoyl]benzoic acid methyl ester and 1.44 g (21%) of 2-[ 3-hydroxy-4-[3-(1-propenyl)]benzoyl]benzoic acid methyl ester as white solids.

2-[3-Hydroxy-2-[3-(1-propenyl)]benzoyl]benzoic acid methyl ester, mp 107°–109° C.; NMR (CDCl$_3$) 7.91 (dd, J=7.8, 2.2 Hz, 1H), 7.43–7.63 (m, 3H), 7.08 (m, 1H), 7.02 (d, J=8 Hz, 1H), 6.80 (dd, J=8, 2 Hz, 1H), 6.15 (m, 1H), 5.42

(bs, 1H, —OH), 5.23 (d, J=16 Hz, 1H), 5.16 (d, J=11 Hz, 1H), 3.81 (d, J=6 Hz, 2H), 3.68 (s, 3H); MS-FD m/e 297 (p+1, 40), 296 (p, 100), 278 (45); IR. Analysis for $C_{18}H_{16}O_4$: Calc: C, 72.96; H, 5.44; Found: C, 73.26; H, 5.54.

2-[3-Hydroxy-4-[3-(1-propenyl)]benzoyl]benzoic acid methyl ester, mp 139°–140° C.; NMR (CDCl$_3$) 8.08 (dd, J=7.9, 3.1 Hz, 1H), 7.63 (t, J=8 Hz, 1H), 7.55 (t, J=8 Hz, 1H), 7.40 (d, J=8 Hz, 1H), 7.35 (s, 1H), 7.16 (s, 2H), 6.00 (m, 1H), 5.62 (bs, 1H, —OH), 5.15 (m, 2H), 3.65 (s, 3H), 3.47 (d, J=5 Hz, 2H); MS-FD m/e 297 (p+1, 20), 296 (p, 100); IR. Analysis for $C_{18}H_{16}O_4$: Calc: C, 72.96; H, 5.44; Found: C, 73.11; H, 5.50.

D. Preparation of 2-[2-[3-(1-propenyl)]-3-[3-[ 2-ethyl-5-(phenylmethoxy)-4-(4-fluorophenyl)phenoxy]propoxy]benzoyl]benzoic acid methyl ester.

2-[3-Hydroxy-2-[3-(1 -propenyl)]benzoyl]benzoic acid methyl ester (520 mg, 1.75 mmol) was alkylated with 2-benzyloxy-1-(4-fluorophenyl)-5-ethyl-4-(3-chloro- 1-propyloxy)benzene as described above for the preparation of Example 66(A). Recrystallization of the crude product from ether/hexane provided 750 mg (65%) of the desired title intermediate as a white solid: mp 90°–91° C.; NMR (CDCl$_3$) 7.91 (m, 1H), 7.53 (m, 4H), 7.45 (m, 1H), 7.32 (m, 5H), 7.02–7.22 (m, 5H), 6.85 (d, J=8 Hz, 1H), 6.61 (s, 1H), 6.10 (m, 1H), 5.04 (d, J=16 Hz, 1H), 5.03 (s, 2H), 4.99 (d, J=11 Hz, 1H), 4.23 (m, 4H), 3.77 (d, J=7 Hz, 2H), 3.66 (s, 3H), 1.64 (q, J=6 Hz, 2H), 2.37 (quintet, J=6 Hz, 2H), 1.19 (t, J=8 Hz, 3H); MS-FD m/e 659 (p+1, 44), 658 (p, 100). Analysis for $C_{42}H_{39}O_6F$: Calc: C, 76.58; H, 5.97; Found: C, 76.79; H, 6.09.

E. Preparation of 2-[2-propyl-3-[3-[2-ethyl- 5-hydroxy-4-(4-fluorophenyl)phenoxy]propoxy]benzoyl]benzoic acid.

2-[2-[3-(1-Propenyl)]-3-[3-[2-ethyl-5-(phenylmethoxy)-4-(4-fluorophenyl)phenoxy]propoxy]benzoyl]benzoic acid methyl ester (318 mg, 0.483 mmol) was submitted to hydrogenation conditions as described above for the preparation of Example 71(C). Hydrolysis of the resulting ester as described above for the preparation of Example 60 and purification via silica gel chromatography (ethyl acetate/hexane) provided 150 mg (56%) of the title product as a glass: NMR (DMSO-d$_6$) 10.15 (bs, 1H, —OH), 7.84 (m, 1H), 7.49 (m, 2H), 7.41 (m, 2H), 6.98–7.23 (m, 5H), 6.96 (s, 1H), 6.62 (d, J=7.2 Hz, 1H), 6.59 (s, 1H), 4.18 (t, J=5.3 Hz, 2H), 4.06 (t, J=5.8 Hz, 2H), 2.85 (m, 2H), 2.49 (m, 2H), 2.20 (quintet, J=5.2 Hz, 2H), 1.57 (hextet, J=5 Hz, 2H), 1.08 (t, J=7.4 Hz, 3H), 0.90 (t, J=7.2 Hz, 3H); IR, MS. Analysis for $C_{34}H_{33}O_6F$: Calc: C, 73.36; H, 5.98; Found: C, 69.71: H, 5.90.

EXAMPLE 79

2-[[2-Propyl-3-[3-[2-ethyl-5-hydroxy-4-(4-fluorophenyl)phenoxy]propoxy]phenyl]methyl]benzoic acid

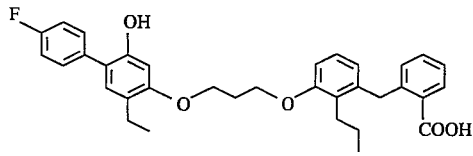

A. Preparation of 2-[(3-hydroxy-2-propylphenyl)methyl] benzoic acid methyl ester.

A mixture of 2-[3-hydroxy-2-3-(1-propenyl)]benzoyl] benzoic acid methyl ester (3.00 g, 10.1 mmol), concentrated sulfuric acid (1 mL), and 5% palladium on carbon (1.5 g) in methanol (95 mL) was hydrogenated at 4 atmospheres for 18 hours. The mixture was concentrated in vacuo to a volume of approximately 30 mL, filtered, and saturated with hydrogen chloride gas. The resulting mixture was stirred for 18 hours, then concentrated in vacuo. The residue was dissolved in diethyl ether and washed with a saturated sodium bicarbonate solution. The aqueous layer was back-extracted with a fresh portion of diethyl ether. The combined organic layers were washed with a saturated sodium chloride solution, dried, filtered, and concentrated in vacuo to provide 2.60 g (90%) of the title intermediate as an orange oil: NMR (CDCl$_3$) 7.97 (d, J=7 Hz, 1H), 7.38 (t, J=7 Hz, 1H), 7.28 (t, J=7 Hz, 1H), 7.02 (m, 2H), 6.70 (d, J=7 Hz, 1H), 6.54 (d, J=7 Hz, 1H), 5.20 (bs, 1H, —OH), 4.45 (s, 2H), 3.89 (s, 3H), 2.58 (t, J=7 Hz, 2H), 1.52 (hextet, J=7 Hz, 2H), 0.92 (t, J=7 Hz, 3H); MS-FD m/e 285 (p+1, 23), 284 (100); IR.

B. Preparation of 2-[[2-propyl-3-[3-[2-ethyl- 5-(phenylmethoxy)-4-(4-fluorophenyl)phenoxy]propoxy]phenyl]methyl] benzoic acid methyl ester.

2-[(3-Hydroxy-2-propylphenyl)methyl]benzoic acid methyl ester (2.00 g, 4.68 mmol) was alkylated with 2-benzyloxy-1-( 4-fluorophenyl)-5-ethyl-4-(3-chloro-1-propyloxy)benzene as described above for the preparation of Example 66(A). Recrystallization of the crude product from hexane provided 1.72 g (38%) of the title intermediate as a white solid: mp 83°–84° C.; NMR (CDCl$_3$) 7.94 (d, J=8 Hz, 1H), 7.53 (m, 2H), 7.25–7.40 (m, 7H), 7.05–7.15 (m, 4H), 7.00 (d, J=7 Hz, 1H), 7.81 (d, J=7 Hz, 1H), 6.62 (s, 1H), 6.58 (d, J=7 Hz, 1H), 5.02 (s, 2H), 4.42 (s, 2H), 4.21 (m, 4H), 3.88 (s, 3H), 2.54–2.68 (m, 4H), 2.32 (quintet, J=6 Hz, 2H), 1.50 (hextet, J=6 Hz, 2H), 1.21 (t, J=8 Hz, 3H), 0.96 (t, J=8 Hz, 3H); MS-FD m/e 648 (p+1, 40), 647 (p, 100); IR (CHCl$_3$, cm$^{-1}$) 2964, 1718, 1603, 1497: 1459, 1143. Analysis for $C_{42}H_{43}O_5F$: Calc: C, 77.99; H, 6.70; Found: C, 79.47; H, 6.76.

C. Preparation of 2-[[2-propyl-3-[3-[2-ethyl- 5-hydroxy-4-(4-fluorophenyl)phenoxy]propoxy]phenyl]methyl]benzoic acid.

2-[[2-Propyl-3-[3-[2-ethyl-5-(phenylmethoxy)-4-( 4-fluorophenyl)phenoxy]propoxy]phenyl]methyl]benzoic acid methyl ester (1.50 mg, 2.32 mmol) was submitted to de-benzylation conditions as described above for the preparation of Example 71(C). Hydrolysis of the resulting ester as described above for the preparation of Example 60 followed by recrystallization of the crude product from ether/hexane provided 860 mg (68%) of the desired title product as a white solid: mp 150°–151° C.; NMR (CDCl$_3$) 8.11 (dd, J=7.3, 0.8 Hz, 1H), 7.45 (m, 2H), 7.30 (t, J=7 Hz, 1H), 6.95–7.25 (m, 5H), 6.81 (d, J=8.0 Hz, 1H), 6.58 (d, J=7.4 Hz, 1H), 6.52 (s, 1H), 4.50 (s, 2H), 4.21 (m, 4H), 2.62 (m, 4H), 2.35 (quintet, J=6.0 Hz, 2H), 1.46 (hextet, J=7.6 Hz, 2H), 1.18 (t, J=7.5 Hz, 3H), 0.93 (t, J=7.4 Hz, 3H); MS-FD m/e 543 (p+1, 40) 542 (p, 100); IR (CHCl$_3$, cm$^{-1}$) 3400 (b), 2966, 1696, 1603, 1496, 1459, 1238, 1146, 1111. Analysis for $C_{34}H_{35}O_5F$: Calc: C, 75.26; H, 6.50; Found: C, 75.26; H, 6.62.

EXAMPLE 80

2-[2-Propyl-3-[3-[2-ethyl-4-(4-fluorophenyl)-5-hydroxyphenoxy]propoxy]thiophenoxy]benzoic acid

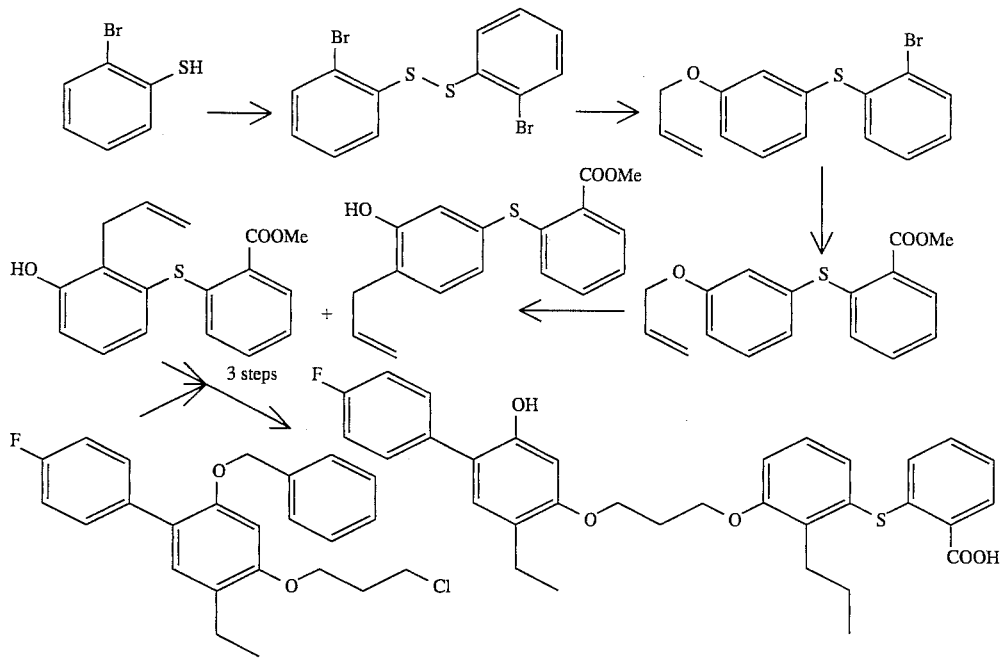

A. Preparation of 2-bromophenyldisulfide.

To a mixture of 2-bromothiophenol (20.0 g, 106 mmol) and 2N sodium hydroxide solution (100 mL) in diethyl ether (400 mL) was added solid iodine (13.4 g, 53.0 mmol) in portions. The mixture was stirred at room temperature for 1 hour at which time the ether layer was separated. The aqueous layer was extracted with a fresh portion of ether and the combined ether layers were washed once with water, once with a saturated sodium chloride solution, dried over sodium sulfate, filtered, and concentrated in vacuo to provide 17.2 g (43%) of intermediate product as a white solid: mp 95°–97° C.; NMR (CDCl$_3$) 7.52 (m, 4H), 7.25 (t, J=9.7 Hz, 2H), 7.06 (t, J=9.7 Hz, 2H); MS-FD m/e 380 (p+4, 20), 379 (p+3, 30), 378 (p+2, 85), 376 (p, 100), 374 (p–2, 75); IR. Analysis for $C_{12}H_8Br_2S_2$: Calc: C, 38.32; H, 2.14; Found: C, 3 8.61; H, 2.13.

B. Preparation of 2-[3-(allyloxy)thiophenoxy]bromobenzene.

To a solution of 3-(allyloxy)bromobenzene (8.20 g, 38.7 mmol) in tetrahydrofuran (600 mL) at −74° C. was added 1.6M n-butyllithium (24.2 mL, 38.7 mmol). After stirring for 30 minutes this solution was cannulated into a solution of 2-bromophenyldisulfide (16.0 g, 42.5 mmol) in tetrahydrofuran (160 mL) at −74° C. The resulting mixture was allowed to warm to room temperature then diluted with saturated ammonium chloride solution and filtered. The aqueous layer was extracted with three times with diethyl ether and the combined organic layers were washed once with water, once with a saturated sodium chloride solution, dried over sodium sulfate, filtered, and concentrated in vacuo to provide a yellow oil. Purification via silica gel chromatography provided 9.40 g (76%) of the title intermediate as a light yellow oil;: NMR (CDCl$_3$) 7.58 (d, J=7 Hz, 1H), 7.27 (t, J=7 Hz, 1H), 7.17 (t, J=7 Hz, 1H), 6.85–7.15 (m, 5H), 6.04 (m, 1H), 5.41 (d, J=14 Hz, 1H), 5.30 (d, J=10 Hz, 1H), 4.52 (d, J=4 Hz, 2H); MS-FD m/e 322 (p, 100), 320 (p, 75); IR (KBr, cm$^{-1}$) 3223 (b), 1688, 1345, 1161, 1013, 678. Analysis for $C_{15}H_{13}OBrS$: Calc: C, 56.09; H, 4.08; Found: C, 56.31; H, 4.22.

C. Preparation of 2-[3-(allyloxy)thiophenoxy]benzoic acid methyl ester.

To a solution of 2-[3-(allyloxy)thiophenoxy]bromobenzene (9.00 g, 28.0 mmol) in tetrahydrofuran (175 mL) at −78° C. was added 1.6M n-butyllithium (19.2 mL, 30.8 mmol) dropwise. After stirring for 15 minutes, the solution was saturated with carbon dioxide gas resulting in a thick gel. Tetrahydrofuran (50 mL) was added and the resulting mixture allowed to warm to room temperature. The mixture was diluted with saturated ammonium chloride solution. The aqueous layer was extracted once with diethyl ether and the combined organic layers were concentrated in vacuo. The residue was dissolved in a fresh portion of ether and extracted with 1N aqueous sodium hydroxide. The aqueous layer was washed with a fresh portion of ether and acidified with aqueous hydrochloric acid. The resulting aqueous layer was extracted with a fresh portion of ether. The organic layer was washed with a saturated sodium chloride solution, dried over sodium sulfate, filtered, and concentrated in vacuo. The crude acid was dissolved in methanol (125 mL) and the resulting solution saturated with hydrogen chloride gas. After stirring for 18 hours, the reaction mixture was concentrated in vacuo, the residue dissolved in ether, and the resulting solution washed with saturated sodium bicarbonate solution. The aqueous layer was back-extracted with a fresh portion of ether and the combined organic layers were washed once with water, once with a saturated sodium chloride solution, dried over sodium sulfate, filtered, and concentrated in vacuo. Purification via silica gel chromatography (ethyl acetate/hexane) provided 4.80 g (68%) of the desired title intermediate as a faint yellow oil: NMR (CDCl$_3$) 7.99 (dd, J=7.8, 1.4 Hz, 1H), 7.33 (t, J=7 Hz, 1H), 7.25 (t, J=7 Hz, 1H), 7.15 (m, 3H), 7.00 (dd, J=8.7, 2.8 Hz, 1H), 6.88 (d, J=8 Hz, 1H), 6.04 (m, 1H), 5.42 (d, J=14 Hz, 1H), 5.30 (d, J=11 Hz, 1H), 4.53 (d, J=3.9 Hz, 2H), 3.97 (s, 3H); MS-FD m/e 301 (p+1, 25), 300 (p, 100); IR (CHCl$_3$, cm$^{-1}$) 3025, 1712, 1590, 1463, 1437, 1254, 1060. Analysis for C$_{17}$H$_{16}$O$_3$S: Calc: C, 67.98; H, 5.37; Found: C, 67.86; H, 5.29.

D. Preparation of 2-[3-hydroxy-2-[3-( 1-propenyl)]-thiophenoxy]benzoic acid methyl ester and 2-[3-hydroxy-4-[ 3-(1-propenyl)]thiophenoxy]benzoic acid methyl ester.

2-[3-(Allyloxy)thiophenoxy]benzoic acid methyl ester (5.40 g, 15.0 mmol) was heated neat at 175° C. for 29 hours. The product mixture was cooled to room temperature and purified via silica gel chromatography (methylene chloride) to provide 2.22 g (41%) of 2-[3-hydroxy-2-[3-(1-propenyl)] thiophenoxy]benzoic acid methyl ester and 1.46 g (27%) of 2-[3-hydroxy-4-[3-( 1-propenyl)]thiophenoxy]benzoic acid methyl ester as white solids.

2-[3-Hydroxy-2-[3-(1 -propenyl)]thiophenoxy]benzoic acid methyl ester, mp 72°–74° C.; NMR (DMSO-d$_6$) 9.79 (s, 1H, —OH), 7.89 (d, J=8 Hz, 1H), 7.33 (t, J=7 Hz, 1H), 7.09–7.23 (m, 2H), 6.94 (m, 2H), 6.62 (dd, J=7, 1 Hz, 1H), 5.78 (m, 1H), 4.70–4.83 (m, 2H), 3.86 (s, 3H), 3.37 (d, J=5 Hz, 2H); MS-FD m/e 301 (p+1, 21), 300 (p, 100); IR (CHCl$_3$, cm$^{-1}$) 3595, 3350 (b), 3029, 3010, 2954, 1711, 1420, 1436, 1273, 1146, 1060. Analysis for C$_{17}$H$_{16}$O$_3$S: Calc: C, 67.98; H, 5.37; Found: C, 68.28; H, 5.41.

2-[3-Hydroxy-4-[3-(1-propenyl)]thiophenoxy]benzoic acid methyl ester, mp 96°–97° C.; NMR (DMSO-d$_6$) 9.78 (s, 1H, —OH), 7.89 (d, J=8 Hz, 1H), 7.40 (t, J=7 Hz, 1H), 7.12–7.25 (m, 2H), 6.93 (s, 1H), 6.91 (d, J=8 Hz, 1H), 6.81 (d, J=8 Hz, 1H), 5.87 (m, 1H), 5.00–5.12 (m, 2H), 3.85 (s, 3H), 3.30 (d, J=4 Hz, 2H); MS-FD m/e 301 (p+1, 45), 300 (p, 100); IR (CHCl$_3$, cm$^{-1}$) 3595, 3300(b), 3029, 3010, 2954, 1711, 1436, 1310, 1255, 942. Analysis for C$_{17}$H$_{16}$O$_3$S: Calc: C, 67.98; H, 5.37; Found: C, 68.04; H, 5.47.

E. Preparation of 2-[2-[3-(1 -propenyl)]-3-[3-[ 2-ethyl-4-(4-fluorophenyl)-5-(phenylmethoxy)phenoxy]propoxy] thiophenoxy] benzoic acid methyl ester.

2-[3-Hydroxy-2-[3-(1-propenyl)]thiophenoxy]benzoic acid methyl ester (2.00 g, 6.66 mmol) was alkylated with 2-benzyloxy-1-(4-fluorophenyl)-5-ethyl-4-(3-chloro- 1-propyloxy)benzene as described above for the preparation of Example 66(A). Purification via silica gel chromatography (hexane/diethyl ether) provided 2.90 g (66%) of desired intermediate product as a white solid: mp 76°–77° C.; NMR (CDCl$_3$) 8.03 (dd, J=7.6, 1.2 Hz, 1H), 7.54 (m, 2H), 7.17–7.40 (m, 8H), 6.98–7.18 (m, 5H), 6.71 (d, J=7.9 Hz, 1H), 6.62 (s, 1H), 5.87 (m, 1H), 5.03 (s, 2H), 4.83–4.95 (m, 2H), 4.26 (t, J=7 Hz, 2H), 4.21 (t, J=7 Hz, 2H), 3.98 (s, 3H), 3.62 (d, J=6.3 Hz, 2H), 2.64 (q, J=7.5 Hz, 2H), 2.33 (quintet, J=5.8 Hz, 2H), 1.22 (t, J=7.5 Hz, 3H); MS-FD m/e 664 (p+2, 40), 663 (p+1, 70), 662 (p, 100); IR (CHCl$_3$, cm$^{-1}$) 3011, 2970, 2940, 2890, 1712, 1497, 1452, 1298, 1255, 1145, 1060. Analysis for C$_{41}$H$_{39}$O$_5$FS: Calc: C, 74.30; H, 5.93; Found: C, 74.46; H, 6.13.

F. Preparation of 2-[2-propyl-3-[3-[2-ethyl-4-( 4-fluorophenyl)-5-hydroxyphenoxy]propoxy]thiophenoxy]benzoic acid methyl ester.

2-[2-[3-(1 -Propenyl)]-3-[3-[2-ethyl-4-( 4-fluorophenyl)-5-(phenylmethoxy)phenoxy]propoxy]thiophenoxy]benzoic acid methyl ester (2.70 g, 4.07 mmol) was hydrogenated as described above for the preparation of Example 71(C) to provide an oil (~2 g). A solution of this material (1.39 g) in methylene chloride (25 mL) at −78° C. was treated with 1M boron tribromide (3.61 mL, 3.61 mmol) and allowed to stir for 1 hour. The reaction mixture was diluted with water and extracted with methylene chloride. The organic layer was washed with water, dried over sodium sulfate, filtered, and concentrated in vacuo to provide a yellow oil. Purification via silica gel chromatography provided 770 mg (47%) of the title intermediate as a white solid: mp 105–106° C.; NMR (CDCl$_3$) 8.02 (dd, J=7.6, 1.2 Hz, 1H), 7.43 (m, 2H), 7.07–7.30 (m, 8H), 6.98 (m, 2H), 6.71 (d, J=7.9 Hz, 1H), 6.57 (s, 1H), 5.10 (bs, 1H, —OH), 4.24 (m, 2H), 3.98 (s, 3H), 2.83 (t, J=7 Hz, 2H), 2.65 (q, J=7.5 Hz, 2H), 2.36 (quintet, J=5 Hz, 2H), 1.52 (hextet, J=6 Hz, 2H), 1.21 (t, J=7.4 Hz, 3H), 0.90 (t, J=7.5 Hz, 3H); MS-FD m/e 575 (p+1, 20), 574 (p, 100); IR.

G. Preparation of 2-[2-propyl-3-[3-[2-ethyl-4-( 4-fluorophenyl)-5-hydroxyphenoxy]propoxy]thiophenoxy]benzoic acid.

2-[2-Propyl-3-[3-[2-ethyl-4-(4-fluorophenyl)- 5-hydroxyphenoxy]propoxy]thiophenoxy]benzoic acid methyl ester (700 mg, 1.22 mmol) was hydrolyzed as described above for the preparation of Example 60 to provide 689 mg (100%) of the desired title product as a white solid: mp 153°–155° C.; NMR (CDCl$_3$) 8.13 (dd, J=8.2, 0.9 Hz, 1H), 7.42 (m, 2H), 7.10–7.33 (6H), 6.99 (m, 2H), 6.72 (d, J=7.9 Hz, 1H), 6.55 (s, 1H), 4.90 (bs, 1H, —OH), 4.24 (m, 4H), 2.82 (t, J=6 Hz, 2H), 2.63 (q, J=7.5 Hz, 2H), 2.34 (quintet, J=6 Hz, 2H), 1.51 (hextet, J=7.5 Hz, 2H), 1.18 (t, J=7.5 Hz, 3H), 0.90 (t, J=7.5 Hz, 3H); MS-FD m/e 561 (p+1, 20), 560 (p, 100).; IR (CHCl$_3$, cm$^{-1}$) 2967, 1700, 1603, 1497, 1451, 1147, 1043. Analysis for C$_{33}$H$_{33}$O$_5$FS:

Calc: C, 70.69; H, 5.93; Found: C, 70.43; H, 5.97.

EXAMPLE 81

2-[2-Propyl-3-[3-[2-ethyl-4-(4-fluorophenyl)-5-hydroxyphenoxy]propoxy]phenylsulfinyl]benzoic acid

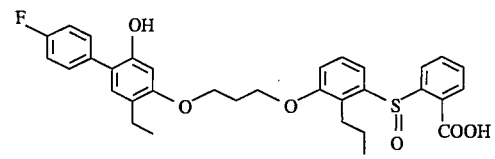

To a solution of 2-[2-propyl-3-[3-[2-ethyl-4-( 4-fluorophenyl)-5-hydroxyphenoxy]propoxy]thiophenoxy]benzoic acid (450 mg, 0.803 mmol) in methylene chloride (10 mL) at −78° C. was added a solution of 85% m-chloroperoxybenzoic acid (138 mg) in methylene chloride (2 mL). After 40 minutes the mixture was concentrated in vacuo. Purification of the residue via silica gel chromatography (95% chloroform/4.5% methanol/0.5% acetic acid) provided 380 mg (80%) of the title product as an off-white solid: mp >100° C. (dec); NMR (CDCl$_3$) 8.53 (d, J=8 Hz, 1H), 8.14 (d, J=8 Hz, 1H), 7.93 (t, J=8 Hz, 1H), 7.63 (t, J=8 Hz, 1H), 7.43 (m, 2H), 7.13 (m, 2H), 6.94–7.06 (m, 2H), 6.88 (d, J=8 Hz, 1H), 6.50 (d, J=8 Hz, 1H), 7.46 (s, 1H), 6.38 (bs, 1H, —OH), 4.15 (m, 4H), 3.32 (m, 1H), 3.08 (m, 1H), 2.57 (q, J=7.5 Hz, 2H), 2.29 (quintet, J=6 Hz, 2H), 1.75 (m, 2H), 1.17 (t, J=7.5 Hz, 3H), 1.05 (t, J=7.3 Hz, 3H); MS (high resolution) calc 577.202642 (MH+), found 577.203800; IR (CHCl$_3$, cm$^{-1}$) 2969, 1708, 1497, 1455, 1266, 1146, 1018. Analysis for C$_{33}$H$_{33}$O$_6$FS: Calc: C, 68.73; H, 5.77; Found: C, 67.54; H, 5.69.

EXAMPLE 82

2-[2-Propyl-3-[3-[2-ethyl-4-(4-fluorophenyl)-5-hydroxyphenoxy]propoxy]phenylsulfonyl]benzoic acid hydrate

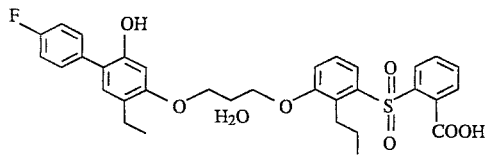

EXAMPLE 83

5-[3-[2-(1-Carboxy)ethyl]-4-[3-[2-ethyl-4-(4-fluorophenyl)-5-hydroxyphenoxy]propoxy]phenyl]-4-pentynoic acid disodium salt 0.4 hydrate

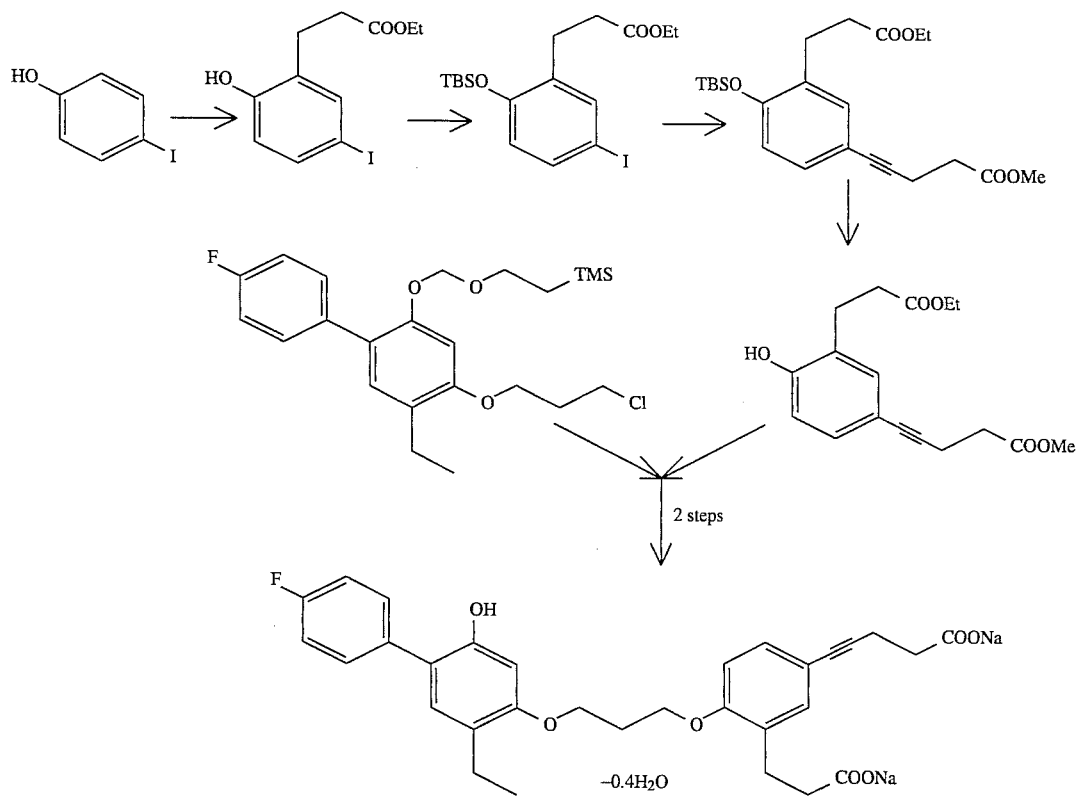

To a solution of 2-[2-propyl-3-[3-[2-ethyl-4-( 4-fluorophenyl)-5-hydroxyphenoxy]propoxy]phenylsulfinyl]benzoic acid (150 mg, 0.260 mmol) in methylene chloride (3.0 mL) at 0° C. was added a solution of 85% m-chloroperoxybenzoic acid (53 mg) in methylene chloride (1 mL). After 1 hour the mixture was warmed to 4° C. and stirred for 18 hours. The mixture was concentrated in vacuo; purification of the residue via silica gel chromatography (90% chloroform/9.5% methanol/0.5% acetic acid) provided 90 mg (58%) of the title product as a white solid: mp 80°–90° C.; NMR (DMSO-$d_6$) 7.88 (m, 2H), 7.55–7.78 (m, 3H), 7.50 (m, 2H), 7.33 (m, 2H), 7.04 (m, 2H), 6.95 (s, 1H), 6.51 (s, 1H), 4.19 (t, J=4.8 Hz, 2H), 4.05 (t, J=5.8 Hz, 2H), 2.69 (m, 2H), 2.44 (q, J=5.8 Hz, 2H), 2.19 (m, 2H), 0.90–1.10 (m, 5H), 0.71 (t, J=4.5 Hz, 3H); MS-FD m/e 595 (p+2, 30), 594 (p+1, 40), 593 (p, 100); IR (CHCl$_3$, cm$^{-1}$) 2966, 1730, 1603, 1497, 1299, 1146. Analysis for $C_{33}H_{33}O_7FS \cdot H_2O$: Calc: C, 64.90; H, 5.78; Found: C, 64.89; H, 5.67.

A. Preparation of 3-(2-hydroxy-5-iodophenyl)propanoic acid ethyl ester.

4-Iodophenyl (6.00 g, 27.3 mmol) was treated with triethylorthoacrylate as described above for the preparation of Example 59(A). The crude material was dissolved in THF (50 mL) and treated with 1N aqueous hydrochloric acid (0.3 mL) at room temperature for 1 hour. The mixture was diluted with water and extracted with ethyl acetate. The organic layer was dried over sodium sulfate, filtered, and concentrated in vacuo to provide an oil. Purification via silica gel chromatography (ethyl acetate/hexane) provided 1.64 g (19%) of the title intermediate as a colorless oil: NMR (CDCl$_3$) 7.60 (bs, 1H, —OH), 7.40 (m, 2H), 6.68 (d, J=9.0 Hz, 1H), 4.17 (q, J=7.1 Hz, 2H), 2.85 (m, 2H), 2.74 (m, 2H), 1.26 (t, J=7.1 Hz, 3H).

B. Preparation of 3-[2-[(1,1-dimethylethyl)dimethylsilyloxy]- 5-iodophenyl]propanoic acid ethyl ester.

A mixture of 3-(2-hydroxy-5-iodophenyl)propanoic acid ethyl ester (1.64 g, 5.13 mmol), tert-butyldimethylsilyl chloride (772 mg, 5.13 mmol), and imidazole (700 mg, 10.3 mmol) in tetrahydrofuran (30 mL) was refluxed for 18 hours. The mixture was cooled to room temperature, diluted with ether, and washed with a saturated sodium bicarbonate solution. The organic layer was dried over sodium sulfate, filtered, and concentrated in vacuo to provide 2.02 g (91%) of the title intermediate as an oil: NMR (CDCl$_3$) 7.46 (d, J=2.3 Hz, 1H), 7.38 (dd, J=8.5, 2.3 Hz, 1H), 6.56 (d, J=8.5 Hz, 1H), 4.15 (q, J=7.2 Hz, 2H), 2.86 (t, J=7.5 Hz, 2H), 2.56 (t, J=8.3 Hz, 2H), 1.26 (t, J=7.1 Hz, 3H), 1.02 (s, 9H), 0.24 (s, 6H); MS-FD m/e 434 (p, 100); IR (CHCl$_3$, cm$^{-1}$) 2933, 1727, 1483, 1258, 1183, 1118, 1044, 918, 843.

C. Preparation of 5-[3-[2-(1-carboethoxy)ethyl]- 4-[(1,1-dimethylethyl)dimethylsilyloxy]phenyl]-4-pentynoic acid methyl ester.

A mixture of 3-[2-[(1,1-dimethylethyl)dimethylsilyloxy]-5-iodophenyl]propanoic acid ethyl ester (1.60 g, 3.68 mmol), 4-pentynoic acid methyl ester (412 mg, 3.68 mmol), copper(I) iodide (25 mg, 0.13 mmol), and bis(triphenylphosphine)palladium(II) chloride (20 mg, 0.028 mmol) in diethylamine (20 mL) was stirred at room temperature for 18 hours. The reaction mixture was filtered and concentrated in vacuo to reveal a dark oil. Purification via silica gel chromatography provided 870 mg (58%) of the title intermediate as an oil: NMR (CDCl$_3$) 7.21 (d, J=2.1 Hz, 1H), 7.13 (dd, J=8.3, 2.1 Hz, 1H), 6.69 (d, J=8.3 Hz, 1H), 4.14 (q, J=7.1 Hz, 2H), 3.73 (s, 3H), 2.87 (t, J=7.4 Hz, 2H), 2.72 (m, 2H), 2.50–2.68 (m, 4H), 1.25 (t, J=7.0 Hz, 3H), 1.01 (s, 9H), 0.24 (s, 6H); MS-FD m/e 419 (p+1, 26), 418 (p, 100); IR (CHCl$_3$, cm$^{-1}$)3450 (b), 3023, 1730, 1603, 1497, 1278, 1043, 842. Analysis for C$_{23}$H$_{34}$O$_5$Si: Calc: C, 65.99; H, 8.19; Found: C, 66.18; H, 8.01.

D. Preparation of 5-[3-[2-(1-carboethoxy)ethyl]- 4-hydroxyphenyl]-4-pentynoic acid methyl ester.

A mixture of 5-[3-[2-(1-carboethoxy)ethyl]-4-[(1,1-dimethylethyl)dimethylsilyloxy]phenyl]-4-pentynoic acid methyl ester (3.70 g, 8.85 mmol) and tetra-n-butylammonium fluoride (2.50 g, 9.58 mmol) in tetrahydrofuran (20 mL) was stirred at room temperature for 2 hours. The mixture was diluted with diethyl ether and washed twice with water. The organic layer was dried over sodium sulfate, filtered, and concentrated in vacuo to reveal a brown oil. Purification via silica gel chromatography (ethyl acetate/ hexane) provided 1.10 g (41%) of the title intermediate as a colorless oil: NMR (CDCl$_3$) 7.62 (s, 1H, —OH), 7.16 (m, 2H), 6.80 (d, J=8 Hz, 1H), 4.15 (q, J=7 Hz, 2H), 3.73 (s, 3H), 2.85 (t, J=7 Hz, 2H), 2.55–2.77 (m, 6H), 1.24 (t, J=7 Hz, 3H); MS-FD m/e 305 (p+1, 18), 304 (100); IR (CHCl$_3$, cm$^{-1}$) 3325 (b), 3028, 1733, 1500, 1379, 1233, 1167. Analysis for C$_{17}$H$_{20}$O$_5$: Calc: C, 67.09; H, 6.62; Found: C, 66.83; H, 6.71.

E. Preparation of 5-[3-[2-(1-carboethoxy)ethyl]-4-[ 3-[2-ethyl-4-(4-fluorophenyl)-5-[2-(trimethylsilyl)ethoxymethoxy] phenoxy]propoxy]phenyl]-4-pentynoic acid methyl ester.

5-[3-[2-(1 -Carboethoxy)ethyl]-4-hydroxyphenyl]-4-pentynoic acid methyl ester (500 mg, 0.942 mmol) was alkylated with 2-[(2-trimethylsilyl)ethoxy]methoxy-1-( 4-fluorophenyl)-5-ethyl-4-(3-chloro-1-propyloxy)benzene as described above for the preparation of Example 66(A). Purification via silica gel chromatography (ethyl acetate/ hexane) provided 320 mg (49%) of title intermediate as a colorless oil: NMR (CDCl$_3$) 7.47 (m, 2H), 7.27 (m, 2H), 7.10 (m, 3H), 6.83 (s, 1H), 6.80 (d, J=8.3 Hz, 1H), 5.15 (s, 2H), 4.23 (m, 4H), 4.13 (q, J=7.2 Hz, 2H), 3.74 (s, 3H), 3.65 (t, J=8.3 Hz, 2H), 2.93 (t, J=7.4 Hz, 2H), 2.75 (m, 2H), 2.58–2.68 (m, 6H), 2.35 (quintet, J=5.9 Hz, 2H), 1.24 (t, J=7.1 Hz, 3H), 1.20 (t, J=7.4 Hz, 3H), 0.00 (s, 9H); MS-FD m/e 637 (p, 100); IR (CHCl$_3$, cm$^{-1}$) 2972, 1731, 1605, 1498, 1234, 1058, 839. Analysis for C$_{40}$H$_{51}$O$_8$Si: Calc: C, 67.96; H, 7.27; Found: C, 68.19; H, 7.28.

F. Preparation of 5-[3-[2-(1-carboxy)ethyl]-4-[3-[ 2-ethyl-4-(4-fluorophenyl)-5-hydroxyphenoxy]propoxy] phenyl]- 4-pentynoic acid disodium salt 0.4 hydrate.

A mixture of 5-[3-[2-(1-carboethoxy)ethyl]-4-[3-[ 2-ethyl-4-(4-fluorophenyl)-5-[ 2-(trimethylsilyl)ethoxymethoxy]-phenoxy]propoxy]phenyl]-4-pentynoic acid methyl ester (300 mg, 0.434 mmol) and tetra-n-butylammonium fluoride (465 mg, 1.78 mmol) in tetrahydrofuran (20 mL) was stirred at 40° C. for 48 hours. The reaction was cooled to room temperature, diluted with diethyl ether, and washed with water. The organic layer was concentrated in vacuo to reveal an oil. Hydrolysis, salt formation, and purification as described above for the preparation of Example 59(D) to provided 112 mg (45%) of title product as an off-white solid: mp 73°–76° C.; NMR (DMSO-d$_6$) 7.54 (m, 2H), 7.04–7.21 (m, 4H), 6.91 (s, 1H), 6.84 (m, 2H), 4.21 (t, J=7.2 Hz, 2H), 4.05 (t, J=3.6 Hz, 2H), 2.71 (t, J=6.0 Hz, 2H), 2.48 (m, 4H), 2.13 (m, 6H), 1.08 (t, J=7.4 Hz, 3H); MS-FAB m/e 580 (p+1, 6), 579 (p, 23); IR (mull, cm$^{-1}$) 2925, 1565, 1502, 1464, 1377, 1241, 1148, 839. Analysis for C$_{31}$H$_{29}$O$_7$FNa$_2$.0.4 H$_2$O: Calc: C, 63.56; H, 5.13; Found: C, 63.68; H, 4.96.

EXAMPLE 84

1-Phenyl-1-(1H-tetrazol-5-yl)-6-(2-ethyl-4-( 4-fluorophenyl)-5-hydroxyphenoxy)hexane

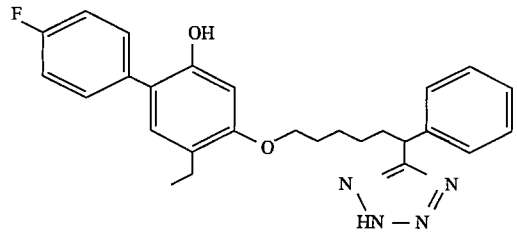

A. Preparation of 7-chloro-2-phenylheptanenitrile.

Lithium diisopropylamine (0.1 mol) was prepared by adding n-butyl lithium in hexane (0.1 mol) to diisopropylamine (10.1 g, 0.1 mol) dissolved in toluene cooled to –78° C. under nitrogen. To this solution was added benzyl cyanide (11.7 g, 0.1 mol). The solution was allowed to stir at –78° C. for 60 minutes then 5-chloro-1-bromopentane was added and the solution slowly allowed to warm to room temperature over 2 hours. The cloudy solution was allowed to stir at room temperature for an additional 3 hours. The toluene solution was then washed with aqueous ammonium chloride solution (250 mL) and the toluene layer separated and dried with magnesium sulfate. The toluene solution was evaporated to an oil which was distilled bulb to bulb at 10 mm of Hg up to an oven temperature of 120° C. to remove unreacted starting materials. The residual oil was the title compound (16.8 g, 76%) which was shown by NMR to contain a small percentage of the corresponding bromide but was otherwise pure and was used as is. NMR.

B. Preparation of 2-phenyl-7-(2-acetyl- 5-benzyloxyphenoxy)heptanenitrile.

2-Hydroxy-5-benzyloxyacetophenone (2.42 g, 0.01 mol) was dissolved in methyl ethyl ketone (100 mL) and 7-chloro- 2-phenylheptanenitrile (2.21 g, 0.01 mol) added followed by finely divided potassium carbonate (5 g) and potassium iodide (1 g). The stirred suspension was refluxed under nitrogen for 20 hours. The solution was then filtered and evaporated to an oil which was chromatographed on a silica gel column eluting with 1:1 ether/hexane to give 2.8 g (65.5%) of the title compound as a colorless oil. NMR.

C. Preparation of 2-phenyl-7-(2-ethyl- 5-benzyloxyphenoxy)heptanenitrile.

2-Phenyl-7-(2-acetyl-5-benzyloxyphenoxy)heptanenitrile (1.4 g, 3.28 mmol) was dissolved in carbon tetrachloride (100 mL) and trifluoroacetic acid (10 mL) added followed by triethylsilane (10 mL). The solution was allowed to stand at room temperature for 6 hours. At this time the NMR spectrum of the reaction mixture showed the reaction to be incomplete and additional trifluoroacetic acid (10 mL) and triethylsilane (5 mL) were added and the solution allowed to stand overnight. The solution was then evaporated to dryness and the residue chromatographed on a silica gel column eluting with ether/hexane (1:1). The title compound was obtained as an oil—yield 1.21 g (89%). NMR.

D. Preparation of 2-phenyl-7-(2-ethyl-4-bromo- 5-benzyloxyphenoxy)heptanenitrile.

2-Phenyl-7-(2-ethyl-5-benzyloxyphenoxy)heptanenitrile (1.23 g, 3 mmol) was dissolved in carbon tetrachloride (50 mL) and a suspension of N-bromosuccinimide (534 mg, 3 mmol) was added. The solution was then stirred at room temperature. After about 40 minutes, a precipitate came out of solution and after 1 hour the reaction was complete as assessed by TLC. The suspension was filtered and evaporated to an oil which was chromatographed on a silica gel column eluting with ether/hexane (1:1) to yield 1.21 g (82%) of the title intermediate as a colorless oil. NMR.

E. Preparation of 2-phenyl-7-(2-ethyl-4-( 4-fluorophenyl)-5-benzyloxyphenoxy)heptanenitrile.

2-Phenyl-7-(2-ethyl-4-bromo- 5-benzyloxyphenoxy)heptanenitrile (1.21 g, 2.46 mmol) was dissolved in benzene (45 mL) and tetrakis(triphenylphosphine)palladium(0) (284.3 mg, 0.246 mmol) was added followed by a solution of 4-fluorophenylboronic acid (516 mg, 3.69 mmol) in ethanol (15 mL). A 2M aqueous sodium carbonate solution (15 mL) was added and the resultant orange solution refluxed for 17 hours under nitrogen. The almost black suspension was then cooled and added to a 10% aqueous ammonia solution (100 mL) and extracted 3 times with dichloromethane. The combined extracts were dried with magnesium sulfate and evaporated to an oil which was chromatographed on a silica gel column eluting with hexane/ether (1:1) to remove triphenylphosphine. The title compound was obtained as an oil in 57.5% (720 mg) yield. NMR.

F. Preparation of 1-phenyl-1-(1H-tetrazol-5-yl)-6-( 2-ethyl-4-(4-fluorophenyl)-5-benzyloxyphenoxy)hexane.

2-Phenyl-7-(2-ethyl-4-(4-fluorophenyl)-5-benzyloxyphenoxy)heptanenitrile (700 mg, 1.38 mmol) was dissolved in dimethylformamide (20 mL) and sodium azide (0.6 g) and triethylamine hydrochloride added (1.2 g) and the stirred suspension heated at 110° C. for 3 days. The suspension was then added to 1M hydrochloric acid (100 mL) and the solution extracted 4 times with chloroform. The combined chloroform extracts were washed with water and dried with magnesium sulfate. On evaporation the solution yielded 680 mg (72%) of the title compound as a crude oil which was then directly deprotected.

G. Preparation of 1-phenyl-1-(1H-tetrazol-5-yl)-6-( 2-ethyl-4-(4-fluorophenyl)-5-hydroxyphenoxy) hexane Crude 1 -phenyl-1-(1H-tetrazol-5-yl)-6-(2-ethyl-4-( 4-fluorophenyl)-5-benzyloxyphenoxy)hexane (150 mg, 0.27 mmol) was dissolved in ethanol (100 mL) and 5% palladium on carbon (0.5 g) added to the solution under a blanket of carbon dioxide. The suspension was then hydrogenated at 50 psi for 3 hours. The catalyst was filtered off and the ethanol evaporated to leave an oil which was purified by reverse phase chromatography on a $C_{18}$ column eluting with methanol/water (9:1). The title compound was the second eluting component which was obtained in 88.5% yield (110 mg) as a colorless oil after evaporation of the solvent. NMR, MS. Analysis for $C_{27}H_{29}N_4O_2$: Calc: C, 70.41; H, 6.35; N, 12.16; Found: C, 70.41; H, 6.46; N, 12.16.

The more polar first eluting component was shown by NMR to be 1-phenyl-1-(1H-tetrazol-5-yl)-6-(2-ethyl- 5-hydroxyphenoxy)hexane, yield 15 mg.

EXAMPLE 85

1-(4-(Carboxymethoxy)phenyl)-1-(1H-tetrazol-5-yl)-6-( 2-ethyl-4-(4-fluorophenyl)-5-hydroxyphenoxy)hexane

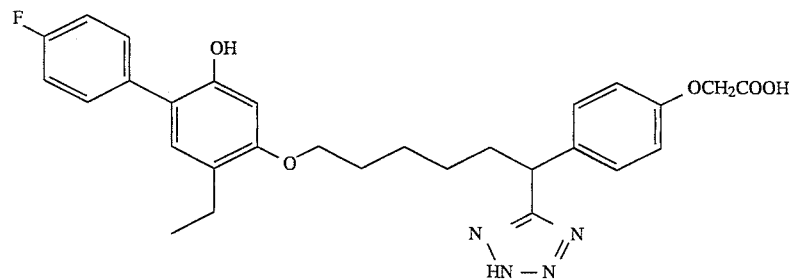

A. Preparation of 7-chloro-2-(4-methoxyphenyl)heptanenitrile.

7-Chloro-2-(4-methoxyphenyl)heptanenitrile was prepared in 71% yield as a pale yellow oil from 4-methoxybenzylnitrile and 5-chloro-1-bromopentane using the procedure described in Example 84(A) except THF was used in place of toluene due to the greater solubility of the lithium salt. NMR.

B. Preparation of 7-chloro-2-(4-hydroxyphenyl)heptanenitrile.

7-Chloro-2-(4-methoxyphenyl)heptanenitrile (4.0 g, 16.7 mmol) was dissolved in dichloromethane (100 mL) and the stirred solution cooled to 0° C. Excess boron tribromide (5 mL) was added to the solution and the reaction mixture allowed to warm to room temperature and stirred overnight.

The solution was then added slowly to a saturated aqueous sodium bicarbonate solution (500 mL) and the mixture extracted 3 times with dichloromethane. The combined dichloromethane extracts were dried and evaporated to a pale yellow oil (yield 3.15 g, 83.6%) which was used directly in the next reaction without purification. NMR.

C. Preparation of 7-chloro-2-(4-(ethoxycarbonylmethoxy)phenyl)heptanenitrile.

7-Chloro-2-(4-hydroxyphenyl)heptanenitrile (1 g, 4.2 mmol) was dissolved in methyl ethyl ketone (100 mL) and freshly ground potassium carbonate (5 g) added to give a slurry. Excess ethyl bromoacetate was added (1.4 g, 8.3 mmol) and the stirred suspension refluxed for 3 hours. The slurry was then poured into water (200 mL) and extracted 3 times with dichloromethane. The combined dichloromethane extracts were dried with magnesium sulfate and evaporated to an oil. Excess bromoester was then removed by azeotroping with toluene yielding the title intermediate in 98% (1.38 g) yield as a pale yellow oil which was essentially pure as judged via the NMR spectrum and used directly in the following reaction. NMR.

D. Preparation of 1-(4-(ethoxycarbonylmethoxy)phenyl)-1-cyano-6-(2-acetyl-5-benzyloxyphenoxy)hexane.

2-Hydroxy-4-benzyloxyacetophenone (1.04 g, 4.3 mmol) was dissolved in dimethylformamide (50 mL) and 7-chloro-2-(4-(ethoxycarbonylmethoxy)phenyl)heptanenitrile (1.4 g, 4.3 mmol) added. Potassium iodide (1.5 g) was then added and the suspension allowed to stir at room temperature for 2 hours. Potassium carbonate (3 g) was added and the stirred suspension heated to 110° C. for 16 hours under nitrogen. The suspension was then added to water (150 mL) and extracted 3 times with chloroform. The combined chloroform extracts were dried with magnesium sulfate and evaporated to a brown oil which was chromatographed on a silica gel column eluting with ether/hexane (1:1). The major component of the mixture was isolated as pale yellow crystals (yield 270 mg, 14%) from hexane/ether, mp 102°–4° C. NMR. A further 180 mg of oily crystals were eventually isolated from the mother liquors.

E. Preparation of 7-iodo-2-(4-(ethoxycarbonylmethoxy)phenyl)heptanenitrile.

7-Chloro-2-(4-(ethoxycarbonylmethoxy)phenyl)heptanenitrile (3.34 g, 10 mmol) was dissolved in methyl ethyl ketone (100 mL). Sodium iodide (3 g) was added and the stirred suspension was then refluxed overnight. The solution was cooled, filtered and evaporated to an oily solid. The oil was dissolved in ether and the solid sodium iodide filtered off. The title compound was obtained as a yellow oil on evaporation of the ether, yield 4.25 g (100%). This crude iodide was used directly in the next reaction.

F. Preparation of 1-(4-(ethoxycarbonylmethoxy)phenyl)-1-cyano-6-(2-acetyl-5-benzyloxyphenoxy)hexane.

2-Hydroxy-4-benzyloxyacetophenone (2.42 g, 10 mmol) was dissolved in dimethylformamide (50 mL) and 7-iodo-2-(4-(ethoxycarbonylmethoxy)phenyl)heptanenitrile (4.3 g, 10 mmol) added followed by potassium carbonate (10 g) and the stirred suspension heated at 110° C. for 24 hours. The reaction mixture was then worked-up as in Example 85(D) to provide 4.5 g (90%) of title compound, mp 102°–4° C. NMR, MS. Analysis for $C_{32}H_{35}NO_6$: Calc: C, 72.57; H, 6.66; N, 2.65; Found: C, 72.84; H, 6.65; N, 2.48.

G. Preparation of 1-(4-(ethoxycarbonylmethoxy)phenyl)-1-cyano-6-(2-ethyl-5-benzyloxyphenoxy)hexane.

1-(4-(Ethoxycarbonylmethoxy)phenyl)-1-cyano-6-(2-acetyl-5-benzyloxy)phenoxyhexane was converted to the title compound using the procedure described in Example 84(C), yield 86%.

H. Preparation of 1-(4-(ethoxycarbonylmethoxy)phenyl)-1-Cyano-6-(2-ethyl-4-bromo-5-benzyloxyphenoxy)hexane.

1-(4-(Ethoxycarbonylmethoxy)phenyl)-1-cyano-6-(2-ethyl-5-benzyloxyphenoxy)hexane (900 mg, 1.8 mmol) was brominated using the procedure described in Example 84(D) except dichloromethane was used as solvent and the product was chromatographed using ether/hexane (3:1). Yield after chromatography was 887 mg (83%). NMR.

I. Preparation of 1-(4-(ethoxycarbonylmethoxy)phenyl)-1-cyano-6-(2-ethyl-4-(4-fluorophenyl)-5-benzyloxyphenoxy)hexane.

The title compound was prepared from 1-(4-(ethoxycarbonylmethoxy)phenyl)-1-cyano-6-(2-ethyl-4-bromo-5-benzyloxyphenoxy)hexane (800 mg, 1.34 mmol) using the procedure in Example 84(E) to provide 672 mg (82%) of a colorless oil. NMR.

J. Preparation of 1-(4-(ethoxycarbonylmethoxy)phenyl)-1-(1H-tetrazol-5-yl)-6-(2-ethyl-4-(4-fluorophenyl)-5-benzyloxyphenoxy) hexane.

1-(4-(Ethoxycarbonylmethoxy)phenyl)-1-cyano-6-(2-ethyl-4-(4-fluorophenyl)-5-benzyloxyphenoxy)hexane (670 mg, 1.09 mmol) was dissolved in dimethylformamide (20 mL). Triethylamine hydrochloride (1.3 g) and sodium azide (0.6 g) were added and the stirred suspension was heated to 117° C. for 24 hours. Additional triethylamine hydrochloride (1.3 g) and sodium azide (0.6 g) were added and the mixture heated at 117° C. for a further 16 hours. The reaction was then worked-up using the procedure of Example 84(F) to provide 690 mg (97%) of the title intermediate as an oil. NMR.

K. Preparation of 1-(4-(ethoxycarbonylmethoxy)phenyl)-1-(1H-tetrazol-5-yl)-6-(2-ethyl-4-(4-fluorophenyl)-5-hydroxyphenoxy)hexane.

The title compound was prepared from crude 1-(4-(ethoxycarbonylmethoxy)phenyl)-1-(1H-tetrazol-5-yl)-6-(2-ethyl-4-(4-fluorophenyl)-5-benzyloxyphenoxy)hexane (680 mg, 1.04 mmol) using the procedure of Example 84(G) to provide 540 mg (92%) of the title intermediate as a colorless oil which contained some ethanol of solvation. NMR.

L. Preparation of 1-(4-(carboxymethoxy)phenyl)-1-(1H-tetrazol-5-yl)-6-(2-ethyl-4-(4-fluorophenyl)-5-hydroxyphenoxy)hexane.

Crude 1-(4-(ethoxycarbonylmethoxy)phenyl)-1-(1H-tetrazol-5-yl)-6-(2-ethyl-4-(4-fluorophenyl)-5-hydroxyphenoxy)hexane (50 mg) was dissolved in ethanol (20 mL). 1M Aqueous sodium carbonate solution was added and the resultant solution stirred at room temperature for 3 hours. The pH of the solution was then adjusted to 2 using 1M hydrochloric acid and the solution extracted 5 times with chloroform. The combined chloroform extracts were dried with magnesium sulfate and evaporated to an oil which was purified on a reverse phase HPLC $C_{18}$ column eluting with methanol/water (85:15) and 0.1% acetic acid. On removal of the solvent 9.7 mg of the title compound was obtained as a colorless oil. MS, NMR.

EXAMPLE 86

1-(4-(Dimethylaminocarbonylmethoxy)phenyl)-1-(1H-tetrazol-5-yl)-6-(2-ethyl-4-(4-fluorophenyl)-5-hydroxyphenoxy)hexane

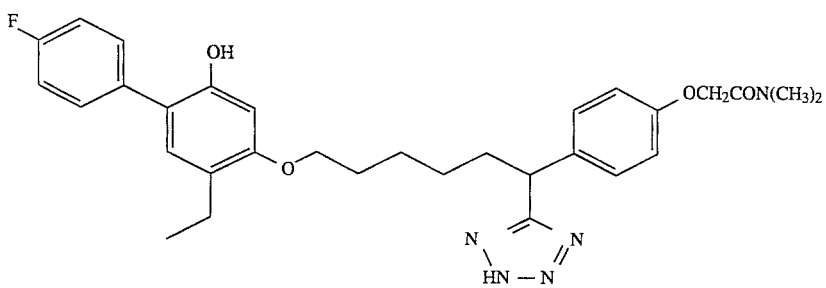

1-(4-(Ethoxycarbonylmethoxy)phenyl)-1-(1H-tetrazol-5-yl)-7-(2-ethyl-4-(4-fluorophenyl)-5-hydroxyphenoxy)hexane (100 mg, 0.18 mmol) was dissolved in ethanol (25 mL) and dimethylamine dissolved in ethanol 33% (25 mL) was added and the solution allowed to stand at room temperature in a sealed flask for 25 days. The solvent was then evaporated and the title compound slowly crystallized from ether, mp 115°–120° C., yield 36.6 mg (36%). NMR, MS. Analysis for $C_{31}H_{36}N_5O_4$: Calc: C, 66.29; H, 6.46; N, 12.47; Found: C, 66.26; H, 6.61; N, 12.29.

EXAMPLE 87

3-(2-(3-(2-Ethyl-4-(4-fluorophenyl)-5-hydroxyphenoxy)propoxy)phenyl)-E-propenoic acid

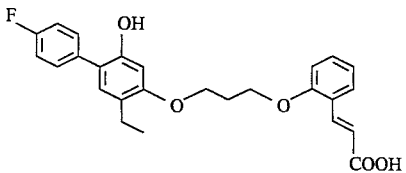

A. Preparation of 2-(2-hydroxyphenyl)-1,3-dioxolane.

2-Hydroxybenzaldehyde (12.2 g, 0.1 mol) was dissolved in toluene (125 mL). Ethylene glycol (12.4 g, 0.2 mol) was added followed by approximately 30 mg para-toluenesulfonic acid as a catalyst. The resultant solution was refluxed under a Dean-Stark trap. After 2 hours an additional 10 mL of ethylene glycol were added and the mixture refluxed for a further 2 hours. The toluene was then decanted off the red resin and washed with aqueous sodium bicarbonate. The toluene layer was then dried with magnesium sulfate and evaporated to a pale yellow oil which was crystallized from ether/hexane to give the title intermediate as white crystals, mp 68°–69° C., yield 10.1 g (61%). NMR.

B. Preparation of 3-(2-ethyl-4-(4-fluorophenyl)- 5-hydroxyphenoxy)propyl chloride.

3-(2-Ethyl-4-(4-fluorophenyl)-5-benzyloxyphenoxy)propyl chloride (0.5 g, 1.25 mmol) was dissolved in ethyl acetate (50 mL) and 10% palladium on carbon catalyst added under an inert atmosphere of carbon dioxide. The suspension was hydrogenated at room temperature at 30 psi for 2 hours. The catalyst was filtered off and the filtrate evaporated to dryness to give an oil which slowly crystallized as the title intermediate, mp 55°–56° C., yield 380 mg (98%). NMR C. Preparation of 3-(2-ethyl-4-(4-fluorophenyl)- 5-acetoxyphenoxy)propyl chloride.

3-(2-Ethyl-4-(4-fluorophenyl)-5-hydroxyphenoxy)propyl chloride (360 mg, 1.16 mmol) was dissolved in dichloromethane and acetic anhydride (85 μl, 1.16 mmol) and triethylamine (117 mg, 1.16 mmol) were added to the stirred solution. After 2 hours an additional 10% equivalent of acetic anhydride and triethylamine was added and the solution stirred for an extra 2 hours at room temperature. The dichloromethane solution was then washed sequentially with aqueous sodium bicarbonate and 1M hydrochloric acid. The dichloromethane solution was then dried with magnesium sulfate and evaporated to an oil to give 400 mg (99%) of the title intermediate. NMR.

D. Preparation of 3-(2-ethyl-4-(4-fluorophenyl)- 5-acetoxyphenoxy)propyl iodide.

3-(2-Ethyl-4-(4-fluorophenyl)-5-acetoxyphenoxy)propyl chloride (400 mg, 1.14 mmol) was dissolved in methyl ethyl ketone (50 mL) and sodium iodide (2.5 g) added. The stirred suspension was then refluxed for 16 hours. The cooled solution was filtered and the methyl ethyl ketone evaporated off to leave a residue which was redissolved in ether. The ether solution was filtered and evaporated to a pale yellow oil. The NMR spectrum showed the crude material to be mainly the required product plus a few minor impurities; because of the unstable nature of the material it was used directly in the next reaction.

E. Preparation of 2-(2-(3-(2-ethyl-4-( 4-fluorophenyl)-5-acetoxyphenoxy)propoxy)phenyl)-1,3-dioxolane.

60% Sodium hydride in oil was washed with hexane and suspended in dry DMSO (50 mL) with stirring under nitrogen. 2-(2-Hydroxyphenyl)-1,3-dioxolane (166 mg, 1 mmol) was dissolved in dry THF (10 mL) and added to the DMSO solution to give a pale yellow solution. After 20 minutes at room temperature 3-(2-ethyl-4-(4-fluorophenyl)- 5-acetoxyphenoxy)propyl iodide (442 mg, 1 mmol) was added as a solution in dry THF (10 mL). After a further 2 hours at room temperature the reaction mixture was poured into pH 7.0 phosphate buffer and the mixture extracted 5 times with ether. The combined ether extracts were washed with water, dried with magnesium sulfate and evaporated to an oil which was chromatographed on a silica gel column eluting with ether/hexane (1:1). The title compound was isolated as an oil which was shown by the NMR spectrum to be contaminated with the starting phenol and a byproduct produced by loss of the acetyl group and alkylation produced with the starting iodide. These impurities could not be conveniently separated at this stage and the partially purified material was taken on to the next step.

F. Preparation of 2-(3-(2-ethyl-4-(4-fluorophenyl)- 5-acetoxyphenoxy)propoxy)benzaldehyde.

2-(2-(3-(2-Ethyl-4-(4-fluorophenyl)- 5-acetoxyphenoxy)propoxy)phenyl)-1,3-dioxolane (300 mg, 0.65 mmol) was dissolved in THF (50 mL) and 1M hydrochloric acid added (10 mL). The resulting colorless solution was allowed to stand at room temperature for 3 hours. The solution was poured into an aqueous sodium bicarbonate solution and extracted 3 times with ether. The combined ether extracts were dried with magnesium sulfate and evaporated to 270 mg of an oil. This material contained some 2-hydroxybenzaldehyde which was removed by passing the oil through a short silica gel column eluting with ether/hexane (1:1). The resulting material still contained the aldehyde of the over-alkylation product formed in the previous reaction which still could not be easily removed but was evident in the NMR spectrum. This crude material was then used in the next reaction.

G. Preparation of 3-(2-(3-(2-ethyl-4-( 4-fluorophenyl)-5-acetoxyphenoxy)propoxy)phenyl)-E-propenoic acid.

2-(3-(2-Ethyl-4-(4-fluorophenyl)-5-acetoxyphenoxy)propoxy)benzaldehyde (210 mg, 0.5 mmol) was dissolved in toluene (25 mL) and pyridine (1 mL), piperidine hydrochloride (100 mg) and malonic acid (1 g) were added. The solution was then refluxed for 3 hours. At that time an extra portion of malonic acid (0.5 g) was added and the solution refluxed for a further hour. The cooled solution was extracted with 1M hydrochloric acid. The aqueous layer was washed 3 times with ether and the combined toluene and ether extracts washed once with water and dried with magnesium sulfate. On evaporation the solution yielded an oil which was a mixture of two compounds with similar Rf values. This compounds were separated on a silica gel column eluting with 1:1 ether/hexane containing 1.0% acetic acid. The title compound was the more polar compound obtained as a glass (yield 107 mg, 46%); NMR. The less polar compound was identified as 3-(2-(3-(2-ethyl-4-( 4-fluorophenyl)-5-(3-(2-ethyl-4-(4-fluorophenyl)- 5-acetoxyphenoxy)propoxy)phenoxy)propoxy)phenyl)-E-propenoic acid by MS and NMR (yield 91 mg obtained as an oil).

H. Preparation of 3-(2-(3-(2-ethyl-4-( 4-fluorophenyl)-5-hydroxyphenoxy)propoxy)phenyl)-E-propenoic acid.

3-(2-(3-(2-Ethyl-4-(4-fluorophenyl)- 5-acetoxyphenoxy)propoxy)phenyl)-E-propenoic acid (90 mg, 0.2 mmol) was dissolved in methanol (10 mL). 0.1M Aqueous potassium carbonate solution was added and the solution stirred under nitrogen overnight. The thin-layer chromatogram showed a single spot of the same Rf as the starting material so additional 1.0M potassium carbonate solution was added and the solution stirred for a further 4 hours. The reaction mixture was poured into 1M hydrochloric acid (50 mL) and the mixture extracted 3 times with chloroform. The combined chloroform extracts were dried with magnesium sulfate and evaporated to provide 63 mg of the title intermediate as an oil which solidified to a glass. MS, NMR.

EXAMPLE 88

3-(2-(3-(2-Ethyl-4-(4-fluorophenyl)-5-hydroxyphenoxy)propoxy)phenyl)-2-methyl-E-propenoic acid

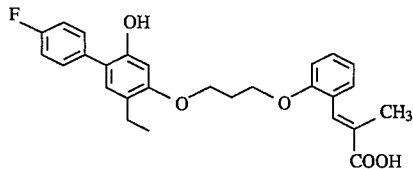

A. Preparation of 3-(2-ethyl-4-(4-fluorophenyl)-5-( 2-(trimethylsilyl)ethoxymethoxyphenoxy)propyl chloride.

3-(2-Ethyl-4-(4-fluorophenyl)-5-hydroxyphenoxy)propyl chloride (400 mg, 1.29 mmol) was dissolved in dichloromethane (25 mL) and the solution cooled to 0° C. under nitrogen. N,N-Diisopropylethylamine (832.0 mg, 6.45 mmol) was added followed by 2-(trimethylsilyl)ethoxymethyl chloride (645 mg, 3.87 mmol) and the mixture allowed to warm to room temperature over 1 hour. The reaction mixture was then poured into 1M hydrochloric acid and extracted 3 times with dichloromethane. The combined dichloromethane extracts were dried over magnesium sulfate and the dichloromethane evaporated to an oil. This oil was then placed under high vacuum for 48 hours at room temperature to remove volatile impurities. The residual oil was the title compound, yield 490 mg (86%). NMR.

B. Preparation of 3-(2-ethyl-4-(4-fluorophenyl)-5-( 2-(trimethylsilyl)ethoxymethoxyphenoxy)propyl iodide.

The title compound was made from corresponding chloride using the procedure described in Example 87(D). The unstable iodide was characterized by NMR and used directly in the next reaction.

C. Preparation of 2-(2-(3-(2-ethyl-4-( 4-fluorophenyl)-5-(2-(trimethylsilyl)ethoxymethoxyphenoxy)propoxy)phenyl). 1,3-dioxolane.

The title compound was prepared using the general procedure described in Example 87(E), yield 86% of an oil after chromatography. NMR.

D. Preparation of 2-(3-(2-ethyl-4-(4-fluorophenyl)- 5-(2-(trimethylsilyl)ethoxymethoxyphenoxy)propoxy)benzaldehyde.

The title compound was prepared from 2-(2-(3-(2-ethyl-4-(4-fluorophenyl)-5-(2-(trimethylsilyl)ethoxymethoxyphenoxy)propoxy)phenyl- 1,3-dioxolane using the general procedure described in Example 87(F), yield 82% as an oil. NMR.

E. Preparation 3-(2-(3-(2-ethyl-4-(4-fluorophenyl)- 5-(2-(trimethylsilyl)ethoxymethoxyphenoxy)propoxy)phenyl)-2-methyl-E-propenoic acid.

The title compound was prepared using the general procedure described in Example 87(G) except methyl malonic acid was used instead of malonic acid. The crude product was found to be a mixture of the title compound plus the 5-hydroxy analog formed by partial loss of the SEM protecting group. The crude product was therefore completely deprotected in the next reaction without further purification. NMR.

F. Preparation 3-(2-(3-(2-ethyl-4-(4-fluorophenyl)- 5-hydroxyphenoxy)propoxy)phenyl)-2-methyl-E-propenoic acid.

Crude 3-(2-(3-(2-ethyl-4-(4-fluorophenyl)-5-( 2-(trimethylsilyl)ethoxymethoxyphenoxy)propoxy)phenyl)- 2-methyl-E-propenoic acid (300 mg) containing some of the title compound was dissolved in THF (50 mL) and tetrabutylammonium fluoride monohydrate (2 g) added as a solution also in THF (20 mL). The resultant yellow solution was allowed to stand at room temperature for 16 hours. The reaction mixture was poured into 1M hydrochloric acid and extracted 3 times with ether. The combined ether extracts were dried with magnesium sulfate and evaporated to dryness to leave an oil. This oil was chromatographed on a silica gel column eluting with 1:1 ether/hexane containing 1% acetic acid. The major component was the title compound with minor impurities present. The oil was further purified on a $C_{18}$ reverse phase HPLC column eluting with methanol/ water (90:10) containing 0.1% acetic acid. The major component was isolated and slowly crystallized from ether/hexane to provide 110 mg of the desired title compound, mp 112°–114° C. The 2D-NOE spectra confirmed the isomer isolated to be the E isomer. NMR, MS. Analysis for $C_{27}H_{27}O_5F$: Calc: C, 71.98; H, 6.04; Found: C, 72.06; H, 6.21.

EXAMPLE 89

5-(2-(2-(3-(2-Ethyl-4-(4-fluorophenyl)-5-hydroxyphenoxy)propoxy)phenyl)ethyl)-1H-tetrazole

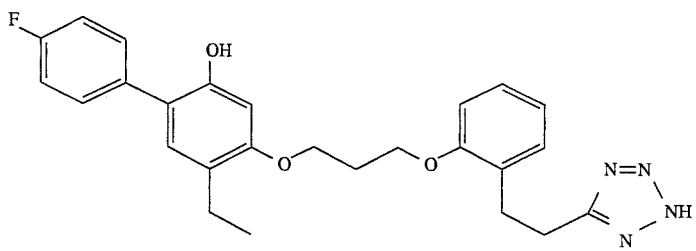

A. Preparation of 3-(2-(3-(2-ethyl-4-( 4-fluorophenyl)-5-benzyloxyphenoxy)propoxy)phenyl)propylnitrile.

3-(2-Ethyl-4-(4-fluorophenyl)-5-benzyloxyphenoxy)propyl chloride (199 mg, 0.5 mmol) was dissolved in methyl ethyl ketone (50 mL) and sodium iodide (0.5 g) added and the resulting suspension stirred at room temperature for 3 hours. 3-(2-Hydroxyphenyl)propylnitrile (73.5 mg, 0.5 mmol) was added followed by potassium carbonate (1 g). The resultant suspension was refluxed under nitrogen for 28 hours. The reaction mixture was then poured into water (50 mL) and the mixture extracted 3 times with chloroform. The combined extracts were dried with magnesium sulfate and evaporated to an oil which was chromatographed on a silica gel column eluting with 1:1 ether/hexane. The title compound was obtain as a colorless oil, yield 131 mg (51%). NMR.

B. Preparation of 5-(2-(2-(3-(2-ethyl-4-( 4-fluorophenyl)-5-benzyloxyphenoxy)propoxy)phenyl)ethyl)-1 H-tetrazole.

3-(2-(3-(2-Ethyl-4-(4-fluorophenyl)- 5-benzyloxyphenoxy)propoxy)phenyl)propylnitrile (120 mg, 0.24 mmol) was dissolved in DMF (20 mL) and sodium azide (0.6 g, 1.0 mmol) and triethylammonium chloride (1.37 g, 1.0 mmol) was added and the stirred mixture heated to 125° C. for 24 hours under nitrogen. An additional 1 mmol of both sodium azide and triethylammonium chloride was then added. After a further 24 hours of heating another aliquot of azide and hydrochloride was added and the mixture heated for a final 6 hours. The reaction mixture was then added to 1M hydrochloric acid (100 mL) and the mixture extracted 3 times with chloroform. The combined extracts were dried with magnesium sulfate and evaporated to an oil which slowly became a waxy solid without a definable melting point. The material was determined to be the DMF solvate of the title compound. NMR.

C. Preparation of 5-(2-(2-(3-(2-ethyl-4-( 4-fluorophenyl)-5-hydroxyphenoxy)propoxy)phenyl)ethyl)-1H-tetrazole.

5-(2-(2-(3-(2-Ethyl-4-(4-fluorophenyl)- 5-benzyloxyphenoxy)propoxy)phenyl)ethyl)-1H-tetrazole (90 mg, 0.16 mmol) was dissolved in ethanol and 10% palladium on carbon catalyst was added under an atmosphere of carbon dioxide. The mixture was then hydrogenated at 30 psi at room temperature for 1 hour. The catalyst was filtered off and the solution evaporated to dryness to give an oil. This oil was then purified by reverse phase HPLC on a $C_{18}$ column eluting with methanol/water (90:10) containing 0.01% acetic acid. The title compound was isolated as an oil (yield 41 mg, 55%) containing 0.3 equivalents of acetic acid. NMR, MS.

EXAMPLE 90

3-(2-(3-(2-Ethyl-4-(4-fluorophenyl)-5-hydroxyphenoxy)propoxy)-4-(4-carboxybutyloxy)phenyl)propionic acid

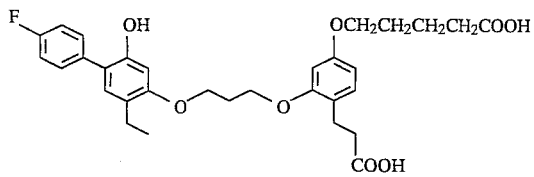

In the same manner as described for Example 5, 3-(2-( 3-(2-ethyl-4-(4-fluorophenyl)-5-benzyloxyphenoxy)propoxy)-4-( 4-carboxybutyloxy)phenyl)propionic acid was debenzylated to provide the title compound in 20% yield. NMR. Analysis for $C_{31}H_{35}FO_8$: Calc: C, 67.14; H, 6.36; Found: C, 67.40; H, 6.45.

EXAMPLE 91

5-[3-[4-(4-Fluorophenyl)-2-ethyl-5-hydroxyphenoxy]propoxy]- 3,4-dihydro-2H- 1-benzopyran-2-one

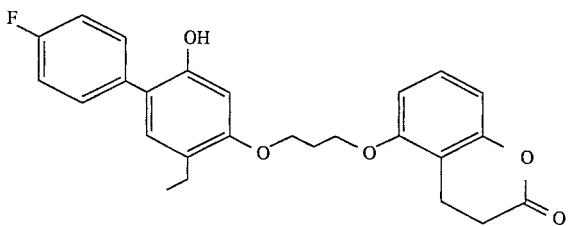

When methyl 3-(2-(3-(2-ethyl-4-(4-fluorophenyl)- 5-hydroxyphenoxy)propoxy)-6-hydroxyphenyl)propionate (Example 12) was hydrolyzed under the conditions of Preparation 26, in addition to the desired product 3-(2-(3-(2-ethyl-4-( 4-fluorophenyl)-5-hydroxyphenoxy)propoxy)-6-hydroxyphenyl)propionic acid (Example 13), the title product was isolated in 10% yield, as isolated by preparative reverse phase HPLC. NMR, MS. Analysis for $C_{26}H_{25}FO_5$: Calc: C, 76.55; H, 5.77; Found: C, 76.39; H, 5.92.

EXAMPLES 92–96

The following compounds were prepared from their corresponding ethyl ester according to the procedure of Preparation 26 using methanol in place of ethanol.

92. 3-(3-{3-[2-Ethyl-4-(4-fluorophenyl)- 5-hydroxyphenyloxy]propoxy}phenyl)propanoic acid, 10% yield, mp 113°–115° C. Analysis for $C_{26}H_{27}FO_5$: Calc: C, 71.22; H, 6.21; Found: C, 70.95; H, 6.42.

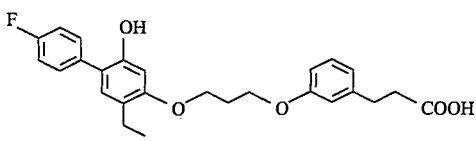

93. 3-(3-{3-[2-Ethyl-4-(4-fluorophenyl)- 5-hydroxyphenyloxy]propoxy}-4-propylphenyl)propanoic acid sodium salt, 23% yield. Analysis for $C_{29}H_{32}FNaO_5$: Calc: C, 69.31; H, 6.42; Found: C, 69.35; H, 6.83.

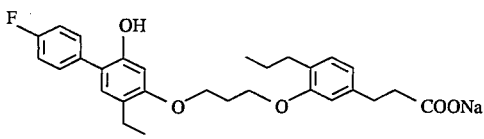

94. 3-(4-{3-[2-Ethyl-4-(4-fluorophenyl)- 5-hydroxyphenyloxy]propoxy}-3-propylphenyl)propanoic acid, 69% yield, mp 118°–120° C. Analysis for $C_{29}H_{33}FO_5$: Calc: C, 72.48 H, 6.92; Found: C, 72.20; H, 7.00.

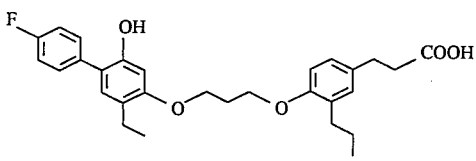

95. 3-(3-{3-[2-Ethyl-4-(4-fluorophenyl)- 5-hydroxyphenyloxy]propoxy}-2-propylphenyl)propanoic acid, 56% yield, mp 125°–127° C. Analysis for $C_{29}H_{33}FO_5$: Calc: C, 72.48; H, 6.92; Found: C, 72.67; H, 7.05.

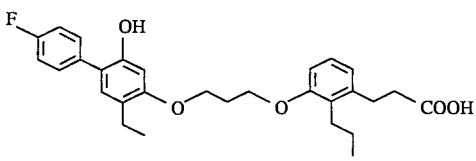

96. 3-{3-[3-(2-Ethyl-5-hydroxyphenyloxy)propoxy]-2-propylphenyl}propanoic acid disodium salt, 18% yield.

Analysis for $C_{29}H_{32}Na_2O_5$: Calc: C, 68.76; H, 6.37; Found: C, 68.00; H, 6.46.

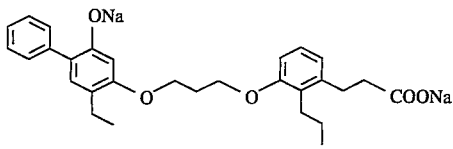

EXAMPLE 97

2-[3-[3-[2-Ethyl-5-hydroxy-4-(4-fluorophenyl)phenoxy]propoxy] benzoyl]benzoic acid disodium salt hemihydrate

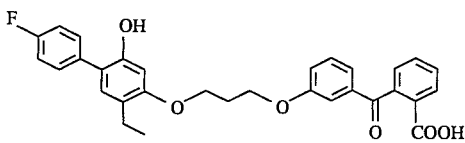

The title compound was hydrolyzed from 400 mg of the corresponding methyl ester as described above in Example 60. The acid was converted to the disodium salt and purified as described above for the preparation of Example 59(D) to provide 170 mg (42%) of the title product as a fluffy white solid. NMR (DMSO-d6) 11.85 (s, 1H, —OH), 7.82 (d, J=7.7 Hz, 1H), 7.53 (m, 2H), 7.28–7.42 (m, 4H), 7.11 (m, 4H), 6.99 (d, J=8.3 Hz, 1H), 6.87 (m, 2H), 3.99 (t, J=4.9 Hz, 2H), 3.84 (t, J=3.9 Hz, 2H), 2,42 (q, J=7.4 Hz, 2H), 1.82 (m, 2H), 1.06 (t, J=7.2 Hz, 3H); MS-FAB m/e 559 (p+Na, 100), 537 (p); IR (CHCl$_3$, cm$^{-1}$) 3450 (br), 3021, 1601, 1370, 1226, 1048. Analysis for $C_{31}H_{26}O_6FNa_2 \cdot 0.5 H_2O$: Calc: C, 65.60; H, 4.80; Found: C, 65.45; H, 4.76.

The compounds of Formula I should be useful in treating any condition, including clinical conditions, which is characterized by the excessive release of leukotriene $B_4$. These conditions include immediate type hypersensitivity reactions such as asthma. The term "excessive release" of leukotriene $B_4$ refers to an amount of the leukotriene sufficient to cause the particular condition associated with such amount. The amount of leukotriene which is considered to be excessive will depend on a variety of factors, including the amount of leukotriene required to cause the particular condition, and the species of the mammal involved. As will be appreciated by those skilled in the art, the success of treating a mammal suffering from or susceptible to a condition characterized by an excessive release of leukotriene with a compound of Formula I will be measured by the regression or prevention of the symptoms of the condition. The effectiveness of compounds of Formula I to inhibit the binding of tritiated LTB$_4$ to guinea pig lung membranes was determined as follows.

[$^3$H]-LTB$_4$ Radioligand Binding Assay in Guinea Pig Lung Membranes

[$^3$H]-LTB$_4$ (196–200 Ci/mmole) was purchased from New England Nuclear (Boston, Mass.). All other materials were purchased from Sigma (St. Louis, Mo.). Incubations (555 μL) were performed in polypropylene minitubes for 45 minutes at 30° C. and contained 25 μg of guinea pig lung membrane protein (Saussy, et al., *Mol. Pharmacol.*, 39, 72

(1991)) in a buffer containing 25 mM MOPS, 10 mM MgCl$_2$, 10 mM CaCl$_2$, pH 6.5, approximately :140 pM [$^3$H]-LTB$_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 μM LTB$_4$ and was usually less than 10% of total binding. Data were analyzed using linear regression analysis of log-logit plots of the values between 10% and 90% of control binding to calculate IC$_{50}$s and slope factors (pseudo-Hill coefficients). IC$_{50}$ values thus obtained were corrected for radioligand concentration (Cheng and Prusoff, *Biochem. Pharmacol.*, 22, 3099 (1973)) to calculate K$_i$ values. The data reported below is the mean -log K$_i$, otherwise known as the pKi, for n experiments.

| Example No. | pKi | n |
|---|---|---|
| 1 | 8.52 | 7 |
| 2 | 8.33 | 7 |
| 3 | 8.08 | 3 |
| 4 | 8.44 | 7 |
| 5 | 9.26 | 6 |
| 6 | 8.30 | 4 |
| 7 | 8.87 | 3 |
| 9 | 8.29 | 3 |
| 9 (cis) | 8.44 | 3 |
| 9 (trans) | 8.41 | 3 |
| 10 | 8.05 | 6 |
| 11 | 7.67 | 3 |
| 13 | 9.01 | 7 |
| 14 | 7.52 | 3 |
| 15 | 8.23 | 3 |
| 16 | 7.76 | 3 |
| 17 | 7.27 | 2 |
| 18 | 6.61 | 3 |
| 19 | 8.82 | 3 |
| 20 | 8.64 | 3 |
| 21 | 7.32 | 3 |
| 23 | 8.43 | 3 |
| 25 | 9.86 | 3 |
| 26 | 7.86 | 3 |
| 27 | 8.64 | 1 |
| 28 | 8.57 | 1 |
| 29 | 8.71 | 3 |
| 30 | 6.73 | 3 |
| 31 | 7.09 | 3 |
| 33 | 9.59 | 3 |
| 42 | 8.59 | 10 |
| 43 | 7.47 | 5 |
| 44 | 7.41 | 3 |
| 45 | 7.23 | 7 |
| 46 | 7.42 | 7 |
| 47 | 7.79 | 7 |
| 48 | 7.18 | 6 |
| 49 | 7.20 | 6 |
| 50 | 9.07 | 3 |
| 51 | 9.66 | 5 |
| 52 | 9.58 | 5 |
| 53 | 8.81 | 4 |
| 54 | 8.92 | 4 |
| 55 | 8.53 | 3 |
| 56 | 8.03 | 5 |
| 57 | 7.69 | 3 |
| 58 | 7.58 | 2 |
| 59 | 7.29 | 5 |
| 60 | 10.19 | 7 |
| 61 | 7.85 | 3 |

-continued

| Example No. | pKi | n |
|---|---|---|
| 62 | 7.24 | 5 |
| 63 | 7.94 | 5 |
| 64 | 7.85 | 2 |
| 65 | 7.91 | 5 |
| 66 | 8.25 | 32 |
| 67 | 10.62 | 1 |
| 68 | 8.46 | 4 |
| 69 | 7.89 | 3 |
| 70 | 8.09 | 3 |
| 71 | 7.77 | 3 |
| 72 | 8.18 | 3 |
| 73 | 7.75 | 3 |
| 74 | 7.86 | 2 |
| 75 | 7.79 | 3 |
| 76 | 7.27 | 3 |
| 77 | 8.09 | 3 |
| 78 | 8.02 | 3 |
| 79 | 7.98 | 3 |
| 80 | 7.95 | 3 |
| 81 | 8.87 | 2 |
| 82 | 7.99 | 2 |
| 83 | 10.18 | 3 |
| 84 | 8.20 | 2 |
| 85 | 9.61 | 3 |
| 86 | 8.42 | 4 |
| 87 | 8.02 | 3 |
| 88 | 8.30 | 3 |
| 89 | 7.85 | 3 |
| 90 | 7.68 | 3 |
| 91 | 9.28 | 3 |
| 92 | 8.08 | 6 |
| 93 | 6.99 | 3 |
| 94 | 7.68 | 4 |
| 95 | 8.26 | 3 |
| 96 | 7.60 | 3 |
| 97 | 7.67 | 2 |

In addition, certain of the compounds of this invention, namely those of Examples 42, 55, and 56, have been shown to be in vitro inhibitors of human synovial and human cytosolic phospholipase A$_2$ (PLA$_2$). Accordingly, the compounds of this invention, particularly those having R$_4$ groups as found in Examples 55 or 56, will be useful in treating conditions, such as arthritis, psoriasis, and asthma, associated with the excessive formation of various eicosanoids which are formed by the action of PLA$_2$ on membrane phospholipids, such as various leukotrienes, prostaglandins, lipoxins, hydroxyeicosatetranoic acids, and thromboxanes.

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma; arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

While all of the compounds illustrated above exemplify $LTB_4$ inhibition activity in vitro, we have also discovered that compounds bearing a single acidic group ($R_6$) are considerably more orally bioactive when administered to mammals compared with those compounds bearing two such acidic groups. Thus, a preferred embodiment when administering compounds of Formula I orally to mammals comprises administering compounds bearing a single acidic $R_6$ functionality.

The following formulation examples may employ as active compounds any of the compounds of this invention. The examples are illustrative only and are not intended to limit the scope of the invention in any way.

FORMULATION EXAMPLE 1

Hard gelatin capsules are prepared using the following ingredients:

|  | Quantity (mg/capsule) |
|---|---|
| 3-(2-(3-(2-Ethyl-4-(4-fluorophenyl)-5-hydroxyphenoxy)propoxy)-6-(4-carboxyphenoxy)phenyl)propanoic acid | 250 |
| Starch | 200 |
| Magnesium stearate | 10 |

The above ingredients are mixed and filled into hard gelatin capsules in 460 mg quantities.

FORMULATION EXAMPLE 2

A tablet is prepared using the ingredients below:

|  | Quantity (mg/tablet) |
|---|---|
| 1-(4-(Carboxymethoxy)phenyl)-1-(1H-tetrazol-5-yl)-6-(2-ethyl-4-(4-fluorophenyl)-5-hydroxyphenoxy)hexane | 250 |
| Cellulose, microcrystalline | 400 |
| Silicon dioxide, fumed | 10 |
| Magnesium stearate | 5 |

The components are blended and compressed to form tablets each weighing 665 mg.

FORMULATION EXAMPLE 3

An aerosol solution is prepared containing the following components:

|  | Weight % |
|---|---|
| 3-[4-[7-Carboxy-9-oxo-3-[3-[2-ethyl-4-(4-fluorophenyl)-5-hydroxyphenoxy]propoxy]-9H-xanthene]]propanoic acid | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

FORMULATION EXAMPLE 4

Tablets each containing 60 mg of active ingredient are made up as follows:

| | |
|---|---|
| 2-[2-Propyl-3-[3-[2-ethyl-5-hydroxy-4-(4-fluorophenyl)phenoxy]propoxy]phenoxy]benzoic acid sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION EXAMPLE 5

Capsules each containing 80 mg of medicament are made as follows:

| | |
|---|---|
| 5-[3-[2-(1-Carboxy)ethyl]-4-[3-[2-ethyl-4-(4-fluorophenyl)-5-hydroxyphenoxy]propoxy]phenyl]-4-pentynoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin Capsules in 200 mg quantities.

FORMULATION EXAMPLE 6

Suppositories each containing 225 mg of active ingredient are made as follows:

| | |
|---|---|
| 3-(5-(6-(4-(4-Fluorophenyl)-5-hydroxy-2-ethylphenoxy)propoxy)-2-carboxymethyl-1,2,3,4-tetrahydronaphthalen-1(2H)-one)propanoic acid | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

FORMULATION EXAMPLE 7

Suspensions each containing 50 mg of medicament per 5 mL dose are made as follows:

| | |
|---|---|
| 2-[2-Propyl-3-[3-[2-ethyl-4-(4-fluorophenyl)-5-hydroxyphenoxy]propoxy]phenoxy]benzoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 mL |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the formula:

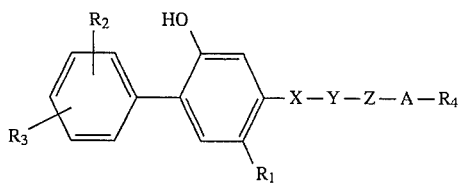

or a pharmaceutically acceptable base addition salt thereof, wherein:

$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substitutedphenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)—S(O)$_q$—, trifluoromethyl, or di-($C_1$–$C_3$ alkyl) amino;

X is —O—, —S—, —C(=O), or —CH$_2$—;

Y is —O— or —CH$_2$—;

or when taken together, —X—Y— is —CH=CH— or —C≡C—;

Z is a straight or branched chain $C_1$–$C_{10}$ alkylidenyl;

A is a bond, —O—, —S—, —CH=CH—, or CR$_a$R$_b$—, where R$_a$ and R$_b$ are each independently hydrogen, $C_1$–$C_5$ alkyl, or R$_7$-substitutedphenyl, or when taken together with the carbon atom to which they are attached form a $C_4$–$C_8$ cycloalkyl ring;

$R_4$ is $R_6$,

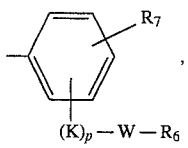

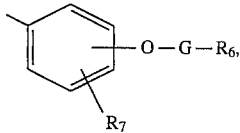

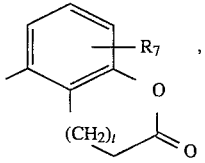

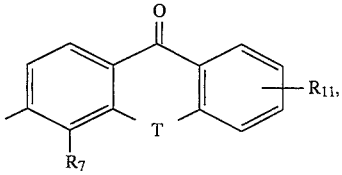

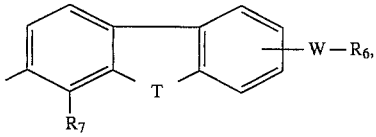

139

-continued

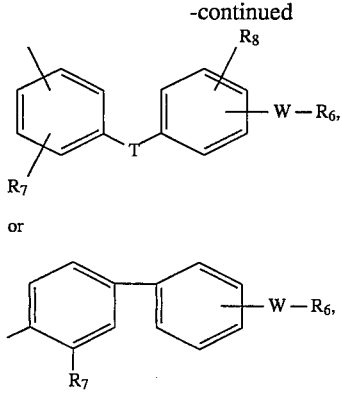

where each $R_6$ is independently —COOH, 5-tetrazolyl, —CON($R_9$)$_2$, or —CONHSO$_2R_{10}$;

each $R_7$ is hydrogen, $C_1$–$C_4$ alkyl, $C_2$–$C_5$ alkenyl, $C_2$–$C_5$ alkynyl, benzyl, methoxy, —W—$R_6$, —T—G—$R_6$, ($C_1$–$C_4$ alkyl)—T— ($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, —W—$R_6$, or —T—G—$R_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)q—;

K is —C(=O)— or —CH(OH)—;

each q is independently 0, 1, or 2;

p is 0 or 1; and t is 0 or 1;

provided when X is —O— or —S—, Y is not —O—;

provided when A is —O— or —S—, $R_4$ is not $R_6$;

and provided W is not a bond when p is 0.

2. A compound of claim 1 of the formula:

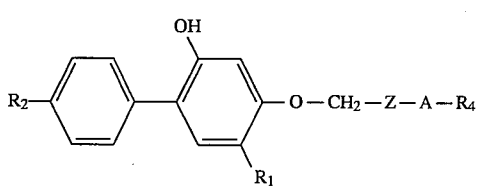

or a pharmaceutically acceptable base addition salt thereof.

3. The compound which is 2-[2-propyl-3-[3-[ 2-ethyl-4-(4-fluorophenyl)-5-hydroxyphenoxy]propoxy]phenoxy]benzoic acid or a pharmaceutically acceptable base addition salt thereof.

4. The compound which is 3(2(3(2ethyl- 4-(4-fluorophenyl)-5-hydroxyphenoxy)propoxy)-6-( 4-carboxyphenoxy)phenyl)propionic acid or a pharmaceutically acceptable base addition salt thereof.

5. The compound which is 1-(4-(carboxymethoxy)phenyl)- 1-(1H-tetrazol-5-yl)-6-(2-ethyl-4-( 4-fluorophenyl)-5-hydroxyphenoxy)hexane or a pharmaceutically acceptable base addition salt thereof.

6. The compound which is 3-[4-[7-carboxy- 9-oxo-3-[3-[2-ethyl-4-(4-fluorophenyl)-5-hydroxyphenoxy]-propoxy]-9H-xanthene]]propanoic acid or a pharmaceutically acceptable base addition salt thereof.

7. The compound which is 5-[3-[2-( 1-carboxy)ethyl]-4-[3-[2-ethyl-4-(4-fluorophenyl)- 5-hydroxyphenoxy]propoxy]phenyl]-4-pentynoic acid or a pharmaceutically acceptable base addition salt thereof.

8. The compound which is 3-(5-(6-(4-( 4-fluoro-phenyl)-5-hydroxy-2-ethylphenoxy)propoxy)- 2-carboxymethyl-1,2,3,4-tetrahydronaphthalen-1 (2H)-one)propanoic acid or a pharmaceutically acceptable base addition salt thereof.

9. A method of treating a mammal suffering from or susceptible to any condition characterized by an excessive release of leukotrienes, which comprises administering to said mammal a leukotriene antagonizing amount of a compound of claim 1 of or a pharmaceutically acceptable base addition salt thereof.

10. A method of treating a mammal suffering from or susceptible to any condition characterized by an excessive release of leukotrienes, which comprises administering to said mammal a leukotriene antagonizing amount of a compound of claim 2.

11. A method of treating a mammal suffering from or susceptible to an immediate hypersensitivity reaction of the type represented by asthma, which comprises administering to said mammal a therapeutically-effective amount of a compound of claim 1 or a pharmaceutically acceptable base addition salt thereof.

12. A method of treating a mammal suffering from or susceptible to an immediate hypersensitivity reaction of the type represented by asthma, which comprises administering to said mammal a therapeutically-effective amount of a compound of claim 2.

13. A pharmaceutical formulation comprising a compound of claim 1 or a pharmaceutically acceptable base addition salt thereof and a pharmaceutically acceptable carrier.

14. A pharmaceutical formulation comprising a compound of claim 2 and a pharmaceutically acceptable carrier.

15. A pharmaceutical formulation comprising 2-[2-propyl-3-[3-[2-ethyl- 4-(4-fluorophenyl)-5-hydroxyphenoxy]propoxy]phenoxy]benzoic acid or a pharmaceutically acceptable base addition salt thereof with a pharmaceutically acceptable carrier.

16. A pharmaceutical formulation comprising 3-(2-(3-(2-ethyl-4-( 4-fluorophenyl)-5-hdyroxyphenoxy)propoxy)-6-( 4-carboxyphenoxy)phenyl)propionic acid or a pharmaceutically acceptable base addition salt thereof with a pharmaceutically acceptable carrier.

17. A pharmaceutical formulation comprising 1-(4-(carboxymethoxyphenyl)-1-(1 H-tetrazol-5-yl)-6-(2-ethyl-4-(4-fluorophenyl)- 5-hydroxyphenoxy)hexane or a pharmaceutically acceptable base addition salt thereof with a pharmaceutically acceptable carrier.

18. A compound of the formula:

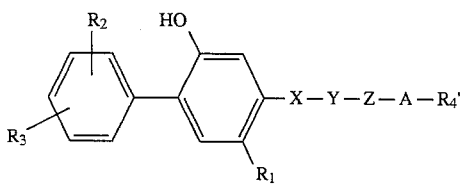

or a pharmaceutically acceptable base addition salt thereof, where $R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substitutedphenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)—S(O)q—, trifluoromethyl, or di-($C_1$–$C_3$ alkyl) amino;

X is —O—, —S—, -C(=O), or —CH$_2$—;

Y is —O— or —CH$_2$—;

or when taken together, —X—Y— is —CH=CH— or —C≡C—;

Z is a straight or branched chain $C_1$–$C_{10}$ alkylidenyl;

A is a bond, —O—, —S—, —CH=CH—, or $CR_aR_b$—, where $R_a$ and $R_b$ are each independently hydrogen, $C_1$–$C_5$ alkyl, or $R_7$-substitutedphenyl, or when taken together with the carbon atom to which they are attached form a $C_4$–$C_8$ cycloalkyl ring;

$R_4'$ is $R_6'$,

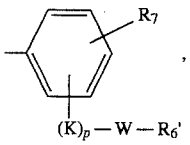

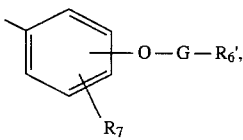

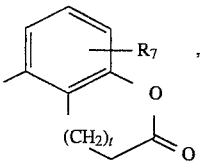

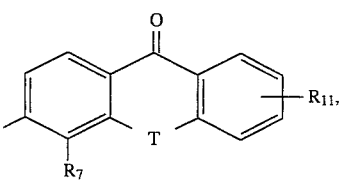

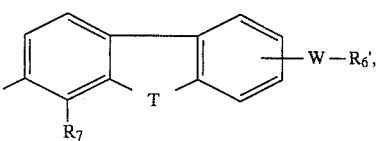

-continued

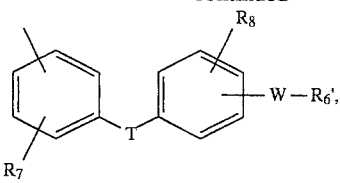

or

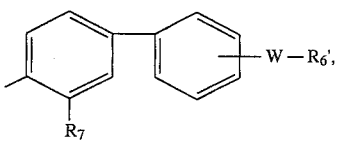

where each $R_6$ is independently —COOH, 5-tetrazolyl, —CON($R_9$)$_2$, —CONHSO$_2$$R_{10}$, —COOR, or —CN;

each $R_7$ is hydrogen, $C_1$–$C_4$ alkyl, $C_2$–$C_5$ alkenyl, $C_2$–$C_5$ alkynyl, benzyl, methoxy, —W—$R_6$, —T—G—$R_6$, ($C_1$–$C_4$ alkyl)—T— ($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, —W—$R_6$, or —T—G—$R_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, -C(=O)—, or —S(O)q—;

K is —C(=O)— or —CH(OH)—;

each q is independently 0, 1, or 2;

p is 0 or 1; and t is 0 or 1;

provided when X is —O— or —S—, Y is not —O—;

provided when A is —O— or —S—, $R_4'$ is not $R_6'$;

provided W is not a bond when p is 0;

and provided that at least one $R_6'$ must be —COOR or —CN.

19. A compound of claim 18 of the formula

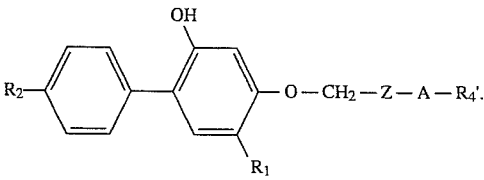

20. A compound which is a $C_1$–$C_6$ alkyl ester of 2-[2-propyl-3-[3-[2-ethyl-4-(4-fluorophenyl)- 5-hydroxyphenoxy]propoxy]phenoxy]benzoic acid.

21. The compound which is 2-[2-propyl-3-[ 3-2-ethyl-4-(4-fluorophenyl)- 5-hydroxyphenoxy]propoxy]phenoxy]-benzoic acid methyl ester.

22. A compound which is a $C_1$–$C_6$ alkyl ester of 3-(2-(3-(2-ethyl-4-(4-fluorophenyl)- 5-hydroxyphenoxy)propoxy)-

6-(4-carboxyphenoxy)phenyl)propionic acid.

23. A compound which is a $C_1-C_6$ alkyl ester of 1-(4-(carboxymethoxy)phenyl)-1-(1H-tetrazol-5-yl)- 6-(2-ethyl-4-(4-fluorophenyl)-5-hydroxyphenoxy)hexane.

24. The compound of claim 1 wherein Z is $C_2-C_4$ alkylidene; and A is —O—, —$CH_2$—, —CH($R_7$-substitutedphenyl)— or —$C(CH_3)_2$—.

25. The compound of claim 1 wherein $R_4$ is

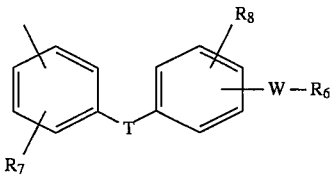

and T is —O— or —S—.

26. The compound of claim 1 wherein Z is —$CH_2$—$CH_2$— or —$CH_2CH_2CH_2CH_2$—; A is —O—, —$CH_2$—, —CH($R_7$-substitutedphenyl)- or —$C(CH_3)_2$—; W is a bond; T is —O— or —S—; $R_4$ is

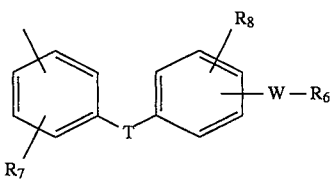

and $R_6$ is —W—COOH.

27. The compound of claim 18 wherein Z is $C_2-C_4$ alkylidene; and A is —O—, —$CH_2$—, —CH($R_7$-substitutedphenyl)- or —$C(CH_3)_2$—.

28. The compound of claim 18 wherein $R_4'$ is

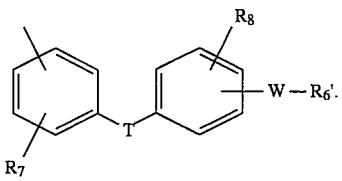

and T is —O— or —S—.

29. The compound of claim 18 wherein Z is —$CH_2$—$CH_2$— or —$CH_2CH_2CH_2CH_2$—; A is —O—, —$CH_2$—, —CH($R_7$-substitutedphenyl)- or —$C(CH_3)_2$—; W is a bond; T is —O— or —S—; $R_4'$ is

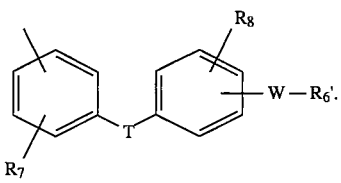

and $R_6'$ is —W—COOH.

30. A method of treating a mammal to regress or prevent the inflammation or allergic disorders of psoriasis, arthritis, chronic lung disease, acute respiratory distress syndrome, shock, asthma, and inflammatory bowel disease; wherein the method comprises administering to said mammal a therapeutically effective amount of a compound of the formula:

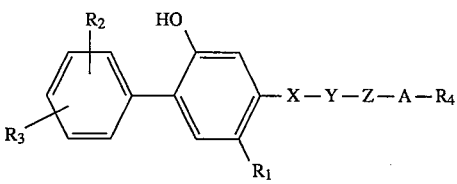

or a pharmaceutically acceptable base addition salt thereof, wherein:

$R_1$ is $C_1-C_5$ alkyl, $C_2-C_5$ alkenyl, $C_2-C_5$ alkynyl, $C_1-C_4$ alkoxy, ($C_1-C_4$ alkyl)thio, halo, or $R_2$-substitutedphenyl;

each $R_2$ and $R_3$ are each independently hydrogen, halo, hydroxy, $C_1-C_4$ alkyl, $C_1-C_4$ alkoxy, ($C_1-C_4$ alkyl)—$S(O)_q$—, trifluoromethyl, or di-($C_1-C_3$ alkyl) amino;

X is —O—, —S—, -C(=O), or —$CH_2$—;

Y is —O— or —$CH_2$—;

or when taken together, —X—Y— is —CH=CH— or —C≡C—;

Z is a straight or branched chain $C_1-C_{10}$ alkylidenyl;

A is a bond, —O—, —S—, —CH=CH—, or $CR_aR_b$—, where $R_a$ and $R_b$ are each independently hydrogen, $C_1-C_5$ alkyl, or $R_7$-substitutedphenyl, or when taken together with the carbon atom to which they are attached form a $C_4-C_8$ cycloalkyl ring;

$R_4$ is $R_6$,

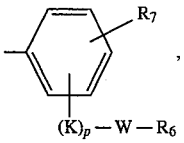

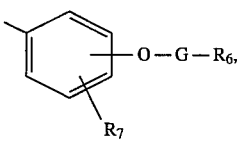

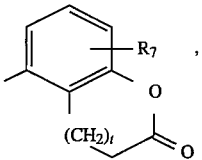

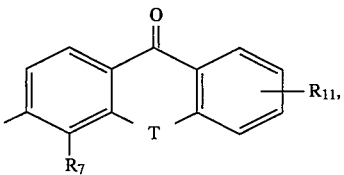

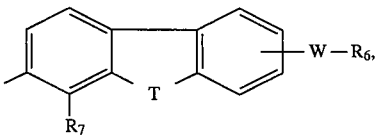

-continued

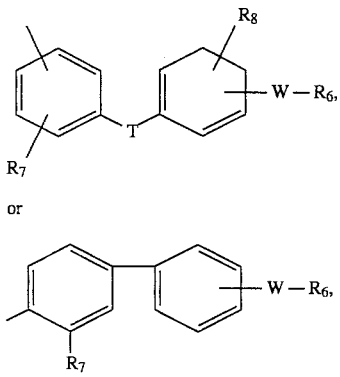

or

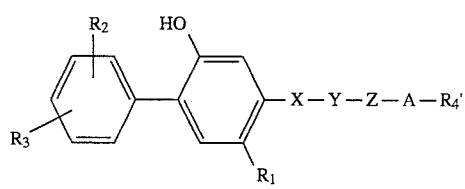

where
each $R_6$ is independently —COOH, 5-tetrazolyl, —CON($R_9$)$_2$, or —CONHSO$_2$R$_{10}$;

each $R_7$ is hydrogen, $C_1$–$C_4$ alkyl, $C_2$–$C_5$ alkenyl, $C_2$–$C_5$ alkynyl, benzyl, methoxy, —W—R$_6$, —T—G—R$_6$, ($C_1$–$C_4$ alkyl)—T— ($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, —W—R$_6$, or —T—G—R$_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)q—;

K is -C(=O)— or —CH(OH)—;

each q is independently 0, 1, or 2;

p is 0 or 1; and t is 0 or 1;

provided when X is —O—or —S—, Y is not —O—;
provided when A is —O—or —S—, R$_4$ is not R$_6$;
and provided W is not a bond when p is 0.

31. The method of claim 30 wherein the mammal is a human.

32. A method of treating a mammal to regress or prevent the inflammation or allergic disorders of psoriasis, arthritis, chronic lung disease, acute respiratory distress syndrome, shock, asthma, and inflammatory bowel disease; wherein the method comprises administering to said mammal a therapeutically effective amount of a compound of the formula:

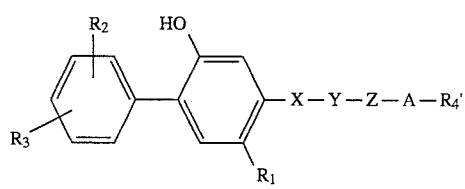

or a pharmaceutically acceptable base addition salt thereof, where $R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substitutedphenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)—S(O)$_q$—, trifluoromethyl, or di-($C_1$–$C_3$ alkyl) amino;

X is —O—, —S—, -C(=O), or —CH$_2$—;

Y is —O— or —CH$_2$—;

or when taken together, —X—Y— is —CH=CH— or —C≡C—;

Z is a straight or branched chain $C_1$–$C_{10}$ alkylidenyl;

A is a bond, —O—, —S—, —CH=CH—, or CR$_a$R$_b$—, where R$_a$ and R$_b$ are each independently hydrogen, $C_1$–$C_5$ alkyl, or R$_7$-substitutedphenyl, or when taken together with the carbon atom to which they are attached form a $C_4$–$C_8$ cycloalkyl ring;

$R_4$' is R$_6$',

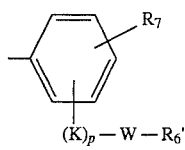

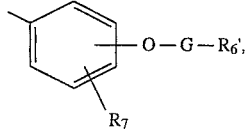

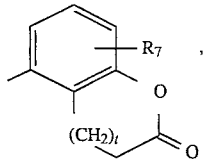

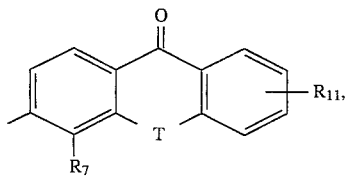

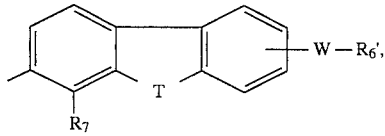

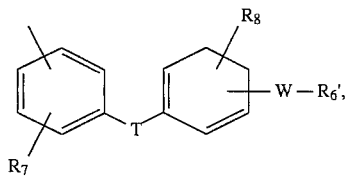

or

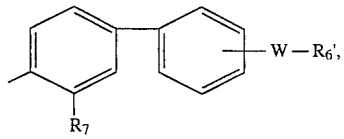

where
each $R_6$' is independently —COOH, 5-tetrazolyl,

—CON(R$_9$)$_2$, —CONHSO$_2$R$_{10}$, —COOR, or —CN;

each R$_7$ is hydrogen, C$_1$–C$_4$ alkyl, C$_2$–C$_5$ alkenyl, C$_2$–C$_5$ alkynyl, benzyl, methoxy, —W—R$_6$, —T—G—R$_6$, (C$_1$–C$_4$ alkyl)—T— (C$_1$–C$_4$ alkylidenyl)—O—, or hydroxy;

R$_8$ is hydrogen or halo;

each R$_9$ is independently hydrogen, phenyl, or C$_1$–C$_4$ alkyl, or when taken together with the nitrogen atom form a morpholino, piperidino, piperazino, or pyrrolidino group;

R$_{10}$ is C$_1$–C$_4$ alkyl or phenyl;

R$_{11}$ is R$_2$, —W—R$_6$', or —T—G—R$_6$';

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)q—;

K is -C(=O)— or —CH(OH)—;

each q is independently 0, 1, or 2;

p is 0 or 1; and t is 0 or 1;

provided when X is —O— or —S—, Y is not —O—;

provided when A is —O— or —S—, R$_4$is not R$_6$;

provided W is not a bond when p is 0;

and provided that at least one R$_6$ must be —COOR or —CN.

33. The method of claim 30 wherein the mammal is a human.

34. A method of treating a mammal to regress or prevent the inflammation or allergic disorders of psoriasis, arthritis, chronic lung disease, acute respiratory distress synfrome, shock, asthma, and inflammatory bowel disease; wherein the method comprises administering to said mammal a therapeutically effective amount of the compound; 2-[2-propyl-3-[3-[2-ethyl-4-(4-fluorophenyl)- 5-hydroxyphenoxy]propoxy]phenoxy]-benzoic acid or a pharmaceutically acceptable base addition salt thereof.

35. A method of treating a human to regress or prevent the inflammation or allergic disorders of psoriasis, arthritis, or asthma; wherein the method comprises administering to said human a therapeutically effective amount of the compound; 2-[2-propyl-3-[3-[2-ethyl-4-( 4-fluorophenyl)-5-hydroxyphenoxy]propoxy]phenoxy]-benzoic acid or a pharmaceutically acceptable base addition salt thereof.

36. The method of claim 35 for treating a human to regress or prevent the inflammation or allergic disorders of psoriasis.

37. The method of claim 35 for treating a human to regress or prevent the inflammation or allergic disorders of arthritis.

38. The method of claim 35 for treating a human to regress or prevent the inflammation or allergic disorders of asthma.

* * * * *

UNITED STATES PATENT AND TRADEMARK OFFICE
CERTIFICATE OF CORRECTION

PATENT NO. : 5,462,954
DATED : October 31, 1995
INVENTOR(S) : S. Richard Baker, et al It is certified that error appears in the above-indentified patent and that said Letters Patent is hereby corrected as shown below:

Column 139, lines 62 through 65 read "4. The compound which is 3(2(3(2ethyl-4-(4-fluorophenyl)-5-hydroxyphenoxy)propoxy)-6-(4-carboxyphenoxy)phenyl)propionic acid or a pharmaceutically acceptable base addition salt thereof." should read -- 4. The compound which is 3-(2-(3-(2-ethyl-4-(4-fluorophenyl)-5-hydroxyphenoxy)propoxy)-6-(4-carboxyphenoxy)phenyl)propionic acid or a pharmaceutically acceptable base addition salt thereof.--

Column 142, line 31 reads "$R_{11}$ is $R_2$, $-W-R_6$ or $-T-G-R_6$," should read -- $R_{11}$ is $R_2$, $-W-R_{6'}$ or $-T-G-R_{6'}$,--

Column 145, first drawing--

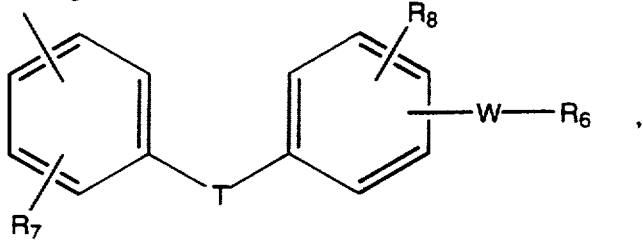

Column 146, line 53, drawing--

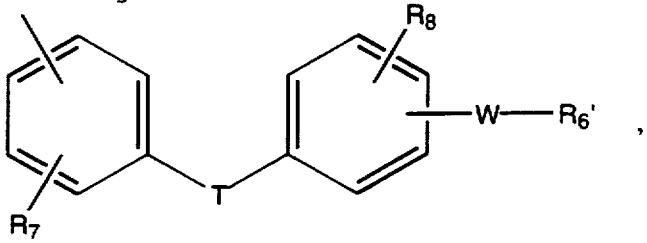

UNITED STATES PATENT AND TRADEMARK OFFICE
CERTIFICATE OF CORRECTION

PATENT NO. : 5,462,954
DATED : October 31, 1995
INVENTOR(S) : S. Richard Baker, et al It is certified that error appears in the above-indentified patent and that said Letters Patent is hereby corrected as shown below:

Column 147, line 3 reads "alkynyl, benzyl, methoxy, $-W-R_6$, $-T-G-R_6$," should read-- alkynyl, benzyl, methoxy, $-W-R_6'$, $-T-G-R_6'$,--

Column 147, line 27, reads "provided when A is -O- or -S-, $R_4$ is not $R_6$," should read --provided when A is -O- or -S-, $R_4'$ is not $R_6'$--

Column 147, line 29, reads "and provided that at least one $R_6$ must be -COOR or ..." should read --and provided that at least one $R_6'$ must be -COOR or--

Signed and Sealed this

Thirtieth Day of April, 1996

Attest:

BRUCE LEHMAN

*Attesting Officer*  *Commissioner of Patents and Trademarks*